United States Patent
Shui et al.

(10) Patent No.: US 12,419,913 B2
(45) Date of Patent: Sep. 23, 2025

(54) MODIFICATION OF CAR-T CELLS

(71) Applicants: DNA Twopointo, Inc., Newark, CA (US); The General Hospital Corporation, Boston, MA (US)

(72) Inventors: Yifang Shui, Boston, MA (US); Jeremy Minshull, Los Altos, CA (US); Maggie Lee, San Jose, CA (US); Feng Shi, Winchester, MA (US); Mark Cobbold, Winchester, MA (US)

(73) Assignees: DNA Twopointo, Inc., Newark, CA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 18/186,901

(22) Filed: Mar. 20, 2023

(65) Prior Publication Data

US 2023/0302054 A1    Sep. 28, 2023

Related U.S. Application Data

(63) Continuation-in-part of application No. 17/429,342, filed as application No. PCT/US2020/017283 on Feb. 7, 2020.

(60) Provisional application No. 63/491,171, filed on Mar. 20, 2023, provisional application No. 63/321,262, filed on Mar. 18, 2022, provisional application No. 62/803,142, filed on Feb. 8, 2019.

(51) Int. Cl.
*A61K 35/17* (2015.01)
*A61P 35/00* (2006.01)
*C07K 14/725* (2006.01)

(52) U.S. Cl.
CPC .............. *A61K 35/17* (2013.01); *A61P 35/00* (2018.01); *C07K 14/7051* (2013.01)

(58) Field of Classification Search
CPC ...... A61K 35/17; C07K 14/7051; A61P 35/00
See application file for complete search history.

(56) References Cited

U.S. PATENT DOCUMENTS

| | | |
|---|---|---|
| 6,143,291 A | 11/2000 | June et al. |
| 6,333,171 B1 | 12/2001 | Klatzmann et al. |
| 9,540,445 B2 | 1/2017 | June et al. |
| 10,457,730 B2 | 10/2019 | Pulé et al. |
| 10,501,539 B2 | 12/2019 | Schneider et al. |
| 10,711,282 B2 | 7/2020 | Slepushkin et al. |
| 11,077,144 B2 | 8/2021 | Galetto et al. |
| 11,377,637 B2 | 7/2022 | Sadelain et al. |
| 2004/0077572 A1 | 4/2004 | Hackett et al. |
| 2010/0240133 A1 | 9/2010 | Brivanlou et al. |
| 2017/0101629 A1 | 4/2017 | Minshull et al. |
| 2018/0258149 A1 | 9/2018 | Motz et al. |
| 2018/0298068 A1 | 10/2018 | Albelda |
| 2019/0040392 A1 | 2/2019 | Kormann et al. |
| 2020/0370012 A1 | 11/2020 | Fraietta et al. |
| 2021/0002366 A1 | 1/2021 | Purwar et al. |
| 2021/0047423 A1 | 2/2021 | He et al. |
| 2021/0309967 A1 | 10/2021 | Schueller et al. |
| 2022/0040234 A1 | 2/2022 | Wang et al. |
| 2022/0090132 A1 | 3/2022 | Jolly et al. |
| 2022/0280566 A1 | 9/2022 | Wang et al. |
| 2022/0348649 A1 | 11/2022 | Aftab |

FOREIGN PATENT DOCUMENTS

| | | | |
|---|---|---|---|
| CN | 107383196 B | 12/2019 | |
| CN | 113710705 A | 9/2020 | |
| CN | 111187352 B | 11/2020 | |
| CN | 110536700 A | 4/2021 | |
| CN | 112210007 B | 7/2022 | |
| CN | 114891115 A | 8/2022 | |
| EP | 3360961 A1 | 8/2018 | |
| EP | 3443096 A2 | 2/2019 | |
| EP | 3488005 A4 | 7/2020 | |
| EP | 3687553 A4 | 1/2022 | |
| EP | 3609536 B1 | 3/2022 | |
| EP | 4069730 A1 | 10/2022 | |
| JP | 2008101003 A | 5/2008 | |
| WO | WO96/34956 | * 11/1996 | ............. C12N 15/12 |
| WO | 2010085699 A2 | 7/2010 | |
| WO | 2017061615 A1 | 4/2017 | |
| WO | 2017062668 A2 | 4/2017 | |
| WO | 2017133633 A1 | 8/2017 | |
| WO | 2018148440 A1 | 8/2018 | |
| WO | WO2018140725 | * 8/2018 | ........... C07K 14/705 |
| WO | 2018170475 A1 | 9/2018 | |
| WO | 2021217130 A3 | 12/2021 | |
| WO | 2022164935 A1 | 8/2022 | |
| WO | 2022222846 A1 | 10/2022 | |

OTHER PUBLICATIONS

Savoldo et al. CD28 costimulation improves expansion and persistence of chimeric antigen receptor-modified T cells in lymphoma patients Clin Invest. 121, 1822-1826, 2011. (Year: 2011).*

Intellectual Property Office of Singapore, Written Opinion issued in Singapore Application No. 11202108665P, dated Apr. 21, 2023 (6 pages).

Intellectual Property Office of Singapore, Search Report issued in Singapore Application No. 11202108665P, dated Apr. 20, 2023 (2 pages).

European search report and European search opinion issued in EP app. No. 20752984.3 dated Dec. 21, 2022.

Boucher Justin C et al: "Mutation of the CD28 Costimulatory Domain Confers Decreased CAR T Cell Exhaustion", Blood, vol. 132, Nov. 29, 2018 (Nov. 29, 2018), p. 966, XP086593720.

(Continued)

*Primary Examiner* — Elly-Gerald Stoica
(74) *Attorney, Agent, or Firm* — Benjamen E. Kern; Charlemagne Kern; Kern Kendrick, LLC

(57) ABSTRACT

Modified immune cells are provided, the modified immune cells expressing a heterologous polynucleotide comprising a nucleotide sequence encoding a function (e.g., at least one of persistence, proliferation, or cytotoxicity) booster, e.g., an apoptosis inhibitor. In one aspect, the modified T cells further comprise a chimeric antigen receptor. Methods, kits, and components for making and using the modified immune cells are also provided.

20 Claims, 42 Drawing Sheets
Specification includes a Sequence Listing.

(56) References Cited

OTHER PUBLICATIONS

International Search Report and Written Opinion issued in PCT/US2020/017283 dated Jul. 17, 2020.
International Preliminary Report on Patentability issued in PCT/US2020/017283 dated Aug. 10, 2021.
Andersson et al. "Activating somatic mutations outside the SH2-domain of STAT3 in LGL leukemia," Leukemia, Sep. 20, 2015, vol. 30, Iss. 5, pp. 1204-1208 and supplemental information, pp. 1-10.
"User Guide: Gateway pcDNA-DEST40 Vector," Invitrogen, Feb. 28, 2013, Cat. No. 12274-015, pp. 1-28.
Yan et al. "Emergence of a STAT3 mutated NK clone in LGL leukemia," Leukemia Research Reports, Dec. 16, 2014, vol. 4, Iss. 1, pp. 4-7.
Gymerek et al., "Functional analysis of acquired CD28 mutations identified in cutaneous T cell lymphoma," Cellular Immunology, Jul. 10, 2017, vol. 319, pp. 28-34.
International Search Report and Written Opinion issued in PCT No. PCT/US2023/64729, dated Oct. 18, 2023.
Notice of Deficiencies of Israel Patent Application No. 2855422, dated Dec. 5, 2023.
Kowolik et al. "CD28 Costimulation Provided through a CD19-Specific Chimeric Antigen Receptor Enhances In vivo Persistence and Antitumor Efficacy of Adoptively Transferred T Cells," Cancer Research, Nov. 15, 2006, vol. 66, Issue 22, pp. 10995-11004 (10 pages).
Japan Patent Office, Notification of Reasons for Rejection issued in Japanese Patent Application No. 2021-547309, dated Feb. 29, 2024 (3 pages).

\* cited by examiner

SEQUENCE LISTING

```
Sequence total quantity: 260
SEQ ID NO: 1            moltype = DNA  length = 14
FEATURE                 Location/Qualifiers
misc_feature            1..14
                        note = Synthetic
source                  1..14
                        mol_type = other DNA
                        organism = synthetic construct
SEQUENCE: 1
ccytttbmct gcca                                                    14

SEQ ID NO: 2            moltype = DNA  length = 14
FEATURE                 Location/Qualifiers
misc_feature            1..14
                        note = Synthetic
source                  1..14
                        mol_type = other DNA
                        organism = synthetic construct
SEQUENCE: 2
tggcagkvaa argg                                                    14

SEQ ID NO: 3            moltype = DNA  length = 15
FEATURE                 Location/Qualifiers
misc_feature            1..15
                        note = Synthetic
source                  1..15
                        mol_type = other DNA
                        organism = synthetic construct
SEQUENCE: 3
cacttggatt gcggg                                                   15

SEQ ID NO: 4            moltype = DNA  length = 15
FEATURE                 Location/Qualifiers
misc_feature            1..15
                        note = Synthetic
source                  1..15
                        mol_type = other DNA
                        organism = synthetic construct
SEQUENCE: 4
cccgacaccg tagtg                                                   15

SEQ ID NO: 5            moltype = DNA  length = 64
FEATURE                 Location/Qualifiers
misc_feature            1..64
                        note = Synthetic
source                  1..64
                        mol_type = other DNA
                        organism = synthetic construct
```

```
SEQUENCE: 5
atcacgcatg ggatacgtcg tggcagtaaa agggcttaaa tgccaacgac gcgtcccata    60
cgtt                                                                 64

SEQ ID NO: 6              moltype = DNA   length = 82
FEATURE                   Location/Qualifiers
misc_feature              1..82
                          note = Synthetic
source                    1..82
                          mol_type = other DNA
                          organism = synthetic construct
SEQUENCE: 6
atgacgcatg ggatacgtcg tggcagtaaa agggcttaaa tgccaacgac gcgtcccata    60
cgttgttggc attttaagtc tt                                             82

SEQ ID NO: 7              moltype = DNA   length = 106
FEATURE                   Location/Qualifiers
misc_feature              1..106
                          note = Synthetic
source                    1..106
                          mol_type = other DNA
                          organism = synthetic construct
SEQUENCE: 7
cctgggtaaa ctaaaagtcc cctcgaggaa aggcccctaa agtgaaacag tgcaaaacgt    60
tcaaaaactg tctggcaata caagttccac tttgggacaa atcggc                  106

SEQ ID NO: 8              moltype = DNA   length = 105
FEATURE                   Location/Qualifiers
misc_feature              1..105
                          note = Synthetic
source                    1..105
                          mol_type = other DNA
                          organism = synthetic construct
SEQUENCE: 8
cctgggtaaa ctaaaagtcc cctcgaggaa aggcccctaa agtgaaacag tgcaaaacgt    60
tcaaaaactg tctggcaata caagttccac tttgaccaaa acggc                   105

SEQ ID NO: 9              moltype = AA    length = 589
FEATURE                   Location/Qualifiers
REGION                    1..589
                          note = Synthetic
source                    1..589
                          mol_type = protein
                          organism = synthetic construct
SEQUENCE: 9
MAKRFYSAEE AAAHCMASSS EEFSGSDSEY VPPASESDSS TEESWCSSST VSALEEPMEV     60
DEDVDDLEDQ EAGDRADAAA GGEPAWGPPC NFPPEIPPFT TVPGVKVDTS NFEPINFFQL    120
FMTEAILQDM VLYTNVYAEQ YLTQNPLPRY ARAHAWHPTD IAEMKRFVGL TLAMGLIKAN    180
SLESYWDTTT VLSIPVFSAT MSRNRYQLLL RFLHFNNNAT AVPPDQPGHD RLHKLRPLID    240
SLSERFAAVY TPCQNICIDE SLLLFKGRLQ FRQYIPSKRA RYGIKFYKLC ESSSGYTSYF    300
LIYEGKDSKL DPPGCPPDLT VSGKIVWELI SPLLGQGFHL YVDNFYSSIP LFTALYCLDT    360
PACGTINRNR KGLPRALLDK KLNRGETYAL RKNELLAIKF FDKKNVFMLT SIHDESVIRE    420
QRVGRPPKNK PLCSKEYSKY MGGVDRTDQL QHYYNATRKT RAWYKKVGIY LIQMALRNSY    480
IVYKAAVPGP KLSYYKYQLQ ILPALLFGGV EEQTVPEMPP SDNVARLIGK HFIDTLPPTP    540
GKQRPQKGCK VCRKRGIRRD TRYYCPKCPR NPGLCFKPCF EIYHTQLHY               589

SEQ ID NO: 10             moltype = AA    length = 589
FEATURE                   Location/Qualifiers
REGION                    1..589
                          note = Synthetic
source                    1..589
                          mol_type = protein
                          organism = synthetic construct
SEQUENCE: 10
MAKRFYSAEE AAAHCMAPSS EEFSGSDSEY VPPASESDSS TEESWCSSST VSALEEPMEV     60
DEDVDDLEDQ EAGDRADAAA GGEPAWGPPC NFPPEIPPFT TVPGVKVDTS NFEPINFFQL    120
FMTEAILQDM VLYTNVYAEQ YLTQNPLPRY ARAHAWHPTD IAEMKRFVGL TLAMGLIKAN    180
SLESYWNTTT VLSIPVFSAT MSRNRYQLLL RFLHFNNNAT AVPPDQPGHD RLHKLRPLID    240
SLSERFAAVY TPCQNICIDE SLLLFKGRLR FRQYIPSKRA RYGIKFYKLC ESSSGYTSYF    300
LIYEGKDSKL DPPGCPPDLT VSGKIVWELI SPLLGQGFHL YVDNFYSSIP LFTALYCLDT    360
PACGTINRTR KGLPRALLDK KLNRGETYAL RKNELLAIKF FDKKNVFMLT SIHDESVIRE    420
QRVGRPPKNK PLCSKEYSKY MGGVDRTDQL QHYYNATRKT SAWYKKVGIY LIQMALRNSY    480
IVYKAAVPGP KLSYYKYQLQ ILPALLFGGV EEQTVPEMLP SDNVARLIGK HFIDTLPPTP    540
GKQRPQKGCK VCRKRGIRRD TRYYCPKCPR NPGLCFKPCF EIYHTQLHY               589

SEQ ID NO: 11             moltype = AA    length = 589
FEATURE                   Location/Qualifiers
REGION                    1..589
                          note = Synthetic
```

```
source                   1..589
                         mol_type = protein
                         organism = synthetic construct
SEQUENCE: 11
MAKRFYSAEE AAAHCMASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NYEPINFFQL   120
FMTEAILQDM VLYTNVYAEQ YLTQNPLPRY ARAHAWHPTD IAEMKRFVGL TLAMGLIKAN   180
SLESYWDTTT VLSIPVFSAT MSRNRYQLLL RFLHFNNNAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHY              589

SEQ ID NO: 12            moltype = AA   length = 589
FEATURE                  Location/Qualifiers
REGION                   1..589
                         note = Synthetic
source                   1..589
                         mol_type = protein
                         organism = synthetic construct
SEQUENCE: 12
MAKRFYSAEE AAAHCMASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQVPLPRY ARAHAWHPTD IAEMKRFVGL TLAMGLIKAN   180
SLESYWDTTT VLNIPVFSAT MSRNRYQLLL RFLEFNNEAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHY              589

SEQ ID NO: 13            moltype = AA   length = 589
FEATURE                  Location/Qualifiers
REGION                   1..589
                         note = Synthetic
source                   1..589
                         mol_type = protein
                         organism = synthetic construct
SEQUENCE: 13
MAKRFYSAEE AAAHCMASSQ EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRY ARAHAWHPTD IAEMKRFVGL TLAMGLIKAN   180
SLESYWDTTT VLSIPVFGAT MSRNRYQLLL RFLHFNNNAT AVPPDQPGHD RLHKLRPLID   240
SLSERFANVY TPCQNICIDE SLLLFKGRLQ FKQYIPSKRA RYGIKFYKLC ESSSGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RHWYKKVGVY LIQMALRNSY   480
IVYKAAVPGP KLSYYKYQLQ ILPALLFGGV EEQTVPEMPD SDNVARLIGK HFIDTLPPTP   540
GKQRPQKGCK VCRKRGIRRD TRYYCPKCPR NPGLCRKPCF EIYHTQLHY              589

SEQ ID NO: 14            moltype = AA   length = 589
FEATURE                  Location/Qualifiers
REGION                   1..589
                         note = Synthetic
source                   1..589
                         mol_type = protein
                         organism = synthetic construct
SEQUENCE: 14
MAKRFYSAEE AAAHCMASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRY ARAHAWHPTD ICEMKRFVGL TLAMGLIKAN   180
SLESYWDTTT VLSIPVFGAT MSRNRYQLLL RFLHFNNNAT AVPPDQPGHD RLHKLRPLID   240
SLSERFANVY TPCQNICIDE SLLLFKGRLQ FRQYIPSKRA RYGIKFYKLC ESSTGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RHWYKKVGVY LIQMALRNSY   480
IVYKAAVPGP KLSYYKYQLQ ILPALLFGGV EEQTVPEMPD SDNVARLIGK HFIDTLPPTP   540
GKQRPQKGCK VCRKRGIRRD TRYYCPKCPR NPGLCRKPCF EIYHTQLHY              589

SEQ ID NO: 15            moltype = AA   length = 589
FEATURE                  Location/Qualifiers
REGION                   1..589
                         note = Synthetic
source                   1..589
                         mol_type = protein
                         organism = synthetic construct
```

```
SEQUENCE: 15
MAKRFYSAEE AAAHCMASSS EQTSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRY ARAHAWHPTD IAEMKRFVGL TLAMGLIKAN   180
SIESYWDTTT VLSIPVFGAT MSRNRYQLLL RFLHFNNNAT AVPPDQPGHD RLHKLRPLID   240
SLSERFANVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPKNK PLCSKEYSKY MGGVDRTDQL QHYYNATRKT RHWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCRKPCF EIYHTQLHY            589

SEQ ID NO: 16          moltype = AA   length = 589
FEATURE                Location/Qualifiers
REGION                 1..589
                       note = Synthetic
source                 1..589
                       mol_type = protein
                       organism = synthetic construct
SEQUENCE: 16
MAKRFYSAEE AAAHCSASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRG ARAHAWHPTD IAEMKRFVGL TLAMGLIKAN   180
SLESYWDTTT VLSIPVFGAT MSRNRYQLLL RFLHFNNNAT AVPPDQPGHD RLHKLRPLID   240
SLSERFANVY TPCQNICIDE SLMLFKGRLQ FRQYIPSKRA RYGIKFYKLC ESSTGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RHWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCRKPCF EIYHTQLHY            589

SEQ ID NO: 17          moltype = AA   length = 589
FEATURE                Location/Qualifiers
REGION                 1..589
                       note = Synthetic
source                 1..589
                       mol_type = protein
                       organism = synthetic construct
SEQUENCE: 17
MAKRFYSAEE AAAHCSASSS EEFSGSDSEY VPPASESDSS TEESWCSSST VSALEEPMEV    60
DEDVDDLEDQ EAHDRADAAA GGEPAWGPPC NFPPEIPPFT TVPGVKVDTS NFEPINFFQL   120
FMTEAILQDM VLYTNVYAEQ YLTQNPLTRG ARAHAWHPTD IAEMKRFVGL TLAMGLIKAN   180
SIESYWDTTT VLSIPVFGAT MSRNRYQLLH RFLHFNNNAT AVPPDQPGHD RLHKLRPLID   240
SLSERFANVY TPCQNICIDE SLMLFKGRLQ FRQYIPSKRA RYGIKFYKLC ESSTGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RHWYKKVGIY LIQMALRNSY   480
IVYKAAVPGP KLSYYKYQLQ ILPALLFGGV EEQTVPEMPP SDSVARLIGK HFIDTLPPTP   540
GKQRPQKGCK VCRKRGIRRD TRYYCPKCPR NPGLCRKPCF EIYHTQLHY            589

SEQ ID NO: 18          moltype = AA   length = 589
FEATURE                Location/Qualifiers
REGION                 1..589
                       note = Synthetic
source                 1..589
                       mol_type = protein
                       organism = synthetic construct
SEQUENCE: 18
MAKRFYSAEE AAAHCSASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRG ARAHAWHPTD IAEMKRFVGL TLAMGLIKAN   180
SIESYWDTTT VLSIPVFGAT MSRNRYQLLL RFLHFNNNAT AVPPDQPGHD RLHKLRPLID   240
SLSERFANVY TPCQNICIDE SLMLFKGRLQ FRQYIPSKRA RYGIKFYKLC ESSTGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RHWYKKVGIY LIQMALRNSY   480
IVYKAAVPGP KLSYYKYQLQ ILPALLFGGV EEQTVPEMPD SDNVARLIGK HFIDTLPPTP   540
GKQRPQKGCK VCRKRGIRRD TRYYCPKCPR NPGLCRKPCF EIYHTQLHY            589

SEQ ID NO: 19          moltype = AA   length = 589
FEATURE                Location/Qualifiers
REGION                 1..589
                       note = Synthetic
source                 1..589
                       mol_type = protein
                       organism = synthetic construct
SEQUENCE: 19
MAKRFYSAEE AAAHCSASSS EQFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
```

```
FMTEAILQDM VLYTNVYAEQ YLTQNPLTRG ARAHAWYPTD IAEMKRFVGL TLAMGLIKAN   180
SIESYWDTTT VLSIPVFGAT MSRNRYQLLL RFLHFNNNAT AVPPDQPGHD RLHKLRPLID   240
SLSERFANVY TPCQNICIDE SLMLFKGRLQ FRQYIPSKRA RYGIKFYKLC ESSTGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPPKNK PLCSKEYSKY MGGVDRGDQL QHYYNATRKT RHWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCRKPCF EIYHTQLHY              589

SEQ ID NO: 20           moltype = AA   length = 589
FEATURE                 Location/Qualifiers
REGION                  1..589
                        note = Synthetic
source                  1..589
                        mol_type = protein
                        organism = synthetic construct
SEQUENCE: 20
MAKRFYSAEE AAAHCSASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRG ARAHAWHPTD IAEMKRFVGL TLAMGLIKAN   180
SIESYWDTTT VLSIPVFGAT MSRNRYQLLL RFLHFNNNAT AVPPDQPGHD RLHKLRPLID   240
SLSERFANVY TPCQNICIDE SLMLFKGRLQ FRQYIPSKRA RYGIKFYKLC ESSTGYMSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPKPNK PLCSKEYSKY MGGVDRTDQL QHYYNATRKT RHWYKKVGIY LIQMALRNSY   480
IVYKAAVPGP KLSYYKYQLQ ILPALLFGGV EEQTVPEMPP SDSVARLIGK HFIDTLPPTP   540
GKQRPQKGCK VCRKRGIRRD TRYYCPKCPR NPGLCRKPCF EIYHTQLHY              589

SEQ ID NO: 21           moltype = AA   length = 589
FEATURE                 Location/Qualifiers
REGION                  1..589
                        note = Synthetic
source                  1..589
                        mol_type = protein
                        organism = synthetic construct
SEQUENCE: 21
MAKRFYSAEE AAAHCMASSS EEFYGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRY ARAHAWHPTD IAEMKRFVGL TLAMGLIKAN   180
SLESYWDTTT VLSIPVFGAT MSRNRYQLLL RFLHFNNNAT AVPPDQPGHD RLHKLRPLID   240
SLSERFANVY TPCQNICIDE SLLLFKGRLQ FKQYIPSKRA RYGIKFYKLC ESSSGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RHWYKKVGIY LIQMALRNSY   480
IVYKAAVPGP KLSYYKYQLQ ILPALLFGGV EEQTVPEMPD SDNVARLIGK HFIDTLPPTP   540
GKQRPQKGCK VCRKRGIRRD TRYYCPKCPR NPGLCRIPCF EIYHTQLHY              589

SEQ ID NO: 22           moltype = AA   length = 589
FEATURE                 Location/Qualifiers
REGION                  1..589
                        note = Synthetic
source                  1..589
                        mol_type = protein
                        organism = synthetic construct
SEQUENCE: 22
MAKRFYSAEE AAAHCSASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRY ARAHAWHPTD ICEMKRFVGL TLAMGLIKAN   180
SIESYWDTTT VLSIPVFGAT MSRNRYQLLL RFLHFNNNAT AVPPDQPGHD RLHKLRPLID   240
SLSERFANVY TPCQNICIDE SLMLFKGRLQ FRQYIPSKRA RYGIKFYKLC ESSTGYTSYF   300
LIYEGKDSKL DPPGCPPDLT VSGKIVWELI SPLLGQGFHL YVDNFYSSIP LFTALYVLNT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RHWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCRKPCF EIYHTQLHY              589

SEQ ID NO: 23           moltype = AA   length = 589
FEATURE                 Location/Qualifiers
REGION                  1..589
                        note = Synthetic
source                  1..589
                        mol_type = protein
                        organism = synthetic construct
SEQUENCE: 23
MAKRFYSAEE AAAHCSASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRY ARAHAWYPTD IAEMKRFVGL TLAMGLIKAN   180
SLESYWDTTT VLSIPVFGAT MSRNRYQLLL RFLHFNNNAT AVPPDQPGHD RLHKLRPLID   240
SLSERFANVY TPCQNICIDE SLMLFKGRLQ FRQYIPSKRA RYGIKFYKLC ESSTGYTSYF   300
```

```
LIYEGKDSKL DPPGCPPDLT VSGKIVWELI SPLLGQGFHL YVDNFYSSIP LFTALYCLNT    360
PACGTINRNR KGLPRALLDK KLNRGETYAL RKNELLAIKF FDKKNVFMLT SIHDESVIRE    420
QRVGRPPKNK PLCSKEYSKY MGGVDRTDQL QHYYNATRKT RHWYKKVGIY LIQMALRNSY    480
IVYKAAVPGP KLSYYKYQLQ ILPALLFGGV EEQTVPEMPP SDNVARLIGK HFIDTLPPTP    540
GKQRPQKGCK VCRKRGIRRD TRYYCPKCPR NPGLCRKPCF EIYHTQLHY                589

SEQ ID NO: 24           moltype = AA  length = 589
FEATURE                 Location/Qualifiers
REGION                  1..589
                        note = Synthetic
source                  1..589
                        mol_type = protein
                        organism = synthetic construct
SEQUENCE: 24
MAKRFYSAEE AAAHCSASSS DEFSGSDSEY VPPASESDSS TEESWCSSST VSALEEPMEV     60
DEDVDDLEDQ EAGDRADAAA GGEPAWGPPC NFPPEIPPFT TVPGVKVDTS NFEPINFFQL    120
FMTEAILQDM VLYTNVYAEQ YLTQNPLTRG ARAHAWYPTD IAEMKRFVGL TLAMGLIKAN    180
SLESYWDTTT VLSIPVFGAT MSRNRYQLLL RFLHFNNNAT AVPPDQPGHD RLHKLRPLID    240
SLSERFANVY TPCQNICIDE SLMLFKGRLQ FRQYIPSKRA RYGIKFYKLC ESSTGYTSYF    300
LIYEGKDSKL DPPGCPPDLT VSGKIVWELI SPLLGQGFHL YVDNFYSSIP LFTALYCLNT    360
PACGTINRNR KGLPRALLDK KLNRGETYAL RKNELLAIKF FDKKNVFMLT SIHDESVIRE    420
QRVGRPPKNK PLCSKEYSKY MGGVDRTDQL QHYYNATRKT RHWYKKVGIY LIQMALRNSY    480
IVYKAAVPGP KLSYYKYQLQ ILPALLFGGV EEQTVPEMPP SDSVARLIGK HFIDTLPPTP    540
GKQRPQKGCK VCRKRGIRRD TRYYCPKCPR NPGLCRKPCF EIYHTQLHY                589

SEQ ID NO: 25           moltype = AA  length = 589
FEATURE                 Location/Qualifiers
REGION                  1..589
                        note = Synthetic
source                  1..589
                        mol_type = protein
                        organism = synthetic construct
SEQUENCE: 25
MAKRFYSAEE AAAHCMASSS EEFSGSDSEY VPPASESDSS TEESWCSSST VSALEEPMEV     60
DEDVDDLEDQ EAGDRADAAA GGEPAWGPPC NFPPEIPPFT TVPGVKVDTS NFEPINFFQL    120
FMTEAILQDM VLYTNVYAEQ YLTQNPLTRY ARAHAWHPTD IAEMKRFVGL TLAMGLIKAN    180
SLESYWDTTT VLSIPVFGAT MSRNRYQLLL RFLHFNNNAT AVPPDQPGHD RLHKLRPLID    240
SLSERFANVY TPCQNICIDE SLLLFKGRLQ FRQYIPSKRA RYGIKFYKLC ESSSGYTSYF    300
LIYEGKDSKL DPPGCPPDLT VSGKIVWELI SPLLGQGFHL YVDNFYSSIP LFTALYCLNT    360
PACGTINRNR KGLPRALLDK KLNRGETYAL RKNELLAIKF FDKKNVFMLT SIHDESVIRE    420
QRVGRPPKNK PLCSKEYSKY MGGVDRTDQL QHYYNATRKT RHWYKKVGIY LIQMALRNSY    480
IVYKAAVPGP KLSYYKYQLQ ILPALLFGGV EEQTVPEMPP SDNVARLIGK HFIDTLPPTP    540
GKQRPQKGCK VCRKRGIRRD TRYYCPKCPR NPGLCRKPCF EIYHTQLHY                589

SEQ ID NO: 26           moltype = AA  length = 589
FEATURE                 Location/Qualifiers
REGION                  1..589
                        note = Synthetic
source                  1..589
                        mol_type = protein
                        organism = synthetic construct
SEQUENCE: 26
MAKRFYSAEE AAAHCMASSS EETSGSDSEY VPPASESDSS TEESWCSSST VSALEEPMEV     60
DEDVDDLEDQ EAGDRADAAA GGEPAWGPPC NFPPEIPPFT TVPGVKVDTS NFEPINFFQL    120
FMTEAILQDM VLYTNVYAEQ YLTQNPLTRY ARAHAWHPTD IAEMKRFVGL TLAMGLIKAN    180
SLESYWDTTT VLSIPVFSAT MSRNRYQLLL RFLHFNNNAT AVPPDQPGHD RLHKLRPLID    240
SLSERFAAVY TPCQNICIDE SLLLFKGRLQ FRQYIPSKRA RYGIKFYKLC ESSSGYTSYF    300
LIYEGKDSKL DPPGCPPDLT VSGKIVWELI SPLLGQGFHL YVDNFYSSIP LFTALYCLNT    360
PACGTINRNR KGLPRALLDK KLNRGETYAL RKNELLAIKF FDKKNVFMLT SIHDESVIRE    420
QRHGRPPKNK PLCSKEYSKY MGGVDRADQL QHYYNATRKT RHWYKKVGIY LIQMALRNSY    480
IVYKAAVPGP KLSYYKYQLQ ILPALLFGGV EEQTVPEMPP SDNVARLIGK HFIDTLPPTP    540
GKQRPQKGCK VCRKRGIRRD TRYYCPKCPR NPGLCRKPCF EIYHTQLHY                589

SEQ ID NO: 27           moltype = AA  length = 589
FEATURE                 Location/Qualifiers
REGION                  1..589
                        note = Synthetic
source                  1..589
                        mol_type = protein
                        organism = synthetic construct
SEQUENCE: 27
MAKRFYSAEE AAAHCMASSS EEFSGSDSEY VPPASESDSS TEESWCSSST VSALEEPMEV     60
DEDVDDLEDQ EAGDRADAAA GGEPAWGPPC NFPPEIPPFT TVPGVKVDTS NFEPINFFQL    120
FMTEAILQDM VLYTNVYAEQ YLTQNPLTRY ARAHAWHPTD IAEMKRFVGL TLAMGLIKAN    180
SLESYWDTTT VLSIPVFSAT MSRNRYQLLL RFLHFNNEAT AVPPDQPGHD RLHKLRPLID    240
SLSERFAAVY TPCQNICIDE SLLLFKGRLQ FRQYIPSKRA RYGIKFYKLC ESSSGYTSYF    300
LIYEGKDSKL DPPGCPPDLT VSGKIVWELI SPLLGQGFHL YVDNFYSSIP LFTALYCLNT    360
PACGTINRNR KGLPRALLDK KLNRGETYAL RKNELLAIKF FDKKNVFMLT SIHDESVIRE    420
QRVGRPPKNK PLCSKEYSKY MGGVDRTDQL QHYYNATRKT RHWYKKVGIY LIQMALRNSY    480
```

```
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCRKPCF EIYHTQLHY              589

SEQ ID NO: 28            moltype = AA   length = 589
FEATURE                  Location/Qualifiers
REGION                   1..589
                         note = Synthetic
source                   1..589
                         mol_type = protein
                         organism = synthetic construct
SEQUENCE: 28
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRY ARAHAWHPTD IAEMKRFVGL TLAMGLIKAN   180
SLESYWDTTT VLSIPVFSAT MSRNRYQLLL RFLHFNNNAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCRKPCF EIYHTQLHY              589

SEQ ID NO: 29            moltype = AA   length = 589
FEATURE                  Location/Qualifiers
REGION                   1..589
                         note = Synthetic
source                   1..589
                         mol_type = protein
                         organism = synthetic construct
SEQUENCE: 29
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRY ARAHAWHPTD IAEMKRFVGL TLAMGLIKAN   180
SLESYWDTTT VLSIPVFSAT MSRNRYQLLL RFLHFNNNAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RHWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCRKPCF EIYHTQLHY              589

SEQ ID NO: 30            moltype = AA   length = 589
FEATURE                  Location/Qualifiers
REGION                   1..589
                         note = Synthetic
source                   1..589
                         mol_type = protein
                         organism = synthetic construct
SEQUENCE: 30
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLPRY ARAHAWHPTD IAEMKRFVGL TLAMGLIKAN   180
SLESYWDTTT VLKIPVFSAT MSRNRYQLLL RFLHFNNNAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RHWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHY              589

SEQ ID NO: 31            moltype = AA   length = 589
FEATURE                  Location/Qualifiers
REGION                   1..589
                         note = Synthetic
source                   1..589
                         mol_type = protein
                         organism = synthetic construct
SEQUENCE: 31
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL   120
FMTEAILQDM VLYTNVYAEQ QLTQNPLPRY ARAHAWHPTD IAEMKRFVGL TLAMGLIKAN   180
SLESYWDTTT VLSIPVFSAT MSRNRYQLLL RFLHFNNNAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDRKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQYHY              589
```

```
SEQ ID NO: 32            moltype = AA  length = 589
FEATURE                  Location/Qualifiers
REGION                   1..589
                         note = Synthetic
source                   1..589
                         mol_type = protein
                         organism = synthetic construct
SEQUENCE: 32
MAKRFYSAEE AAAHCMASSS EEPSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLPRY ARAHAWHPTD IAEMKRFVGL TLAMGLIKAN   180
SLESYWDTTT VLSIPVFSAT MSRNRYQLLL RFLHFNNNAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTHLYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQYHY              589

SEQ ID NO: 33            moltype = AA  length = 592
FEATURE                  Location/Qualifiers
REGION                   1..592
                         note = Synthetic
source                   1..592
                         mol_type = protein
                         organism = synthetic construct
SEQUENCE: 33
MAKRFYSAEE AAAHCMASSQ EEFSGSDSEY VPPASESDSS TEESWCSSST VSALEEPMEV    60
DEDVDDLEDQ EAGDRVDAAA GGEPAWGPPC NFPPEIPPFT TVPGVKVDTS NFEPINFFQL   120
FMTEAILQDM VLYTNVYAEQ YLTQNPLPRY ARAHAWHPTD IAEMKRFVGL TLAMGLIKAN   180
SLESYWDTTT VLSIPVFSAT MSRNRYQLLL RFLHFNNNAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHYG RR          592

SEQ ID NO: 34            moltype = AA  length = 592
FEATURE                  Location/Qualifiers
REGION                   1..592
                         note = Synthetic
source                   1..592
                         mol_type = protein
                         organism = synthetic construct
SEQUENCE: 34
MAKRFYSAEE AAAHCMASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNKLPRY ARAHAWHPTD IAEMKRFVGL TLAMGLIKAN   180
SLESYWDTGT VHSIPVFSAT MSRNRYQLLL RFLHFNNNAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHYG RR          592

SEQ ID NO: 35            moltype = AA  length = 592
FEATURE                  Location/Qualifiers
REGION                   1..592
                         note = Synthetic
source                   1..592
                         mol_type = protein
                         organism = synthetic construct
SEQUENCE: 35
MAKRFCSAEE AAAHCMASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRY ARAHAWHPTD IAEMKRFVGL TLAMGLIKAN   180
SLESYWDTTT VLSIPVFSAT MSRNRYQLLL RFLHFNNNAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIATLPPTP   540
GKQRPQKGCK VCRKRGIRRD TRYYCPKCPR NPGLCFKPCF EIYHTQLHYG RR          592

SEQ ID NO: 36            moltype = AA  length = 592
FEATURE                  Location/Qualifiers
REGION                   1..592
```

```
                        note       = Synthetic
source                  1..592
                        mol_type   = protein
                        organism   = synthetic construct
SEQUENCE: 36
MAKRFYSAEE AAAHCMASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQVPLTRY ARAHAWHPTD IAEMKRFVGL TLAMGLIKKN   180
SLESYWDTTT VLSIPVFSAT MSRNRYQLLL RFLHFNNNAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHYG RR           592

SEQ ID NO: 37           moltype = AA    length = 592
FEATURE                 Location/Qualifiers
REGION                  1..592
                        note       = Synthetic
source                  1..592
                        mol_type   = protein
                        organism   = synthetic construct
SEQUENCE: 37
MAKRFYSAEE AAAHCMASSS EEFSGSDQEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNKLTRY ARAHAWHPTD IAEMKRFVGL TLAMGLIKAN   180
SLESYWDTTT VLSIPVFSAT MSRNRYQLLL RFLHFNNNAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHYG RR           592

SEQ ID NO: 38           moltype = AA    length = 592
FEATURE                 Location/Qualifiers
REGION                  1..592
                        note       = Synthetic
source                  1..592
                        mol_type   = protein
                        organism   = synthetic construct
SEQUENCE: 38
MAKRFYSAEE AAAHCMASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNVLPRY ARAHAWHPTD IAEMKRFVGL TLAMGLIKAN   180
SLESYWDTTT VLSIPVFSAT MSRNRYQLLL RFLHFNNDAT AVPPDQPGHD RLHKLRPLID   240
SLTERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHYG RR           592

SEQ ID NO: 39           moltype = AA    length = 592
FEATURE                 Location/Qualifiers
REGION                  1..592
                        note       = Synthetic
source                  1..592
                        mol_type   = protein
                        organism   = synthetic construct
SEQUENCE: 39
MAKRFYSAEE AAAHCMASSS EEFSGSDSEY VPPASESDSS TEESWCSSST VSALEEPMEV    60
DEDVDDLEDQ EAGDRADAAP GGEPAWGPPC NFPPEIPPFT TVPGVKVDTS NFEPINFFQL   120
FMTEAILQDM VLYTNVYAEQ YLTQVPLPRY ARAHAWHPTD IAEMKRFVGL TLAMGLIKAN   180
SLESYWDTTT VLSIPVFSAT MSRNRYQLLL RFLHFNNEAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHYG RR           592

SEQ ID NO: 40           moltype = AA    length = 592
FEATURE                 Location/Qualifiers
REGION                  1..592
                        note       = Synthetic
source                  1..592
                        mol_type   = protein
```

```
                       organism = synthetic construct
SEQUENCE: 40
MAKRFYSAEE AAAHCMASSS EEFSGSDSEY VPPASESDSS TEESWCSSST VSALEEPMEV   60
DEDVDDLEDQ EAGDRVDAAA GGEPAWGPPC NFPPEIPPFT TVPGVKVDTS NFEPINFFQL  120
FMTEAILQDM VLYTNVYAEQ YLTQNPLPRY ARAHAWHPTD IAEMKRFVGL TLAMGLIKAN  180
SLESYWDTTT VLSIPVFSAT MSRNRYQLLL KFLHFNNEAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTALYCLDT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RAWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCFKPCF EIYHTQLHYG RR          592

SEQ ID NO: 41              moltype = AA  length = 592
FEATURE                    Location/Qualifiers
REGION                     1..592
                           note = Synthetic
source                     1..592
                           mol_type = protein
                           organism = synthetic construct
SEQUENCE: 41
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL  120
FMTEAILQDM VLYTNVYAEQ YLTQVPLPRY ARAHAWHPTD IAEMKRFVGL TLAMGLIKAN  180
SLESYWDTTT VLNIPVFSAT MSRNRYQLLL RFLEFNNNAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTALYCLDT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RAWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCFKPCF EIYHTQLHYG RR          592

SEQ ID NO: 42              moltype = DNA  length = 16
FEATURE                    Location/Qualifiers
misc_feature               1..16
                           note = Synthetic
source                     1..16
                           mol_type = other DNA
                           organism = synthetic construct
SEQUENCE: 42
cccggcgagc atgagg                                                   16

SEQ ID NO: 43              moltype = DNA  length = 16
FEATURE                    Location/Qualifiers
misc_feature               1..16
                           note = Synthetic
source                     1..16
                           mol_type = other DNA
                           organism = synthetic construct
SEQUENCE: 43
cctcatgctc gccggg                                                   16

SEQ ID NO: 44              moltype = DNA  length = 205
FEATURE                    Location/Qualifiers
misc_feature               1..205
                           note = Synthetic
source                     1..205
                           mol_type = other DNA
                           organism = synthetic construct
SEQUENCE: 44
cagggtatct catacccdtgg taaaatttta agttgtgta ttttataaaa ttttcgtctg   60
acaacactag cgcgctcagt agctggaggc aggagcgtgc gggaggggat agtggcgtga  120
tcgcagtgtg gcacgggaca ccggcgagat attcgtgtgc aaacctgttt cgggtatgtt  180
ataccctgcc tcattgttga cgtat                                        205

SEQ ID NO: 45              moltype = DNA  length = 192
FEATURE                    Location/Qualifiers
misc_feature               1..192
                           note = Synthetic
source                     1..192
                           mol_type = other DNA
                           organism = synthetic construct
SEQUENCE: 45
tttaagaaaa agattaataa ataataataa tttcataatt aaaaacttct ttcattgaat   60
gccattaaat aaaccattat tttcaaaat aagatcaaca taattgagta aataataata  120
agaacaatat tatagtacaa caaaatatgg gtatgtcata ccctgccaca ttcttgatgt  180
aactttttt ca                                                      192

SEQ ID NO: 46              moltype = AA  length = 610
```

```
FEATURE                 Location/Qualifiers
REGION                  1..610
                        note = Synthetic
source                  1..610
                        mol_type = protein
                        organism = synthetic construct
SEQUENCE: 46
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRHRQTKT AAENSSAETS   180
FYMQETTLCE LKALIALLYL AGLIKSNRQS LKDLWRTDGT GVDIFRTTMS LQRFQFLQNN   240
IRFDDKSTRD ERKQTDNMAA FRSIFDQFVQ CCQNAYSPSE FLTIDEMLLS FRGRCLFRVY   300
IPNKPAKYGI KILALVDAKN FYVVNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEK QLGEPSPRHV NVPGRYVRCQ DCPYKKDRKT KRSCNACAKP ICMEHAKFLC   600
ENCAELDSSL                                                         610

SEQ ID NO: 47           moltype = AA   length = 610
FEATURE                 Location/Qualifiers
REGION                  1..610
                        note = Synthetic
source                  1..610
                        mol_type = protein
                        organism = synthetic construct
SEQUENCE: 47
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRHRQTKT AAENSSAETS   180
FYMQETTLCE LKALIALLYL AGLIKSNRQS LKDLWRTDGT GVDIFRTTMS LQRFQFLQNN   240
IRFDDKSTRD ERKQTDNMAA FRSIFDQFVQ CCQNAYSPSE FLTIDEMLLS FRGRCLFRVY   300
IPNKPAKYGI KILALVDAKN FDVVNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELSANYNVSR   480
NSKRWPMTLF YGVLNMAAIN ACIIYRANKN VTIKRTEFIR SLGLSMIYEH LHSRNKKKNI   540
PTYLRQRIEK QLGEPSPRHV NVPGRYVRCQ DCPYKKDRKT KHSCNACAKP ICMEHAKFLC   600
ENCAELDSSL                                                         610

SEQ ID NO: 48           moltype = AA   length = 610
FEATURE                 Location/Qualifiers
REGION                  1..610
                        note = Synthetic
source                  1..610
                        mol_type = protein
                        organism = synthetic construct
SEQUENCE: 48
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRWRQTKT AAENSSAETS   180
FYMQETTLCE LKALIGLLYI AGLIKSNRQS LKDLWRTDGT GVDIFRTTMS LQRFQFLQNN   240
IRFDDKSTRD ERKQTDNMAA FRSIFDQFVQ SCQNAYSPSE FLTIDEMLLS FRGRCLFRVY   300
IPNKPAKYGI KILALVDAKN FYVHNLEVYA GKQPSGPYAV SNRPFEVVER LIQPVARSHR   360
NVTFDNWFTG YEVMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEK QLGEPSPRHV NVPGRYVRCQ DCPYKKDRKT KRSCNACAKP ICMEHAKFLC   600
ENCAHLDSSL                                                         610

SEQ ID NO: 49           moltype = AA   length = 610
FEATURE                 Location/Qualifiers
REGION                  1..610
                        note = Synthetic
source                  1..610
                        mol_type = protein
                        organism = synthetic construct
SEQUENCE: 49
MDIERQEERI RAMLEEELSD YSDESSSEDE TDHCSEHEVN YDTEEERIDS VDVPSNSRQE    60
EANAIIANES DSDPDDDLPL SLVRERASAS RQVSGPFYTS KDGTKWYKNC QRPNVRLRSE   120
NIVTEQAQVK NIARDASTEY ECWNIFVTSD MLQEILTHTN SSIRWRQTKT AAENSSAETS   180
FYMQETTLCE LKALIGLLYI AGLIKSNRQS LKDLWRTDGT GVDIFRTTMS LQRFQFLQNN   240
IRFDDKSTRD ERKQTDNMAA FRSIFDQFVQ SCQNAYSPSE FLTIDEMLLS FRGRCLFRVY   300
IPNKPAKYGI KILALVDAKN FYVKNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELQANYNVSR   480
NSKRWPMTLF YGVLNMAAIN ACIIYRTNKN VTIKRTEFIR SLGLSMIKEH LHSRNKKKNI   540
PTYLRQRIEK QLGEPSPRHV NVPGRYVRCQ DCPYKKDRKT KRSCNACAKP ICMEHAKFLC   600
ENCAELDSSI                                                         610
```

```
SEQ ID NO: 50            moltype = AA  length = 610
FEATURE                  Location/Qualifiers
REGION                   1..610
                         note = Synthetic
source                   1..610
                         mol_type = protein
                         organism = synthetic construct
SEQUENCE: 50
MDIERQEERI RAMLEEELSD YSDESSSEDE TDHCSEHEVN YDTEEERIDS VDVPSNSRQE   60
EANAIIANES DSDPDDDLPL SLVRQRASAS RAVSGPFYTS KDGTKWYKNC QRPNVRLRSE  120
NIVTEQAQVK NIARDASTEY ECWNIFVTSD MLQEILTHTN SSIRHRQTKT AAENSSAETS  180
FYMQETTLCE LKALIGLLYI AGLIKSNRQS LKDLWRTDGT GVDIFRTTMS LQRFQFLLNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVKNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRCNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAELDSSL                                                        610

SEQ ID NO: 51            moltype = AA  length = 610
FEATURE                  Location/Qualifiers
REGION                   1..610
                         note = Synthetic
source                   1..610
                         mol_type = protein
                         organism = synthetic construct
SEQUENCE: 51
MDIERQEERI RAMLEEELSD YSDESSSEDE TDHCSEHEVN YDTEEERIDS VDVPSNSRQE   60
EANAIIANES DSDPDDDLPL SLVRQRASAS RQMSGPHYTS KDGTKWYKNC QRPNVRLRSE  120
NIVTEQAQVK NIARDASTEY ECWNIFVTSD MLQEILTHTN SSIRWRQTKT AAENSSASTS  180
FYMQETTLCE LKALIGLLYI AGLIKSNRQS LKDLWRTDGT GVDIFRTTMS LQRFQFLQNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVKNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRTNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAELDSHL                                                        610

SEQ ID NO: 52            moltype = AA  length = 610
FEATURE                  Location/Qualifiers
REGION                   1..610
                         note = Synthetic
source                   1..610
                         mol_type = protein
                         organism = synthetic construct
SEQUENCE: 52
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRWRQTKT AAENSSASTS  180
FYMQETTLCE LKALIGLLYI AGLIKSNRQS LKDLWRTDGT GVDIFRTTMS LQRFQFLLNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVKNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRTNKN VTIKRTEFIR SLGLSMIYEH LHSRNKKKNI  540
PTYLRQRIAM QLGEPSPRHV NVPGRYVRCQ DCPYKKDRKT KRSCNACAKP ICMEHAKFLC  600
ENCAELDSSL                                                        610

SEQ ID NO: 53            moltype = AA  length = 610
FEATURE                  Location/Qualifiers
REGION                   1..610
                         note = Synthetic
source                   1..610
                         mol_type = protein
                         organism = synthetic construct
SEQUENCE: 53
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRWRQTKT AAENSSAETS  180
FYMQETTLCE LKALIGLLYI AGLIKSNRQS LKDLWRTDGT GVDIFRTTMS LQRFQFLLNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVKNLEVYA GKQPSGPYAV SNRPFEVVER LIQPVARSHR  360
NVTFDNWFTG YELMLHLLNE YRLTSVGTVR KNKTQIPENF IRTDRQPNSS VFGFQKDITL  420
VSYAPKKNKV VVVMSTMHHD NSIDESTGEK QKPEMITFYN STKAGVDVVD ELQANYNVSR  480
NSKRWPMTLF YGVLNMAAIN ACIIYRTNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAELDSSL                                                        610
```

```
SEQ ID NO: 54            moltype = AA   length = 610
FEATURE                  Location/Qualifiers
REGION                   1..610
                         note = Synthetic
source                   1..610
                         mol_type = protein
                         organism = synthetic construct
SEQUENCE: 54
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRWRQTKT AAENSSAETS   180
FYMQETTLCE LKALIGLLYL AGLIKSNRQS LKDLWRTDGT GVDIFRTTMS LQRFQFLQNN   240
IRFDDKSTRD ERKQTDNMAA FRSIFDQFVQ SCQNAYSPSE FLTIDEMLLS FRGRCLFRVY   300
IPNKPAKYGI KILALVDAKN FYVVNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELQANYNVSR   480
NSKRWPMTLF YGVLNMAAIN ACIIYRTNKN VTIKRTEFIR SLGLSMIKEH LHSRNKKKNI   540
PTYLRQRIEK QLGEPSPRHV NYPGRYVRCQ DCPYKKDRKT KRSCNACAKP ICMEHAKFLC   600
ENCAELDSSL                                                         610

SEQ ID NO: 55            moltype = AA   length = 610
FEATURE                  Location/Qualifiers
REGION                   1..610
                         note = Synthetic
source                   1..610
                         mol_type = protein
                         organism = synthetic construct
SEQUENCE: 55
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRWRQTKT AAENSSAETS   180
FYMQETTLCE LKALIGLLYI AGLIKSNRQS LKDLWRTDGT GVDIFRTTMS LQRFQFLQNN   240
IRFDDKSTRD ERKQTDNMAA FRSIFDQFVQ SCQNAYSPSE FLTIDEMLLS FRGRCLFRVY   300
IPNKPAKYGI KILALVDAKN FYVKNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEK QLGEPSPRHV NYPGRYVRCQ DCPYKKDRKT KRSCNACAKP ICMEHAKFLC   600
ENCAELDSSL                                                         610

SEQ ID NO: 56            moltype = AA   length = 610
FEATURE                  Location/Qualifiers
REGION                   1..610
                         note = Synthetic
source                   1..610
                         mol_type = protein
                         organism = synthetic construct
SEQUENCE: 56
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRWRQTKT AAENSSAETS   180
FYMQETTLCE LKALIGLLYL AGLIKSNRQS LKDLWRTDGT GVDIFRTTMS LQRFQFLQNN   240
IRFDDKSTRD ERKQTDNMAA FRSIFDQFVQ SCQNAYSPSE FLTIDEMLLS FRGRCLFRVY   300
IPNKPAKYGI KILALVDAKN FYVVNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIKEH LHSRNKKKNI   540
PTYLRQRIEK QLGEPSPRHV NYPGRYVRCQ DCPYKKDRKT KRSCNACAKP ICMEHAKFLC   600
ENCAELHSSL                                                         610

SEQ ID NO: 57            moltype = AA   length = 610
FEATURE                  Location/Qualifiers
REGION                   1..610
                         note = Synthetic
source                   1..610
                         mol_type = protein
                         organism = synthetic construct
SEQUENCE: 57
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRHRQTKT AAENSSAETS   180
FYMQETTLCE LKALIGLLYL AGLIKSNRQS LKDLWRTDGT GVDIFRTTMS LQRFQFLQNN   240
IRFDDKSTRD ERKQTDNMAA FRSIFDQFVQ SCQNAYSPSE FLTIDEMLLS FRGRCLFRVY   300
IPNKPAKYGI KILALVDAKN FYVKNLEVYA GKQPSGPYAV SNRPFEVVER LIQPVARSHR   360
NVTFDNWFTG YELMLHLLNE YRLTSVGTVR KNKRQIPESF IRTSRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEK QLGEPSPRHV NYPGRYVRCQ DCPYKKDRKT KRSCNACAKP ICMEHAKFLC   600
```

```
ENCAELDSSL                                                                    610

SEQ ID NO: 58            moltype = AA  length = 610
FEATURE                  Location/Qualifiers
REGION                   1..610
                         note = Synthetic
source                   1..610
                         mol_type = protein
                         organism = synthetic construct
SEQUENCE: 58
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRHRQTKT AAENSSAETS  180
FYMQETTLCE LKALIGLLYI AGLIKSNRQS LKDLWRTDGT GVDIFRTTMS LQRFQFLQNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVKNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRTNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAELDSSL                                                                    610

SEQ ID NO: 59            moltype = AA  length = 610
FEATURE                  Location/Qualifiers
REGION                   1..610
                         note = Synthetic
source                   1..610
                         mol_type = protein
                         organism = synthetic construct
SEQUENCE: 59
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRHRQTKT AAENSSAETS  180
FYMQETTLCE LKALIGLLYI AGLIKSNRQS LKDLYRTDGT GVDIFRTTMS LQRFQFLQNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVVNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELQANYNVSR  480
NSKRWPMTLF YGVLNMAAIN ACIIYRTNKN VTIKRTEFIR SLGLSMIYEH LHSRNKKKNI  540
PTYLRQRIEK QLGEPSPRHV NYPGRYVRCQ DCPYKKDRKT KRSCNACAKP ICMEHAKFLC  600
ENCAELDSSL                                                                    610

SEQ ID NO: 60            moltype = AA  length = 610
FEATURE                  Location/Qualifiers
REGION                   1..610
                         note = Synthetic
source                   1..610
                         mol_type = protein
                         organism = synthetic construct
SEQUENCE: 60
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRHRQTKT AAENSSAETS  180
FYMQETTLCE LKALIALLYI AGLIKSNRQS LKDLWRKDGT GVDIFRTTMS LQRFQFLLNN  240
IRFDDISTRD ERKQTDNMAA FRSIFDQFVQ CCQNAYSPSE FLTIDEMLLS FRGRCLFRVY  300
IPNKPAKYGI KILALVDAKN FYVHNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKKWPMTLF YGVLNMAAIN ACIIYRTNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAELDSSL                                                                    610

SEQ ID NO: 61            moltype = AA  length = 610
FEATURE                  Location/Qualifiers
REGION                   1..610
                         note = Synthetic
source                   1..610
                         mol_type = protein
                         organism = synthetic construct
SEQUENCE: 61
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRHRQTKT AAENSSAETS  180
FYMQETTLCE LKALIALLYI AGLIKSNRQS LKDLWRTDGT GVDIFRTTMS LQRFQFLINN  240
IRFDDKSTRD ERKQTDNMAA FRSIFDQFVQ CCQNAYSPSE FLTIDEMLLS FRGRCLFRVY  300
IPNKPAKYGI KILALVDAKN WYVVNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRTNKN VTIKRTEFIR SLGLSMIYEH LHSRNKKKNI  540
```

```
PTYLRQRIEK QLGEPSPRHV NVPGRYVRCQ DCPYKKDRKT KRSCNACAKP ICMEHAKFLC  600
ENCAELDSSL                                                        610

SEQ ID NO: 62           moltype = AA  length = 610
FEATURE                 Location/Qualifiers
REGION                  1..610
                        note = Synthetic
source                  1..610
                        mol_type = protein
                        organism = synthetic construct
SEQUENCE: 62
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRHRQTKT AAENSSAETS  180
FYMQETTLCE LKALIALLYL AGLIKSNRQS AKDLWRTDGT GVDIFRTTMS LQRFYFLQNN  240
IRFDDKSTRD ERKQTDNMAA FRSIFDQFVQ CCQNAYSPSE FLTIDEMLLS FRGRCLFRVY  300
IPNKPAKYGI KILALVDAKN FYVKNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRTNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAELDSSL                                                        610

SEQ ID NO: 63           moltype = AA  length = 610
FEATURE                 Location/Qualifiers
REGION                  1..610
                        note = Synthetic
source                  1..610
                        mol_type = protein
                        organism = synthetic construct
SEQUENCE: 63
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRHRQTKT AAENSSAETS  180
FYMQETTLPE LKALIALLYL AGLIKSNRQS LKDLWRTDGT GVDVFRTTMS LQRFQFLQNN  240
IRFDDKSTRD ERKQTDNMAA FRSIFDQFVQ CCQNAYSPSE FLTIDEMLLS FRGRCLFRVY  300
IPNKPAKYGI KILALVDAKN FYVVNLEVYV GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRTNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAELDSSL                                                        610

SEQ ID NO: 64           moltype = AA  length = 610
FEATURE                 Location/Qualifiers
REGION                  1..610
                        note = Synthetic
source                  1..610
                        mol_type = protein
                        organism = synthetic construct
SEQUENCE: 64
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRERQTKT AAENSSAETS  180
FYMQETTLCE LKALIALLYL AGLIKSNRQS LKDLWRTDGT GVDVFRTTMS LQRFQFLQNN  240
IRFDDKSTRD ERKQTDNMAA FRSIFDQFVQ CCQNAYSPSE FLTIDEMLLS FRGRCLFRVY  300
IPNKPAKYGI KILALVDAKN FYVKNLEVYV GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRTNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAELDSSL                                                        610

SEQ ID NO: 65           moltype = AA  length = 610
FEATURE                 Location/Qualifiers
REGION                  1..610
                        note = Synthetic
source                  1..610
                        mol_type = protein
                        organism = synthetic construct
SEQUENCE: 65
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRHRQTKT AAENSSAETS  180
FYMQETTLCE LKALIALLYL AGLIKSNRQS LKDLWRTDGT GVDIFRTTMS LQRFQFLQNN  240
IRFDDISTRD ERKQTDNMAA FRSIFDQFVQ CCQNAYSPSE FLTIDEMLLS FRGRCLFRVY  300
IPNKPAKYGI KILALVDAKN DYVVNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
```

```
NSKRWPMTLF YGVLNMAAIN ACIIYRTNKN VTIKRTEFIR SLGLSMIYEH LHSRNKKKNI    540
PTYLRQRIEK QLGEPSPRHV NYPGRYVRCQ DCPYKKDRKT KRSCNACAKP ICMEHAKFLC    600
ENCAELDSSL                                                          610

SEQ ID NO: 66           moltype = AA   length = 610
FEATURE                 Location/Qualifiers
REGION                  1..610
                        note = Synthetic
source                  1..610
                        mol_type = protein
                        organism = synthetic construct
SEQUENCE: 66
MDIERQEERI RAMLEEELSD YSDESSSEDE TDHCSEHEVN YDTEEERIDS VDVPSNSRQE     60
EANAIIANES DSDPDDDLPL SLVRQRASAS RQVSGPFYTS KDGTKWYKNC QRPNVRLRSE    120
NIVTEQAQVK NIARDASTEY ECWNIFVTSD MLQEILTHTN SSIRHRQTKT AAENSSAETS    180
FYMQETTLCE LKALIGLLYL AGLIKSNRQS LKDLYRTDGT GVDIFRTTMS LQRFGFLQNN    240
IRFDDKSTRD ERKQTDNMAA FRSIFDQFVQ CCQNAYSPSE FLTIDEMLLS FRGRCLFRVY    300
IPNKPAKYGI KILALVDAKN FYVVNLEVYA GKQPSGPYAV SNRPFEVVER LIQPVARSHR    360
NVTFDNWFTG YELMLHLLNE YRLTSVGTVR KNKRQIPESF IRTDRQPNSS VFGFQKDITL    420
VSYAPKKNKV VVVMSTMHHD NSIDESTGEK QKPEMITFYN STKAGVDVVD ELCANYNVSR    480
NSKRWPMTLF YGVLNMAAIN ACIIYRTNKN VTIKRTEFIR SLGLSMIYEH LHSRNKKKNI    540
PTYLRQRIEK QLGEPSPRHV NYPGRYVRCQ DCPYKKDRKT KRSCNACAKP ICMEHAKFLC    600
ENCAELDSSL                                                          610

SEQ ID NO: 67           moltype = AA   length = 610
FEATURE                 Location/Qualifiers
REGION                  1..610
                        note = Synthetic
source                  1..610
                        mol_type = protein
                        organism = synthetic construct
SEQUENCE: 67
MDIERQEERI RAMLEEELSD YSDESSSEDE TDHCSEHEVN YDTEEERIDS VDVPSNSRQE     60
EANAIIANES DSDPDDDLPL SLVRQRASAS RQVSGPFYTS KDGTKWYKNC QRPNVRLRSE    120
NIVTEQAQVK NIARDASTEY ECWNIFVTSD MLQEILTHTN SSIRHRQTKT AAENSSAETS    180
FYMQETTLCE LKALIGLLYL AGLIKSNRQS LKDLWRTDGT GVDIFRTTMS LQRFQFLQNN    240
IRFDDKSTRD ERKQTDNMAA FRSIFDQFVQ CCQNAYSPSE FLTIDEMLLS FRGRCLFRVY    300
IPNKPAKYGI KILALVDAKN FYVVNLEVYA GKQPSGPYAV SNRPFEVVER LIQPVARSHR    360
NVTFDNWFTG YELMLHLLNE YRLTSVGTVR KNKRQIPESF IRTDRQPNSS VFGFQKDITL    420
VSYAPKKNKV VVVMSTMHHD NSIDESTGEK QKPEMITFYN STKAGVDVVD ELCANYNVSR    480
NSKRWPMTLF YGVLNMAAIN ACIIYRTNKN VTIKRTEFIR SLGLSMIYEH LHSRNKKKNI    540
PTILRQRIEK QLGEPSPRHV NYPGRYVRCQ DCPYKKDRKT KRSCNACAKP ICMEHAKFLC    600
VNCAELDSSL                                                          610

SEQ ID NO: 68           moltype = AA   length = 610
FEATURE                 Location/Qualifiers
REGION                  1..610
                        note = Synthetic
source                  1..610
                        mol_type = protein
                        organism = synthetic construct
SEQUENCE: 68
MDIERQEERI RAMLEEELSD YSDESSSEDE TDHCSEHEVN YDTEEERIDS VDVPSNSRQE     60
EANAIIANES DSDPDDDLPL SLVRQRASAS RQVSGPFYTS KDGTKWYKNC QRPNVRLRSE    120
NIVTEQAQVK NIARDASTEY ECWNIFVTSD MLQEILTHTN SSIRHRQTKT AAENSSAETS    180
FYMQETTLCE LKALIGLLYL AGLIKSNRQS LKDLWRTDGT GVDIFRTTMS LQRFQFLQNN    240
IRFDDKSTRD ERKQTDNMAA FRSIFDQFVQ SCQNAYSPSE FLTIDEMLLS FRGRCLFRVY    300
IPNKPAKYGI KILALVDAKN FYVVNLEVYA GKQPSGPYAV SNRPFEVVER LIQPVARSHR    360
NVTFDNWFTG YELMLHLLNE YRLTSVGTVR KNKRQIPESF IRTDRQPNSS VFGFQKDITL    420
VSYAPKKNKV VVVMSTMHHD NSIDESTGEK QKPEMITFYN STKAGVDVVD ELCANYNVSR    480
NSKRWPMTLF YGVLNMAAIN ACIIYRTNKN VTIKRTEFIR SLGLSMIYEH LHSRNKKKNI    540
PTYLRQRIEK QLGEPSPRHV NYPGRYVRCQ DCPYKKDRKT KRSCNACAKP ICMEHAKFLC    600
ENCAELDSSL                                                          610

SEQ ID NO: 69           moltype = AA   length = 610
FEATURE                 Location/Qualifiers
REGION                  1..610
                        note = Synthetic
source                  1..610
                        mol_type = protein
                        organism = synthetic construct
SEQUENCE: 69
MDIERQEERI RAMLEEELSD YSDESSSEDE TDHCSEHEVN YDTEEERIDS VDVPSNSRQE     60
EANAIIANES DSDPDDDLPL SLVRQRASAS RQVSGPFYTS KDGTKWYKNC QRPNVRLRSE    120
NIVTEQAQVK NIARDASTEY ECWNIFVTSD MLQEILTHTN SSIRHRQTKT AAENSSAETS    180
FYMQETTLCE LKALIALLYL AGLIKSNRQS LKDLWRTDGT GVDIFRTTMS LQRFQFLQNN    240
IRFDDKSTRD ERKQTDNMAA FRSIFDQFVQ CCQNAYSPSE FLTIDEMLLS FRGRCLFRVY    300
IPNKPAKYGI KILALVDAKN FYVVNLEVYA GKQPSGPYAV SNRPFEVVER LIQPVARSHR    360
NVTFDNWFTG YECMLHLLNE YRLTSVGTVR KNKRQIPESF IRTDRQPNSS VFGFQKDITL    420
```

```
VSYAPKKNKV VVVMSTMHHD NSIDESTGEK QKPEMITFYN STKAGVDVVD ELCANYNVSR    480
NSKRWPMTLF YGVLNMAAIN ACIIYRTNKN VTIKRTEFIR SLGLSMIYEH LHSRNKKKNI    540
PTYLRQRIEM QLGEPSPRHV NVPGRYVRCQ DCPYKKDRKT KRSCNACAKP ICMEHAKFLC    600
ENCAELKSSL                                                          610

SEQ ID NO: 70           moltype = DNA   length = 15
FEATURE                 Location/Qualifiers
misc_feature            1..15
                        note = Synthetic
source                  1..15
                        mol_type = other DNA
                        organism = synthetic construct
SEQUENCE: 70
cacttggatt gcggg                                                    15

SEQ ID NO: 71           moltype = DNA   length = 15
FEATURE                 Location/Qualifiers
misc_feature            1..15
                        note = Synthetic
source                  1..15
                        mol_type = other DNA
                        organism = synthetic construct
SEQUENCE: 71
cccgacaccg tagtg                                                    15

SEQ ID NO: 72           moltype = DNA   length = 262
FEATURE                 Location/Qualifiers
misc_feature            1..262
                        note = Synthetic
source                  1..262
                        mol_type = other DNA
                        organism = synthetic construct
SEQUENCE: 72
aaacgagtta agtcggctcg cgtgaattgc gcgtactccg cgggagccgt cttaactcgg    60
ttcatataga tttgcggtgg agtgcgggaa acgtgtaaac tcgggccgat tgtaactgcg    120
tattaccaaa tatttgtttc caagcttggt accgagctcg gatcccgtac gctgcaggtc    180
gacggatccc cgggttaatt aaggcgcgcc agatctgttt agcttgcctc gtccccgccg    240
ggtcacccgg ccagcgacat gg                                            262

SEQ ID NO: 73           moltype = DNA   length = 227
FEATURE                 Location/Qualifiers
misc_feature            1..227
                        note = Synthetic
source                  1..227
                        mol_type = other DNA
                        organism = synthetic construct
SEQUENCE: 73
tgtcgaagaa ttcggcggcc gcatgcatct agagaattat ttatgtactg aatagataaa    60
aaaatgtctg tgattgaata aatttttcat ttttacacaa gaaaccgaaa atttcatttc    120
aatcgaaccc atacttcaaa agatataggc atttaaaact aactctgatt ttgcgcggga    180
aacctaaata attgcccgcg ccatcttata ttttggcggg aaattca                 227

SEQ ID NO: 74           moltype = AA    length = 567
FEATURE                 Location/Qualifiers
REGION                  1..567
                        note = Synthetic
source                  1..567
                        mol_type = protein
                        organism = synthetic construct
SEQUENCE: 74
MSQHSDYSDD EFCADKLSNY SCDSDLENAS TSDEDSSDDE VMVRPRTLRR RRISSSSSDS    60
ESDIEGGREE WSHVDNPPVL EDFLGHQGLN TDAVINNIED AVKLFIGDDF FEFLVEESNR    120
YYNQNRNNFK LSKKSLKWKD ITPQEMKKFL GLIVLMGQVR KDRRDDYWTT EPWTETPYFG    180
KTMTRDRFRQ IWKAWHFNNN ADIVNESDRL CKVRPVLDYF VPKFINIYKP HQQLSLDEGI    240
VPWRGRLFFR VYNAGKIVKY GILVRLLCES DTGYICNMEI YCGEGKRLLE TIQTWSPYTD    300
SWYHIYMDNY YNSVANCEAL MKNKPFRICGT IRKNRGIPKD FQTISLKKGE TKFIRKNDIL    360
LQVWQSKKPV YLISSHSAEM EESQNIDRTS KKKIVKPNAL IDYNKHMKGV DRADQYLSYY    420
SILRRWKWTK RLAMYMINCA LFNSYAVYKS VRQRKMGFKM FLKQTAHWLT DDIPEDMDIV    480
PDLQPVPSTS GMRAKPPTSD PPCRLSMDMR KHTLQAIVGS GKKKNILRRC RVCSVHKLRS    540
ETRYMCKFCN IPLHKGACFE KYHTLKN                                       567

SEQ ID NO: 75           moltype = DNA   length = 13
FEATURE                 Location/Qualifiers
misc_feature            1..13
                        note = Synthetic
source                  1..13
                        mol_type = other DNA
                        organism = synthetic construct
SEQUENCE: 75
```

```
ccctagaaag ata                                                          13

SEQ ID NO: 76          moltype = DNA  length = 13
FEATURE                Location/Qualifiers
misc_feature           1..13
                       note = Synthetic
source                 1..13
                       mol_type = other DNA
                       organism = synthetic construct
SEQUENCE: 76
tatctttcta ggg                                                          13

SEQ ID NO: 77          moltype = DNA  length = 296
FEATURE                Location/Qualifiers
misc_feature           1..296
                       note = Synthetic
source                 1..296
                       mol_type = other DNA
                       organism = synthetic construct
SEQUENCE: 77
gtctgcgtaa aattgacgca tgcattcttg aaatattgct ctctctttct aaatagcgcg        60
aatccgtcgc tgtgcattta ggacatctca gtcgccgctt ggagctcccg tgaggcgtgc       120
ttgtcaatgc ggtaagtgtc actgattttg aactataacg accgcgtgag tcaaaatgac       180
gcatgattat cttttacgtg acttttaaga tttaactcat acgataatta tattgttatt       240
tcatgttcta cttacgtgat aacttattat atatatattt tcttgttata gatatc          296

SEQ ID NO: 78          moltype = DNA  length = 218
FEATURE                Location/Qualifiers
misc_feature           1..218
                       note = Synthetic
source                 1..218
                       mol_type = other DNA
                       organism = synthetic construct
SEQUENCE: 78
tttgttactt tatagaagaa attttgagtt tttgtttttt tttaataaat aaataaacat        60
aaataaattg tttgttgaat ttattattag tatgtaagtg taaatataat aaaacttaat       120
atctattcaa attaataaat aaacctcgat atacagaccg ataaaacaca tgcgtcaatt       180
ttacgcatga ttatctttaa cgtacgtcac aaatatgat                              218

SEQ ID NO: 79          moltype = AA   length = 594
FEATURE                Location/Qualifiers
REGION                 1..594
                       note = Synthetic
source                 1..594
                       mol_type = protein
                       organism = synthetic construct
SEQUENCE: 79
MGSSLDDEHI LSALLQSDDE LVGEDSDSEV SDHVSEDDVQ SDTEEAFIDE VHEVQPTSSG        60
SEILDEQNVI EQPGSSLASN RILTLPQRTI RGKNKHCWST SKSTRRSRVS ALNIVRSQRG       120
PTRMCRNIYD PLLCFKLFFT DEIISEIVKW TNAEISLKRR ESMTSATFRD TNEDEIYAFF       180
GILVMTAVRK DNHMSTDDLF DRSLSMVYVS VMSRDRFDPL IRCLRMDDKS IRPTLRENDV       240
FTPVRKIWDL FIHQCIQNYT PGAHLTIDEQ LLGFRGRCPF RVYIPNKPSK YGIKILMMCD       300
SGTKYMINGM PYLGRGTQTN GVPLGEYYVK ELSKPVHGSC RNITCDNWFT SIPLAKNLLQ       360
EPYKLTIVGT VRSNKREIPE VLKNSRSRPV GTSMFCFDGP LTLVSYKPKP AKMVYLLSSC       420
DEDASINEST GKPQMVMYYN QTKGGVDTLD QMCSVMTCSR KTNRWPMALL YGMINIACIN       480
SFIIYSHNVS SKGEKVQSRK KFMRNLYMSL TSSFMRKRLE APTLKRYLRD NISNILPKEV       540
PGTSDDSTEE PVMKKRTYCT YCPSKIRRKA NASCKKCKKV ICREHNIDMC QSCF             594

SEQ ID NO: 80          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 80
cccttgrcat gcctggta                                                     18

SEQ ID NO: 81          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 81
taccaggcat gycaaggg                                                     18

SEQ ID NO: 82          moltype = DNA  length = 297
```

-continued

```
FEATURE                 Location/Qualifiers
misc_feature            1..297
                        note = Synthetic
source                  1..297
                        mol_type = other DNA
                        organism = synthetic construct
SEQUENCE: 82
gggtttatta gacccaccac tttgaaaaac ctatgatatt tttttaaatt gaaggctatt    60
gttgacgtgt gttatagtag cttcgcgcaa taaaccggcg gccatttttga cgagcgaact  120
tcagtctcac gtgagcgtgc gtgcgagtag cacgtgtgta aagtgcgcgc gggcccgtgg  180
gaccctacca ggcatacaac gtaacattct gtcggtaaga atattttctt tattttttgg  240
catttctttg tttaatgtgt taaattataa tacgaaaaaa atattgttgc agtagaa     297

SEQ ID NO: 83           moltype = DNA  length = 337
FEATURE                 Location/Qualifiers
misc_feature            1..337
                        note = Synthetic
source                  1..337
                        mol_type = other DNA
                        organism = synthetic construct
SEQUENCE: 83
atcttttcga ttatccaaag ataatagtat tttagttgat ttattagtgc cttaaattaa    60
tgaaagtctg acttcgatct ctgcattata tgtaagattg ttaattatag aactaagagt  120
ttaatttctg ttaattaaaa ttaagcgatt tgaataatt gttaaataaa gatattttca  180
catacattta catattttat ttattatctg taataataat acattctaaa agacataaat  240
ataaaacaaa attttcctag cttgttcatt tgtgtaaaac atgtatttc aatatcgggt   300
ttgacagacc caccaggcat gccgtgtgat ttttatg                           337

SEQ ID NO: 84           moltype = AA  length = 588
FEATURE                 Location/Qualifiers
REGION                  1..588
                        note = Synthetic
source                  1..588
                        mol_type = protein
                        organism = synthetic construct
SEQUENCE: 84
MARGLTDLEI NQILELEDVE NDVIFDESGD ESDHVSIRVE SDTEEVEIPT LEPQQGSSDS    60
ENDQPLSNLA RRSFYKGKDN TIWNRAPPNP RVRTRSENIV TGTPGVKRQA KNALLELDCF  120
HLFVNESILS VILEHTNHKI RSERQGKNTS NEYAYSETTL TELRAVIGLL YLAGLFKSGR  180
QNLQDLWASD GTGIEIFPMT MSLRRFAFIV NCLRFDDSDT REERAAIDRL APIRQIYEEF  240
VKNCKDVYTP YENLTIDEEL VAFRGRCKFR QYLPNKPAKY GIKIIALVDA YTYYSLNMEI  300
YAGDQPDGPY KVSNKPHDVV DRIVQPISQT GRNVTMDNWF TSYPTYAHLL KNHKLTAVGT  360
MKSNKTCIPP KFRERREINT SLFGFQDDFT IVSYIPKRNK NVFMLSSLHH DSEIDSETGE  420
QQKPSIITFY NKTKSGVDNV DKLIRTYDVS RNSRRWPLTI FFWILNTAGI NAKIVQMLNS  480
SDNTPTRRAF IKKLGMSLIA PHQAERKTNS KIPVSLRKRI GSHLGESSAS PAKIPNVGVK  540
KRCYICPVKK DRKSKYICIS CTSHICLEHA NFVCENCRRN EEENSDSS              588

SEQ ID NO: 85           moltype = DNA  length = 19
FEATURE                 Location/Qualifiers
misc_feature            1..19
                        note = Synthetic
source                  1..19
                        mol_type = other DNA
                        organism = synthetic construct
SEQUENCE: 85
cctttarctr ctgaggtgg                                                 19

SEQ ID NO: 86           moltype = DNA  length = 19
FEATURE                 Location/Qualifiers
misc_feature            1..19
                        note = Synthetic
source                  1..19
                        mol_type = other DNA
                        organism = synthetic construct
SEQUENCE: 86
ccacctcagy agytaaagg                                                 19

SEQ ID NO: 87           moltype = DNA  length = 273
FEATURE                 Location/Qualifiers
misc_feature            1..273
                        note = Synthetic
source                  1..273
                        mol_type = other DNA
                        organism = synthetic construct
SEQUENCE: 87
gggcttttcg agcctagcga aagtgaaatt gttcccctcc tccttccccc cgcgcgcgac    60
aaacccgtaa cttctagtag cttcgatgtt agttgcgcct aggccgtcag aagcttgca   120
cgtgttttcg tgcgcaattc ggtaagtaaa ttcaatttga aatttgtcgc gggcttctta  180
ggccccacct cagtgtttac gtaacttttt tgtaaatagt ttcgattaag ttattgtgtt  240
```
ttttttttgc agtagcttga aaacgtttga aaa                                         273

SEQ ID NO: 88          moltype = DNA   length = 370
FEATURE                Location/Qualifiers
misc_feature           1..370
                       note = Synthetic
source                 1..370
                       mol_type = other DNA
                       organism = synthetic construct
SEQUENCE: 88
ttttggtgct tgtattttt ttcttcccat aatacaaaga taattatgaa tgtgcctaat     60
gctaaaaaga ctgttaaaaa ttaatatttt atgtaagttt gttgattatt tctaatattt   120
taatgaatac tttgtgattt ttgatctcat gtgattttgc caaaaatttt gctaagtgtt   180
ttttaaaaac actcaaaagt taattataaa taaaaaaatt aaacaaaaaa cattttattt   240
tatttaaaat ctatccacaa aagcttatta ttatacaata aaacctaaaa accccaaata   300
ttttaaaata tgaacattta tatacacggg ccgcggaggc ccccacgtca gtacttacgt   360
gaaaataatt                                                          370

SEQ ID NO: 89          moltype = AA   length = 613
FEATURE                Location/Qualifiers
REGION                 1..613
                       note = Synthetic
source                 1..613
                       mol_type = protein
                       organism = synthetic construct
SEQUENCE: 89
MEPSTSSGRK RSIGNVHNQR AAKNRRAVVP GTRDFGTTLT SWLDNEDSSG SEVEDIGDNF     60
TPERHEIESD TISQSESEEQ VADHVTEEHN MSSDDDAPLS TRRSFYGKNR YKWACQPLSR    120
AVRVPQHNII QRTNVSNLTE DDPKDPFSIW NKLMDDEILQ ETLKWTNEKI IQYRSKFSDK    180
DRPELRNLDM VELHAPIGLL LFTAVFKSNH ENVNYLFATD GTGREIFRCV MSKNRFLVIL    240
HCLRFDNPDD REERRESDKI AAISYIFTKF VGNCQKIYNV CEYATVDEML VPFRGRTHLM    300
IYMPMKPAKY GLKLMCLCDA NNGYFYNCYI YTGRGSDGAG LTEEEKKPMV PTQSVIHLAK    360
PLFGSNRNIT CDNWFTSIEL IEYLKKKGLT CVGTMKKNKR EIPKEFLPSK QRDVGSSLYG    420
YAGQNTILSH VPKKNKAVIL LSSMHHAEAV DETTGKPEII GFYNKTKGGV DEIDKKCAIY    480
TSSRRTRRWP MVVFYRMLDI STVNSHLIYD IHHDKTTERG MFLKQLARTL VLPQMKRRAL    540
NERLPRELRL SLARVLGPDM PVPDPQEVDE TFKTRRRCHT CPLKLQRKST HTCYTCKKHV    600
CLQCAKQVCA DCV                                                      613

SEQ ID NO: 90          moltype = DNA   length = 15
FEATURE                Location/Qualifiers
misc_feature           1..15
                       note = Synthetic
source                 1..15
                       mol_type = other DNA
                       organism = synthetic construct
SEQUENCE: 90
ccctcrtatt atgtt                                                     15

SEQ ID NO: 91          moltype = DNA   length = 15
FEATURE                Location/Qualifiers
misc_feature           1..15
                       note = Synthetic
source                 1..15
                       mol_type = other DNA
                       organism = synthetic construct
SEQUENCE: 91
aacataatay gaggg                                                     15

SEQ ID NO: 92          moltype = DNA   length = 328
FEATURE                Location/Qualifiers
misc_feature           1..328
                       note = Synthetic
source                 1..328
                       mol_type = other DNA
                       organism = synthetic construct
SEQUENCE: 92
cagtgttctt caacctgtgt tccgcggaac cctagggttc cacccaaagg ctttcggggt     60
tccgcgagtc attgcttcaa ttcgagagac gtcggccgcg ccgctcttca aatgcacat    120
gcgtcaatcg gagtttcatg ttgaaacatg ttatccattc gcatagttga cttacactgg   180
acttaacctt aattttcaaa aatatgtaac tgtacttgtg gtcgtagttt tgttgttgtt   240
ttaggtttag acaagcaaag gtaagttaac ttacagtttt aaaataaatt gtattttgtt   300
tgatcctaac ctagaatcgt tcagaaat                                      328

SEQ ID NO: 93          moltype = DNA   length = 145
FEATURE                Location/Qualifiers
misc_feature           1..145
                       note = Synthetic
source                 1..145
                       mol_type = other DNA

```
                         organism = synthetic construct
SEQUENCE: 93
ccaaagcacg ggctcacctt gttcgtaaca agtcaacgca gctgtcccta aaatctcatc        60
tgggtgtatt actaaatgaa gggttccata aaaaaaaata tctcgacaaa gggttccgcc       120
ggatggcaaa ggttgaagaa cactg                                             145

SEQ ID NO: 94            moltype = DNA  length = 401
FEATURE                  Location/Qualifiers
misc_feature             1..401
                         note = Synthetic
source                   1..401
                         mol_type = other DNA
                         organism = synthetic construct
SEQUENCE: 94
aagggtcaat ttgacccatt tcagttttg gtttgaccaa agaactggtt atcctttctt         60
tttcttcacg aaagttggtg acttttcctc atctagggtc atgaacttgt gtgtaaaatc       120
tggatactgt gaagtgtcgt ggaatgtctg tgaacagttt gtatacaaag atgatgttgc       180
gggtcatttg gacccacaca cttttgatgt agcaagtagc tgtccagatc cgaaataaac       240
atgtctcttt gatgcacttt attttgattg ctaaattatt tatatttga ctgtctctga        300
atagaccttc agatcagaga cccaggtgtg tgtgggggag gagctttctc tcccttgtcc       360
ttgtcactgt tctcgtgtca tctctttgag aaacagcaaa a                           401

SEQ ID NO: 95            moltype = DNA  length = 247
FEATURE                  Location/Qualifiers
misc_feature             1..247
                         note = Synthetic
source                   1..247
                         mol_type = other DNA
                         organism = synthetic construct
SEQUENCE: 95
agatactgaa tattgaaaat ctcagaaaat gtgacaagtt aaattacaaa aaaaagtgt         60
ttgtgaagga aaaaaatatt aaatatagtg ttggaataaa aaaatagtat tgtttgtctc       120
tttcctaaat gttgaaatat tctaaaataa agttgatatc agtttaacct gttttttat        180
tgtttttgagt ggatttacac agtatgggtc aaaatgaccc gcaacataat caaggtaatt      240
tttttc                                                                  247

SEQ ID NO: 96            moltype = AA   length = 579
FEATURE                  Location/Qualifiers
REGION                   1..579
                         note = Synthetic
source                   1..579
                         mol_type = protein
                         organism = synthetic construct
SEQUENCE: 96
MSSRRFTAEE ALLLFFDSDA EEEISEIEDL SDAEDNDIDD PDFQFSDDEE DSEDESAVVS         60
PSDENLGMEQ SSSTEGTWAS KDGNIKWSTS PHQSRGRLSS SNIIKMTPGP TRFAVTRVDD       120
IQSAFQLFIS QPIERIILDM TNLEGRRVFQ EKWKSLDQTF LNAYIGILIL AGVYRSKGEA       180
TSSLWNEENG RPIFRATMSL ETFHMISRVI RFDNRDTRVG RRESDKLAAI RDVWDKWVEI       240
LPLLYNPGPH VTVDERLVPF RGRCPFRQYM PNKPAKYGIK IWAACDAKSS YAWKMQVYTG       300
KSPGGAPEKN QGMRVVLEMS EGLQGHNITC DNFFTSYRLG EELQKRKLTM LGTVRRNKPE       360
LPSEILKIQG RPMHSSIFAF TEKATVVSYC PKRNKNVLVM STMHTDASLS TRDDMKPQMI       420
LDYNSTKGGV DNLDKVTATY SCQRKTARWP MAIFFNIVDV SAYNAYVLWS EINQEWNAGK       480
LYRRRLFLEE LGKALITPKI QRRARPARSP AAAAVIEKIK FRTSNQFAMD PVDTDVKKRK       540
RCQVCPSRDD SKTSTSCVKC KNFICRKHTV TFCPSCGEH                              579

SEQ ID NO: 97            moltype = DNA  length = 16
FEATURE                  Location/Qualifiers
misc_feature             1..16
                         note = Synthetic
source                   1..16
                         mol_type = other DNA
                         organism = synthetic construct
SEQUENCE: 97
ccctagaagc ccaatc                                                        16

SEQ ID NO: 98            moltype = DNA  length = 16
FEATURE                  Location/Qualifiers
misc_feature             1..16
                         note = Synthetic
source                   1..16
                         mol_type = other DNA
                         organism = synthetic construct
SEQUENCE: 98
gattgggctt ctaggg                                                        16

SEQ ID NO: 99            moltype = DNA  length = 303
FEATURE                  Location/Qualifiers
misc_feature             1..303
                         note = Synthetic
```

```
source                          1..303
                                mol_type = other DNA
                                organism = synthetic construct
SEQUENCE: 99
tacgtaaatt tgacgtatac cgcggcgaaa tatatctgtc tctttcacgt ttaccgtcgg       60
attcccgcta acttcggaac caactcagta gccattgaga actcccagga cacagttgcg      120
tcatctcggt aagtgccgcc attttgttgt aatagacagg ttgcacgtca ttttgacgta      180
taattgggct tgtgtaact tttgaaatta tttataattt ttattgatgt gatttatttg       240
agttaatcgt attgtttcgt tacattttc atatgatatt aatattttca gattgaatat       300
aaa                                                                    303

SEQ ID NO: 100                  moltype = DNA   length = 347
FEATURE                         Location/Qualifiers
misc_feature                    1..347
                                note = Synthetic
source                          1..347
                                mol_type = other DNA
                                organism = synthetic construct
SEQUENCE: 100
agactgtttt ttttaaaagg cttataaagt attactattg cgtgatttaa ttttataaaa       60
atatttaaaa ccagttgatt tttttaataa ttacctaatt ttaagaaaaa atgttagaag      120
cttgatattt ttgttgattt ttttctaaga tttgattaaa aggccataat tgtattaata      180
aagagtattt ttaacttcaa atttattta tttattaatt aaaacttcaa ttatgataat       240
acatgcaaaa atatagttca tcaacagaaa aatataggaa aactctaata gttttatttt      300
tacacgtcat tttacgtat gattgggctt tatagctagt caaatat                     347

SEQ ID NO: 101                  moltype = AA    length = 598
FEATURE                         Location/Qualifiers
REGION                          1..598
                                note = Synthetic
source                          1..598
                                mol_type = protein
                                organism = synthetic construct
SEQUENCE: 101
MESRQRLNQD EIATILENDD DYSPLDSDSE AEDRVVEDDV WSDNEDAMID YVEDTSRQED        60
PDNNIASQES ANLEVTSLTS HRIISLPQRS ICGKNNHVWS TTKGRTTGRT SAINIIRTNR       120
GPTRMCRNIV DPLLCFQLFI TDEIIHEIVK WTNVEMIVKR QNLIDISASY RDTNTMEMWA       180
LVGILTLTAV MKDNHLSTDE LFDATFSGTR YVSVMSRERF EFLIRCMRMD DKTLRPTLRS       240
DDAFIPVRKL WEIFINQCRL NYVPGGNLTV DEQLLGFRGR CPFRMYIPNK PDKYGIRFPM       300
MCDAATKYMI DAIPYLGKST KTNGLPLGEF YVKELTKTVH GTNRNVTCDN WFTSIPLAKN       360
MLQAPYNLTI VGTIRSNKRE IPEEIKNSRS RPVGSSMFCF DGPLTLVSYK PKPSRMVFLL       420
SSCDENAVIN ESNGKPDMIL FYNQTKGGVD SFDQMCKSMS ANRKTNRWPM AVFYGMLNMA       480
FVNSYIIYCH NKINKQKKPI NRKEFMKNLS TDLTTPWMQE RLKAPTLKRT LRDNITNVLK       540
NVVPPSPANN SEEPGPKKRS YCGFCSYKKR RMTKTQFYKC KKAICGEHNI DVCQDCVG        598

SEQ ID NO: 102                  moltype = DNA   length = 16
FEATURE                         Location/Qualifiers
misc_feature                    1..16
                                note = Synthetic
source                          1..16
                                mol_type = other DNA
                                organism = synthetic construct
SEQUENCE: 102
ccctagaagc ccaatc                                                       16

SEQ ID NO: 103                  moltype = DNA   length = 16
FEATURE                         Location/Qualifiers
misc_feature                    1..16
                                note = Synthetic
source                          1..16
                                mol_type = other DNA
                                organism = synthetic construct
SEQUENCE: 103
gattgggctt ctaggg                                                       16

SEQ ID NO: 104                  moltype = DNA   length = 304
FEATURE                         Location/Qualifiers
misc_feature                    1..304
                                note = Synthetic
source                          1..304
                                mol_type = other DNA
                                organism = synthetic construct
SEQUENCE: 104
tacgtaaatt tgacgtatac cgcggcgaaa tatctctgtt actttcacgt ttacgtcgg        60
atcgccgcta acttctgaac caactcagta gccattggga cctcgcagga cacagttgca     120
tcatctcggt aagtgccgcc attttgttgt aatagagagg ttgcacgtca ttttgacgta     180
taattgggct tgtgtaact tttgaaattg tttaaatttt tttaaatttg tgatttattt      240
gagttaatcg tattgtttcg ttacatttta catgtaatat taatattttc aggttgaata     300
caaa                                                                   304
```

```
SEQ ID NO: 105          moltype = DNA  length = 370
FEATURE                 Location/Qualifiers
misc_feature            1..370
                        note = Synthetic
source                  1..370
                        mol_type = other DNA
                        organism = synthetic construct
SEQUENCE: 105
tgtttgtcaa gactgtatat aaagactgtt ttttctaag aaacttataa aatattatta    60
caagttgatt taattttatg aaaaaattta aaactagttg attttttta taattacata   120
attttaagaa aaagtgttag aggcttgatt ttttgtttt ttttttcta aggtttgatt   180
gaaatgccat aatagtatta ataaagagta ttttttaact aaaatctat tttatttatt   240
aattaaaact tcaattatga taactcatgc aaaaatatag ttcattaaca gaaaaatctt   300
ggaaaactct gaagttttat tttacacgt cattttacg tatgattggg ctttataact   360
agttaaatat                                                         370

SEQ ID NO: 106          moltype = AA  length = 598
FEATURE                 Location/Qualifiers
REGION                  1..598
                        note = Synthetic
source                  1..598
                        mol_type = protein
                        organism = synthetic construct
SEQUENCE: 106
MASRQRLNHD EIATILENDD DYSPLDSESE KEDCVVEDDV WSDNEDAIVD FVEDTSAQED    60
PDNNIASRES PNLEVTSLTS HRIITLPQRS IRGKNNHVWS TTKGRTTGRT SAINIIRTNR   120
GPTRMCRNIV DPLLCFQLFI TDEIIHEIVK WTNVEIIVKR QNLKDISASY RDTNTMEIWA   180
LVGILTLTAV MKDNHLSTDE LFDATFSGTR YVSVMSRERF EFLIRCIRMD DKTLRPTLRS   240
DDAFLPVRKI WEIFINQCRQ NHVPGSNLTV DEQLLGFRGR CPFRMYIPNK PDKYGIKFPM   300
MCAAATKYMI DAIPYLGKST KTNGLPLGEF YVKDLTKTVH GTNRNITCDN WFTSIPLAKN   360
MLQAPYNLTI VGTIRSNKRE MPEEIKNSRS RPVGSSMFCF DGPLTLVSYK PKPSKMVFLL   420
SSCDENAVIN ESNGKPDMIL FYNQTKGGVD SFDQMCKSMS ANRKTNRWPM AVFYGMLNMA   480
FVNSYIIYCH NKINKQEKPI SRKEFMKKLS IQLTTPWMQE RLQAPTLKRT LRDNITNVLK   540
NVVPASSENI SNEPEPKKRR YCGVCSYKKR RMTKAQCCKC KKAICGEHNI DVCQDCIG    598

SEQ ID NO: 107          moltype = DNA  length = 32
FEATURE                 Location/Qualifiers
misc_feature            1..32
                        note = Synthetic
source                  1..32
                        mol_type = other DNA
                        organism = synthetic construct
SEQUENCE: 107
cagttgaagt cggaagttta catacactta ag                                 32

SEQ ID NO: 108          moltype = DNA  length = 32
FEATURE                 Location/Qualifiers
misc_feature            1..32
                        note = Synthetic
source                  1..32
                        mol_type = other DNA
                        organism = synthetic construct
SEQUENCE: 108
ctaaggtgta tgtaaacttc cgacttcaac tg                                 32

SEQ ID NO: 109          moltype = DNA  length = 227
FEATURE                 Location/Qualifiers
misc_feature            1..227
                        note = Synthetic
source                  1..227
                        mol_type = other DNA
                        organism = synthetic construct
SEQUENCE: 109
cagttgaagt cggaagttta catacactta agtggagtc attaaaactc gtttttcaac    60
tacaccacaa atttcttgtt aacaaacaat agttttggca agtcagttag gacatctact   120
ttgtgcatga cacaagtcat ttttccaaca attgtttaca gacagattat ttcacttata   180
attcactgta tcacaattcc agtgggtcag aagtttacat acactaa                227

SEQ ID NO: 110          moltype = DNA  length = 229
FEATURE                 Location/Qualifiers
misc_feature            1..229
                        note = Synthetic
source                  1..229
                        mol_type = other DNA
                        organism = synthetic construct
SEQUENCE: 110
ttgagtgtat gttaacttct gacccactgg gaatgtgatg aaagaaataa aagctgaaat    60
gaatcattct ctctactatt attctgatat ttcacattct taaaataaag tggtgatcct   120
```

```
aactgacctt aagacaggga atctttactc ggattaaatg tcaggaattg tgaaaaagtg   180
agtttaaatg tatttggcta aggtgtatgt aaacttccga cttcaactg              229

SEQ ID NO: 111          moltype = AA   length = 340
FEATURE                 Location/Qualifiers
REGION                  1..340
                        note = Synthetic
source                  1..340
                        mol_type = protein
                        organism = synthetic construct
SEQUENCE: 111
MGKSKEISQD LRKRIVDLHK SGSSLGAISK RLAVPRSSVQ TIVRKYKHHG TTQPSYRSGR    60
RRVLSPRDER TLVRKVQINP RTTAKDLVKM LEETGTKVSI STVKRVLYRH NLKGHSARKK   120
PLLQNRHKKA RLRFATAHGD KDRTFWRNVL WSDETKIELF GHNDHRYVWR KKGEACKPKN   180
TIPTVKHGGG SIMLWGCFAA GGTGALHKID GIMDKENYVD ILKQHLKTSV RKLKLGRKWV   240
FQHDNDPKHT SKVVAKWLKD NKVKVLEWPS QSPDLNPIEN LWAELKKRVR ARRPTNLTQL   300
HQLCQEEWAK IHPNYCGKLV EGYPKRLTQV KQFKGNATKY                        340

SEQ ID NO: 112          moltype = DNA   length = 16
FEATURE                 Location/Qualifiers
misc_feature            1..16
                        note = Synthetic
source                  1..16
                        mol_type = other DNA
                        organism = synthetic construct
SEQUENCE: 112
cagtgttctt caacct                                                   16

SEQ ID NO: 113          moltype = DNA   length = 16
FEATURE                 Location/Qualifiers
misc_feature            1..16
                        note = Synthetic
source                  1..16
                        mol_type = other DNA
                        organism = synthetic construct
SEQUENCE: 113
aggttgaaga acactg                                                   16

SEQ ID NO: 114          moltype = DNA   length = 328
FEATURE                 Location/Qualifiers
misc_feature            1..328
                        note = Synthetic
source                  1..328
                        mol_type = other DNA
                        organism = synthetic construct
SEQUENCE: 114
cagtgttctt caacctgtgt tccgcggaac cctagggttc cacccaaagg ctttcggggt    60
tccgcgagtc attgcttcaa ttcgagagac gtcggccgcg ccgctcttca gaatgcacat   120
gcgtcaatcg gagtttcatg ttgaaacatg ttatccattc gcatagttga cttacactgc   180
acttaacctt aattttcaaa aatatgtaac tgtacttgtg gtcgtagttt tgttgttgtt   240
ttaggtttag acaagcaaag gtaagttaac ttacagtttt aaaataaatt gtattttgtt   300
tgatcctaac ctagaatcgt tcagaaat                                     328

SEQ ID NO: 115          moltype = DNA   length = 145
FEATURE                 Location/Qualifiers
misc_feature            1..145
                        note = Synthetic
source                  1..145
                        mol_type = other DNA
                        organism = synthetic construct
SEQUENCE: 115
ccaaagcacg ggctcacctt gttcgtaaca agtcaacgca gctgtcccta aaatctcatc    60
tgggtgtatt actaaatgaa gggttccata aaaaaaaata tctcgacaaa gggttccgcc   120
ggatggcaaa ggttgaagaa cactg                                        145

SEQ ID NO: 116          moltype = AA   length = 636
FEATURE                 Location/Qualifiers
REGION                  1..636
                        note = Synthetic
source                  1..636
                        mol_type = protein
                        organism = synthetic construct
SEQUENCE: 116
MMLNWLKSGK LESQSQEQSS CYLENSNCLP PTLDSTDIIG EENKAGTTSR KKRKYDEDYL    60
NFGFTWTGDK DEPNGLCVIC EQVVNNSSLN PAKLKRHLDT KHPTLKGKSE YFKRKCNELN   120
QKKHTFERYV RDDNKNLLKA SYLVSLRIAK QGEAYTIAEK LIKPCTKDLT TCVFGEKFAS   180
KVDLVPLSDT TISRRIEDMS YFCEAVLVNR LKNAKCGFTL QMDESTDVAG LAILLVFVRY   240
IHESSFEEDM LFCKALPTQT TGEEIFNLLN AYFEKHSIPW NLCYHICTDG AKAMVGIKGS   300
VIARIKKLVP DIKASHCCLH RHALAVKRIP NALHEVLNDA VKMINFIKSR PLNARVFALL   360
```

```
CDDLGSLHKN LLLHTEVRWL SRGKVLTRFW ELRDEIRIFF NEREFAGKLN DTSWLQNLAY    420
IADIFSYLNE VNLSLQGPNS TIFKVNSRIN SIKSKLKLWE ECITKNNTEC FANLNDFLET    480
SNTALDPNLK SNILEHLNGL KNTFLEYFPP TCNNISWVEN PFNECGNVDT LPIKEREQLI    540
DIRTDTTLKS SFVPDGIGPF WIKLMDEFPE ISKRAVKELM PFVTTYLCEK SFSVYVATKT    600
KYRNRLDAED DMRLQLTTIH PDIDNLCNNK QAQKSH                              636

SEQ ID NO: 117           moltype = DNA   length = 554
FEATURE                  Location/Qualifiers
misc_feature             1..554
                         note = Synthetic
source                   1..554
                         mol_type = other DNA
                         organism = synthetic construct
SEQUENCE: 117
ggagacgatg acgtcgagga gaagttcccc aactttcccg cctctcagcc tttgaaagaa     60
agaaagggga gggggcaggc cgcgtgcagc cgcgagcggt gctgggctcc ggctccaatt    120
ccccatctca gtcgttccca aagtcctcct gtttcatcca agcgtgtaag ggtcccgtc     180
cttgactccc tagtgtcctg ctgcccacag tccagtcctg ggaaccagca ccgatcacct    240
cccatcgggc caatctcagt cccttccccc ctacgtcggg gcccacacgc tcggtgcgtg    300
cccagttgaa ccaggcggct gcggaaaaaa aaaagcgggg agaaagtagg gcccggctac    360
tagcggtttt acgggcgcac gtagctcagg cctcaagacc ttgggctggg actggctgag    420
cctggcggga ggcggggtcc gagtcaccgc ctgccgccgc gcccccggtt tctataaatt    480
gagcccgcag cctcccgctt cgctctctgc tcctcctgtt cgacagtcag ccgcatcttc    540
ttttgcgtcg ccag                                                      554

SEQ ID NO: 118           moltype = DNA   length = 646
FEATURE                  Location/Qualifiers
misc_feature             1..646
                         note = Synthetic
source                   1..646
                         mol_type = other DNA
                         organism = synthetic construct
SEQUENCE: 118
ggagacgcga agaacaacga gaagatcctc aacttctcct aagcttttc actaataggg      60
agaagttcga tggggcagcc ttgggcagac ccacacttct gctccatttc cctggttcct    120
gcagctctca gattctccca ttttattcgg gaagcagctt tctggtttct gggtcctgga    180
tgtcctggt gcacactcca aggactcctc gtccttaatc catagtctgt attccctgag     240
tcctatcctg ggaaccctca tccggtcact tcctcggcgg acaatctca gctcccctcc     300
ccctctcagg tcggagccca cacgtctggt gcgtgcacat ttcaaaaacg aggcgggtcc    360
aaaaagaggg agggggggaa tgagagaggc ccagctactc gcggctttac gggtgcacgt    420
agctcaggcc tctgcgccct tgagctggga ctggatgagc cgagcgggag gcggggcgcg    480
cgtcatcagc tcccccacc atccagttcc tataaatacg gactgcagcc ctccctggtg     540
ctctctgctc ctccctgttc tagagacagc cgcatcttc tgtgcagtgc caggctctct    600
gctcctcctg ttcgacagtc agccgcatct tcttttgcgt cgccag                  646

SEQ ID NO: 119           moltype = DNA   length = 218
FEATURE                  Location/Qualifiers
misc_feature             1..218
                         note = Synthetic
source                   1..218
                         mol_type = other DNA
                         organism = synthetic construct
SEQUENCE: 119
gggaatgaga gaggcccagc tactcgcggc tttacgggtg cacgtagctc aggcctctgc     60
gcccttgagc tgggactgga tgagccgagc gggaggcggg gcgcgcgtca tcagctcccc    120
ccaccatcca gttcctataa atacggactg cagcccctcc tggtgctctc tgctcctccc    180
tgttctagag acagccgcat cttcttgtgc agtgccag                            218

SEQ ID NO: 120           moltype = DNA   length = 519
FEATURE                  Location/Qualifiers
misc_feature             1..519
                         note = Synthetic
source                   1..519
                         mol_type = other DNA
                         organism = synthetic construct
SEQUENCE: 120
cgaagaacaa cgaggagaag atcctcaact tttccgcagc cttttcaata atggggagag     60
gttcgatgat gcagtggcag ggagaccac acttctccat ttcccctgtt ctcccatttt    120
actcgggaag cagcattcag gtctctgggt cctggatgtc cttggtgcac actccaagga    180
ctcctcgtcc ttaagttcat agtctgtatt ccctgagtcc tatcctggga accatcaccc    240
ggtcacctcc tgagcgggc aatctcagct cccctcccccc tatcagttcg agcccacac     300
gcttggtgcg tgcacatttc aaaaatgagg cgggtccaaa gagagggagg aggggaaatg    360
agagaggccc agctactcgc ggctttacgg gtgcacgtag ctcaggcctc tgcgcccttg    420
agctaggact ggataagcag gcggggaggc ggggcgcgcg tcatcagctc cccccacca    480
tccgggttcc tataaatacg gactgcagcc ctccctggt                           519

SEQ ID NO: 121           moltype = DNA   length = 215
FEATURE                  Location/Qualifiers
misc_feature             1..215
```

```
                        note = Synthetic
source                  1..215
                        mol_type = other DNA
                        organism = synthetic construct
SEQUENCE: 121
acgctcggtg cgtgcccagt tgaaccaggc ggctgcggaa aaaaaaaagc ggggagaaag    60
tagggcccgg ctactagcgg tttttacggg gcacgtagct caggcctcaa gacctttgggc  120
tgggactggc tgagcctggc gggaggcggg gtccgagtca ccgcctgccg ccgcgccccc   180
ggtttctata aattgagccc gcagcctccc gcttc                              215

SEQ ID NO: 122          moltype = DNA   length = 103
FEATURE                 Location/Qualifiers
misc_feature            1..103
                        note = Synthetic
source                  1..103
                        mol_type = other DNA
                        organism = synthetic construct
SEQUENCE: 122
ccttgggctg ggactggctg agcctggcgg gaggcgggt ccgagtcacc gcctgccgcc     60
gcgcccccgg tttctataaa ttgagcccgc agcctcccgc ttc                     103

SEQ ID NO: 123          moltype = DNA   length = 353
FEATURE                 Location/Qualifiers
misc_feature            1..353
                        note = Synthetic
source                  1..353
                        mol_type = other DNA
                        organism = synthetic construct
SEQUENCE: 123
tcctatcctg ggaaccctca tccggtcact tcctcggcgg gacaatctca gctcccctcc    60
ccctctcagg tcggagccca cacgcttggt gcgtgcacat ttcaaaaacg aggcgggtcc   120
aaaaagaggg aggggggaa tgagagaggc ccagctactc gcggctttac gggtgcacgt    180
agctcaggcc tctgcgccct tgagctggga ctggatgagc cgagcgggag gcggggcgcg   240
cgtcatcagc tcccccacc atccagttcc tataaatacg gactgcagcc ctccctggtg   300
ctctctgctc ctccctgttc tagagacagc cgcatcttct tgtgcagtgc cag          353

SEQ ID NO: 124          moltype = DNA   length = 151
FEATURE                 Location/Qualifiers
misc_feature            1..151
                        note = Synthetic
source                  1..151
                        mol_type = other DNA
                        organism = synthetic construct
SEQUENCE: 124
agctgggact ggatgagccg agcgggaggc ggggcgcgcg tcatcagctc cccccaccat    60
ccagttccta taaatacgga ctgcagccct cctggtgct ctctgctcct ccctgttcta   120
gagacagccg catcttcttg tgcagtgcca g                                 151

SEQ ID NO: 125          moltype = DNA   length = 99
FEATURE                 Location/Qualifiers
misc_feature            1..99
                        note = Synthetic
source                  1..99
                        mol_type = other DNA
                        organism = synthetic construct
SEQUENCE: 125
agctaggact ggataagcag ggcgggaggc ggggcgcgcg tcatcagctc cccccccacca   60
tccgggttcc tataaatacg gactgcagcc ctccctggt                          99

SEQ ID NO: 126          moltype = DNA   length = 524
FEATURE                 Location/Qualifiers
misc_feature            1..524
                        note = Synthetic
source                  1..524
                        mol_type = other DNA
                        organism = synthetic construct
SEQUENCE: 126
atcctcaact tttccacagc ctttgcataa aggggagagg gtcggcggtg cagctgtggc    60
acacacgcac ttctgctcaa cccgcccccc cccgccccg ttcctgttcc ttcccaggtt   120
ctccccattt tatcggggcg gcaacttta ggtccctggg tcctggaagt ccttagtaca    180
cactcttcgt cctaagtcc atagtctgta ttccctcggt cctatcctgt cccccatcac   240
cgggtcacct ccccagcgaa gcaatctcag ttccctccc cctctcagcc ccgagccac    300
acgtttggtg cgtgcacatt tcaaaaacga ggcgggtcca aagagagggg gtgggaggt   360
gccgagtggc ccagctactc gcggctttac gggtgcacgt agctcaggcc tcagcgccct   420
tgagctgtga ctggatggat gagcggggcg ggaggcgggg cgagcgtcct cggcgctccc   480
caccacccca gttcctataa atacggactg cagcccctccc cggt                   524

SEQ ID NO: 127          moltype = DNA   length = 497
FEATURE                 Location/Qualifiers
```

```
misc_feature              1..497
                          note = Synthetic
source                    1..497
                          mol_type = other DNA
                          organism = synthetic construct
SEQUENCE: 127
ttcctcagct tgcccgcctc ccagcctttg aaagaatagg ggaaggggt ggcgcgtgct    60
gtccccaggc gaccgggctc aggctccgac tccccatgcc agccgctccc gggtcgtccg   120
tgcggcccct tggcgcggcc tgggctcctg gacctctctg gttcccacca ggatccccat   180
ccccgagtct atagtggctt gcgtgcccat agtcccgtcc cgggaacctt tagccatcac   240
tgcccccgcg ggccacctcg gtccctccc cctctcaggc ctgggcccac atgcctggtg    300
cgtgcactgg ggaacaaggc gggcccgcaa aaagaaaaac gaggaggccc ggctactcgc   360
gggtttacgg gcgcacgtag ctcaggcctc ctcgcccttg ggctgggact gggcgagcag   420
cacgggaggc ggggcgcacg tcacccacgc cccgccgccc ccagtcccta taaattgagg   480
ctgcgggttc ctccggt                                                  497

SEQ ID NO: 128           moltype = DNA  length = 457
FEATURE                  Location/Qualifiers
misc_feature             1..457
                         note = Synthetic
source                   1..457
                         mol_type = other DNA
                         organism = synthetic construct
SEQUENCE: 128
ctaccgggta ggggaggcgc ttttcccaag gcagtctgga gcatgcgctt tagcagcccc    60
gctgggcact tggcgctaca caagtggcct ctggcctcgc acacattcca catccaccgg   120
taggcgccaa ccggctccgt tctttggtgg ccccttcgcg ccaccttcta ctcctcccct   180
agtcaggaag ttccccccg ccccgcagct cgcgtcgtgc aggacgtgac aaatggaagt    240
agcacgactc actagtctcg tgcagatgga cagcaccgct gagcaatgga agcgggtagg   300
cctttggggc agcggccaat agcagctttg ctccttcgct ttctgagagc agcggccggg   360
aaggggcggt gcgggaggcg gggtgtgggg cggtagtgtg ggccctgttc ctgcccgcgc   420
ggtgttccgc attctgcaag cctccggagc gcacgtc                            457

SEQ ID NO: 129           moltype = DNA  length = 507
FEATURE                  Location/Qualifiers
misc_feature             1..507
                         note = Synthetic
source                   1..507
                         mol_type = other DNA
                         organism = synthetic construct
SEQUENCE: 129
ctaccgggta ggggaggcgc ttttcccaag gcagtctgga gcatgcgctt tagcagcccc    60
gctgggcact tggcgctaca caagtggcct ctggcctcgc acacattcca catccaccgg   120
taggcgccaa ccggctccgt tctttggtgg ccccttcgcg ccaccttcta ctcctcccct   180
agtcaggaag ttccccccg ccccgcagct cgcgtcgtgc aggacgtgac aaatggaagt    240
agcacgactc actagtctcg tgcagatgga cagcaccgct gagcaatgga agcgggtagg   300
cctttggggc agcggccaat agcagctttg ctccttcgct ttctgggctc agaggctggg   360
aaggggtggg tccggggggcg ggctcagggg cgggctcagg ggcggggcgg cgcgcccgaag  420
gtcctccgga ggcccggcat tctgcacgct tcaaaagcgc acgtctgccg cgctgttctc   480
ctcttcctca tctccgggcc tttcgtc                                       507

SEQ ID NO: 130           moltype = DNA  length = 460
FEATURE                  Location/Qualifiers
misc_feature             1..460
                         note = Synthetic
source                   1..460
                         mol_type = other DNA
                         organism = synthetic construct
SEQUENCE: 130
ctaccgggta ggggaggcgc ttttcccaag gcagtctgga gcatgcgctt tagcagcccc    60
gctgggcact tggcgctaca caagtggcct ctggcctcgc acacattcca catccaccgg   120
taggcgccaa ccggctccgt tctttggtgg ccccttcgcg ccaccttcta ctcctcccct   180
agtcaggaag ttccccccg ccccgcagct cgcgtcgtgc aggacgtgac aaatggaagt    240
agcacgactc actagtctcg tgcagatgga cagcaccgct gagcaatgga agcgggtagg   300
cctttggggc agcggccaat agcagctttg ctccttcgct ttctgggctc aggggcgggg   360
cgggcgcccg aaggtcctcc ggaggcccgg cattctgcac gcttcaaaag cgcacgtctg   420
ccgcgctgtt ctcctcttcc tcatctccgg gcctttcgtc                         460

SEQ ID NO: 131           moltype = DNA  length = 466
FEATURE                  Location/Qualifiers
misc_feature             1..466
                         note = Synthetic
source                   1..466
                         mol_type = other DNA
                         organism = synthetic construct
SEQUENCE: 131
cggggttggg gttgcgcctt ttccaaggca gccctgggtt tgcgcaggga cgcggctgct    60
ctgggcgtgt ttccgggaaa cgcagcgcg ccgaccctgg gcctcgcaca ttcttcacgt    120
ccgttcgcag cgtcacccgg atcttcgccg ctaccccttgt gggcccccg gcgacgcttc   180
```

```
ctcgtccgcc cctaagtcgg gaaggttcct tgcggttcgc ggcgtgccgg acgtgacaaa  240
cggaagccgc acgtctcact agtaccctcg cagacggaca gcgccaggga gcaatggcag  300
cgcgccgacc gcgatgggct gtggccaata gcggctgctc agcagggcgc gccgagagca  360
gcggccggga aggggcggtg cgggaggcgg ggtgtgsggc ggtagtgtgg gccctgttcc  420
tgcccgcgcg gtgttccgca ttctgcaagc ctccggagcg cacgtc                  466

SEQ ID NO: 132        moltype = DNA  length = 502
FEATURE               Location/Qualifiers
misc_feature          1..502
                      note = Synthetic
source                1..502
                      mol_type = other DNA
                      organism = synthetic construct
SEQUENCE: 132
cctctcccgg ccagaggagc aaggtatgcg ggaggcgacc aggaggatag cggggctgac  60
gtcgggaggt ggcctccgtg ggaaggacac ccggatcttg acacagcctt ggcagcggag  120
tcaggaagag taggggtagg ttctggacgc cctcttggcc agctcatcgc cgccccaccc  180
tctgctgag cacagagtaa ttcatacaaa aggagggatc gccttcgcaa ggggagagcc  240
cagggaccgt ccctaaattc tcacagaccc aaatccctgt agccgcccca cgacagcgcg  300
aggagcatgc gcccagggct gagcgcgggt agatcagagc acacaagctc acagtccccg  360
gcggtggggg gaggggcgcg ctgagcgggg gccaggagc tggcgcgggg caaactggga  420
aagtggtgtc gtgtgctggc tccgccctct tcccgagggt gggggagaac ggtatataag  480
tgcggtagtc gccttggacg tt                                            502

SEQ ID NO: 133        moltype = DNA  length = 455
FEATURE               Location/Qualifiers
misc_feature          1..455
                      note = Synthetic
source                1..455
                      mol_type = other DNA
                      organism = synthetic construct
SEQUENCE: 133
caacctttgg agctaagcca gcaatggtag agggaagatt ctgcacgtcc cttccaggcg  60
gcctcccgt caccaccccc cccaacccgc cccgaccgga gctgagagta attcatacaa  120
aaggactcgc ccctgccttg gggaatccca gggaccgtcg ttaaactccc actaacgtag  180
aacccagaga tcgctgcgtt cccgcccct cacccgcccg ctctcgtcat cactgaggtg  240
gagaatagca tgcgtgaggc tccggtgccc gtcagtgggc agagcgcaca tcgcccacag  300
tccccgagaa gttgggggga ggggtcggca attgaacggg tgcctagaga aggtggcgcg  360
gggtaaactg ggaaagtgat gtcgtgtact ggctccgcct ttttcccgag ggtgggggag  420
aaccgtatat aagtgcagta gtcgccgtga acgtt                              455

SEQ ID NO: 134        moltype = DNA  length = 178
FEATURE               Location/Qualifiers
misc_feature          1..178
                      note = Synthetic
source                1..178
                      mol_type = other DNA
                      organism = synthetic construct
SEQUENCE: 134
gcacatcgcc cacagtcccc gagaagttgg ggggaggctc tggctgcagg taattgaacc  60
ggtgcctaga gaaggtggcg cggggtaaac tgggaaagtg atgtcgtgta ctggctccgc  120
cttttttccg agggtggggg agaaccgtat ataagtgcag tagtcgccgt gaacgttc    178

SEQ ID NO: 135        moltype = DNA  length = 369
FEATURE               Location/Qualifiers
misc_feature          1..369
                      note = Synthetic
source                1..369
                      mol_type = other DNA
                      organism = synthetic construct
SEQUENCE: 135
acccgccccg accggagctg agagtaattc atacaaaagg actcgcccct gccttgggga  60
atcccaggga ccgtcgttaa actcccacta acgtagaacc cagagatcgc tgcgttcccg  120
cccctcacc cgcccgctct cgtcatcact gaggtggaga atagcatgcg tgaggctccg  180
gtgcccgtca gtgggcagag cgcacatcgc ccacagtccc cgagaagttg ggaggggtcg  240
gcaattgaac cggtgcctag agaaggtggc gcggggtaaa ctgggaaagt gatgtcgtgt  300
actggctcag ccttttttccc gagggtgggg gagaaccgta taagtgcag tagtcgcccg  360
tgaacgttc                                                           369

SEQ ID NO: 136        moltype = DNA  length = 369
FEATURE               Location/Qualifiers
misc_feature          1..369
                      note = Synthetic
source                1..369
                      mol_type = other DNA
                      organism = synthetic construct
SEQUENCE: 136
acccgccccg accggagctg agagtaattc atacaaaagg actcgcccct gccttgggga  60
atcccaggga ccgtcgttaa actcccacta acgtagaacc cagagatcgc tgcgttcccg  120
```

```
cccccctcacc cgcccgctct cgtcatcact gaggtggaga atagcatgcg tgaggctccg    180
gtgcccgtca gtgggcagag cgcacatcgc ccacagtccc cgagaagttg ggaggggtcg    240
gcaattgaac cggtgcctag agaaggtggc gcggggtaaa ctgggaaagt gatgtcgtgt    300
actggctccg ccttttttccc gagggtgggg gagaaccgta tataagtgca gtagtcgccg    360
tgaacgttc                                                            369

SEQ ID NO: 137        moltype = DNA  length = 372
FEATURE               Location/Qualifiers
misc_feature          1..372
                      note = Synthetic
source                1..372
                      mol_type = other DNA
                      organism = synthetic construct
SEQUENCE: 137
acccgccccg accggagctg agagtaattc atacaaaagg actcgcccct gccttgggga    60
atcccaggga ccgtcgttaa actcccacta acgtagaacc cagagatcgc tgcgttcccg   120
cccccctcacc cgcccgctct cgtcatcact gaggtggaga atagcatgcg tgaggctccg   180
gtgcccgtca gtgggcagag cgcacatcgc ccacagtccc cgagaagttg ggggagggg    240
tcggcaattg aaccggtgcc tagagaaggt ggcgcggggt aaactgggaa agtgatgtcg   300
tgtactggct ccgccttttt cccgagggtg ggggagaacc gtatataagt gcagtagtcg   360
ccgtgaacgt tc                                                        372

SEQ ID NO: 138        moltype = DNA  length = 372
FEATURE               Location/Qualifiers
misc_feature          1..372
                      note = Synthetic
source                1..372
                      mol_type = other DNA
                      organism = synthetic construct
SEQUENCE: 138
acccgccccg accggagctg agagtaattc atacaaaagg actcgcccct gccttgggga    60
atcccaggga ccgtcgttaa actcccacta acgtagaacc cagagatcgc tgcgttcccg   120
cccccctcacc cgcccgctct cgtcatcact gaggtggaga atagcatgcg tgaggctccg   180
gtgcccgtca gtgggcagag cgcacatcgc ccacagtccc cgagaagttg ggggagggg    240
tcggcaattg aacgggtgcc tagagaaggt ggcgcggggt aaactgggaa agtgatgtcg   300
tgtactggct ccgccttttt cccgagggtg ggggagaacc gtatataagt gcagtagtcg   360
ccgtgaacgt tc                                                        372

SEQ ID NO: 139        moltype = DNA  length = 372
FEATURE               Location/Qualifiers
misc_feature          1..372
                      note = Synthetic
source                1..372
                      mol_type = other DNA
                      organism = synthetic construct
SEQUENCE: 139
acccgccccg accggagctg agagtaattc atacaaaagg actcgcccct gccttgggga    60
atcccaggga ccgtcgttaa actcccacta acgtagaacc cagagatcgc tgcgttcccg   120
cccccctcacc cgcccgctct cgtcatcact gaggtggaga atagcatgcg tgaggctccg   180
gtgcccgtca gtgggcagag cgcacatcgc ccacagtccc cgagaagttg ggggagggg    240
tcggcaattg atccggtgcc tagagaaggt ggcgcggggt aaactgggaa agtgatgtcg   300
tgtactggct ccgccttttt cccgagggtg ggggagaacc gtatataagt gcagtagtcg   360
ccgtgaacgt tc                                                        372

SEQ ID NO: 140        moltype = DNA  length = 570
FEATURE               Location/Qualifiers
misc_feature          1..570
                      note = Synthetic
source                1..570
                      mol_type = other DNA
                      organism = synthetic construct
SEQUENCE: 140
ctgggctgag acccgcagag gaagacgctc tagggatttg tcccggacta gcgagatggc    60
aaggctgagg acgggaggct gattgagagg cgaaggtaca ccctaatctc aatacaaccct   120
ttggagctaa gccagcaatg gtagagggaa gattctgcac gtcccttcca ggcggcctcc   180
ccgtcaccac ccccccaac ccgccccgac cggagctgag agtaattcat acaaaaggac   240
tcgcccctgc cttggggaat cccagggacc gtcgttaaac tcccactaac gtagaaccca   300
gagatcgctg cgttcccgcc cctcacccg cccgctctcg tcatcactga ggtggagaag    360
agcatgcgtg aggctccggt gcccgtcagt gggcagagcg cacatcgccc acagtcccg    420
agaagttggg ggagggtc ggcaattgaa ccggtgccta gagaaggtgg cgcggggtaa    480
actgggaaag tgatgtcgtg tactggctcc gccttttttcc cgagggtggg ggagaaccgt   540
atataagtgc agtagtcgcc gtgaacgttc                                    570

SEQ ID NO: 141        moltype = DNA  length = 168
FEATURE               Location/Qualifiers
misc_feature          1..168
                      note = Synthetic
source                1..168
                      mol_type = other DNA
```

```
                        organism = synthetic construct
SEQUENCE: 141
gcacatcgcc cacagtcccc gagaagttgg gaggggtcgg caattgaacc ggtgcctaga    60
gaaggtggcg cggggtaaac tgggaaagtg atgtcgtgta ctggctccgc cttttttcccg   120
agggtggggg agaaccgtat ataagtgcag tagtcgccgt gaacgttc                 168

SEQ ID NO: 142          moltype = DNA   length = 171
FEATURE                 Location/Qualifiers
misc_feature            1..171
                        note = Synthetic
source                  1..171
                        mol_type = other DNA
                        organism = synthetic construct
SEQUENCE: 142
gcacatcgcc cacagtcccc gagaagttgg ggggagggt cggcaattga accggtgcct     60
agagaaggtg gcgcggggta aactgggaaa gtgatgtcgt gtactggctc cgcctttttc    120
ccgagggtgg gggagaaccg tatataagtg cagtagtcgc cgtgaacgtt c             171

SEQ ID NO: 143          moltype = DNA   length = 171
FEATURE                 Location/Qualifiers
misc_feature            1..171
                        note = Synthetic
source                  1..171
                        mol_type = other DNA
                        organism = synthetic construct
SEQUENCE: 143
gcacatcgcc cacagtcccc gagaagttgg ggggagggt cggcaattga acgggtgcct     60
agagaaggtg gcgcggggta aactgggaaa gtgatgtcgt gtactggctc cgcctttttc    120
ccgagggtgg gggagaaccg tatataagtg cagtagtcgc cgtgaacgtt c             171

SEQ ID NO: 144          moltype = DNA   length = 168
FEATURE                 Location/Qualifiers
misc_feature            1..168
                        note = Synthetic
source                  1..168
                        mol_type = other DNA
                        organism = synthetic construct
SEQUENCE: 144
gcacatcgcc cacagtcccc gagaagttgg gaggggtcgg caattgaacc ggtgcctaga    60
gaaggtggcg cggggtaaac tgggaaagtg atgtcgtgta ctggctcagc ctttttcccg    120
agggtggggg agaaccgtat ataagtgcag tagtcgccgt gaacgttc                 168

SEQ ID NO: 145          moltype = DNA   length = 171
FEATURE                 Location/Qualifiers
misc_feature            1..171
                        note = Synthetic
source                  1..171
                        mol_type = other DNA
                        organism = synthetic construct
SEQUENCE: 145
gcacatcgcc cacagtcccc gagaagttgg ggggagggt cggcaattga tccggtgcct     60
agagaaggtg gcgcggggta aactgggaaa gtgatgtcgt gtactggctc cgcctttttc    120
ccgagggtgg gggagaaccg tatataagtg cagtagtcgc cgtgaacgtt c             171

SEQ ID NO: 146          moltype = DNA   length = 440
FEATURE                 Location/Qualifiers
misc_feature            1..440
                        note = Synthetic
source                  1..440
                        mol_type = other DNA
                        organism = synthetic construct
SEQUENCE: 146
agcggggctg acgtcgggag gtggcctccg tgggaaggga cacccggatc ttgacacagc    60
cttggcagcg gagtaaggaa gagtagggat agattctggc cgccctcttg gccagcttct   120
cgccgcccca ccctccgcta gggccaagag taattcatac aaaaggaggg atcgccttcg   180
caagggagag cccagggac cgtccctaaa ttctcacaga cccaaatccc tgtagccgcc    240
ccacgacagc gcgaggagca tgcgctcagg gctgagcgcg gggagagcag agcacacaag   300
ctcatagacc ctggtcgtgg gggaggac cggggagctg cgcgcgggca aactgggaaa     360
gcggtgtcgt gtgctggctc cgccctcttc ccgagggtgg gggagaacgg tatataagtg   420
cggcagtcgc cttggacgtt                                                440

SEQ ID NO: 147          moltype = DNA   length = 480
FEATURE                 Location/Qualifiers
misc_feature            1..480
                        note = Synthetic
source                  1..480
                        mol_type = other DNA
                        organism = synthetic construct
SEQUENCE: 147
```

```
agcggggctg acgtcgggag gtggcctccg tgggaaggga caccccggatc ttgacacagc    60
cttggcagcg gagtaaggaa gagtagggat agattctggc cgccctcttg gccagcttct   120
cgccgcccca ccctccgcta gggccaagag taattcatac aaaaggaggg atcgccttcg   180
cctggggaag tcccagggac cgtcgctaaa ttctcataac ccataatccc ggtacccgcc   240
ccaccacagt gcgaggagca tgcgctcagg gctgagcgcg gggagagcag agcacacaag   300
ctcatagacc ctggtcgtgg ggggaggggc gcactgagcg ggggggggg gggtgatggg    360
ggggaggacc ggggagctgg cgcggggcaa actgggaaag cggtgtcgtg tgctggctcc   420
gccctcttcc cgagggtggg ggagaacggt atataagtgc ggcagtcgcc ttggacgttc   480

SEQ ID NO: 148         moltype = DNA  length = 316
FEATURE                Location/Qualifiers
misc_feature           1..316
                       note = Synthetic
source                 1..316
                       mol_type = other DNA
                       organism = synthetic construct
SEQUENCE: 148
ggagccgaga gtaattcata caaaaggagg gatcgccttc gcaagggag agcccaggga     60
ccgtccctaa attctcacag acccaaatcc ctgtagccgc cccacgacag cgcgaggagc   120
atgcgcccag ggctgagcgc gggtagatca gagcacacaa gctcacagtc cccggcggtg   180
ggggagggg cgcgctgagc gggggccagg agctggcgcg gggcaaaact gggaaagtgg   240
tgtcgtgtgc tggctccgcc ctcttcccga gggtggggga gaacgtata taagtgcggt    300
agtcgccttg gacgtt                                                   316

SEQ ID NO: 149         moltype = DNA  length = 503
FEATURE                Location/Qualifiers
misc_feature           1..503
                       note = Synthetic
source                 1..503
                       mol_type = other DNA
                       organism = synthetic construct
SEQUENCE: 149
cctctcccgg ccagaggagc aaggtatgcg ggaggcgacc aggaggatag cggggctgac    60
gtcgggaggt ggcctccgtg gaaggacac ccggatcttg acacagcctt ggcagcggag   120
tcaggaagag tagggtagg ttctggacgc cctcttggcc agctcatcgc cgccccaccc   180
tctgctggag cacagagtaa ttcatacaaa aggagggatc gccttcgcaa ggggagagcc   240
cagggaccgt ccctaaattc tcacagaccc aaatccctgt agccgcccca cgacagcgcg   300
aggagcatgc gcccagggct gagcgcgggt agatcagagc acacaagctc acagtccccg   360
gcggtggggg gagggcgcg ctgagcgggg gccaggagc tggcgcgggg caaactggga   420
aagtggtgtc gtgtgctggc tccgccctct tcccgagggt ggggagaac ggtatataag   480
tgcggtagtc gccttggacg ttc                                           503

SEQ ID NO: 150         moltype = DNA  length = 503
FEATURE                Location/Qualifiers
misc_feature           1..503
                       note = Synthetic
source                 1..503
                       mol_type = other DNA
                       organism = synthetic construct
SEQUENCE: 150
cctctcccgg ccagaggagc aaggtatgcg ggaggcgacc aggaggatag cggggctgac    60
gtcgggaggt ggcctccgtg gaaggacac ccggatcttg acacagcctt ggcagcggag   120
tcaggaaagag tagggtagg ttctggacgc cctcttggcc agctcttcgc cgccccaccc  180
tctgctggag cacagagtaa ttcatacaaa aggagggatc gccttcgcaa ggggagagcc   240
cagggaccgt ccctaaattc tcacagaccc aaatccctgt agccgcccca cgacagcgcg   300
aggagcatgc gcccagggct gagcgcgggt agatcagagc acacaagctc acagtccccg   360
gcggtggggg gagggcgcg ctgagcgggg gccaggagc tggcgcgggg caaactggga   420
aagtggtgtc gtgtgctggc tccgccctct tcccgagggt ggggagaac ggtatataag   480
tgcggtagtc gccttggacg ttc                                           503

SEQ ID NO: 151         moltype = DNA  length = 301
FEATURE                Location/Qualifiers
misc_feature           1..301
                       note = Synthetic
source                 1..301
                       mol_type = other DNA
                       organism = synthetic construct
SEQUENCE: 151
ggagccgaga gtaattcata caaaaggagg gatcgccttc gcaagggag agcccaggga     60
ccgtccctaa attctcacag acccaaatcc ctgtagccgc cccacgacag cgcgaggagc   120
atgcgctcag ggctgagcgc gggagagca gagcacacaa gctcatagac cctggtcgtg   180
ggggggagga ccggggagct ggcgcgggc aaactgggaa agcggtgtcg tgtgctggct   240
ccgccctctt cccgagggtg ggggagaacg gtatataagt gcggcagtcg ccttggacgt   300
t                                                                   301

SEQ ID NO: 152         moltype = DNA  length = 459
FEATURE                Location/Qualifiers
misc_feature           1..459
                       note = Synthetic
```

```
source                  1..459
                        mol_type = other DNA
                        organism = synthetic construct
SEQUENCE: 152
ggcggggctg acgtcgggag gtggcctcca cgggaaggga cacccggatc tcgacacagc    60
cttggcagtg gagtcaggaa gggtaggaca gattctggac gccctcttgg ccagtcctca   120
ccgcccccacc cccgatggag ccgagagtaa ttcatacaaa aggagggatc gccttcgccc   180
ctgggaatcc cagggaccgt cgctaaattc tggccggcct cccagccggg aaccgctgtg   240
cccgcccagc gcggcgggag gagcctgcgc ctagggcgga tcgcgggtcg gcgggagagc   300
acaagcccac agtccccggc ggtgggggag gggcgcgctg agcggggggcc cgggagccag   360
cgcggggcaa actgggaaag tggtgtcgtg tgctggctcc gccctcttcc cgagggtggg   420
ggagaacggt ataaaagtgc ggtagtcgcg ttggacgtt                          459

SEQ ID NO: 153          moltype = DNA   length = 415
FEATURE                 Location/Qualifiers
misc_feature            1..415
                        note = Synthetic
source                  1..415
                        mol_type = other DNA
                        organism = synthetic construct
SEQUENCE: 153
ggagacgggg tccgaatttc aaagtccttt ttattgactt acaaggtttt caaggaaaat    60
cttggaagta actgtgttcc gaagaatcta cgtttaaaaa ccgacccctg gatctttgcc   120
ttgggtccaa ggaccgagct ggccacgccc cagccgcgcc gcagccactc ccaaggcagt   180
tcaagtgtta agcccgaaag gtagagctct gcgcatgtgc acacccgtcc atagctgggt   240
cccagccaac caggccggag gagcacccgc gccgtgccca accggcgtcg                300
acctataaaa ggccgggcgt tgacgtcagc ggactcttcc gccgcagcca ccgccatcgt   360
cggcgcgctt ccctgttcac ctctgtattt gagaatccga cgccatctgc cacca        415

SEQ ID NO: 154          moltype = DNA   length = 416
FEATURE                 Location/Qualifiers
misc_feature            1..416
                        note = Synthetic
source                  1..416
                        mol_type = other DNA
                        organism = synthetic construct
SEQUENCE: 154
ggagacgcgg tccgaatttc aaagtctttt tcctattgac ctacaaggtt ttcaagaatc    60
atgttgtaag caactgtgtt ctgaggaatc tatgtttaaa aacccatccg tggatcttgg   120
cccagggtcc agagactgag ctagccacgc cccggccgcg ccgcagccac tcccacggca   180
gttcaagtgt taagtcccaa agaccgcgct ctgtgcatgc gcagaccgt ccacagctgg    240
ctcctagcca acccggccgg acgagcaccc ggcgccgtca cgtgacgcac caaccggcg   300
tcgacctata aaaggccggg cgttgacgtc agcgttctct tccgccgcag ccgccgcat    360
cgtcggcgcg cttccctgtt cacctctgac tctgagaatc cgtcgccatc cgccag       416

SEQ ID NO: 155          moltype = DNA   length = 1367
FEATURE                 Location/Qualifiers
misc_feature            1..1367
                        note = Synthetic
source                  1..1367
                        mol_type = other DNA
                        organism = synthetic construct
SEQUENCE: 155
ggagacgcgg tccgaatttc aaagtctttt tcctattgac ctacaaggtt ttcaagaatc    60
atgttgtaag caactgtgtt ctgaggaatc tatgtttaaa aacccatccg tggatcttgg   120
cccagggtcc agagactgag ctagccacgc cccggccgcg ccgcagccac tcccacggca   180
gttcaagtgt taagtcccaa agaccgcgct ctgtgcatgc gcagaccgt ccacagctgg    240
ctcctagcca acccggccgg acgagcaccc ggcgccgtca cgtgacgcac caaccggcg   300
tcgacctata aaaggccggg cgttgacgtc agcgttctct tccgccgcag ccgccgcat    360
cgtcggcgcg cttccctgtt cacctctgac tctgagaatc cgtcgccatc cgccaggtga   420
gtctcctcgg ctccgctaga ctcggggacc gagaggaatc tctgggcag cgggacgtgg    480
ctgtagcggg acgctgagag ggacgggagg aagagacatg gctgccctgg cccggggcgg   540
aggacgtggt cgggccgcgg cgccatatct gcgcgtccct gagggccttg ggagtgtcaa   600
ctgccgaggt cggggtgttt tcttgaagtc cttcaactcc ccgcggccgc cggggtgact   660
gcgggagggg ttgtgcttgg tgatgtggca gcgggcaaag cgccgtcccc gcgccctgg    720
tgacgggcgg agggtgtcct cggaggtga cagcctgtag gctggcttc cttgacacc     780
tccagtgggc tgaacgcctt ccgggccctt tccggtagcc ccgtgtctg tttctatct    840
gagttcacac gtgagcaccg gtcccccataa tctaagaaag tggctcactg ggcctagtgg   900
cgcattgtgg cctttgatcc gggctttgac cttggcgcac agcacccagt ggttttggga   960
agaggtgtgt gtagcagagg aggttttttc gtgctttggt cccaatcaat ccggcatctt  1020
tgcagtgccg aggtggccgt gcaccttggc tttgaattct tgtgctgagg ttatgtgact  1080
tgagcctcaa gatagggtgt tctagcacag gcttgctctt aagtgtcgca gttgtcggtt  1140
tcggcgtttg tttagagctg tggacacatc tgtgaacttg tgatgcttat ttcagaggtc  1200
ctgggtgtta cgtttgagtc acactgtgag gtcagctcca atcttgggcc gacatctggt  1260
tcctgccccct gctgtggggt gctattgacc caccgatgcc tgccaagttg ggttcccaga  1320
atcagcctgg ctgcccatcc ccccaccaca ggtgaacttc gtctcag                 1367

SEQ ID NO: 156          moltype = DNA   length = 783
FEATURE                 Location/Qualifiers
```

```
misc_feature              1..783
                          note = Synthetic
source                    1..783
                          mol_type = other DNA
                          organism = synthetic construct
SEQUENCE: 156
tattaatagc aatcttagct aattaaaata gatagcgttt attgagcgtt gggtatcagg    60
cacggtccta attcttttag atgtctttag ttcgtttcac tctccccaa acaataggg    120
ggtattgatc acctccgagc aggtgaaatt gaggcacaga gaaatcctag tagctggtag   180
aagaacacgc agtgtggtca agctagcaag gtgtttggtc cactgctata tctacaaaac   240
ccctaacaat gcctggtgta tagatgctca gtatgcattt gtgggatcag tgattccgat   300
gcctgcttct tataaagttt ttatttagaa ataattacag gtaaggagtt gcaaaaacag   360
tatagtggga tcgagtgtcc tttttccctc ggcttctccc aggggtatcg tcttacgtaa   420
caatgtccaa acagggaaat tgacttgggt ataatccaca gactctattc accttgtaga   480
ttggttttaa tagaagtaac tggacaactt gtaagctaat atcgttgcta tggttctcgt   540
tctcagctaa aacggcgctc tttactttgt gcacctgaac actgcacacc gagggcgacc   600
accgccccg agatgcccag cttctattct agagcgccgc gccggcgccg aatgggttaa   660
cgggcggggg gacacgcctc cgtgcgcttg cgcggcgtcc cttcgccccg ccttcgcagc   720
gcagtcacat gacccgccca accggcgtcc gcctataaaa agctgagtgt tgacgtcagc   780
gtt                                                                783

SEQ ID NO: 157             moltype = DNA  length = 335
FEATURE                    Location/Qualifiers
misc_feature               1..335
                           note = Synthetic
source                     1..335
                           mol_type = other DNA
                           organism = synthetic construct
SEQUENCE: 157
ggatccaact tctaagtccg ttttttattg atctaaaagg cctttttgcga atcatcttga    60
aggcaatcgc gttctgagcc acctcagctt tggcacacag cgcggggact gtcgcgaggg   120
gtttagggcc caagcaggac acaccccgaa atctccgcag ccaccccac cccacgcccc    180
cggctcttga gggttaaatc gcaggcgcag gttctcgcac gcgcacatca tcccgcaggc   240
gagccccagc acccagccca gggtgcgcgc gcgccgtcac gtgacacgcc caaccggcgt   300
cgccgtataa aagcgcgggc gttgacgtca gcggt                              335

SEQ ID NO: 158             moltype = DNA  length = 335
FEATURE                    Location/Qualifiers
misc_feature               1..335
                           note = Synthetic
source                     1..335
                           mol_type = other DNA
                           organism = synthetic construct
SEQUENCE: 158
ggatccaact tctaagtccg ttttttattg atctaaaagg cctttttgcga atcatcttga    60
aggcaatcgc gttctgagcc acctcagctt tggcacacag cgcggggact gtcgcgaggg   120
gtttagggcc caagcaggac acaccccgaa atctccgcag ccaccccac cccacgcccc    180
cggctcttga gggttaaatc gcaggcgctg gttctcgcac gcgcacatca tcccgcaggc   240
gagccccagc acccagccca gggtgcgcgc gcgccgtcac gtgacacgcc caaccggcgt   300
cgccgtataa aagcgcgggc gttgacgtca gcgtt                              335

SEQ ID NO: 159             moltype = DNA  length = 343
FEATURE                    Location/Qualifiers
misc_feature               1..343
                           note = Synthetic
source                     1..343
                           mol_type = other DNA
                           organism = synthetic construct
SEQUENCE: 159
tgacttgggt ataatccaca gactctattc accttgtaga ttggttttaa tagaagtaac    60
tggacaactt gtaagctaat atcgttgcta tggttctcgt tctcagctaa aacggcgctc   120
tttactttgt gcacctgaac actgcacacc gagggcgacc accgccccg agatgcccag   180
cttctattct agagcgccgc gccggcgccg aatgggttaa cgggcggggg gacacgcctc   240
cgtgcgcttg cgcggcgtcc cttcgccccg ccttcgcagc gcagtcacat gacccgccca   300
accggcgtcc gcctataaaa agctgagtgt tgacgtcagc gtt                    343

SEQ ID NO: 160             moltype = DNA  length = 329
FEATURE                    Location/Qualifiers
misc_feature               1..329
                           note = Synthetic
source                     1..329
                           mol_type = other DNA
                           organism = synthetic construct
SEQUENCE: 160
cggtccgaat tcaaagtct tttttcctatt gacctacaag gttttcaaga atcatgttgt    60
aagcaactgt gttctgagga atctatgttt aaaaacccat ccgtggatct tggcccaggg   120
tccagagact gagctagcca cgccccggcc gcgccgcagc cactcccacg gcagttcaag   180
tgttaagtcc caaagaccgc gctctgtgca tgcgcagacc cgtccacagc tggctcctag   240
ccaacccggc cggacgagca cccggcgccg tcacgtgacg cacccaaccg gcgtcgacct   300
```

```
ataaaaggcc gggcgttgac gtcagcggt                                     329
```

SEQ ID NO: 161         moltype = DNA   length = 329
FEATURE                Location/Qualifiers
misc_feature           1..329
                       note = Synthetic
source                 1..329
                       mol_type = other DNA
                       organism = synthetic construct
SEQUENCE: 161
```
cggtccgaat tcaaagtct ttttcctatt gacctacaag gttttcaaga atcatgttgt    60
aagcaactgt gttctgagga atctatgttt aaaaacccat ccgtggatct tggcccaggg   120
tccagagact gagctagcca cgccccggcc gcgccgcagc cactcccacg gcagttcaag   180
tgttaagtcc caaagaccgc gctctgtgca tgcgcagacc cgtccacagc tggctcctag   240
ccaacccggc cggacgagca cccggcgccg tcacgtgacg cacccaaccg cgtcgacct    300
ataaaaggcc gggcgttgac gtcagcgtt                                     329
```

SEQ ID NO: 162         moltype = DNA   length = 325
FEATURE                Location/Qualifiers
misc_feature           1..325
                       note = Synthetic
source                 1..325
                       mol_type = other DNA
                       organism = synthetic construct
SEQUENCE: 162
```
gggtccgaat tcaaagtcc tttttattga cttacaaggt tttcaaggaa aatcttggaa    60
gtaactgtgt tccgaagaat ctacgtttaa aaaccgaccc ctggatcttt gccttgggtc   120
caaggaccga gctggccacg ccccagccgc gccgcagcca ctcccaaggc agttcaagtg   180
ttaagcccga aaggtagagc tctgcgcatg tgcacacccg tccatagctg ggtcccagcc   240
aaccaggccg gaggagcacc cgcgccgtca cgtgacgtgc ccaaccggcg tcgacctata   300
aaaggccggg cgttgacgtc agcgg                                         325
```

SEQ ID NO: 163         moltype = DNA   length = 326
FEATURE                Location/Qualifiers
misc_feature           1..326
                       note = Synthetic
source                 1..326
                       mol_type = other DNA
                       organism = synthetic construct
SEQUENCE: 163
```
gggtccgaat tcaaagtcc tttttattga cttacaaggt tttcaaggaa aatcttggaa    60
gtaactgtgt tccgaagaat ctacgtttaa aaaccgaccc ctggatcttt gccttgggtc   120
caaggaccga gctggccacg ccccagccgc gccgcagcca ctcccaaggc agttcaagtg   180
ttaagcccga aaggtagagc tctgcgcatg tgcacacccg tccatagctg ggtcccagcc   240
aaccaggccg gaggagcacc cgcgccgtca cgtgacgtgc ccaaccggcg tcgacctata   300
aaaggccggg cgttgacgtc agcgtt                                        326
```

SEQ ID NO: 164         moltype = DNA   length = 294
FEATURE                Location/Qualifiers
misc_feature           1..294
                       note = Synthetic
source                 1..294
                       mol_type = other DNA
                       organism = synthetic construct
SEQUENCE: 164
```
aagtttccag agctttcgag gaaggtttct tcaactcaaa ttcatccgcc tgataatttt    60
cttatatttt cctaaagaag gaagagaagc gcatagagga gaagggaaat aattttttag   120
gagcctttct tacggctatg aggaatttgg ggctcagttg aaaagcctaa actgcctctc   180
gggaggttgg gcgcggcgaa ctactttcag cggcgcacgc agacggcgtc tacgtgaggg   240
gtgataagtg acgcaacact cgttgcataa atttgcgctc cgccagcccg gagc         294
```

SEQ ID NO: 165         moltype = DNA   length = 332
FEATURE                Location/Qualifiers
misc_feature           1..332
                       note = Synthetic
source                 1..332
                       mol_type = other DNA
                       organism = synthetic construct
SEQUENCE: 165
```
ggcctccgcg ccgggttttg gcgccccccg cgggcgcccc ctcctcacgg cgagcgctgc    60
cacgtcagac gaagggcgca cgagcgtcct gatccttccg cccggacgct caggacagcg   120
gcccgctgct cataagactc ggccttagaa ccccagtatc agcagaagga catttttagga  180
cgggacttgg gtgactctag ggcactggtt ttcttttccag agagcggaac aggcgaggaa   240
aagtagtccc ttctcggcga ttctgcggag ggatctccgt ggggcggtga acgccgatga   300
ttatataagg acgcgccggg tgtggcacag ct                                 332
```

SEQ ID NO: 166         moltype = DNA   length = 334
FEATURE                Location/Qualifiers
misc_feature           1..334

```
                    note = Synthetic
source              1..334
                    mol_type = other DNA
                    organism = synthetic construct
SEQUENCE: 166
ggcctccgcg ccgggttttg gcgcctcccg cgggcgcccc cctcctcacg gcgagcgctg   60
ccacgtcaga cgaagggcgc agcgagcgtc ctgatccttc cgcccggacg ctcaggacag  120
cggcccgctg ctcataagac tcggccttag aaccccagta tcagcagaag gacattttag  180
gacgggactt gggtgactct agggcactgg ttttctttcc agagagcgga acaggcgagg  240
aaaagtagtc ccttctcggc gattctgcgg agggatctcc gtggggcggt gaacgccgat  300
gattatataa ggacgcgccg ggtgtggcac agct                              334

SEQ ID NO: 167      moltype = DNA   length = 334
FEATURE             Location/Qualifiers
misc_feature        1..334
                    note = Synthetic
source              1..334
                    mol_type = other DNA
                    organism = synthetic construct
SEQUENCE: 167
ggcctccgcg ccgggttttg gcgcctcccg cgggcgcccc cctcctcacg gcgagcgctg   60
ccacgtcaga cgaagggcgc agcgagcgtc ctgatccttc cgcccggacg ctcaggacag  120
cggcccgctg ctcataagac tcggccttag aaccccagta tcagcagaag gacattttag  180
gacgggactt gggtgactct agggcactgg ttttctttcc agagagcgga acaggcgagg  240
aaaagtagtc ccttctcggc gattctgcgg agggatctcc gtggggcggt gaacgccgat  300
gattatataa ggacgcgccg ggtgtggcac agct                              334

SEQ ID NO: 168      moltype = DNA   length = 944
FEATURE             Location/Qualifiers
misc_feature        1..944
                    note = Synthetic
source              1..944
                    mol_type = other DNA
                    organism = synthetic construct
SEQUENCE: 168
gtgagtggcg ggtgtggctt ccgcgggccc cggagctgga gccctgctct gagcgggccg   60
ggctgatatg cgagtgtcgt ccgcagggtt tagctgtgag cattcccact tcgagtggcg  120
ggcggtgcgg gggtgagagt gcgaggccta gcggcaaccc cgtagcctcg cctcgtgtcc  180
ggcttgaggc ctagcgtggt gtccgccgcc gcgtgccact ccggccgcac tatgcgtttt  240
ttgtccttgc tgccctcgat tgccttccag cagcatgggc taacaaaggg agggtgtggg  300
gctcactctt aaggagccca tgaagcttac gttggatagg aatggaaggg caggaggggc  360
gactggggcc cgcccgcctt cggagcacat gtccgacgcc acctggatgg ggcgaggcct  420
gtggcttttcc gaagcaatcg ggcgtgagtt tagcctacct gggccatgtg gccctagcac  480
tgggcacggt ctggcctggc ggtgccgcgt tcccttgcct cccaacaagg gtgaggccgt  540
cccgccggc accagttgct tgcgcggaaa gatggccgct cccggggccc tgttgcaagg  600
agctcaaaat ggaggacgcg gcagcccggt ggagcgggcg ggtgagtcac ccacacaaag  660
gaagagggcc ttgcccctcg cccgccgctg cttcctgtga ccccgtgtgtc tatcggccgc  720
atagtcacct cgggcttctc ttgagcaccg ctcgtcgcgg cgggggggagg ggatctaatg  780
gcgttggagt ttgttcacat ttggtgggtg gagactagtc aggccagcct ggcgctggaa  840
gtcattcttg gaatttgccc ctttgagttt ggagcgaggc taattctcaa gcctcttagc  900
ggttcaaagg tattttctaa acccgtttcc aggtgttgtg aaag                   944

SEQ ID NO: 169      moltype = DNA   length = 252
FEATURE             Location/Qualifiers
misc_feature        1..252
                    note = Synthetic
source              1..252
                    mol_type = other DNA
                    organism = synthetic construct
SEQUENCE: 169
gtgaaaagaa aagaaaaaaa aaggactggg ccgcaggagg ccggagagga atggaaatta   60
ggaatggggg gaaggacgct gtacgggttt aggggcgctg gtgcgaggtc cggaagccga  120
gcccaggctc cgcattgcag aggatggtag aggacgtgat ggggcatgcg gcgggaatgg  180
aggcgggtgg gggagggga ctggccacgc taatctgact ttcttctccc gcagcctctt  240
ctcatagaca ag                                                      252

SEQ ID NO: 170      moltype = DNA   length = 874
FEATURE             Location/Qualifiers
misc_feature        1..874
                    note = Synthetic
source              1..874
                    mol_type = other DNA
                    organism = synthetic construct
SEQUENCE: 170
gtgagtgtcc gcggcgcggc aagacttggg gactgtgacg agacttcggg gcagcggagg   60
gtggccggag cgggacccgg aaaagaaagg agacatggct gcctctgcat gggtggcggg  120
acgtggtcgc ctcgcggcgc catatctgca cctcctctgc ccgtctttgg gagtgtcggc  180
ctcctgaagt tggagtgttt tctctaattc cttcgtccag ctctccttc cgagaacgct  240
ggggtggctg tgggaggggc ggcgtttgct gatgtgcag cggacataat gctgtatagc   300
```

```
cctgtgccca tggtgacagg gtgatggtgc tcccgggaag tgacagcctg caggggtggc    360
tcacatggtg acctctagtg agctgagcct cttccgccct ggcctttatc tccttccttg    420
gtccgcacaa tggaaccggt ccctccaag ctgagaaaat ggctcatggg cctaggggcc    480
tattgtggcc tttgatccca gcatttgacc ttggcgcaca aggcgggttg gcagtgtgta    540
gcaggcgagg ttttgtcggc ctgtgtgggc cccatctggc gcgggccctc tgtcgcctgc    600
attgttggac tgctgggtg gcagtccagc ttggcgttga ttacgtgctg cggtcacagc    660
ctaggctccc tggtactctt gttctagttg tcatttttggt tagggttggg ttcctgacac    720
atctggtgac tcttgatgct tcttaggtgg taggcttgta ggtgtgagtc gaatgagcgc    780
cagttttggg gagacagctc tttggaaccc cacaatgggg tgctatcgac ccgagttccc    840
agaatcagtc ctgaccgccc ttcccccacc acag                                 874

SEQ ID NO: 171       moltype = DNA  length = 292
FEATURE              Location/Qualifiers
misc_feature         1..292
                     note = Synthetic
source               1..292
                     mol_type = other DNA
                     organism = synthetic construct
SEQUENCE: 171
gtaggctgag caccgtggcg ggcggcagcg ggtggcggtc ggggttgttt ctggcggagg     60
tgctgctgat gatgtaatta aagtaggcgg tcttgagagg gcggatggtc gaggtgaggt    120
gtggcaggct tgagatccag ctgttgggg gagtactccc tctcaaaagc gggcattact    180
tctgcgctaa gattgtcagt ttccaaaaac gaggaggatt tgatattcac ctggcccgat    240
ctggccatac acttgagtga caatgacatc cactttgcct ttctctccac ag            292

SEQ ID NO: 172       moltype = DNA  length = 701
FEATURE              Location/Qualifiers
misc_feature         1..701
                     note = Synthetic
source               1..701
                     mol_type = other DNA
                     organism = synthetic construct
SEQUENCE: 172
gtactggccc acagccgtaa agagctgcgg gggcgtgaga gggggggaatg ggtgaggtca     60
agctggaggc ttcttggggt tgggtgggcc gctgagggga gggagggcg aggtgacgcg    120
acaccggcc tttctgggag agtgggcctt gttgacctaa gggggcgag ggcagttggc    180
acgcgcacgc gccgacagaa actaacagac attaaccaac agcgattccg tcgcgtttac    240
ttgggaggaa ggcggaaaag aggtagtttg tgtggcttct ggaaacccta aatttggaat    300
cccagtatga gaatggtgtc ccttcttgtg tttcaatggg attttttactt cgcgagtctt    360
gtgggtttgg ttttgttttc agtttgccta acaccgtgct taggtttgag gcagattgga    420
gttcggtcgg gggagtttga atatccggaa cagttagtgg ggaaagctgt ggacgcttgg    480
taagagagcg ctctggattt tccgctgttg acgttgaaac cttgaatgac gaatttcgta    540
ttaagtgact tagcctttgta aaattgaggg gaggcttgcg gaatattaac gtatttaagg    600
cattttgaag gaatagttgc taattttgaa gaatattagg tgtaaaagca agaaatacaa    660
tgatcctgag gtgacacgct tatgttttac ttttaaacta g                        701

SEQ ID NO: 173       moltype = DNA  length = 280
FEATURE              Location/Qualifiers
misc_feature         1..280
                     note = Synthetic
source               1..280
                     mol_type = other DNA
                     organism = synthetic construct
SEQUENCE: 173
tgtatactct atattatact ctatgttata ctctgtaatc ctactcaata aacgtgtcac     60
gcctgtgaaa ccgtactaag tctcccgtgt cttcttatca ccatcaggtg acatcctcgc    120
ccaggctgtc aatcatgccg gtatcgattc cagtagcacc ggcccacgc tgacaaccca    180
ctcttgcagc gttagcagcg cccctcttaa caagccgacc cccaccagcg tcgcggttac    240
taacactcct ctccccgggg catccgctac tcccgagctc                           280

SEQ ID NO: 174       moltype = DNA  length = 280
FEATURE              Location/Qualifiers
misc_feature         1..280
                     note = Synthetic
source               1..280
                     mol_type = other DNA
                     organism = synthetic construct
SEQUENCE: 174
tgtatactct atattatact ctatgttata ctctgtaatc ctactcaata aacgtgtcac     60
gcctgtgaaa ccgtactaag tctcccgtga cttcttatca ccatcaggtg acatcctcgc    120
ccaggctgtc aatcatgccg gtatcgattc cagtagcacc ggcccacgc tgacaaccca    180
ctcttgcagc gttagcagcg cccctcttaa caagccgacc cccaccagcg tcgcggttac    240
taacactcct ctccccgggg catccgctac tcccgagctc                           280

SEQ ID NO: 175       moltype = DNA  length = 328
FEATURE              Location/Qualifiers
misc_feature         1..328
                     note = Synthetic
source               1..328
```

```
                            mol_type = other DNA
                            organism = synthetic construct
SEQUENCE: 175
actattgtat atatatatca gttactgtta tggatcccac gtcactattg tatactctat    60
attatactct atgttatact ctgtaatcct actcaataaa cgtgtcacgc ctgtgaaacc   120
gtactaagtc tcccgtgtct tcttatcacc atcaggtgac atcctcgccc aggctgtcaa   180
tcatgccggt atcgattcca gtagcaccgg ccccacgctg acaacccact cttgcagcgt   240
tagcagcgcc cctcttaaca agccgacccc caccagcgtc gcggttacta acactcctct   300
ccccggggca tccgctactc ccgagctc                                      328

SEQ ID NO: 176          moltype = DNA   length = 328
FEATURE                 Location/Qualifiers
misc_feature            1..328
                        note = Synthetic
source                  1..328
                        mol_type = other DNA
                        organism = synthetic construct
SEQUENCE: 176
actattgtat atatatatca gttactgtta tggatcccac gtcactattg tatactctat    60
attatactct atgttatact ctgtaatcct actcaataaa cgtgtcacgc ctgtgaaacc   120
gtactaagtc tcccgtgtct tgttatcacc atcaggtgac atcctcgccc aggctgtcaa   180
tcatgccggt atcgattcca gtagcaccgg ccccacgctg acaacccact cttgcagcgt   240
tagcagcgcc cctcttaaca agccgacccc caccagcgtc gcggttacta acactcctct   300
ccccggggca tccgctactc ccgagctc                                      328

SEQ ID NO: 177          moltype = DNA   length = 343
FEATURE                 Location/Qualifiers
misc_feature            1..343
                        note = Synthetic
source                  1..343
                        mol_type = other DNA
                        organism = synthetic construct
SEQUENCE: 177
atccacaagc ccagctcccc acccatcacc atggacaatg tttttttact aacacttgga    60
caatgatgga tacttttta ctaacacttg gacaatgatg atgatacact cctcacctgc   120
ccacttagac acaattacta acaccacacc ccctctttta tttctctgta cttaatgttt   180
tctgaataaa gtgatcctat tgtacccaca ttaaagactt cttaactct ttatggttca    240
caggacccga gatgaacata gatattgtta cagcagcggc ctccatgtca ggtataacta   300
ctgcctcaca cagcgccctg ccaatcagaa gaccaaaac ccc                      343

SEQ ID NO: 178          moltype = DNA   length = 331
FEATURE                 Location/Qualifiers
misc_feature            1..331
                        note = Synthetic
source                  1..331
                        mol_type = other DNA
                        organism = synthetic construct
SEQUENCE: 178
atccacaagc ccagctcccc acccatcacc atggacaatg tttttttact aacacttgga    60
caatgatgga tacttttta ctaacacttg gacaatgatg atgatacact cctcacctgc   120
ccacttagac acaattacta acaccacacc ccctctttta tttctctgta cttaatgttt   180
tctgaataaa gtgatcctat tgtacccaca ttaaagactt cttaactct ttatggttca    240
caggacccga gatgaacata gatattgtta cagcagcggc ctccatgtca ggtataacta   300
ctgcctcaca cagcgccctg ccaatcagaa g                                  331

SEQ ID NO: 179          moltype = DNA   length = 270
FEATURE                 Location/Qualifiers
misc_feature            1..270
                        note = Synthetic
source                  1..270
                        mol_type = other DNA
                        organism = synthetic construct
SEQUENCE: 179
atattacccc taacacctgc caccccagtc ttaatcagtg gtggaagaac ggtctcagaa    60
ctgtttgtct caattggcca tttaagttta atagtgaaag actggttaat gataacaatg   120
catcggaaaa ccttcaggag gaaaggagaa tgttttgtgg aacattttg tgtgtgtggc   180
agttttaagt tattagtttt caaaatcagt acttttaat ggaaacaact tgaccaaaaa    240
tctgtcacag aattttgaga cccattaaaa                                    270

SEQ ID NO: 180          moltype = DNA   length = 292
FEATURE                 Location/Qualifiers
misc_feature            1..292
                        note = Synthetic
source                  1..292
                        mol_type = other DNA
                        organism = synthetic construct
SEQUENCE: 180
atattacccc taacacctgc caccccagtc ttaatcagtg gtggaagaac ggtgtcagaa    60
ctgtttgtct caattggcca tttaagttta atagtgaaag actggttaat gataacaatg   120
```

```
catcggaaaa ccttcaggag gaaaggagaa tgttttgtgg aacattttg tgtgtgtggc    180
agttttaagt tattagtttt caaaatcagt acttttaat ggaaacaact tgaccaaaaa    240
tctgtcacag aattttaga cccattaaaa tacaagttta atgagaagtc tg            292

SEQ ID NO: 181         moltype = DNA   length = 573
FEATURE                Location/Qualifiers
misc_feature           1..573
                       note = Synthetic
source                 1..573
                       mol_type = other DNA
                       organism = synthetic construct
SEQUENCE: 181
attatcccta atacctgcca ccccactctt aatcagtggt ggaagaacgg tctcagaact    60
gtttgtttca attggccatt taagtttagt agtaaaagac tggttaatga taacaatgca   120
tcgtaaaacc ttcagaagga aaggagaatg ttttgtggac cactttggtt ttctttttg   180
cgtgtggcag ttttaagtta ttagttttta aaatcagtac tttttaatgg aaacaacttg   240
accaaaaatt tgtcacagaa ttttgagacc cattaaaaaa gttaaatgag aaacctgtgt   300
gttcctttgg tcaacaccga gacatttagg tgaaagacat ctaattctga ttttacgaat   360
ctggaaactt cttgaaaatg taattcttga gttaacactt ctgggtggag aatagggttg   420
ttttccccc acataattgg aagggaagg aatatcattt aaagctatgg gagggttgct    480
ttgattacaa cactggagag aaatgcagca tgttgctgat tgcctgtcac taaaacaggc   540
caaaaactga gtccttgggt tgcatagaaa gct                                573

SEQ ID NO: 182         moltype = DNA   length = 280
FEATURE                Location/Qualifiers
misc_feature           1..280
                       note = Synthetic
source                 1..280
                       mol_type = other DNA
                       organism = synthetic construct
SEQUENCE: 182
attatcccta atacctgcca ccccactctt aatcagtggt ggaagaacgg tgtcagaact    60
gtttgtttca attggccatt taagtttagt agtaaaagac tggttaatga taacaatgca   120
tcgtaaaacc ttcagaagga aaggagaatg ttttgtggac cactttggtt ttcttttg   180
cgtgtggcag ttttaagtta ttagttttta aaatcagtac tttttaatgg aaacaacttg   240
accaaaaatt tgtcacagaa ttttgacacc cattaaaaaa                         280

SEQ ID NO: 183         moltype = DNA   length = 186
FEATURE                Location/Qualifiers
misc_feature           1..186
                       note = Synthetic
source                 1..186
                       mol_type = other DNA
                       organism = synthetic construct
SEQUENCE: 183
gcatatactg agattgagat taacttcctg tgaaacccag tgtcttagac aactgtggct    60
tgagcaccac ctgctggtat tcattacaaa cttgctcact acaataaatg aatttttaagc  120
tttaagatga agtggcattt cttttaacag ttactatgtt ggaattggtt acaaatttg   180
gagtgg                                                               186

SEQ ID NO: 184         moltype = DNA   length = 186
FEATURE                Location/Qualifiers
misc_feature           1..186
                       note = Synthetic
source                 1..186
                       mol_type = other DNA
                       organism = synthetic construct
SEQUENCE: 184
gcatatactg agattgagat taacttcctg tgaaacccag tgtcttagac aactgtggct    60
tgagcaccac ctgttggtat tcattacaaa cttgctcact acaataaatg aatttttaagc  120
tttaagatga agtggcattt cttttaacag ttactatgtt ggaattggtt acaaatttg   180
gagtgg                                                               186

SEQ ID NO: 185         moltype = DNA   length = 337
FEATURE                Location/Qualifiers
misc_feature           1..337
                       note = Synthetic
source                 1..337
                       mol_type = other DNA
                       organism = synthetic construct
SEQUENCE: 185
atattatccc taatacttgc cacccactc ttaatcagtg gtggaagaac ggtgtcagaa    60
ctgtttgttt caattggcca tttaagttta gtagtaaaag actggttaat gataacaatg   120
catcgtaaaa ccttcagaag gaaaggagaa tgttttgtgg accactttgg ttttctttct   180
tgcgtgtggc agttttaagt tattagtttt taaaatcagt acttttaat ggaaacaact   240
tgaccaaaaa tttgtcacag aattttgaga tccattaaaa aagttaaatg agaaacctgt   300
gtgttccttt ggtcaacacc gagacattta ggtgaaa                            337

SEQ ID NO: 186         moltype = DNA   length = 185
```

```
FEATURE                 Location/Qualifiers
misc_feature            1..185
                        note = Synthetic
source                  1..185
                        mol_type = other DNA
                        organism = synthetic construct
SEQUENCE: 186
ttgccagcca tctgttgttt gcccctcccc cgtgccttcc ttgaccctgg aaggtgccac   60
tcccactgtc ctttcctaat aaaatgagga aattgcatcg cattgtctga gtaggtgtca  120
ttctattctg gggggtgggg tggggcagga cagcaagggg gaggattggc aagacaatag  180
caggc                                                              185

SEQ ID NO: 187          moltype = DNA  length = 251
FEATURE                 Location/Qualifiers
misc_feature            1..251
                        note = Synthetic
source                  1..251
                        mol_type = other DNA
                        organism = synthetic construct
SEQUENCE: 187
ttgccagcca tctgttgttt gcccctcccc cgtgccttcc ttgaccctgg aaggtgccac   60
tcccactgtc ctttcctaat aaaatgagga aattgcatcg cattgtctga gtaggtgtca  120
ttctattctg gggggtgggg tgggcagga cagcaagggg gaggattggg aatacaatag  180
caggcatgct ggggatgcgg tgggctctat gggtacccag gtgctgaaga attgacccgg  240
ttcctcctgg g                                                       251

SEQ ID NO: 188          moltype = DNA  length = 99
FEATURE                 Location/Qualifiers
misc_feature            1..99
                        note = Synthetic
source                  1..99
                        mol_type = other DNA
                        organism = synthetic construct
SEQUENCE: 188
ttgccagcca tctgttgttt gcccctcccc cgtgccttcc ttgaccctgg aaggtgccac   60
tcccactgtc ctttcctaat aaaatgagga aattgcatc                          99

SEQ ID NO: 189          moltype = DNA  length = 479
FEATURE                 Location/Qualifiers
misc_feature            1..479
                        note = Synthetic
source                  1..479
                        mol_type = other DNA
                        organism = synthetic construct
SEQUENCE: 189
acgggtggca tccctgtgac ccctccccag tgcctctcct ggccctggaa gttgccactc   60
cagtgcccac cagccttgtc ctaataaaat taagttgcat cattttgtct gactaggtgt  120
ccttctataa tattatgggg tggaggggggg tggtatggag caaggggcaa gttgggaaga  180
caacctgtag ggcctgcggg gtctattggg aaccaagctg gagtgcagtg gcacaatctt  240
ggctcactgc aatctccgcc tcctgggttc aagcgattct cctgcctcag cctcccgagt  300
tgttgggatt ccaggcatgc atgaccaggc tcagctaatt tttgttttt tggtagagac  360
ggggttttcac catattggcc aggctggtct ccaactccta atctcaggtg atctaccac  420
cttggcctcc caaattgctg ggattacagg cgtgaaccac tgctcccttc cctgtcctt   479

SEQ ID NO: 190          moltype = DNA  length = 202
FEATURE                 Location/Qualifiers
misc_feature            1..202
                        note = Synthetic
source                  1..202
                        mol_type = other DNA
                        organism = synthetic construct
SEQUENCE: 190
ctgcccgggt ggcatccctg tgacccctcc ccagtgcctc tcctggccct ggaagttgcc   60
actccagtgc ccaccagcct tgtcctaata aaattaagtt gcatcatttt gtctgactag  120
gtgtccttct ataatattat ggggtggagg ggggtggtat ggagcaaggg gcccaagttg  180
ggaagaaacc tgtagggcct gc                                           202

SEQ ID NO: 191          moltype = DNA  length = 210
FEATURE                 Location/Qualifiers
misc_feature            1..210
                        note = Synthetic
source                  1..210
                        mol_type = other DNA
                        organism = synthetic construct
SEQUENCE: 191
ctcgctttct tgctgtccaa tttctattaa aggttccttt gttccctaag tccaactact   60
aaactggggg atattatgaa gggccttgag catctggatt ctgcctaata aaaacatttt  120
attttcattg caatgatgta tttaaattat ttctgaatat tttactaaaa agggaatgtg  180
ggaggtcagt gcatttaaaa cataaagaaa                                   210
```

```
SEQ ID NO: 192          moltype = DNA   length = 210
FEATURE                 Location/Qualifiers
misc_feature            1..210
                        note = Synthetic
source                  1..210
                        mol_type = other DNA
                        organism = synthetic construct
SEQUENCE: 192
ctcgctttct tgctgtccaa tttctattaa aggttccttt gttccctaag tccaactact    60
aaactggggg atattatgaa gggccttgag catctggatt ctgcctaata aaaaacattt   120
attttcattg caatgatgta tttaaattat ttctgaatat tttactaaaa agggaatgtg   180
ggagatcagt gcatttaaaa cataaagaaa                                    210

SEQ ID NO: 193          moltype = DNA   length = 387
FEATURE                 Location/Qualifiers
misc_feature            1..387
                        note = Synthetic
source                  1..387
                        mol_type = other DNA
                        organism = synthetic construct
SEQUENCE: 193
tggctaataa aggaaattta ttttcattgc aatagtgtgt tggaattttt tgtgtctctc    60
actcggaagg acatatggga gggcaaatca tttaaaacat cagaatgagt atttggttta   120
gagtttggca acatatgccc atatgctggc tgccatgaac aaaggttggc tataaagagg   180
tcatcagtat atgaaacagc cccctgctgt ccattcctta ttccatagaa aagccttgac   240
ttgaggttag attttttta tattttgttt tgtgttattt ttttctttaa catccctaaa   300
attttcctta catgttttac tagccagatt tttcctcctc tcctgactac tcccagtcat   360
agctgtccct cttctcttat ggagatc                                       387

SEQ ID NO: 194          moltype = DNA   length = 527
FEATURE                 Location/Qualifiers
misc_feature            1..527
                        note = Synthetic
source                  1..527
                        mol_type = other DNA
                        organism = synthetic construct
SEQUENCE: 194
ttcactcctc aggtgcaggc tgcctatcag aaggtggtgg ctggtgtggc caatgccctg    60
gctcacaaat accactgaga tcttttttccc tctgccaaaa attatgggga catcatgaag   120
cccccttgagc atctgacttc tggctaataa aggaaattta ttttcattgc aatagtgtgt   180
tggaattttt tgtgtctctc actcggaagg acatatggga gggcaaatca tttaaaacat   240
cagaatgagt atttggttta gagtttggca acatatgccc atatgctggc tgccatgaac   300
aaaggttggc tataaagagg tcatcagtat atgaaacagc cccctgctgt ccattcctta   360
ttccatagaa aagccttgac ttgaggttag attttttta tattttgttt tgtgttattt   420
ttttctttaa catccctaaa attttcctta catgttttac tagccagatt tttcctcctc   480
tcctgactac tcccagtcat agctgtccct cttctcttat ggagatc                 527

SEQ ID NO: 195          moltype = DNA   length = 387
FEATURE                 Location/Qualifiers
misc_feature            1..387
                        note = Synthetic
source                  1..387
                        mol_type = other DNA
                        organism = synthetic construct
SEQUENCE: 195
tggctaataa aggaaattta ttttcattgc aatagtgtgt tggaattttt tgtgtctctc    60
actcggaaga acatatggga gggcaaatca tttaaaacat cagaatgagt atttggttta   120
gagtttggca acatatgccc atatgctggc tgccatgaac aaaggttggc tataaagagg   180
tcatcagtat atgaaacagc cccctgctgt ccattcctta ttccatagaa aagccttgac   240
ttgaggttag attttttta tattttgttt tgtgttattt ttttctttaa catccctaaa   300
attttcctta catgttttac tagccagatt tttcctcctc tcctgactac tcccagtcat   360
agctgtccct cttctcttat ggagatc                                       387

SEQ ID NO: 196          moltype = DNA   length = 387
FEATURE                 Location/Qualifiers
misc_feature            1..387
                        note = Synthetic
source                  1..387
                        mol_type = other DNA
                        organism = synthetic construct
SEQUENCE: 196
aggctaataa aggaaattta ttttcattgc aatagtgtgt tggaattttt tgtgtctctc    60
actcggaagg acatatggga gggcaaatca tttaaaacat cagaatgagt atttggttta   120
gagtttggca acatatgccc atatgctggc tgccatgaac aaaggttggc tataaagagg   180
tcatcagtat atgaaacagc cccctgctgt ccattcctta ttccatagaa aagccttgac   240
ttgaggttag attttttta tattttgttt tgtgttattt ttttctttaa catccctaaa   300
attttcctta catgttttac tagccagatt tttcctcctc tcctgactac tcccagtcat   360
agctgtccct cttctcttat ggagatc                                       387
```

```
SEQ ID NO: 197          moltype = DNA  length = 99
FEATURE                 Location/Qualifiers
misc_feature            1..99
                        note = Synthetic
source                  1..99
                        mol_type = other DNA
                        organism = synthetic construct
SEQUENCE: 197
gacctctggc taataaagga aatttatttt cattgcaata gtgtgttgga atttttttgtg    60
tctctcactc ggaaggacat atgggagggc aaatcattt                           99

SEQ ID NO: 198          moltype = DNA  length = 155
FEATURE                 Location/Qualifiers
misc_feature            1..155
                        note = Synthetic
source                  1..155
                        mol_type = other DNA
                        organism = synthetic construct
SEQUENCE: 198
gtgcgacggc cggcaagccc ccgctccccg ggctctcgcg gtcgcacgag gatgcttggc    60
acgtaccccc tgtacatact tcccgggcgc ccagcatgga aataaagcac ccagcgctgc   120
cctgggcccc tgcgagactg tgatggttct ttcca                              155

SEQ ID NO: 199          moltype = DNA  length = 860
FEATURE                 Location/Qualifiers
misc_feature            1..860
                        note = Synthetic
source                  1..860
                        mol_type = other DNA
                        organism = synthetic construct
SEQUENCE: 199
agggagaagt gcccccacct gctcctcagt tccagcctga ccccctccca tcctttggcc    60
tctgacccctt tttccacagg ggacctaccc ctattgcggt cctccagctc atctttcacc   120
tcacccccct cctcctcctt ggctttaatt atgctaatgt tggaggagaa tgaataaata   180
aagtgaatct ttgcacctgt ggtttctctc tttcctcatt taataattat tatctgttgt   240
tttaccaact actcaatttc tcttataagg gactaaatat gtagtcatcc taaggcgcat   300
aaccatttat aaaaatcatc cttcattcta ttttacccta tcatcctctg caagacagtc   360
ctccctcaaa cccacaagcc ttctgtcctc acagtcccct gggccatggt aggagagact   420
tgcttccttg ttttccctc ctcagcaagc cctcatagtc ctttttaagg gtgacaggtc   480
ttacagtcat atatcctttg attcaattcc ctgagaatca accaaagcaa attttcaaa    540
agaagaaacc tgctataaag agaatcattc attgcaacat gatataaaat aacaacacaa   600
taaaagcaat taaataaaca aacaataggg aaatgtttaa gttcatcatg gtacttagac   660
ttaatggaat gtcatgcctt atttacattt ttaaacaggt actgagggac tcctgtctgc   720
caagggccgt attgagtact ttccacaacc taatttaatc cacactatac tgtgagatta   780
aaaacattca ttaaaatgtt gcaaaggttc tataaagctg agagacaaat atattctata   840
actcagcaat cccacttcta                                                860

SEQ ID NO: 200          moltype = DNA  length = 983
FEATURE                 Location/Qualifiers
misc_feature            1..983
                        note = Synthetic
source                  1..983
                        mol_type = other DNA
                        organism = synthetic construct
SEQUENCE: 200
gtgcgacggc cggcaagccc ccgctccccg ggctctcgcg gtcgcacgag gatgcttggc    60
acgtaccccc tgtacatact tcccgggcgc ccagcatgga aataaagcac ccagcgctgc   120
cctgggcccc tgcgagactg tgatggttct ttccacgggt caggccgagt ctgaggcctg   180
agtgacgatga gggaggcaga gcgggtccca ctgtccccac actgcccag gctgtgcagg   240
tgtgcctggg ccgcctaggg tggggctcag ccaggggctg ccctcggcag ggtggggat    300
tgccagcgt ggccctccct ccagcagcac ctgcctggg ctgggccacg ggaagcccta    360
ggagccctg gggacagaca cacagcccct gcctctgtag gagactgtcc tgttctgtga   420
gcgccctgtc ctccgacctc catgcccact cggggcatg cctagtccat gtgcgtaggg   480
acaggccctc cctcacccat ctaccccac ggcactaacc cctggctgcc ctgcccagcc   540
tcgcacccgc atggggacac aaccgactcc ggggacatgc actctcgggc cctgtggagg   600
gactggtgca gatgcccaca cacacactca gcccagaccc gttcaacaaa ccccgcactg   660
aggttggccg gccacacggc caccacacac acacgtgcac gcctcacaca cggagcctca   720
cccgggcgaa ctgcacagca ccagaccag agcaaggtcc tcgcacacgt gaacactcct   780
cggacacagg ccccacgag ccccacgcgg cacctcaagg cccacgagcc tctcggcagc   840
ttctccacat gctgacctgc tcagacaaac ccagccctcc tctcacaagg gtgccctgc    900
agccgccaca cacacacagg ggatcacaca ccacgtcacg tccctggccc tggcccactt   960
cccagtgccg cccttccctg cag                                           983

SEQ ID NO: 201          moltype = DNA  length = 223
FEATURE                 Location/Qualifiers
misc_feature            1..223
                        note = Synthetic
source                  1..223
```

```
                        mol_type = other DNA
                        organism = synthetic construct
SEQUENCE: 201
cagacatgat aagatacatt gatgagtttg gacaaaccac aactagaatg cagtgaaaaa    60
aatgctttat ttgtgaaatt tgtgatgcta ttgctttatt tgtaaccatt ataagctgca   120
ataaacaagt taacaacaac aattgcattc attttatgtt tcaggttcag ggggagatgt   180
gggaggtttt ttaaagcaag taaaacctct acaaatgtgg taa                     223

SEQ ID NO: 202          moltype = DNA  length = 222
FEATURE                 Location/Qualifiers
misc_feature            1..222
                        note = Synthetic
source                  1..222
                        mol_type = other DNA
                        organism = synthetic construct
SEQUENCE: 202
cagacatgat aagatacatt gatgagtttg gacaaaccac aactagaatg cagtgaaaaa    60
aatgctttat ttgtgaaatt tgtgatgcta ttgctttatt tgtaaccatt ataagctgca   120
ataaacaagt taacaacaac aattgcattc attttatgtt tcaggttcag ggggaggtgt   180
gggaggtttt ttaaagcaag taaaacctct acaaatgtgg ta                      222

SEQ ID NO: 203          moltype = DNA  length = 129
FEATURE                 Location/Qualifiers
misc_feature            1..129
                        note = Synthetic
source                  1..129
                        mol_type = other DNA
                        organism = synthetic construct
SEQUENCE: 203
aacttgttta ttgcagctta taatggttac aaataaagca atagcatcac aaatttcaca    60
aataaagcat ttttttcact gcattctagt tgtggtttgt ccaaactcat caatgtatct   120
tatcatgtc                                                           129

SEQ ID NO: 204          moltype = DNA  length = 249
FEATURE                 Location/Qualifiers
misc_feature            1..249
                        note = Synthetic
source                  1..249
                        mol_type = other DNA
                        organism = synthetic construct
SEQUENCE: 204
gacatgataa gatacattga tgagtttgga caaaccacaa ctagaatgca gtgaaaaaaa    60
tgcttttattt gtgaaatttg tgatgctatt gctttatttg tgaaatttgt gatgctattg   120
ctttatttgt aaccattata agctgcaata aacaagttaa caacaacaat tgcattcatt   180
ttatgtttca ggttcagggg gaggtgtggg aggtttttta aagcaagtaa aacctctaca   240
aatgtggta                                                           249

SEQ ID NO: 205          moltype = DNA  length = 271
FEATURE                 Location/Qualifiers
misc_feature            1..271
                        note = Synthetic
source                  1..271
                        mol_type = other DNA
                        organism = synthetic construct
SEQUENCE: 205
ggggaggct aactgaaaca cggaaggaga caataccgga aggaacccgc gctatgacgg     60
caataaaaag acagaataaa acgcacgggt gttgggtcgt ttgttcataa acgcggggtt   120
cggtcccagg gctggcactc tgtcgatacc ccaccgagac cccattgggg ccaatacgcc   180
cgcgtttctt cctttttcccc accccacccc ccaagttcgg gtgaaggccc agggctcgca   240
gccaacgtcg gggcggcagg ccctgccata g                                  271

SEQ ID NO: 206          moltype = DNA  length = 271
FEATURE                 Location/Qualifiers
misc_feature            1..271
                        note = Synthetic
source                  1..271
                        mol_type = other DNA
                        organism = synthetic construct
SEQUENCE: 206
ggggaggct aactgaaaca cggaaggaga caataccgga aggaacccgc gctatgacgg     60
caataaaaag acagaataaa acgcacgggt gttgggtcgt ttgttcataa acgcggggtt   120
cggtcccagg gctggcactc tgtcgatacc ccaccgagtc cccattgggg ccaatacgcc   180
cgcgtttctt cctttttcccc accccacccc ccaagttcgg gtgaaggccc agggctcgca   240
gccaacgtcg gggcggcagg ccctgccata g                                  271

SEQ ID NO: 207          moltype = DNA  length = 194
FEATURE                 Location/Qualifiers
misc_feature            1..194
                        note = Synthetic
```

```
source                  1..194
                        mol_type = other DNA
                        organism = synthetic construct
SEQUENCE: 207
gcggccgcgt cgaaattcac gcgtaagctt ctcgaccggg agatggggga ggctaactga    60
aacacggaag gagacaatac cggaaggaac ccgcgctatg acggcaataa aaagacagaa   120
taaaacgcac gggtgttggg tcgtttgttc ataaacgcgg ggttcgggat ctcgaggcta   180
gtctcgtgat cgat                                                    194

SEQ ID NO: 208          moltype = DNA   length = 223
FEATURE                 Location/Qualifiers
misc_feature            1..223
                        note = Synthetic
source                  1..223
                        mol_type = other DNA
                        organism = synthetic construct
SEQUENCE: 208
taccacattt gtagaggttt tacttgcttt aaaaaacctc ccacacctcc ccctgaacct    60
gaaacataaa atgaatgcaa ttgttgttgt taacttgttt attgcagctt ataatggtta   120
caaataaagc aatagcatca caaatttcac aaataaagca tttttttcac tgcattctag   180
ttgtggtttg tccaaactca tcaatgtatc ttatcatgtc tgg                    223

SEQ ID NO: 209          moltype = DNA   length = 279
FEATURE                 Location/Qualifiers
misc_feature            1..279
                        note = Synthetic
source                  1..279
                        mol_type = other DNA
                        organism = synthetic construct
SEQUENCE: 209
gctggagcct cggtagccgt tcctcctgcc cgctgggcct cccaacgggc cctcctcccc    60
tccttgcacc ggcccttcct ggtctttgaa taaagtctga gtgggcggca gcctgtgtgt   120
gcctgggttc tctctgtccc ggaatgtgcc aacaatggag gtgtttacct gtctcagacc   180
aaggacctct ctgcagctgc atggggctgg ggagggagaa ctgcagggag tatgggaggg   240
gaagctgagg tgggcctgct caagagaagg tgctgaacc                         279

SEQ ID NO: 210          moltype = DNA   length = 255
FEATURE                 Location/Qualifiers
misc_feature            1..255
                        note = Synthetic
source                  1..255
                        mol_type = other DNA
                        organism = synthetic construct
SEQUENCE: 210
ctgtcttctc agcctcgact gtgccttcta gttgccagcc atctgttgtt tgccctccc    60
ccgtgccttc cttgaccctg gaaggtgcca ctcccactgt cctttcctaa taaaatgagg   120
aaattgcatc aaatcgataa tatatggtag ggttcatagc cagagtaacc ttttttttta   180
attttattt tattttattt ttgagtcggg cgcgccaaaa tgaagtgaag ttcctatact   240
ttctagagaa gacag                                                  255

SEQ ID NO: 211          moltype = DNA   length = 449
FEATURE                 Location/Qualifiers
misc_feature            1..449
                        note = Synthetic
source                  1..449
                        mol_type = other DNA
                        organism = synthetic construct
SEQUENCE: 211
gatccttttc cctctgacca gaattatggg aacatcatga agccccttga gcatctagct    60
tctggctaat aaaggaaatt tattttcatt gcaatagtgt gttggaattt tttgtgtctc   120
tcactcggaa ggacatatgg gagggcaaat catttaaaac atcagaatga gtatttggtt   180
tagagtttgg caacatatgc ccatatgctg gctgccatga caaaggttg gctataaaga   240
ggtcatcagt atatgaaaca gccccctgct gtccattcct tattccatag aaaagccttg   300
acttgaggtt agatttttt tatatttgt tttgtgttat tttttttctt aacatcccta   360
aaattttcct tacatgtttt actagccaga ttttttcctcc tctcctgact actcccagtc   420
atagctgtcc ctcttctctt atggagatc                                    449

SEQ ID NO: 212          moltype = DNA   length = 449
FEATURE                 Location/Qualifiers
misc_feature            1..449
                        note = Synthetic
source                  1..449
                        mol_type = other DNA
                        organism = synthetic construct
SEQUENCE: 212
gatccttttc cctctgacca gaattatggg aacatcatga agccccttga gcatctagct    60
tctggctaat aaaggaaatt tattttcatt gcaatagtgt gttggaattt tttgtgtctc   120
tcactcggaa ggacatatgg gagggcaaat catttaaaac atcagaatga gtatttggtt   180
tagagtttgg caacatatgc ccatatgctg gctgccatga caaaggttg gctataaaga   240
```

```
ggtcatcagt atatgaaaca gcccctgct gtccattcct tattccatag aaaagccttg    300
acttgaggtt agatttttt tatattttgt tttgtgttat ttttttcttt aacatccta    360
aaattttcct tacatgtttt actagccaga ttttcctcc tctcctgact actcccagtc   420
atagctgtcc ctcttctctt atggagatc                                    449
```

```
SEQ ID NO: 213              moltype = DNA   length = 330
FEATURE                     Location/Qualifiers
misc_feature                1..330
                            note = Synthetic
source                      1..330
                            mol_type = other DNA
                            organism = synthetic construct
SEQUENCE: 213
ctgtacttgg ctcactctcc ttctccttac ataggaaatt acccagttat gaaattaata    60
aaaagccagt gatccccaca tttgtctgtg cctctgccta ggggctggcc tgggagggga   120
gaaaaaggcc agaataattc caggaaccgc caagaaggca ggtcagagat cttgctggac   180
aaacagtggc tgaactctgt tccttaacag agtcagcagc aggggaggg ggggcggcg    240
cgcagtgtgg atcttatatc tagtcccag ggggagggg caataaaaga tctttatttt    300
cattagatct gtgtgttggt tttttgtgtg                                   330
```

```
SEQ ID NO: 214              moltype = DNA   length = 353
FEATURE                     Location/Qualifiers
misc_feature                1..353
                            note = Synthetic
source                      1..353
                            mol_type = other DNA
                            organism = synthetic construct
SEQUENCE: 214
ttgacttgac tcatgcttgt ttcactttca catggaattt cccagttatg aaattaataa    60
aaatcaatgg tttccacatc tgtgtgtgcc tgtgtcaccg acccaggtag ggctggcctt   120
gggggagggg gaggccagaa tgactccaag agctacagga aggcaggtca gagatcccac   180
tggacaaaca gtggctggac tctgcaccat aacacacaat caacagggga gtgagctgga   240
tccaggggga ggggggggcg gcgcgcagtg tggatcttat atctagtccc caggggagg   300
gggcaataaa agatctttat tttcattaga tctgtgtgtt ggttttttgt gtg          353
```

```
SEQ ID NO: 215              moltype = DNA   length = 284
FEATURE                     Location/Qualifiers
misc_feature                1..284
                            note = Synthetic
source                      1..284
                            mol_type = other DNA
                            organism = synthetic construct
SEQUENCE: 215
ttgacttgac tcatgcttgt ttcactttca catggaattt cccagttatg aaattaataa    60
aaatcaatgg tttccacatc tgtgtgtgcc tgtgtcaccg acccaggtag ggctggcctt   120
gggggagggg gaggccagaa tgactccaag agctacagga aggcaggtca gagaagggg   180
aggggggggc ggcgcgcagt gtggatctta tatctagtcc caggggag ggggcaataa   240
aagatcttta ttttcattag atctgtgtgt tggttttttg tgtg                   284
```

```
SEQ ID NO: 216              moltype = DNA   length = 280
FEATURE                     Location/Qualifiers
misc_feature                1..280
                            note = Synthetic
source                      1..280
                            mol_type = other DNA
                            organism = synthetic construct
SEQUENCE: 216
tgtatactct atattatact ctatgttata ctctgtaatc ctactcaata aacgtgtcac    60
gcctgtgaaa ccgtactaag tctcccgtgt cttcttatca ccatcaggtg acatcctcgc   120
ccaggctgtc aatcatgccg gtatcgattc cagtagcacc ggcccacgc tgacaaccca   180
ctcttgcagc gttagcagcg cccctcttaa caagccgacc cccaccagcg tcgcggttac   240
taacactcct ctccccgggg catccgctac tcccgagctc                        280
```

```
SEQ ID NO: 217              moltype = DNA   length = 347
FEATURE                     Location/Qualifiers
misc_feature                1..347
                            note = Synthetic
source                      1..347
                            mol_type = other DNA
                            organism = synthetic construct
SEQUENCE: 217
ctgtcttcat ccacaagccc agctcccac ccatcaccat ggacaatgtt tttttactaa    60
cacttggaca atgatggata cttttttact aacacttgga caatgatgat gatacactcc   120
tcacttgccc acttagacac aattactaac accacaccc ctcttttatt tctctgtact   180
taatgttttc tgaataaagt gatcctattg tacccacatt aaagacttct ttaactcttt   240
atggttcaca ggacccgaga tgaacataga tattgttaca gcagcggcct ccatgtcagg   300
tataactact gcctcacaca gcgccctgcc aatcagaagg aagacag                347
```

```
SEQ ID NO: 218              moltype = DNA   length = 332
```

```
FEATURE              Location/Qualifiers
misc_feature         1..332
                     note = Synthetic
source               1..332
                     mol_type = other DNA
                     organism = synthetic construct
SEQUENCE: 218
ctgtcttccc acagacctgg tgaccgtcag gaagaagatt cagtgagagg acacgaggta    60
tgtcatggtt tttaatcaat aaataaagag gttttattca tcggacagtc gttgtagcct   120
gtaaaagact cgccccggag ggggttcccc cgatgtgagg ggcatgcagt agtatggtgt   180
cctgagtgtc tcggatgcgt ccttgaactc gcactctacc gccgtggggg ttaataaagt   240
tttgctgcgc cggtaggggg ggaggccgag gataataaag ttgctacgta ctggttgaag   300
tctaacaatc tctcgggggg atccgaagac ag                                 332

SEQ ID NO: 219       moltype = DNA   length = 138
FEATURE              Location/Qualifiers
misc_feature         1..138
                     note = Synthetic
source               1..138
                     mol_type = other DNA
                     organism = synthetic construct
SEQUENCE: 219
ctgtcttctc agcctcgact gtgccttcta gttgccagcc atctgttgtt tgcccctccc    60
ccgtgccttc cttgaccctg gaaggtgcca ctcccactgt cctttcctaa taaaatgagg   120
aaattgcatc gaagacag                                                 138

SEQ ID NO: 220       moltype = DNA   length = 403
FEATURE              Location/Qualifiers
misc_feature         1..403
                     note = Synthetic
source               1..403
                     mol_type = other DNA
                     organism = synthetic construct
SEQUENCE: 220
ctgtcttctg gctaataaag gaaatttatt ttcattgcaa tagtgtgttg gaatttttg    60
tgtctctcac tcggaaggac atatgggagg gcaaatcatt taaaacatca gaatgagtat   120
ttggtttaga gtttgcaac atatgcccat atgctggctg ccatgaacaa aggttggcta    180
taaagaggtc atcagtatat gaaacagccc cctgctgtcc attccttatt ccatagaaaa   240
gccttgactt gaggttagat ttttttata ttttgttttg tgttattttt ttctttaaca    300
tccctaaaat tttccttaca tgttttacta gccagatttt tcctcctctc ctgactactc   360
ccagtcatag ctgtccctct tctcttatgg agatcgaaga cag                     403

SEQ ID NO: 221       moltype = DNA   length = 287
FEATURE              Location/Qualifiers
misc_feature         1..287
                     note = Synthetic
source               1..287
                     mol_type = other DNA
                     organism = synthetic construct
SEQUENCE: 221
ctgtcttcgg gggaggctaa ctgaaacacg gaaggagaca ataccggaag gaacccgcgc    60
tatgacggca ataaaaagac agaataaaac gcacgggtgt tgggtcgttt gttcataaac   120
gcggggttcg gtcccagggc tggcactctg tcgataccc accgagtccc cattggggcc    180
aatacgcccg cgtttcttcc ttttcccac cccaccccc aagttcgggt gaaggcccag    240
ggctcgcagc caacgtcggg gcggcaggcc ctgccatagg aagacag                 287

SEQ ID NO: 222       moltype = DNA   length = 462
FEATURE              Location/Qualifiers
misc_feature         1..462
                     note = Synthetic
source               1..462
                     mol_type = other DNA
                     organism = synthetic construct
SEQUENCE: 222
tcttctttct agactgacca aagactttt gtcaacttgt acaatctgaa gcaatgtctg     60
gcccacagac agctgagctg taaacaaatg tcacatggaa ataaatactt tatcttgtga   120
actcacttta ttgtgaagga atttgttttg ttttcaaac cttcctgcg gtgttgacag    180
cccaaggatt atctgaatag agcctaggaa ctggaaatgg aacagtgcag tctgatggta   240
cttaagggag aaaaggaa aaggtgtg gaagaagaaa aaagagaagc aagggggagg      300
ggagaaaggg agagggagag ggagagggag agggagaggg agagggaggag gggagaggag   360
aggagaggag agggagagag ggagggggag agagagagag agagagagag agagagagag   420
agagagagag agagagagag agagcatgca ctctaacagc aa                      462

SEQ ID NO: 223       moltype = DNA   length = 463
FEATURE              Location/Qualifiers
misc_feature         1..463
                     note = Synthetic
source               1..463
                     mol_type = other DNA
```

```
                        organism = synthetic construct
SEQUENCE: 223
tcttctttct agactgacca aagactttt  gtcaacttgt acaatctgaa gcaatgtctg   60
gcccacagac agctgagctg taaacaaatg tcacatggaa ataaatactt tatcttgtga  120
actcacttta ttgtgaagga atttgttttg tttttcaaac ctttcctgcg gtgttgacag  180
cccaaggatt atctgaatag agcctaggaa ctggaaatgg aacagtgcag tctgatggta  240
cttaagggag aaagagggaa aggaggtgtg gaagaagaaa aaagagaagc aaggggagg   300
gggagaaagg gagagggaga gggagaggga gaggagagg gagagggaga gggagaggga   360
gagggagagg gagagggagg gggagggga gagagagaga gagagagaga gagagagaga   420
gagagagaga gagagagaga gagagcatgc actctaacag caa                    463

SEQ ID NO: 224           moltype = DNA  length = 415
FEATURE                  Location/Qualifiers
misc_feature             1..415
                         note = Synthetic
source                   1..415
                         mol_type = other DNA
                         organism = synthetic construct
SEQUENCE: 224
tcttctttct agactgacca aagactttt  gtcaacttgt acaatctgaa gcaatgtctg   60
gcccacagac agctgagctg taaacaaatg tcacatggaa ataaatactt tatcttgtga  120
actcacttta ttgtgaagga atttgttttg tttttcaaac ctttcctgcg gtgttgacag  180
cccaaggatt atctgaatag agcctaggaa ctggaaatgg aacagtgcag tctgatggta  240
cttaagggag aaagagggaa aggaggtgtg gaagaagaaa aaagagaagc aaggggagg   300
gggagaaagg gagagggaga gggagaggga gggagagagg gagagggaga gggagaggga   360
gagggagagg gagagggagg gggaggggga gagagagcat gcactctaac agcaa        415

SEQ ID NO: 225           moltype = DNA  length = 463
FEATURE                  Location/Qualifiers
misc_feature             1..463
                         note = Synthetic
source                   1..463
                         mol_type = other DNA
                         organism = synthetic construct
SEQUENCE: 225
tcttctttct agactgacca aagactttt  gtcaacttgt acaatctgaa gcaatgtctg   60
gcccacagac agctgagctg taaacaaatg tcacatggaa ataaatactt tatcttgtga  120
actcacttta ttgtgaagga atttgttttg tttttcaaac ctttcctgcg gtgttgacag  180
cccaaggatt atctgaatag agcctaggaa ctggaaatgg aacagtgcag tctgatggta  240
cttaagggag aaagagggaa aggaggtgtg gaagaagaaa aaagagaagc acggggagg   300
gggagaaagg gagagggaga gggagaggga gggagagagg gagagggaga gggagaggga   360
gagggagagg gagagggagg gggaggggga gagagagaga gagagagaga gagagagaga   420
gagagagaga gagagagaga gagagcatgc actctaacag caa                    463

SEQ ID NO: 226           moltype = DNA  length = 461
FEATURE                  Location/Qualifiers
misc_feature             1..461
                         note = Synthetic
source                   1..461
                         mol_type = other DNA
                         organism = synthetic construct
SEQUENCE: 226
tcttctttct agactgacca aagactttt  gtcaacttgt acaatctgaa gcaatgtctg   60
gcccacagac agctgagctg taaacaaatg tcacatggaa ataaatactt tatcttgtga  120
actcacttta ttgtgaagga atttgttttg tttttcaaac ctttcctgcg gtgttgacag  180
cccaaggatt atctgaatag agcctaggaa ctggaaatgg aacagtgcag tctgatggta  240
cttaagggag aaagagggaa aggaggtgtg gaagaggaaa gaagagaagc aaggggagg   300
gggagaaagg gagagggaga gggagaggga gggagagagg gagagggaga gggagaggga   360
gagggagagg gagagggagg gggaggggga gagagagaga gagagggaga gagagagaga   420
gagagagaga gagagagaga gagcatgcac tctaacagca a                      461

SEQ ID NO: 227           moltype = DNA  length = 147
FEATURE                  Location/Qualifiers
misc_feature             1..147
                         note = Synthetic
source                   1..147
                         mol_type = other DNA
                         organism = synthetic construct
SEQUENCE: 227
ctgtcttccc aacttgttta ttgcagctta taatggttac aaataaagca atagcatcac   60
aaatttcaca aataaagcat ttttttcact gcattctagt tgtggtttgt ccaaactcat  120
caatgtatct tatcatgtcg aagacag                                      147

SEQ ID NO: 228           moltype = DNA  length = 239
FEATURE                  Location/Qualifiers
misc_feature             1..239
                         note = Synthetic
source                   1..239
                         mol_type = other DNA
```

```
                        organism = synthetic construct
SEQUENCE: 228
ctgtcttcca gacatgataa gatacattga tgagtttgga caaaccacaa ctagaatgca       60
gtgaaaaaaa tgctttattt gtgaaatttg tgatgctatt gctttatttg taaccattat      120
aagctgcaat aaacaagtta acaacaacaa ttgcattcat tttatgtttc aggttcaggg      180
ggagatgtgg gaggtttttt aaagcaagta aaacctctac aaatgtggta agaagacag       239

SEQ ID NO: 229          moltype = DNA   length = 231
FEATURE                 Location/Qualifiers
misc_feature            1..231
                        note = Synthetic
source                  1..231
                        mol_type = other DNA
                        organism = synthetic construct
SEQUENCE: 229
cagcatgat aagatacatt gatgagtttg acaaaccac aactagaatg cagtgaaaaa         60
aatgctttat ttgtgaaatt tgtgatgcta ttgctttatt tgtaaccatt ataagctgca      120
ataaacaagt taacaacaac aattgcattc attttatgtt tcaggttcag ggggagatgt      180
ggggaggtttt ttaaagcaag taaaacctct acaaatgtgg taagaagaca g              231

SEQ ID NO: 230          moltype = DNA   length = 65
FEATURE                 Location/Qualifiers
misc_feature            1..65
                        note = Synthetic
source                  1..65
                        mol_type = other DNA
                        organism = synthetic construct
SEQUENCE: 230
ctgtcttcaa taaagatct ttattttcat tagatctgtg tgttggtttt ttgtgtggaa        60
gacag                                                                   65

SEQ ID NO: 231          moltype = DNA   length = 1296
FEATURE                 Location/Qualifiers
misc_feature            1..1296
                        note = Synthetic
source                  1..1296
                        mol_type = other DNA
                        organism = synthetic construct
SEQUENCE: 231
cagcaggtgg gccgcctact gcgcacgcgc gggtttgcgg gcagccgcct gggctgtggg       60
agcagcccgg gcagagctct cctgcctctc caccagccca cccgccgcc tgaccgcccc      120
ctccccaccc cccaccccc accccgaa aacgcgtcgt cccctgggct gggtggagac        180
ccccgtcccg cgaaacaccg ggccccgcgc agcgtccggg cctgacaccg ctccggcggc     240
tcgcctccta tgcgccccg cgccaccgtc gcccgcccgc ccgggcccct gcagccgccc      300
aggtgccagc acggagcgcc tggcggcgga acgcagaccc caggcccggc gcacaccggg     360
gacgctgagc gttccaggcg ggagggaagg cgggcagaga tggagagagg aacgggagac     420
ctagagggggc ggaaggacgg gcggagggac gttaggaggg agggagggag gcagggaggc    480
agggaggaac ggagggaaag acagagcgac gcagggactg ggggcgggcg ggagggagcc     540
ggggaacggg gggaggaagg cagggaggaa aagcggtcct cggcctccgg gagtagcggg     600
accccccgccc tccgggaaaa cggtcagcgt ccggcgcggg ctgagggctg ggcccacagc    660
cgccgccgcg gccggcgggg caccaccca tcgcccccgt tccgtggccc agggagtggg      720
cggtttcctc cgggacaaaa gaccgggact cgggttgccg tcgggtcttc acccgcgcgg     780
ttcacagacc gcacatcccc aggctgagcc ctgcaacgcg gcgcgaggcc gacagccccg     840
gccacggagg agccacacgc aggacgacgg aggcgtgatt ttggtttccg cgtggctttg     900
ccctccgcaa ggcggcctgt tgctcacgtc tctccggccg tcaaaaggct ggccatgccgg    960
actgttttgct cccggagctc tgcgggcacc cggaaacatg cagggaaggg tgcaagcccg   1020
gcacggtgcc ttcgctctcc ttgccaggtt ccaaaccggc cacactcag actccccacg     1080
ttgccgcacg cgggaatcca tcgtcaggcc atcacgccgg ggaggcatct cctctctggg    1140
gtctcgctct ggtcttctac gtggaaatga acgagagcca cacgcctgcg tgtgcgagac    1200
cgtccccggca acggcgacgc ccacaggcat tgccctcctc acgagagag ggcctggcac    1260
actcaagact cccacggagg ttcagttcca cactcc                              1296

SEQ ID NO: 232          moltype = DNA   length = 1296
FEATURE                 Location/Qualifiers
misc_feature            1..1296
                        note = Synthetic
source                  1..1296
                        mol_type = other DNA
                        organism = synthetic construct
SEQUENCE: 232
caccaggtgg gccgcctact gcgcacgcgc gggtttgcgg gcagccgcct gggctgtggg       60
agcagcccgg gcagagctct cctgcctctc caccagccca cccgccgcc tgaccgcccc      120
ctccccaccc cccaccccc accccgaa aacgcgtcgt cccctgggct gggtggtgac        180
ccccgtcccg cgaaacaccg ggccccgcgc agcgtccggg cctgacaccg ctccggcggc     240
tcgcctccta tgcgccccg cgccaccgtc gcccgcccgc ccgggcccct gcagccgccc      300
aggtgccagc acggagcgcc tggcggcgga acgcagaccc caggcccggc gcacaccggg     360
gacgctgagc gttccaggcg ggagggaagg cgggcagaga tggagagagg aacgggagtc     420
ctagaggggc ggaaggacgg gcggagggac gttaggaggg agggagggag gcagggaggc     480
agggaggaac ggagggaaag acagagcgac gcagggactg ggggcgggcg ggagggagcc     540
```

```
ggggaacggg gggaggaagg cagggaggaa aagcggtcct cggcctccgg gagtagcggg    600
accccgccc tccgggaaaa cggtcagcgt ccggcgcggg ctgagggctg ggcccacagc    660
cgccgcgccg gccggcgggg caccacccat tccgccccgt tccgtggccc agggagtggg    720
cggtttcctc cgggacaaaa gaccgggact cgggttgccg tcgggtgttc acccgcgcgg    780
ttcacagacc gcacatcccc aggctgagcc ctgcaacgcg gcgcgaggcc gacagccccg    840
gccacggagg agccacacgc aggacgacgg aggcgtgatt ttggttccg cgtggctttg    900
ccctccgcaa ggcggcctgt tgctcaagtc tctccggccc ccgaaaggct ggccatgccg    960
actgtttgct cccggagctc tgcgggcacc cggaaacatg cagggaaggg tgcaagcccg   1020
gcacggtgcc ttcgctctcc ttgccaggtt ccaaaccggc cacactgcag actccccacg   1080
ttgccgcacg cgggaatcca tcgtcaggcc ggaggcatct cctctctggg                1140
gtgtcgctct ggacttctac gtggaaatga acgagagcca cacgcctgcg tgtgccagac   1200
cgtcccggca acgcgacgc ccacaggcat tgcctccttc acggagagag ggcctggcac    1260
actcaagact cccacggagg ttcagttcca cactcc                              1296

SEQ ID NO: 233          moltype = DNA   length = 433
FEATURE                 Location/Qualifiers
misc_feature            1..433
                        note = Synthetic
source                  1..433
                        mol_type = other DNA
                        organism = synthetic construct
SEQUENCE: 233
ggcgggaggg aaggcgggca gagatggaga gaggaacggg agacctagag gggcggaagg     60
acgggcggag ggacgttagg agggagggag ggaggcaggg aggcagggag gaacggaggg    120
aaagacagag cgacgcaggg actggggggcg ggcgggaggg agccggggaa cggggggagg   180
aaggcaggga ggaaaagcgg tcctcggcct ccgggagtga aggggacccc gccctccggg    240
aaaacggtca gcgtccggcg cgggctgagg gctgggccca cagccgccgc gccggccggc    300
ggggcaccac ccattcgccc cggttccgtg gcccagggag tgggcggtttt cctccgggac   360
aaaagaccgg gactcgggtt gccgtcgggt cttcacccgc gcggttcaca gaccgcacat    420
ccccaggctg agc                                                       433

SEQ ID NO: 234          moltype = DNA   length = 433
FEATURE                 Location/Qualifiers
misc_feature            1..433
                        note = Synthetic
source                  1..433
                        mol_type = other DNA
                        organism = synthetic construct
SEQUENCE: 234
ggcgggaggg aaggcgggca gagatggaga gaggaacggg agtcctagag gggcggaagg     60
acgggcggag ggacgttagg agggagggag ggaggcaggg aggcagggag gaacggaggg    120
aaagacagag cgacgcaggg actggggggcg ggcgggaggg agccggggaa cggggggagg   180
aaggcaggga ggaaaagcgg tcctcggcct ccgggagtga aggggacccc gccctccggg    240
aaaacggtca gcgtccggcg cgggctgagg gctgggccca cagccgccgc gccggccggc    300
ggggcaccac ccattcgccc cggttccgtg gcccagggag tgggcggtttt cctccgggac   360
aaaagaccgg gactcgggtt gccgtcgggt gttcacccgc gcggttcaca gaccgcacat    420
ccccaggctg agc                                                       433

SEQ ID NO: 235          moltype = DNA   length = 65
FEATURE                 Location/Qualifiers
misc_feature            1..65
                        note = Synthetic
source                  1..65
                        mol_type = other DNA
                        organism = synthetic construct
SEQUENCE: 235
agaggggcgg aagggacgtt aggagggagg cagggaggca gggaggcagg gaggaacgga     60
gggag                                                                 65

SEQ ID NO: 236          moltype = DNA   length = 1213
FEATURE                 Location/Qualifiers
misc_feature            1..1213
                        note = Synthetic
source                  1..1213
                        mol_type = other DNA
                        organism = synthetic construct
SEQUENCE: 236
gcgagctcac ggggacagcc ccccccaaa gccccagggg atgtaattac gtccctcccc      60
cgctaggggg cagcagcgag ccgcccgggg ctccgctccg gtccggcgct ccccccgcat    120
ccccgagccg gcagcgtgcg gggacagccc gggcacgggg aaggtggcac gggatcgctt    180
tcctctgaac gcttctcgct gctctttgag cctgcagaca cctgggggga tacgggggaaa    240
aagctttagg ctgaaagaga gatttagaat gacagaatca tagaacggcc tgggttgcaa    300
aggagcacag tgctcatcca gatccaaccc cctgctatgt gcagggtcat caaccagcag    360
ccccaggctgc ccagagccac atccagcctg gccttgaatg cctgcaggga tggggcatcc    420
acagcctcct tggcaacct gttcagtgcg tcaccaccct ctgggggaaa aactgcctcc    480
tcatatccaa cccaaacctc ccctgtctca gtgtaaagcc attcccccttt gtcctatcaa    540
gggggagttt gctgtgacat tgttggtctg ggtgacaca tgtttgccaa ttcagtgcat    600
cacgagagg cagatcttgg ggataaggaa gtgcaggaca gcatggacgt gggacatgct    660
ggtgttgagg gctctgggac actctccaag tcacagcgtt cagaacagcc ttaaggataa    720
```

```
gaagatagga tagaaggaca aagagcaagt taaaacccag catggagagg agcacaaaaa  780
ggccacagac actgctggtc cctgtgtctg agcctgcatg tttgatggtg tctggatgca  840
agcagaaggg gtggaagtgc ttgcctggag agatacagct gggtcagtag gactgggaca  900
ggcagctgga gaattgccat gtagatgttc atacaatcgt caaatcatga aggctggaaa  960
agccctccaa gatccccaag accaacccca acccaccccac cgtgcccact ggccatgtcc 1020
ctcagtgcca catccccaca gttcttcatc acctccaggg acggtgaccc ccccacctcc 1080
gtgggcagct gtgccactgc agcaccgctc tttggagaag gtaaatcttg ctaaatccag 1140
cccgaccctc ccctggcaca acgtaaggcc attatctctc atccaactcc aggacggagt 1200
cagtgagaat att                                                    1213

SEQ ID NO: 237          moltype = DNA   length = 246
FEATURE                 Location/Qualifiers
misc_feature            1..246
                        note = Synthetic
source                  1..246
                        mol_type = other DNA
                        organism = synthetic construct
SEQUENCE: 237
gcgagctcac ggggacagcc cccccccaaa gccccagggg atgtaattac gtccctcccc   60
cgctaggggg cagcagcgag ccgccggggg ctccgctccg gtccggcgct ccccccgcat  120
ccccgagccg gcagcgtgcg gggacagccc gggcacgggg aaggtggcac gggatcgctt  180
tcctctgaac gcttctcgct gctctttgag cctgcagaca cctgggggga tacggggaaa  240
aagctt                                                             246

SEQ ID NO: 238          moltype = AA    length = 220
FEATURE                 Location/Qualifiers
REGION                  1..220
                        note = Synthetic
source                  1..220
                        mol_type = protein
                        organism = synthetic construct
SEQUENCE: 238
MLRLLLALNL FPSIQVTGNK ILVKQSPMLV AYDNAVNLSC KYSYNLFSRE FRASLHKGLD   60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                        220

SEQ ID NO: 239          moltype = AA    length = 233
FEATURE                 Location/Qualifiers
REGION                  1..233
                        note = Synthetic
source                  1..233
                        mol_type = protein
                        organism = synthetic construct
SEQUENCE: 239
MSQSNRELVV DFLSYKLSQK GYSWSQFSDV EENRTEAPEG TESEMETPSA INGNPSWHLA   60
DSPAVNGATG HSSSLDAREV IPMAAVKQAL REAGDEFELR YRRAFSDLTS QLHITPGTAY  120
QSFEQVVNEL FRDGVNWGRI VAFFSFGGAL CVESVDKEMQ VLVSRIAAWM ATYLNDHLEP  180
WIQENGGWDT FVELYGNNAA AESRKGQERF NRWFLTGMTV AGVVLLGSLF SRK         233

SEQ ID NO: 240          moltype = AA    length = 142
FEATURE                 Location/Qualifiers
REGION                  1..142
                        note = Synthetic
source                  1..142
                        mol_type = protein
                        organism = synthetic construct
SEQUENCE: 240
MGAPTLPPAW QPFLKDHRIS TFKNWPFLEG CACTPERMAE AGFIHCPTEN EPDLAQCFFC   60
FKELEGWEPD DDPIEEHKKH SSGCAFLSVK KQFEELTLGE FLKLDRERAK NKIAKETNNK  120
KKEFEETAKK VRRAIEQLAA MD                                           142

SEQ ID NO: 241          moltype = AA    length = 220
FEATURE                 Location/Qualifiers
REGION                  1..220
                        note = Synthetic
source                  1..220
                        mol_type = protein
                        organism = synthetic construct
SEQUENCE: 241
MLRLLLALNL FPSIQVTGNK ILVKQSPMLV AYDNAVNLSC KYSYNLFSRE FRASLHKGLD   60
SAVEVCVVYG NYSQQLQVYS KTGFNCDGKL GNESVTFYLQ NLYVNQTDIY FCKIEVMYPP  120
PYLENEKSNG TIIHVKGKHL CPSPLFPGPS KPFWVLVVVG GVLACYSLLV TVAFIIFWVR  180
SKRSRLLHSD YMNMPPRRPG PTRKHYQPYA PPRDFAAYRS                        220

SEQ ID NO: 242          moltype = AA    length = 239
FEATURE                 Location/Qualifiers
REGION                  1..239
                        note = Synthetic
```

```
source                        1..239
                              mol_type = protein
                              organism = synthetic construct
SEQUENCE: 242
MAHAGRTGYD NREIVMKYIH YKLSQRGYEW DAGDVGAAPP GAAPAPGIFS SQPGHTPHPA    60
ASRDPVARTS PLQTPAAPGA AAGPALSPVP PVVHLTLRQA GDDFSRRYRR DFAEMSSQLH   120
LTPFTARGRF ATVVEELFRD GVNWGRIVAF FEFGGVMCVE SVNREMSPLV DNIALWMTEY   180
LNRHLHTWIQ DNGGWDAFVE LYGPSMRPLF DFSWLSLKTL LSLALVGACI TLGAYLGHK    239

SEQ ID NO: 243                moltype = AA  length = 706
FEATURE                       Location/Qualifiers
REGION                        1..706
                              note = Synthetic
source                        1..706
                              mol_type = protein
                              organism = synthetic construct
SEQUENCE: 243
MASPADSCIQ FTRHASDVLL NLNRLRSRDI LTDVVIVVSR EQFRAHKTVL MACSGLFYSI    60
FTDQLKCNLS VINLDPEINP EGFCILLDFM YTSRLNLREG NIMAVMATAM YLQMEHVVDT   120
CRKFIKASEA EMVSAIKPPR EEFLNSRMLM PQDIMAYRGR EVVENNLPLR SAPGCESRAF   180
APSLYSGLST PPASYSMYSH LPVSSLLFSD EEFRDVRMPV ANPFPKERAL PCDSARPVPG   240
EYSRPTLEVS PNVCHSNIYS PKETIPEEAR SDMHYSVAEG LKPAAPSARN APYFPCDKAS   300
KEEERPSSED EIALHFEPPN APLNRKGLVS PQSPQKSDCQ PNSPTESCSS KNACILQASG   360
SPPAKSPTDP KACNWKKYKF IVLNSLNQNA KPEGPEQAEL GRLSPRAYTA PPACQPPMEP   420
ENLDLQSPTK LSASGEDSTI PQASRLNNIV NRSMTGSPRS SSESHSPLYM HPPKCTSCGS   480
QSPQHAEMCL HTAGPTFPEE MGETQSEYSD SSCENGAFFC NECDCRFSEE ASLKRHTLQT   540
HSDKPYKCDR CQASFRYKGN LASHKTVHTG EKPYRCNICG AQFNRPANLK THTRIHSGEK   600
PYKCETCGAR FVQVAHLRAH VLIHTGEKPY PCEICGTRFR HLQTLKSHLR IHTGEKPYHC   660
EKCNLHFRHK SQLRLHLRQK HGAITNTKVQ YRVSATDLPP ELPKAC                  706

SEQ ID NO: 244                moltype = DNA  length = 9014
FEATURE                       Location/Qualifiers
misc_feature                  1..9014
                              note = Synthetic
source                        1..9014
                              mol_type = other DNA
                              organism = synthetic construct
SEQUENCE: 244
atgtcacagt ccaaccgcga gctcgtggtg gacttcctga gctataagct gtcccagaag    60
ggctactcgt ggagccagtt cagcgacgtg gaagagaaca ggactgaagc acctgaaggg   120
accgagagcg agatggaaac cccgtcggcc atcaacggaa accttcttg gcaccttgcc    180
gactccccgg ccgtgaacgg cgcgaccgga cattcatcct ccctggatgc ccgcgaagtc   240
attccaatgg ccgctgtgaa gcaggccctt cgcgaggccg ggacgaatt cgagctgaga   300
tacagacggg cgttctccga cttgacctcg caactccaca tcaccccgg aaccgcgtac    360
cagtcgtttg aacaagtcgt caacgaactc ttccgggatg cgtgaactg gggacggatc    420
gtggcctttc tctcctttgg tggcgctctg tgcgtcgagt ccgtggacaa agagatgcaa   480
gtgctggtgt ccagaatcgc agcctggatg gccacctacc tcaacgatca cctgagccc    540
tggattcagg aaaacggcgg atgggacact ttcgtggagc tgtacggaaa caatgccgct   600
gccgaatccc ggaagggcca ggaaaggttc aatcgctggt tcttgacggg gatgactgtg   660
gccggagtgg tcctgctggg tagcctgttc tcacggaagt gataaaagct taattaatgg   720
ctaataaagg aaatttattt tcattgcaat agtgtgttgg aatttttgt gtctctcaat    780
cggaagaaca tatgggaggg caaatcattt aaaacatcag aatgagtatt tggtttagag   840
tttggcaaca tatgcccata tgctggctgc catgaacaaa ggttggctat aaagaggtca   900
tcagtatatg aaacagcccc ctgctgtcca ttccttattc catagaaaag ccttgacttg   960
aggttagatt tttttatat tttgttttgt gttattttt tctttaacat ccctaaaatt    1020
ttccttacat gttttactag ccagattttt cctcctctcc tgactactcc cagtcatagc   1080
tgtccctctt ctcttatgga gatcagaaaa ttttgtgtcg cccttcgctg aacaccaggt   1140
gggccgccta ctgcgcacgc gcgggttttgc gggcagccgc ctgggctgtg ggagcagccc   1200
gggcagagct ctcctgcctc tccaccagcc caccccgccg cctgaccgcc ccctccccac   1260
ccccacccc ccaccccgg aaaacgcgtc gtccctgcg ctgggtggtg accccgtcc       1320
cgcgaaacac cgggccccgc gcagcgtccg ggcctgacac cgctccggcg gctcgcctcc   1380
tatgcgcccc cgcgccaccg tcgcccgccc gcccgggccc ctgcagccgc caggtgcca    1440
gcacggagcg cctggcggcg gaacgcagac cccaggcccg gcgcacaccg gggacgctga   1500
gcgttccagg cggaggggaa ggcgggcaga gatggagaga ggaacgggag tcctagaggg   1560
gcggaaggac gggcggaggg acgttaggag ggagggaggg aggcagggag gcaggaggag   1620
acggaggaa agacagagcg acgcagggac tgggggcggg cggagggag ccggggaacg     1680
gggggaggaa ggcaggaggg aaaagcggtc ctcggcctcc gggagtagcg gaccccgc     1740
cctccgggaa aacggtcagc gtccggcgcg ggctgagggc tgggcccaca gccgccgcgc   1800
cggccgcggg ggcaccaccc attcgcccgc gttccgtggc ccaggagtg ggcggtttcc    1860
tccgggacaa aagaccggga ctcggttgc cgtcgggtgt tcacccgcgc ggttcacaga    1920
ccgcacatcc ccaggctgag ccctgcaacg cggcgcgagg ccgacagccc cggccacgga   1980
ggagccacac gcaggacgac ggaggcgtga ttttggttc cgcgtggctt tgcctccgc     2040
aaggcggcct gttgctcaag tctctccggc ccccgaaagg ctggccatgc cgactgtttg   2100
ctcccgggagc tctgcgggca cccggaaaca tgcagggaag tgcaaggcc cggcacggtg    2160
ccttcgctct ccttgccagg ttccaaaccg gccacactgc agactcccca cgttgccgca   2220
cgcgggaatc catcgtcagg ccatcacgcc gggaggcat ctcctctctg gggtgtcgct    2280
ctggacttct acgtggaaat gaacgagagc cacacgcctg cgtgtgccag accgtccggg   2340
caacggcgac gcccacaggc attgcctcct tcacggagag agggcctggc acactcaaga   2400
ctcccacgga ggttcagttc cacactccac ctaggtcata ttttttagttt aaaaaaataa   2460
```

```
ttatatgttt tataatgaaa agaatctcat tatctttcag tattaggttg atttatattc   2520
caaagaataa tattttttgtt aaattgttga tttttgtaaa cctctaaatg tttgttgcta   2580
aaattactgt gtttaagaaa aagattaata aataataata atttcataat taaaaacttc   2640
tttcattgaa tgccattaaa taaaccatta ttttacaaaa taagatcaac ataattgagt   2700
aaataataat aagaacaata ttatagtaca acaaaatatg ggtatgtcat accctgccac   2760
attcttgatg taacttttttt tcacctcatg ctcgccgggt taagggctac aatgaactcg   2820
aaacgaccgg tttgcatttt tagacattta gaagcctata tcttgttaca gaattggaat   2880
tacacaaaaa ttctaccata ttttgaaagc ttaggttgtt ctgaaaaaaa caatatattg   2940
ttttcctggg taaactaaaa gtcccctcga ggaaaggccc ctaaagtgaa acagtgcaaa   3000
acgttcaaaa actgtctggc aatacaagtt ccactttgac caaaacggct ggcagtaaaa   3060
gggttaagcg gccgctcagc cttgagcggg atcagctcac tcaaaggcgg taatacggtt   3120
atccacagaa tcaggggata acgcaggaaa gaacatgtga gcaaaaggcc agcaaaaggc   3180
caggaaccgt aaaaaggccg cgttgctggc gttttttccat aggctccgcc cccctgacga   3240
gcatcacaaa aatcgacgct caagtcagag gtggcgaaac ccgacaggac tataaagata   3300
ccaggcgttt cccctggaa gctcccctcgt gcgctctcct gttccgaccc tgccgcttac   3360
cggatacctg tccgcctttc tcccttcggg aagcgtggcg ctttctcata gctcacgctg   3420
taggtatctc agttcggtgt aggtcgttcg ctccaagctg ggctgtgtgc acgaaccccc   3480
cgttcagccc gaccgctgcg ccttatccgg taactatcgt cttgagtcca acccggtaag   3540
acacgactta tcgccactgg cagcagccac tggtaacagg attagcagag cgaggtatgt   3600
aggcggtgct acagagttct tgaagtggtg gcctaactac ggctacacta gaagaacagt   3660
atttggtatc tgcgctctgc tgaagccagt taccttcgga aaaagagttg gtagctcttg   3720
atccggcaaa caaaccaccg ctggtagcgg tggttttttt gtttgcaagc agcagattac   3780
gcgcagaaaa aaaggatctc aagaagatcc tttgatcttt tctacggggt ctgacgctca   3840
gtggaacgac gcgcgcgtaa ctcacgttaa gggattttgg tcatgagtta gaaaaactca   3900
tcgagcatca aatgaaactg caatttattc atatcaggat tatcaatacc atattttga   3960
aaaagccgtt tctgtaatga aggagaaaac tcaccgaagc agttccatag gatgccaaga   4020
tcctggtatc ggtctgcgat tccgactcgt ccaacatcaa tacaacctat taatttcccc   4080
tcgtcaaaaa taaggttatc aagtgagaaa tcaccatgag tgacgactga atccggtgag   4140
aatggcaaaa gtttatgcat ttcttttccag acttgttcaa caggccagcc attacgctcg   4200
tcatcaaaat cactcgcatc aaccaaaccg ttattcattc gtgattgcgc ctgagcgagg   4260
cgaaatacgc gatcgctgtt aaaaggacaa ttacaaacag gaatcgagtg caaccggcgc   4320
aggaacactg ccagcgcatc aacaatattt tcacctgaat caggatattc ttctaatacc   4380
tggaacgctg ttttttccggg gatcgcagtg gtgagtaacc atgcatcatc aggagtacgg   4440
ataaaatgct tgatggtcgg aagtggcata aattccgtca gccagtttag tctgaccatc   4500
tcatctgtaa catcattggc aacgctacct ttgccatgtt tcagaaacaa ctctggcgca   4560
tcgggcttcc catacaagcg atagattgtc gcacctgatt gcccgacatt atcgcgagcc   4620
catttatacc catataaatc agcatccatg ttggaattta atcgcggcct cgacgtttcc   4680
cgttggatat ggctcatttt ttacttcctc accttgtcgt attatactat gccgatatac   4740
tatgccgatg attaattgtc gacactgcgg gggctctggc gcgccttaac cttttttactg   4800
ccaatgacgc atgggatacg tcgtggcagt aaaagggctt aaatgccaac gacgcgtccc   4860
atacgttgtt ggcattttaa ttcttctctc tgcagcggca gcatgtgccg ccgctgcaga   4920
gagtttctag cgatgacagc ccctctggc aacgagccgg gggggctgtc ccatgacgcg   4980
gctagacatg cacgaccatt aacccagcga gcatgaggca gggtatctca taccctggta   5040
aaattttaaa gttgtgtatt ttataaaatt ttcgtctgac aacactacgc cgctcagtag   5100
ctggaggcag gagcgtgcgg gagggggtag tggcgtgatc gcagtgtggc acgggacacc   5160
ggcgagatat tcgtgtgcaa acctgtttcg ggtatgttat accctgcctc attgttgacg   5220
tattttttttt atgtaatttt tccgattatt aatttcaact gttttattgg tattttttatg   5280
ttatccattg ttctttttttt atgatttact gtatcggttg tctttcgttc ctttagttga   5340
gttttttttttt attattttca gttttttgatc aaagctagcg cgagctcacg gggacagccc   5400
cccccaaag cccccaggga tgtaattacg tccctccccc gctaggggc agcagcgagc   5460
cgcccgggc tccgctccgg tccggcgctc ccccgcatc cccgagccgg cagcgtgcgg   5520
ggacagcccg ggcacgggga aggtggcacg ggatcgcttt cctctgaacg cttctcgctg   5580
ctctttgagc ctgcagacac ctgggggat acggggaaaa agcttaggc tgaaagagag   5640
atttagaatg acagaatcat agaacggcct gggttgcaaa ggagcacagt gctcatccag   5700
atccaacccc ctgctatgtg caggtcatc aaccagcagc ccaggctgcc cagagccaca   5760
tccagcctgg ccttgaatgc ctgcaggat ggggcatcca cagcctcctt gggcaacctg   5820
ttcagtgcgt caccaccctc tgggggaaaa actgcctcct catatccaac ccaaacctcc   5880
cctgtctcag tgtaaagcca ttcccccttg tcctatcaag ggggagttg ctgtgacatt   5940
gttggtctgg ggtgacacat gtttgccaat tcagtgcatc acggagaggc agatcttggg   6000
gataaggaag tgcaggacag catggacgtg ggacatgctg gtgttgaggg ctctgggaca   6060
ctctccaagt cacagcgttc agaacagcct taaggataag aagataggat agaaggacaa   6120
agagcaagtt aaaacccagc atggagagga gcacaaaaag gccacagaca ctgctggtcc   6180
ctgtgtctga gcctgcatgt ttgatggtgt ctggatgcaa gcagaagggg tggaagtgct   6240
tgcctggaga gatacagctg ggtcagtagg actgggacag gcagctggag aattgccatg   6300
tagatgttca tacaatcgtc aaatcatgaa ggctgaaaa gccctccaag atccccaaga   6360
ccaaccccaa cccaccacc gtgcccactg gccatgtccc tcagtgccac atccccacag   6420
ttcttcatca cctccaggga cggtgacccc cccacctccg tgggcagctg tgccactgca   6480
gcaccgctct ttggagaagg taaatcttgc taaatccagc ccgaccctcc cctggcacaa   6540
cgtaaggcca ttatctctca ggacgagtc agtgagaata ttggctaccgg   6600
ggtgtggtgt cttcttaacc tcacccagga ggaaccgggt caattcttca gcacctgggt   6660
acccatagag cccaccgcat ccccagcatg cctgctattg tattcccaat cctccccctt   6720
gctgtcctgc cccacccccac ccccagaat agaatgacac ctactcagac aatgcgatgc   6780
aattcctca ttttattagg aaaggacagt gggagtggca ccttccaggg tcaaggaagg   6840
ggggagg gggcaaacaa cagatggctg gcaagagagc aggtttactg ataggtatcg   6900
agatcgacgg ccttgaccac ttccaccagg cacatgtgat ctctcctctc atcgcggtct   6960
ttggagagct tagtgtgata agtgatatga tggtagcgcg gaatgtggac agccgctgaa   7020
ccggccagtg gccgattcat ctggctacac ttggtcacca gcttctccgt caccccctcg   7080
atgtcgtagg cttgattgaa ctccacgcgg attccgttgt tcacagtgtc ggggagaatg   7140
taaaggatgc tgggagggca ctggaaggcg acattcttcc gaagaatatg cccgtccttc   7200
```

```
ttaaagtttt ctccagtcag agtcacccgg ttgtagatag atcccctctc ataggtgacc   7260
atcgcgcggg tcttgtacac tccatctccc tcaaaagaaa tggtgcgctc ttgggtataa   7320
ccttccggca tggcggattt gaagaagtcc ttaatgtggc tagggtactt agcaaaacac   7380
tgcactccat acgagagggt tgacacaagg gtggcccaag gcactggcag atctccagtg   7440
gtacagatat acttggcctt aatggttcca gtcgtagcgt ccccggttcc ttctcccttg   7500
atgatgaact tcattccttc gacgtcccct tccagctcgg tgatgtacgg aatctccttc   7560
tcaaacagct tagcaccttc ggtcagggca gtcatggtgg cggccttcct gcaaaaagaa   7620
caagcaagct cttgtctatg agaagaggct gcgggagaaa aaagtcagat tagcgtggcc   7680
agtccctcc ccccacccgc ctccattccc gccgcatgcc ccatcacgtc ctctaccatc   7740
ctctgcaatg cggagcctgg gctcggcttc cggacctcgc accagcgccc ctaaacccgt   7800
acagcgtcct tccccccatt cctaatttcc attcctctcc ggcctcctgc ggcccagtcc   7860
ttttttttct tttcttttc acctggcact gcacaagaag atgcggctgt ctctagaaca   7920
gggaggagca gagagcacca gggagggctg cagtccgtat ttataggaac tggatggtgg   7980
ggggagctga tgacgcgcgc cccgcctccc gctcggctca tccagtccca gctcaaggc   8040
gcagaggcct gagctacgtg caccctgtaaa gccgcgagta gctgggcctc tctcattccc   8100
cccctccctc tttttggacc cgcctcgttt ttgaaatgtg cacgcaccaa gcgtgttgggc   8160
tccgacctga gaggggagg ggagctgaga ttgtcccgcc gaggaagtga ccggatgagg   8220
gttcccagga taggactcag ggaatacaga ctatggatta aggacgagga gtccttggag   8280
tgtgcaccaa ggacatccag gacccagaaa ccagaaagct gcttcccgaa taaaatggga   8340
gaatctgaga gctgcaggaa ccagggaaat ggagcagaag tgtgggtctg cccaaggctg   8400
ccccatcgaa cttctcccta ttagtgaaaa ggcttaggag aagttgagga tcttctcgtt   8460
gttcttcgga agactactct ggagacgtct accgggtagg ggagcgctt ttcccaaggc   8520
agtctggagc atgcgcttta gcagcccgc tgggcacttg gcgctacaca agtggcctc   8580
ggcctcgcac acattccaca tccaccggta ggcgccaacc ggctccgttc tttggtggcc   8640
ccttcgcgcc accttctact cctcccctag tcaggaagtt ccccccgcc ccgcagctcg   8700
cgtcgtgcag gacgtgacaa atggaagtag cacgactcac tagtctcgtg cagatggaca   8760
gcaccgctga gcaatggaag cgggtaggc tttggggcag cggccaatag cagctttgct   8820
ccttcgcttt ctgagagcag cggccggaa ggggcggtgc gggaggcggg gtgtggggc   8880
gtagtgtggg ccctgttcct gcccgcgcgg tgttccgcat tctgcaagcc tccggagcgc   8940
acgtccgtct caggggcagc ttgcttgttc tttttgcaga agctcagaat aaacgctcaa   9000
ctttggccgc cacc                                                    9014
```

```
SEQ ID NO: 245           moltype = DNA  length = 8741
FEATURE                  Location/Qualifiers
misc_feature             1..8741
                         note = Synthetic
source                   1..8741
                         mol_type = other DNA
                         organism = synthetic construct
SEQUENCE: 245
atgggagcac ccaccctgcc tcccgcttgg caaccgttcc tgaaagacca ccggatttcg   60
accttcaaga attggccgtt cctcgagggc tgtgcctgca ctcctgagcg gatggccgag   120
gccggttca tccactgtcc aaccgagaac gaacctgacc tggcccagtg cttcttctgc   180
tttaaggaac ttgaggggttg ggagccggac gatgacccca tcgaagaaca caagaagcat   240
tcctccggct gcgccttcct gagcgtgaag aaacagttcg aagaactgac tctgggagag   300
ttcttgaagc tcgacagaga gcgcgccaag aacaagatcg cgaaggaaac caacaacaag   360
aagaaagaat ttgaggaaac cgcgaagaag gtccgcaagg cgattgaaca gctggctgcc   420
atggattgat aaaaagctta ttaatggcta ataaaggaaa tttattttca ttgcaatagt   480
gtgttggaat ttttttgtgtc tctcactcgg aagaacatat gggagggcaa atcatttaaa   540
acatcagaat gagtatttgg tttagagttt ggcaacatat gcccatatgc tggctgccat   600
gaacaaaggt tggctataaa gaggtcatca gtatatgaaa cagcccccctg ctgtccattc   660
cttattccat agaaaagcct tgacttgagg ttagattttt tttatattt gttttgtgtt   720
atttttttct ttaacatccc taaaattttc cttacatgtt ttactagcca gatttttcct   780
cctctcctga ctactcccag tcatagctgt ccctcttctc ttatggagat cagaaaattt   840
tgtgtcgccc ttcgctgaac accaggtggg ccgcctactg cgcacgcggg ggtttgcgg   900
cagccgcctg ggctgtggga gcagcccggg cagagctctc ctgcctctcc accagcccac   960
cccgccgcct gaccgcccc tcccaccccc ccaccccca ccccggaaa acgcgtcgtc   1020
ccctgggctg gtggtgacc cccgtcccgc gaaacaccgg gccccgcgca gcgtccgggc   1080
ctgacaccgc tccggcggct cgcctcctat gcgccccgc gccaccgtcg cccgcccgcc   1140
cgggccctg cagccgccca ggtgccagca cggagcgct ggcggcggaa cgcagaccc   1200
aggccccgg cacaccgggg acgctgagcg ttccaggcgg gagggaaggc gggcagagat   1260
ggagagagga acgggagtcc tagaggggcg gaaggacggg cggagggacg ttaggaggga   1320
gggaggggag caggaggaga gggaggaacg gagggaaaga cagagcgacg cagggactgg   1380
gggcgggcgg gagggagccg gggaacgggg ggaggaaggc aggggaaa agccgtcctc   1440
ggcctccggg agtagcggga ccccgcgcct ccgggaaaac ggtcagcgtc cggcgcgggc   1500
tgagggctgg gccacagcc gccgcgccgg ccggcggggc accaccatt cgccccggtt   1560
ccgtggccca gggagtgggc ggtttcctcc gggacaaaag accgggactc gggttgccgt   1620
cgggtgttca cccgcgcggt tcacagaccg cacatccca ggctgagccc tgcaacgcgg   1680
cgcgaggccg acagccccgg ccacggagga gccacacgca ggacgacgga ggcgtgattt   1740
tggtttccgc gtggctttgc cctccgcaag gcggcctgtt gctcaagtct ctccggcccc   1800
cgaaaggctg gccatgccga ctgtttgctc ccggagctct gcgggcaccc ggaaacatgc   1860
agggaagggt gcaagcccgg cacggtgcct tcgctctcct tgccaggttc caaaccggcc   1920
acactgcaga ctccccacgt tgccgcacgc gggaatccta cgtcaggcca tcacgccggg   1980
gaggcatctc ctctctgggg tgtcgctctg gacttctacg tggaaatgaa gagagccac   2040
acgcctgcgt gtgccagacc gtcccggcaa cggcgacgcc acaggcatt gcctccttca   2100
cggagagagg gcctggcaca ctcaagactc ccacggaggt tcagttccac actccaccta   2160
ggtcatattt ttagttttaaa aaataatta tatgttttat aatgaaaaga atctcattat   2220
ctttcagtat taggttgatt tatattccaa agaataatat tttgttaaa ttgttgattt   2280
ttgtaaaacct ctaaatgttt gttgctaaaa ttactgtgtt taagaaaaag attaataaat   2340
```

```
aataataatt tcataattaa aaacttcttt cattgaatgc cattaaataa accattattt    2400
tacaaaataa gatcaacata attgagtaaa taataataag aacaatatta tagtacaaca    2460
aaatatgggt atgtcatacc ctgccacatt cttgatgtaa cttttttca cctcatgctc     2520
gccgggttaa gggctacaat gaactcgaaa cgaccggttt gcattttag acatttagaa     2580
gcctatatct tgttacagaa ttggaattac acaaaaattc taccatattt tgaaagctta    2640
ggttgttctg aaaaaaacaa tatattgttt tcctgggtaa actaaaagtc ccctcgagga    2700
aaggcccta aagtgaaaca gtgcaaaacg ttcaaaaact gtctggcaat acaagttcca     2760
cttttgaccaa aacggctggc agtaaaaggg ttaagcggcc gctcagcctt gagcggtatc   2820
agctcactca aaggcggtaa tacggttatc cacagaatca ggggataacg caggaaagaa    2880
catgtgagca aaaggccagc aaaaggccag gaaccgtaaa aaggccgcgt tgctggcgtt    2940
tttccatagg ctccgccccc ctgacgagca tcacaaaaat cgacgctcaa gtcagaggtg    3000
gcgaaacccg acaggactat aaagatacca ggcgtttccc cctggaagct ccctcgtgcg    3060
ctctcctgtt ccgaccctgc cgcttaccgg atacctgtcc gcctttctcc cttcgggaag    3120
cgtggcgctt tctcatagct cacgctgtag gtatctcagt tcggtgtagg tcgttcgctc    3180
caagctgggc tgtgtgcacg aaccccccgt tcagcccgac cgctgcgcct tatccggtaa    3240
ctatcgtctt gagtccaacc cggtaagaca cgacttatcg ccactggcag cagccactgg    3300
taacaggatt agcagagcga gtatgtagg cggtgctaca gagttcttga agtggtgggc     3360
taactacggc tacactagaa gaacagtatt tggtatctgc gctctgctga agccagttac    3420
cttcggaaaa agagttggta gctcttgatc cggcaaacaa accaccgctg gtagcggtgg    3480
tttttttgtt tgcaagcagc agattacgcg cagaaaaaaa ggatctcaag aagatccttt    3540
gatcttttct acggggtctg acgctcagtg gaacgacgcg cgcgtaactc acgttaaggg    3600
attttggtca tgagttagaa aaactcatcg agcatcaaat gaaactgcaa tttattcata    3660
tcaggattat caataccata tttttgaaaa agccgtttct gtaatgaagg agaaaactca    3720
ccgaggcagt tccataggat ggcaagatcc tggtatcggt ctgcgattcc gactcgtcca    3780
acatcaatac aacctattaa tttcccctcg tcaaaaataa ggttatcaag tgagaaatca    3840
ccatgtgtga cgactgaatc cggtgagaat ggcaaaagtt tatgcatttc tttccagact    3900
tgttcaacag gccagccatt acgctcgtca tcaaaatcac tcgcatcaac caaaccgtta    3960
ttcattcgtg attgcgcctg agcgaggcga aatacgcgat cgctgttaaa aggacaatta    4020
caaacaggaa tcgagtgcaa ccggcgcagg aacactgcca gcgcatcaac aatattttca    4080
cctgaatcag gatattcttc taatacctcg aacgctgttt ttccggggat cgcagtggtg    4140
agtaaccatg catcatcagg agtacggata aaatgcttga tggtcggaag tggcataaat    4200
tccgtcagcc agtttagtct gaccatctca tctgtaacat cattggcaac gctacctttg    4260
ccatgtttca gaaacaactc tggcgcatcg ggcttcccat acaagcgata gattgtcgca    4320
cctgattgcc cgacattatc gcgagcccat ttatacccat ataaatcagc atccatgttg    4380
gaatttaatc gcggcctcga cgtttcccgt tggatatggc tcattttta cttcctcacc     4440
ttgtcgtatt atactatgcc gatatactat gccgatgatt aattgtcgac actgcggggg    4500
ctctggcgcg ccttaacctt tttactgcca atgacgcatg ggatacgtcg tggcagtaaa    4560
agggcttaaa tgccaacgac gcgtcccata cgttgttggc atttaattc ttctctctgc     4620
agcggcagca tgtgccgccg ctgcagagag tttctagcga tgacagcccc tctgggcaac    4680
gagccggggg ggctgtccca tgacgcggct agacatgcac gaccattaac ccggcgagca    4740
tgaggcaggg tatctcatac cctggtaaaa ttttaaagtt gtgtatttta taaaattttc    4800
gtctgacaac actagcgcgc tcagtagctg gaggcaggag cgtgcgggag gggatagtgg    4860
cgtgatcgca gtgtggcacg ggacaccggc gagatattcg tgtgcaaacc tgtttcggtg    4920
atgttatacc ctgcctcatt gttgacgtat ttttttatg taattttcc gattattaat      4980
ttcaactgtt ttattggtat ttttatgtta tccattgttc tttttttatg atttactgta    5040
tcggttgtct ttcgttcctt tagttgagtt tttttttatt atttcagtt tttgatcaaa     5100
gctagcgcga gctcacgggg acagcccccc cccaaagccc ccaggatgt aattacgtcc     5160
ctccccccgct aggggggcagc agcgagccgc ccggggctcc gctccggtcc ggcgctcccc   5220
ccgcatcccc gagccggcag cgtgcgggga cagcccgggc acggggaagg tggcacggga    5280
tcgctttcct ctgaacgctt ctcgctgctc tttgagcctg cagacacctg gggggatacg    5340
gggaaaaagc tttaggctga aagagagatt tagaatgaca gaatcataga acggcctaga    5400
ttgcaaagga gcacagtgct catccagatc caaccccctg ctatgtgcag ggtcatcaac    5460
cagcagccca ggctgcccag agccacatcc agcctggcct tgaatgcctg cagggatggg    5520
gcatccacag cctccttggg caacctgttc agtgcgtcac caccctctgg gggaaaaact    5580
gcctcctcat atccaaccca aacctcccct gtctcagtgt aaagccattc cccccttgtcc   5640
tatcaagggg gagtttgctg tgacattgtt ggtctggggt gacacatgtt tgccaattca    5700
gtgcatcacg gagaggcaga tcttggggat aaggaagtgc aggacagcat ggacgtggga    5760
catgctggtt ttgagggctc tgggacactc tccaagtcac agcgttcaga acagcctaa     5820
ggataagaag ataggataga aggacaaaga gcaagttaaa acccagcatg gagaggagca    5880
caaaaaggcc acagacactg ctggtccctg tgtctgagcc tgcatgtttg atggtgtctg    5940
gatgcaagca gaagggtgg aagtgcttgc ctggagagat acagctgggt cagtaggact      6000
gggacaggca gctggagaat tgccatgtag atgttcatac aatcgtcaaa tcatgaaggc    6060
tggaaaagcc ctcaagatc cccaagacca accccaaccc acccaccgtg cccactggcc     6120
atgtccctca gtgccacatc cccacagttc ttcatcacct ccagggacgg tgacccccca    6180
acctccgtgg gcagctgtgc cactgcagca ccgctctttg gagaaggtaa atcttgctaa    6240
atccagcccg acccctcccct ggcacaacgt aaggccatta tctctcatcc aactccagga   6300
cggagtcagt gagaatattg gtaccggggt gtggtgtctt cttaacctca cccaggagga    6360
accgggtcaa ttcttcagca cctgggtacc catgagccc accgcatccc cagcatgcct    6420
gctattgtat tcccaatcct cccccttgct gtcctgcccc accccaccccc ccagaataga    6480
atgacaccta ctcagacaat gcgatgcaat ttcctcattt tattaggaaa ggacagtggg    6540
agtggcacct tccagggtca aggaaggcac gggggagggg caaacaacag atggctggca    6600
agagagcagg tttactgata ggtatcgaga tcgacgcct tgaccacttc caccaggcac      6660
atgtgatctc tcctctcatc gcggtctttg gagagcttag tgtgataagt gatatgatgg    6720
tagcgcggaa tgtggacagc cgctgaaccg gcgcaggggcc gattcatctg gctacacttg    6780
gtcaccagct tctccgtcac cccctcgatg tcgtaggctt gattgaactc cacgcggatt    6840
ccgttgttca cagtgtcggg gagaatgtaa aggatgctgg gagggcactg gaaggcgaca    6900
ttcttccgaa gaatatgccc gtccttctta aagtttctc cagtcagagt cacccggttg     6960
tagatagatc ccctctcata ggtgaccatc gcgcgggtct tgtacactcc atctccctca    7020
aaagaaatgg tgcgctcttg ggtataaccct tccggcatgg cggatttgaa gaagtcctta   7080
```

-continued

```
atgtggctag ggtacttagc aaaacactgc actccatacg agagggttga cacaagggtg    7140
gcccaaggca ctggcagatc tccagtggta cagatatact tggccttaat ggttccagtc    7200
gtagcgtccc cggttccttc tcccttgatg atgaacttca ttccttcgac gtcccctcc     7260
agctcggtga tgtacggaat ctccttctca aacagcttag caccttcggt cagggcagtc    7320
atggtggcgg cccttctgca aaaagaacaa gcaagctctt gtctatgaga agaggctgcg    7380
ggagaagaaa gtcagattag cgtggccagt cccctccccc cacccgcctc cattcccgcc    7440
gcatgcccca tcacgtcctc taccatcctc tgcaatgcgg agcctgggct cggcttccgg    7500
acctcgcacc agcgcccta aaccgtaca gcgtccttcc ccccattcct aatttccatt      7560
cctctccggc ctcctgcggc ccagtccttt tttttctttt cttttttcacc tggcactgca   7620
caagaagatg cggctgtctc tagaacaggg aggagcagag agcaccaggg agggctgcag    7680
tccgtattta taggaactgg atggtggggg gagctgatga cgcgcgcccc gcctcccgct    7740
cggctcatcc agtcccagct caagggcgca gaggcctgag ctacgtgcac ccgtaaagcc    7800
gcgagtagct gggcctctct cattcccccc ctccctcttt ttggacccgc ctcgttttg     7860
aaatgtgcac gcaccaagcg tgtgggctcc gacctgagga gggagggga gctgagattg     7920
tcccgccgag gaagtgaccg gatgagggtt cccaggatga gactcaggga atacagacta    7980
tggattaagg acgaggagtc cttggagtgt gcaccaagga catccaggac ccagaaacca    8040
gaaagctgct tcccgaataa aatgggagaa tctgagagct gcaggaacca gggaaatgga    8100
gcagaagtgt gggtctgccc aaggctgccc catcgaactt ctcccctatta gtgaaaaggc   8160
ttaggagaag ttgaggatct tctcgttgtt cttcggaaga ctactctgga gacgtctacc    8220
gggtagggga ggcgcttttc ccaaggcagt ctggagcatg cgctttagca gccccgctgg    8280
gcacttggcg ctacacaagt ggcctctggc ctcgcacaca ttccacatcc accggtaggc    8340
gccaaccggc tccgttcttt ggtggcccct tcgcgccacc ttctactcct ccccttagtca   8400
ggaagttccc ccccgccccg cagctcgcgt cgtgcaggac gtgacaaatg gaagtagcac    8460
gactcactag tctcgtgcag atggacagca ccgctgagca atggaagcgg gtaggccttt    8520
ggggcagcgg ccaatagcag ctttgctcct tcgctttctg agagcagcgg ccgggaaggg    8580
gcggtgcggg aggcggggtg tggggcggta gtgtgggcgc tgttcctgcc cgcgcggtgt    8640
tccgcattct gcaagcctcc ggagcgcacg tccgtctcag gggcagcttg cttgttcttt    8700
ttgcagaagc tcagaataaa cgctcaactt tggccgccac c                        8741
```

```
SEQ ID NO: 246          moltype = DNA  length = 8975
FEATURE                 Location/Qualifiers
misc_feature            1..8975
                        note = Synthetic
source                  1..8975
                        mol_type = other DNA
                        organism = synthetic construct
SEQUENCE: 246
atgctgaggc tgctgctggc tctgaacttg tttccatcaa ttcaagtcac cggcaacaag    60
atccttgtga agcagagccc catgctcgtg gcgtacgata atgccgtgaa cctgagctgc    120
aaatattcgt acaacctgtt ctcgcgcgag ttccgggcct cgctgcacaa gggcctggac    180
tccgccgtgg aagtctgcgt ggtgtacggg aactacagcc agcagctcca agtgtacagc    240
aagaccggat tcaactgtga cggaaagctc gggaacgaat ccgtgacttt ctacctccaa    300
aacctttacg tgaatcagac cgacatctac ttctgcaaga tgtaagtcat gtaccctcct    360
ccctacctgg agaacgagaa gtccaacggt accatcatcc acgtgaaggg caaaacctg    420
tgcccgtccc ctctgttccc gggaccgtcc aagcccttct gggtgctcgt ggtcgtcggt    480
ggcgtgctgg cctgttactc cttgctcgtg actgtgcat tcattatctt ttgggtccgg     540
tccaagagat ctcggctgct gcactccgat tacatgaaca tgcccccgag gcgcccggga    600
ccgaccagaa agcattatca gccatacgcg ccccctcgcg acttcgccgc ctaccggtca    660
tgataaaagc ttaattaatg gctaataaag gaaatttatt tcattgcaa tagtgtgttg     720
gaattttttg tgtctctcac tcggaagaac atatgggagg gcaaatcatt taaaacatca    780
gaatgagtat ttggtttaga gtttggcaac atatgcccat atgctggctg ccatgaacaa    840
aggttggcta taagaggtc atcagtatat gaaacagccc cctgctgtcc attccttatt     900
ccatagaaaa gccttgactt gaggttagat ttttttttata ttttgttttg tgttatttt    960
ttctttaaca tccctaaaat tttccttaca tgttttacta gccagatttt tcctcctctc    1020
ctgactactc ccagtcatag ctgtccctct tctcttatgg agatcagaaa attttgtgtc    1080
gcccttcgct gaacaccagg tgggccgcct actgcgcacg cgcgggtttg cgggcagccg    1140
cctgggctgt gggagcagcc cggcagagc tctcctgcct ctccaccagc ccacccgcc     1200
gcctgaccgc cccctcccca ccccccaccc ccacccccg gaaaacgcgt cgtccctgg     1260
gctgggtggt gacccccgtc ccgcgaaaca cgggcccg cgcagcgtcc gggcctgaca    1320
ccgctccggc ggctcgcctc ctatgcgccc ccgcgccacc gtcgccccgc cgcccggggcc   1380
cctgcagccg cccaggtgcc agcacgagc gcctggcggc ggaacgcaga ccccaggccc    1440
ggcgcacacc ggggacgctg agcgttccag gcgggaggga aggcgggcag agtggagag    1500
aggaacggga gtcctagagg ggcggaagga cgggcggagg gacgttagga gggagggagg    1560
gaggcaggga ggcagggagg aacgaggga aagacagagc gacgcaggga ctgggggcgg    1620
gcgggaggga gccggggaac ggggggagga aggcagggag gaaaagcggt cctcggcctc    1680
cgggagtagc gggaccccg ccctccggga aaacggtcag cgtccggcgc gggctgaggg     1740
ctgggcccac agccgccgcg ccggccgcgc gggcaccacc cattcgcccc ggttccgtgg    1800
cccagggagt gggcggtttc ctccgggaca aaagaccggg actcggggttg ccgtcgggtg   1860
ttcacccgcg cggttcacag accgcacatc cccaggctga gccctgcaac gcggcgcgag    1920
gccgacagcc ccggccacgg aggagccaca cgcaggacga cggaggcgtg attttggttt    1980
ccgcgtggct ttgccctccg caaggcgcc tgttgctcaa gtctctcgg cccccgaaag      2040
gctggccatg ccgactgttt gctcccggag ctctgcgggc accggaaaac atgcaggaa    2100
gggtgcaagc ccggcacggt gccttcgctc tccttgccag gttccaaacc ggccacactg    2160
cagactcccc acgttgccgc acgcgggaat ccatcgtcag cgcccacgc cgggaggca    2220
tctcctctct ggggtgtcgc tctgacttc tacgtggaaa tgaacgagag ccacacgcct     2280
gcgtgtgcca gaccgtcccg gcaacggcga cgcccacagg cattgcctcc ttcacggaga    2340
gagggcctgg cacactcaag actcccacg aggttcagtt ccacactcca cctaggtcat    2400
atttttagtt taaaaaaata attatatgtt ttataatgaa aagaatctca ttatctttca    2460
gtattaggtt gatttatatt ccaaagaata atattttgt taaattgttg attttttgtaa   2520
```

```
acctctaaat gtttgttgct aaaattactg tgtttaagaa aaagattaat aaataataat  2580
aatttcataa ttaaaaactt ctttcattga atgccattaa ataaaccatt attttacaaa  2640
ataagatcaa cataattgag taaataataa taagaacaat attatagtac aacaaaatat  2700
gggtatgtca taccctgcca cattcttgat gtaactttt ttcacctcat gctcgccggg  2760
ttaaggtgcta caatgaactc gaaacgaccg gtttgcattt ttagacattt agaagcctat  2820
atcttgttac agaattggaa ttacacaaaa attctaccat atttttgaaag cttaggttgt  2880
tctgaaaaaa acaatatatt gttttcctgg gtaaactaaa agtcccctcg aggaaaggcc  2940
cctaaagtga aacagtgcaa aacgttcaaa aactgtctgg caatacaagt tccactttga  3000
ccaaaacggc tggcagtaaa agggttaagc ggccgctcag ccttgagcgg tatcagctca  3060
ctcaaaggcg gtaatacggt tatccacaga atcaggggat aacgcaggaa agaacatgtg  3120
agcaaaaggc cagcaaaagg ccaggaaccg taaaaaggcc gcgttgctgg cgttttccca  3180
taggctccgc cccctgacg agcatcacaa aaatcgacgc tcaagtcaga ggtggcgaaa  3240
cccgacagga ctataaagat accaggcgtt tccccctgga agctccctcg tgcgctctcc  3300
tgttccgacc ctgccgctta ccggatacct gtccgccttt ctcccttcgg gaagcgtggc  3360
gctttctcat agctcacgct gtaggtatct cagttcggtg taggtcgttc gctccaagct  3420
gggctgtgtg cacgaacccc ccgttcagcc cgaccgctgc gccttatccg gtaactatcg  3480
tcttgagtcc aacccggtaa gacacgactt atcgccactg gcagcagcca ctggtaacag  3540
gattagcaga gcgaggtatg taggcggtgc tacagagttc ttgaagtggt gggctaacta  3600
cggctacact agaagaacag tatttggtat ctgcgctctg ctgaagccag ttaccttcgg  3660
aaaaagagtt ggtagctctt gatccggcaa acaaaccacc gctggtagcg gtggtttttt  3720
tgtttgcaag cagcagatta cgcgcagaaa aaaggatct caagaagatc ctttgatctt  3780
ttctacgggg tctgacgctc agtggaacga cgcgcgtat actcacgtta agggattttg  3840
gtcatgagtt agaaaaactc atcgagcatc aaatgaaact gcaatttatt catatcagga  3900
ttatcaatac catattttg aaaaagccgt ttctgtaatg aaggagaaaa ctcaccgagg  3960
cagttccata ggatggcaag atcctggtat cggtctgcga ttccgactcg tccaacatca  4020
atacaaccta ttaatttccc ctcgtcaaaa ataaggttat caagtgagaa atcaccatga  4080
gtgacgactg aatccggtga gaatggcaaa agtttatgca tttctttcca gacttgttca  4140
acaggccagc cattacgctc gtcatcaaaa tcactcgcat caaccaaacc gttattcatt  4200
cgtgattgcg cctgagcgag gcgaaatacg cgatcgctgt taaaaggaca attacaaaca  4260
ggaatcgagt gcaaccggcg caggaacact gccagcgcat caacaatatt ttcacctgaa  4320
tcaggatatt cttctaatac ctggaacgct gtttttccgg ggatcgcagt ggtgagtaac  4380
catgcatcat caggagtacg gataaaatgc ttgatggtcg gaagtggcat aaattccgtc  4440
agccagttta gtctgaccat ctcatctgta acatcattgg caacgctacc tttgccatgt  4500
ttcagaaaca actctggcgc atcgggcttc ccatacaagc gatagattgt cgcacctgat  4560
tgcccgacat tatcgcgagc ccatttatac ccatataaat cagcatccat gttggaattt  4620
aatcgcggcc tcgacgtttc ccgttggata tggctcattt tttacttcct caccttgtcg  4680
tattatacta tgccgatata ctatgccgat gattaattgt cgacactgcg ggggctctgg  4740
cgcgccttaa ccttttact gccaatgacg catgggatac gtcgtggcag taaaagggct  4800
taaatgccaa cgacgcgtcc catacgttgt tggcatttta attcttctct ctgcagcgga  4860
agcatgtgcc gccgctgcag agagtttcta gcgatgacga cccctctggg caacgagccg  4920
gggggggctgt cccatgacgc ggctagacat gcacgaccat taacccggcg agcatgaggc  4980
agggtatctc ataccctggt aaaattttaa agttgtgtat tttataaaat tttcgtctga  5040
caacactagc gcgctcagta gctggaggca ggagcgtgca gaggggata gtggcgtgat  5100
cgcagtgtgg cacgggacac cggcgagata ttcgtgtgca aacctgtttc gggtatgtta  5160
taccctgcct cattgttgac gtatttttt tatgtaattt ttccgattat aatttcaac  5220
tgtttattg gtatttttat gttatccatt gttcttttt tatgatttac tgtatcggtt  5280
gtctttcgtt cctttagttg agttttttt tattatttc agttttttgat caaagctagc  5340
gcgagctcac ggggacagcc cccccccaaa gccccagggg atgtaattac gtccctcccc  5400
cgctaggggg cagcagcgag ccgccgggg ctccgctccg gtccggcgct ccccccgcat  5460
ccccgagccg cagcgtgcg gggacagccc gggcacgggg aagtggcac gggatcgctt  5520
tcctctgaac gcttctcgct gctctttgag cctgcagaca cctgggggga tacggggaaa  5580
aagcttagg ctgaaagaga gatttagaat gacagaatca tagaacggcc tgggttgcaa  5640
aggagcacag tgctcatcca gatccaaccc cctgctatgt gcagggtcat caaccagcag  5700
cccaggctgc ccagagccac atccagcctg gccttgaatg cctgcaggga tggggcatcc  5760
acagcctcct tgggcaacct gttcagtgcg tcaccaccct ctggggggaaa aactgcctcc  5820
tcatatccaa cccaaacctc ccctgtctca gtgtaaagcc attcccctt gtcctatcca  5880
ggggagttt gctgtgacat tgttggtctg gggtgacaca tgtttgccaa ttcagtgcat  5940
cacggagagg cagatcttgg ggataaggaa gtgcaggaca gcatggacgt gggacatgct  6000
ggtgttgagg gctctgggac actctccaag tcacagcgtt cagaacagcc ttaaggataa  6060
gaagatagga tagaaggaca aagagcaagt taaaacccag catggagagg agcacaaaaa  6120
ggccacagac actgctggtc cctgtgtctg agcctgcatg tttgatggtg tctggatgca  6180
agcagaaggg gtgaagtgc ttgcctggag agatacagct gggtcagtag gactgggaca  6240
ggcagctgga gaattgccat gtagatgttc atacaatcgt caaatcatga aggctggaaa  6300
agccctccaa gatcccccaag accaaccca acccacccac cgtgcccact ggccatgtcc  6360
ctcagtgcca catccccaca gttcttcatc acctccaggg acggtgaccc cccacctcc  6420
gtgggcagct gtgccactgc agcaccgctc tttggagaag gtaaatcttg ctaaatccag  6480
cccgaccctc cctggcaca acgtaaggcc attatctctc atccaactcc aggacggagt  6540
cagtgagaat attggtaccg gggtgtggtg tcttcttaac ctcacccagg aggaaccggg  6600
tcaattcttc agcacctggg taccataga gcccaccgga tcccagcag gcctgctatt  6660
gtattcccaa tcctcccct tgctgtcctg ccccaccccca cccccagaa tagaatgaca  6720
cctactcaga caatgcgatg caatttcctc atttattag gaaaggacag tgggagtggc  6780
accttccagg gtcaaggaag gcacggggga gggcaaaca acagatggct ggcaagagag  6840
caggtttact gataggtatc gagatcgacg gccttgacca cttccaccag gcacatgtga  6900
tctctcctct catcgcggtc tttggagagc ttagtgtgat aagtgatatg atgtagcgc  6960
ggaatgtgga cagccgctga accggccagt ggccgattca tctggctaca cttggtcacc  7020
agcttctccg tcacccctc gatgtcgtag cttcattga actccacgcg gattcgttg  7080
ttcacagtgt cgggagaat gtaaaggatg ctggagggc actggaaggc gacattcttc  7140
cgaagaatat gcccgtcctt cttaaagttt tctccagtca gagtcacccg gttgtagata  7200
gatcccctct cataggtgac catcgcgcgg gtcttgtaca ctccatctcc ctcaaaagaa  7260
```

```
atggtgcgct cttgggtata accttccggc atggcggatt tgaagaagtc cttaatgtgg    7320
ctagggtact tagcaaaaca ctgcactcca tacgagaggg ttgacacaag ggtggcccaa    7380
ggcactggca gatctccagt ggtacagata tacttggcct taatggttcc agtcgtagcg    7440
tccccggttc cttctccctt gatgatgaac ttcattcctt cgacgtcccc ttccagctcg    7500
gtgatgtacg gaatctcctt ctcaaacagc ttagcaccct cggtcagggc agtcatggtg    7560
gcggcccttc tgcaaaaaga acaagcaagc tcttgtctat gagaagaggc tgcgggagaa    7620
gaaagtcaga ttagcgtggc cagtccccte ccccaccog cctccattcc cgccgcatgc    7680
cccatcacgt cctctaccat cctctgcaat gcggagcctg ggctcggctt ccggacctcg    7740
caccagcgcc cctaaacccg tacagcgtcc ttcccccat tcctaatttc cattcctctc    7800
cggcctcctg cggcccagtc cttttttttc ttttcttttt cacctggcac tgcacaagaa    7860
gatgcggctg tctctagaac agggaggagc agagagcacc agggagggct gcagtccgta    7920
tttataggaa ctgatggtg gggggagctg atgacgcgcg ccccgcctcc cgctcggctc    7980
atccagtccc agctcaaggg cgcagaggcc tgagctacgt gcaccgtaa agccgcgagt    8040
agctgggcct ctctcattcc cccctccct cttttggac ccgcctcgt tttgaaatgt    8100
gcacgcacca agcgtgtggg ctccgacctg agagggggag gggagctgag attgtccgc    8160
cgaggaagtg accggatgag ggttccccagg ataggactca gggaataccag actatggatt    8220
aaggacgagg agtccttgga gtgtgcacca aggacatcca ggacccagaa accagaagc    8280
tgcttcccga ataaaatggg agaatctgag agctgcagga accagggaaa tggagcagaa    8340
gtgtgggtct gcccaaggct gccccatcga acttctccct attagtgaaa aggcttagga    8400
gaagttgagg atcttctcgt tgttcttcgg aagactactc tggagacgtc taccgggtag    8460
gggaggcgct tttcccaagg cagtctggag catgcgcttt agcagcccccg ctgggcactt    8520
ggcgctacac aagtggccte tggcctcgca cacattccac atccaccggt aggcgccaac    8580
cggctccgtt ctttggtggc cccttcgcgc caccttctac tcctcccta gtcaggaagt    8640
tccccccgc cccgcagctc gcgtcgtgca ggacgtgaca aatggaagta gcacgactca    8700
ctagtctcgt gcagatggac agcaccgctg agcaatggaa gcgggtaggc ctttgggca    8760
gcggccaata gcagctttgc tccttcgctt tctgagagca gggccggaa aggggcggtg    8820
cgggaggcgg ggtgtggggc ggtagtgtgg gccctgttcc tgcccgcgcg gtgttccgca    8880
ttctgcaagc ctccggagcg cacgtccgtc tcaggggcag cttgcttgtt cttttttgcag    8940
aagctcagaa taaacgctca actttggccg ccacc                               8975

SEQ ID NO: 247           moltype = DNA   length = 1845
FEATURE                  Location/Qualifiers
misc_feature             1..1845
                         note = Synthetic
source                   1..1845
                         mol_type = other DNA
                         organism = synthetic construct
SEQUENCE: 247
cgaagaacaa cgagaagatc ctcaacttct cctaagcctt ttcactaata gggagaagtt     60
cgatggggca gccttgggca gacccacact tctgctccat ttccctggtt cctgcagctc    120
tcagattctc ccatttatt cgggaagcag cttttctggtt tctgggtcct ggatgtcctt    180
ggtgcacact ccaaggactc ctcgtcctta atccatagtc tgtattccct gagtcctatc    240
ctgggaaccc tcatccgtc acttcctcgg cgggacaatc tcagctcccc tcccccctcc    300
aggtcggagc ccacacgctt ggtgcgtgca catttcaaaa acgaggcggg tccaaaaaga    360
gggaggggg gaatgagaga ggcccagcta ctcgcggctt tacgggtgca cgtagctcag    420
gcctctcgcg ccttgagctg ggactggatg agccgagcgg gaggcgggc gcgcgtcatc    480
agctcccccc accatccagt tcctataaat acggactgca cccctccctg gtgctctctg    540
ctcctccctg ttctagagac agccgcatct tcttgtgcag tgccaggtga aaaagaaaag    600
aaaaaaaagg actgggccgc aggaggccgg agaggaatgg aaattaggaa tgggggaag    660
gacgctgtac gggtttaggg gcgctggtgc gaggtccgga agccgagccc aggctccgca    720
ttgcagagga tggtagagga cgtgatgggg catgcggcgg gaatggaggc gggtgggggg    780
aggggactgg ccacgctaat ctgactttct tctcccgcag cctcttctca tagacaagag    840
cttgcttgtt cttttttgcag aagggccgcc accatgactg ccctgaccga aggtgctaag    900
ctgtttgaga aggagattcc gtacatcacc gagctggaag gggacgtcga aggaatgaag    960
ttcatcatca agggagaagg aaccggggac gctacgacg gaacacattaa ggccaagtat   1020
atctgtacca ctggagatct gccagtgcct tgggccaccc ttgtgtcaac cctctctat   1080
ggagtgcagt gttttgctaa gtaccctagc cacattaagg acttcttcaa atccgccatg    1140
ccggaaggtt ataccccaaga gcgcaccatt tcttttgagg gagatggagt gtacaagacc    1200
cgcgcgatgg tcacctatga gaggggatct atctacaacc gggtgactct gactggaga    1260
aacttttaaga aggacgggca tattcttcgg aagaatgtcg ccttccagtg ccctcccagc    1320
atcctttaca ttctccccga cactgtgaac aacggaatcc gcgtgagtt caatcaagcc    1380
tacgacatcg aggggtgac ggagaagctg gtgaccaagt gtagccagat gaatcggcca    1440
ctggccggtt cagcggctgt ccacattccg cgctaccatc atatcactta tcacactaag    1500
ctctccaaag accgcgatga gaggagagat cacatgtgcc tggtggaagt ggtcaaggcc    1560
gtcgatctcg atacctatca gtaaacctgc tctcttgcca gccatctgtt gtttgcccct    1620
ccccccgtgcc ttccttgacc ctggaagtg ccactccac tgtcctttcc taataaaatg    1680
aggaaattgc atcgcattgt ctgagtaggt gtcattctat tctgggggt ggggtgggc    1740
aggacagcaa ggggaggat tgggaataca atagcaggca tgctggggat gcggtgggct    1800
ctatgggtac ccaggtgctg aagaattgac ccggttcctc ctggg                   1845

SEQ ID NO: 248           moltype = DNA   length = 14
FEATURE                  Location/Qualifiers
misc_feature             1..14
                         note = Synthetic
source                   1..14
                         mol_type = other DNA
                         organism = synthetic construct
SEQUENCE: 248
cctttttact gcca                                                       14
```

```
SEQ ID NO: 249            moltype = DNA  length = 82
FEATURE                   Location/Qualifiers
misc_feature              1..82
                          note = Synthetic
source                    1..82
                          mol_type = other DNA
                          organism = synthetic construct
SEQUENCE: 249
atgacgcatg ggatacgtcg tggcagtaaa agggcttaaa tgccaacgac gcgtcccata   60
cgttgttggc attttaattc tt                                            82

SEQ ID NO: 250            moltype = DNA  length = 14
FEATURE                   Location/Qualifiers
misc_feature              1..14
                          note = Synthetic
source                    1..14
                          mol_type = other DNA
                          organism = synthetic construct
SEQUENCE: 250
tggcagtaaa aggg                                                     14

SEQ ID NO: 251            moltype = DNA  length = 2052
FEATURE                   Location/Qualifiers
misc_feature              1..2052
                          note = Synthetic
source                    1..2052
                          mol_type = other DNA
                          organism = synthetic construct
SEQUENCE: 251
gagcttgctt gttcttttg cagaagctca gaataaacgc tcaactttgg ccgccaccat    60
ggcacccaaa aagaaacgta aagtgatggc aaaaagattc tattccgccg aagaagccgc  120
tgcccattgc atggcgtcgt ccagcgaaca gacctccggc tcggactccg aatacgtgcc  180
gccggcttcc gagtccgaca gctccaccga ggaatcctgg tgttcatcga gcactgtgcc  240
agccctcgag gagcccatgg aagtggatga ggacgtggac gatcttgagg atcaggaagc  300
cggagacaga gcggatgcgg cagccggagg ggagcctgca tggggtcctc cctgcaattt  360
ccctcctgaa atcccccct tcaccaccgt ccctggagtg aaggtcgaca cttcgaactt   420
cgagccgatt aatttcttcc aactgttcat gaccgaggcg atactgcaag atatggtcct  480
gtacaccaac gtgtacgcgg agcagtactt gacacaaaac ccgctgaccc gctacgctcg  540
ggcccacgca tggcacccta ccgacattgc cgagatgaag cggttcgtcg gcctgactct  600
ggccatgggg ctgattaagg ccaactccat tgagtcctac tgggacacta ccactgtgct  660
gagcatccca gtgttcggcg ccactatgag ccggaaccgg tatcagctgt tgcttcggtt  720
cctgcacttc aacaacaacg ccacgcccgt gccccggcac gaccaggac acgatagact    780
gcataagctg cgcccgctca tcgactccct gtcggagagg ttcgcgaacg tgtacactcc  840
gtgtcaaaac atttgcatcg atgaaagcct gctgctgttc aagggacgcc tccagttccg  900
gcagtacatc ccctcgaaaa gagcccgcta tgggatcaag ttctcaagc tgtgcgagtc   960
gagcagcggc tacacctcat actttctgat ctacgaggga aaagactcca agctcgaccc 1020
acctggatgc ccgccggatc tcaccgtgtc cgggaagatt gtgtgggagc tcatcagccc 1080
cttgctggga cagggcttcc acctctacgt ggataacttc tactcctcaa tccctctgtt 1140
caccgccctg tactgcctca cactccggc atgcggtacc atcaaccgga accgcaaagg 1200
actgccccgg gccctgcttg acaagaagct gaaccgcggc gaaacctacg ccctcggaa   1260
gaacgaactc ctggccatca agttcttcga caagaagaac gtgttttatgc tgacctcgat 1320
ccacgatgaa tctgtgattc gggagcagcg cgtcggcagg aagcctaaga caagcctct   1380
gtgctctaag gagtactcaa agtacatggg gggagtggac cgcaccgacc agctgcagca 1440
ttactacaat gccacccgaa agaccagaca ctggtacaag aaagtcggca tctacctgat 1500
ccaaatggcg cttcggaact cctacattgt gtacaaggcc gcagtgccgg gacccaagct 1560
ttcctactac aagtaccagc tccaaattct cccgcccctg ctgttcggag gggtggaaga 1620
acagacggtg ccagagatgc cgccgtccga acgtggct cgcctgattg aaagcactt   1680
catcgatacc ctgccccaa ccctgggaa gcagaggccg cagaagggtt gcaaggtctg  1740
cagaaagcgc ggcatccgga gggacactcg gtactattgc cctaagtgcc ctcggaaccc 1800
cggtttgtgt aggaagccgt gttttgagat ctaccatacg cagctgcact actgaggttg 1860
agatctttt ccctctgcca aaaattatgg ggacatcatg aagcccttg agcatctgac  1920
ttctggctaa taaggaaat ttattttcat tgcaaaaaaa aaaaaaaaaa aaaaaaaaaa  1980
aaaaaaaaaa aaaaaaaaa aaaaaaaa aaaaaaaaaa aaaaaaaaaa aaaaaaaaaa   2040
aaaaaaaaaa aa                                                     2052

SEQ ID NO: 252            moltype = AA  length = 486
FEATURE                   Location/Qualifiers
REGION                    1..486
                          note = Synthetic
source                    1..486
                          mol_type = protein
                          organism = synthetic construct
SEQUENCE: 252
MALPVTALLL PLALLLHAAR PDIQMTQTTS SLSASLGDRV TISCRASQDI SKYLNWYQQK   60
PDGTVKLLIY HTSRLHSGVP SRFSGSGSGT DYSLTISNLE QEDIATYFCQ QGNTLPYTFG  120
GGTKLEITGG GGSGGGGSGG GGSEVKLQES GPGLVAPSQS LSVTCTVSGV SLPDYGVSWI  180
RQPPRKGLEW LGVIWGSETT YYNSALKSRL TIIKDNSKSQ VFLKMNSLQT DDTAIYYCAK  240
HYYYGGSYAM DYWGQGTSVT VSSTTTPAPR PPTPAPTIAS QPLSLRPEAC RPAAGGAVHT  300
```

```
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                            486

SEQ ID NO: 253          moltype = DNA   length = 375
FEATURE                 Location/Qualifiers
misc_feature            1..375
                        note = Synthetic
source                  1..375
                        mol_type = other DNA
                        organism = synthetic construct
SEQUENCE: 253
gtttacctga ctcatggtcc tttcactttc acatgggatt cccagttat gaaattaata    60
aaaatcagtg atttccacat ctgtgtgtgc ctgtgccagg ctgggtgggg aacaggaggc  120
cgagatgatt ccgggaactg tcagaaggaa tcaatgattt ccacatcctg tctgtcttat  180
gtcttggggg gtggggaggc caggaagatt ccaggaaggt cagagtcaat caatggtttc  240
cacatctctc agtgcctcta tctgaggcc aggtagggct ggcctgggg gaggggagg    300
ccagaatgac tccaagagct acaggaaggg gggaggggga aaaggccag aataattcca   360
ggaaccgcca agaag                                                   375

SEQ ID NO: 254          moltype = DNA   length = 9773
FEATURE                 Location/Qualifiers
misc_feature            1..9773
                        note = Synthetic
source                  1..9773
                        mol_type = other DNA
                        organism = synthetic construct
SEQUENCE: 254
atggcactcc ctgtcaccgc cctcctcctc ccactcgccc tcttgctgca cgccgctcgc   60
ccggatattc agatgacgca gaccacctca agtctgtcgg cctcccttgg tgatcgggtc  120
accatttcct gccgagccag ccaggacatc tccaagtacc tgaactggta ccagcagaag  180
cccgacggga ccgtgaagct gctgatctac catacctccc ggctgcatag cggggtgccg  240
tcaaggttta gcggatcggg atccggcacc gactactgc tgactatctc caacttggaa    300
caagaggaca tcgccaccta cttctgtcaa caagggaata ctctgcccta cactttcggg  360
gggggaacca agctcgagat cactggcggg ggcggctcgg gcggtggtgg atccgggggc  420
ggtggctccg aggtcaagct tcaggaatcc ggacccggcc tggtggcacc gtcacaatcc  480
ctatccgtga catgcaccgt cagcgagtg tcgctgcccg attacggagt gtcttggatt   540
aggcagccc cgcgcaaagg tcttgagtgg ctgggagtga tctgggatc agagactacc    600
tactacaaca gcgccctcaa gtcgaggctc accatcatca aggacaactc caagtcccaa   660
gtgtttctga agatgaactc cctgcaaact gacgacaccg ccatctacta ctgcgcgaag   720
cactactact acggggaag ctacgctatg gactattgg gacaggaac ttccgtgact     780
gtgtccagca ccacgcacc agccccgcgc ccgccgacc cgccccgac cattgcgagc    840
cagccgctga gccttcggcc ggaagcctgc aggcccgcgg ccggcggagc cgtgcacacc  900
agaggactgg acttcgcctg cgatatctat atctgggcgc tctgccgg aacctgtgga    960
gtcctgctgc tgtcactcgt gattactctg tactgcaagc gcgtcggaa gaagctgctc  1020
tacattttca gcaaccttt catgcggcca gtgcagacca ctcaggaaga agatgctgt   1080
tcctgccggt tccctgaaga agaaggggc ggctgcgaat tgagagtgaa gttctcccgc  1140
tcggctgacg ctcccgccta caaacaggg cagaaccagc tgtataacga actgaacctc  1200
gggcgccgcg aggaatacga cgtgctggac aagcggagag gccgcgatcc tgagatgggg  1260
ggaaagcccc ggagaaagaa ccctcaggag gcctgtaca atgagctgca gaaagacaaa  1320
atggccgagg cgtacagcga gatcggcatg aagggcgaac gccggagagg aaagggacac  1380
gacggactgt accagggact gtccaccgcg accaaggata cctacgacgc cctgcacatg  1440
caggcactgc cacctcggtg ataaaagctt aattaatggc taataaagga aattattt    1500
cattgcaata gtgtgttgga attttttgtg tctctcactc ggaagaact atgggaggc   1560
aaatcattta aaacatcaga atgagtattt ggtttagagt ttggcaacat atgcccat    1620
gctggctgcc atgaacaaag gttggctata aagaggtcat cagtatatga aacagccccc  1680
tgctgtccat tccttattcc atagaaaagc cttgacttga ggttagatt tttttatt    1740
ttgttttgtg ttattttttt cttaacatc cctaaaattt tccttacatg tttactagc   1800
cagatttttc ctcctctcct gactactccc agtcatagct gtccctcttc tcttatggag  1860
atcagaaat tttgtgtcgc ccttgctga acaccaggtg gccgcctac tgcgcacgcg    1920
cgggtttgcg ggcagccgcc tgggctgtgg gagcagcccg gcagagctc tcctgcctct  1980
ccaccagccc accccgccgc ctgaccgccc ctccccacc ccccaccccc cacccccgga   2040
aaacgctcg tccccctggc tgggtggtga ccccgcgcg cgaaaacacc gggccccgga   2100
cagcgtccgg gcctgacacc gctccggcgg ctcgcctcct atgcgccccc gcgccaccgt  2160
cgcccgcccg cccgggcccc tgcagccgcc caggtgccag cacggagcgc ctggcggcgg  2220
aacgcagacc caggcccgg cgcacaccgg ggacgctgag cgttccaggc gggagggaag  2280
gcgggcagag atggagagag gaacgggagt cctagagggg cggaaggacg gcggaggga   2340
cgttaggagg gagggaggga ggcagggagg caggagaaa gacagagcga                        2400
cgcagggact gggggcggc ggaaggagc cggggaacgg gggagggaag gcagggagga   2460
aaagcggtcc tcggcctccg ggagtagcgg gaccccgcc ctcgggaaa acggtcagcg   2520
tccggcgcgg gctgagggct gggcccacag ccgccgcgcc ggccggcggg caccaccca   2580
ttcgccccgg ttccgtggcc cagggagtgg gcggtttcct ccgggacaaa agaccgggac  2640
tcgggttgcc tcggggtgtt cacccgcgcg gttcacagac cgcacatccc caggctgcgg  2700
cctgcaacgc ggcgcgaggc cgacagcccc ggccacggag agccacacg caggacgacg   2760
gaggcgtgat tttggtttcc gcgtggcttt gcctccgca aggcggcctg ttgctcaagt   2820
ctctccggcc cccgaaaggc tggccatgcc gactgtttgc tcccgagct ctgcgggcac   2880
ccggaaacat gcagggaagg gtgcaagccc ggcacggtgc cttcgctctc cttgccaggt   2940
tccaaaccgg ccacactgca gactcccac gttgccgcac gcgggaatcc atcgtcaggc   3000
```

```
catcacgccg gggaggcatc tcctctctgg ggtgtcgctc tggacttcta cgtggaaatg   3060
aacgagagcc acacgcctgc gtgtgccaga ccgtcccggc aacggcgacg cccacaggca   3120
ttgcctcctt cacggagaga gggcctggca cactcaagac tcccacggag gttcagttcc   3180
acactccacc taggtcatat ttttagttta aaaaaataat tatatgtttt ataatgaaaa   3240
gaatctcatt atctttcagt attaggttga tttatattcc aaagaataat attttttgtta  3300
aattgttgat ttttgtaaac ctctaaatgt ttgttgctaa aattactgtg tttaagaaaa   3360
agattaataa ataataataa tttcataatt aaaaacttct ttcattgaat gccattaaat   3420
aaaccattat tttacaaaat aagatcaaca taattgagta ataataata agaacaatat   3480
tatagtacaa caaaatatgg gtatgtcata ccctgccaca ttcttgatgt aacttttttt   3540
caccctcatgc tcgccgggtt aagggctaca atgaactcga aacgaccggt ttgcattttt   3600
agacatttag aagcctatat cttgttacag aattggaatt acacaaaaat tctaccatat   3660
tttgaaagct taggttgttc tgaaaaaaac aatatattgt tttcctgggt aaactaaaag   3720
tccctcgag gaaaggcccc taaagtgaaa cagtgcaaaa cgttcaaaaa ctgtctggca    3780
atacaagttc cactttgacc aaaacgctg gcagtaaagg ggttaagcgg ccgctcagcc    3840
ttgagcggta tcagctcact caaaggcggt aatacggtta ccacagaat caggggataa    3900
cgcaggaaag aacatgtgag caaaaggcca gcaaaaggcc aggaaccgta aaaaggccgc   3960
gttgctggcg ttttttccata ggctccgccc ccctgacgag catcacaaaa atcgacgctc   4020
aagtcagagg tggcgaaacc cgacaggact ataaagatac caggcgtttc ccccctggaag   4080
ctccctcgtg cgctctcctg ttccgaccct gccgcttacc ggatacctgt ccgcctttct    4140
cccttcggga agcgtggcgc tttctcatag ctcacgctgt aggtatctca gttcggtgta    4200
ggtcgttcgc tccaagctgg gctgtgtgca cgaaccccc gttcagcccg accgctgcgc    4260
cttatccggt aactatcgtc ttgagtccaa cccggtaaga cacgacttat cgccactggc    4320
agcagccact ggtaacagga ttagcagagc gaggtatgta ggcggtgcta cagagttctt    4380
gaagtggtgg gctaactacg gctacactag aagaacagta tttggtatct gcgctctgct    4440
gaagccagtt accttcggaa aaagagttgg tagctcttga tccggcaaac aaaccaccgc    4500
tggtagcggt ggtttttttg tttgcaagca gcagattacg gcagaaaaaa aaggatctca    4560
agaagatcct ttgatctttt ctacggggtc tgacgctcag tggaacgacg cgcgcgtaac   4620
tcacgttaag ggattttggt catgagttag aaaaactcat cgagcatcaa atgaaactgc    4680
aatttattca tatcaggatt atcaataca tattttgaa aaagccgttt ctgtaatgaa     4740
ggagaaaact caccgaggca gttccatagg atggcaagat cctggtatcg gtctgcgatt    4800
ccgactcgtc caacatcaat acaacctatt aatttcccct cgtcaaaaat aaggttatca    4860
agtgagaaat caccatgagt gacgactgaa tccggtgaga atggcaaaag tttatgcatt    4920
tctttccaga cttgttcaac aggccagcca ttacgctcgt catcaaaatc actcgcatca    4980
accaaaccgt tattcattcg tgattgcgcc tgagcgaggc gaaatacgcg atcgctgtta    5040
aaaggacaat tacaaacagg aatcgagtgc aaccggcgca ggaacactgc cagcgcatca   5100
acaatatttt cacctgaatc aggatattct tctaataacct ggaacgctgt ttttccgggg   5160
atcgcagtgg tgagtaacca tgcatcatca ggagtacgga taaatgctt gatggtcgga   5220
agtggcataa attccgtcag ccagtttagt ctgaccatct catctgtaac atcattggca   5280
acgctacctt tgccatgttt cagaaacaac tctggcgcat cgggcttccc atacaagcga   5340
tagattgtcg cacctgattg cccgacatta tcgcgagccc atttatacc atataaatca    5400
gcatccatgt tggaatttaa tcgcggcctc gacgtttccc gttggatatg gctcattttt    5460
tacttcctca ccttgtcgta ttatactatg ccgatatact atgccgatga ttaattgtcg    5520
acactgcggg ggctctggcg cgccttaacc ttttactgcg caatgacgca tgggatacgt    5580
cgtggcagta aaagggctta aatgccaacg acgcgtccca tacgttgttg gcattttaat    5640
tcttctctct gcagcggcag catgtgccgc cgctgcagag agtttctagc gatgacagcc    5700
cctctgggca acgagccggg ggggctgtcc catgacgcgg ctagacatgc acgaccatta    5760
acccggcgag catgaggcag ggtatctcat accctgtaa aatttttaaag ttgtgtattt   5820
tataaaattt tcgtctgaca acactagcgc gctcagtagc tggaggcagg agcgtgcggg   5880
aggggatagt ggcgtgatcg cagtgtggca cgggacaccg gcgagatatt cgtgtgcaaa   5940
cctgtttcgg gtatgttata ccctgcctca ttgttgacgt atttttttta tgtaattttt    6000
ccgattatta attcaactg ttttattggt attttttatgt tatccattgt tctttttta    6060
tgatttactg tatcggttgt ctttcgttcc tttagttgag tttttttttta ttattttcag   6120
tttttgatca aagctagcgc gagctcacgg ggacagcccc cccccaaagc ccccagggat    6180
gtaattacgt ccctcccccg ctaggggca gcagcgagcc gcccgggct ccgctccggt    6240
ccggcgtctcc ccccgcatcc ccgagccggc agcgtgcggg gacagcccgg gcacggggaa   6300
ggtggcacgg gatcgctttc ctctgaacgc ttctcgctgc tctttgagcc tgcagacacc   6360
tgggggata cggggaaaaa gctttaggct gaaagagaga tttagaatga cagaatcata    6420
gaacggcctg ggttgcaaag gagcacagtg ctcatccaga tccaaccccc tgctatgtgc    6480
agggtcatca accagcagcc caggctgccc agagccacat ccagcctggc cttgaatgcc    6540
tgcagggatg gggcatccac agcctccttg gcaacctgt tcagtgcgtc accaccctcc    6600
gggggaaaaa ctgcctcctc atatccaacc caaacctccc ctgtctcagt gtaaagccat    6660
tccccctttgt cctatcaagg gggagtttgc tgtgacattg ttggtctggg gtgacacatg   6720
tttgccaatt cagtgcatca cggagaggca gatcttgggg ataaggaagt gcaggacagc   6780
atggacgtgg gacatgctgg tgttgagggc tctgggacac tctccaagtc acagcgttca   6840
gaacagcctt aaggataaga agataggata gaaggacaaa gagcaagtta aaacccagca    6900
tggagaggag cacaaaaagg ccacagacac tgctggtccc tgtgtctgag cctgcatgtt    6960
tgatggtgtc tggatgcaag cagaaggggt ggaagtgctt gcctgagag atacagctgg    7020
gtcagtagga ctgggacagg cagctggaga attgccatgt agatgttcat acaatcgtca    7080
aatcatgaag gctggaaaag ccctccaaga tccccaagac caacccaac ccacccaccg    7140
tgcccactgg ccatgtccct cagtgccaca tccccacagt tcttcatcac ctccagggac    7200
ggtgacccccc ccacctccgt gggcagctgt gccactgcag caccgctctt tggagaaggt   7260
aaatcttgct aaatccagcc cgaccctccc ctggcacaac gtaaggccat tatctctcat    7320
ccaactccag gacggagtca gtgagaatat tggtaccggg gtgtggtgtc ttcttaacct    7380
caccagagag gaacgggtc aatcttcag cacctggta cccatagagc ccaccccacc    7440
cccagcatgc ctgctattgt attcccaatc ctccccttg ctgtcctgcc caccccacc    7500
ccccagaata gaatgacacc tactcagaca atgcgatgca atttctcat ttttattagga    7560
aaggacagtg ggagtggcac cttccagggt caaggaaggc acgggggagg ggcaaacaac    7620
agatggctgc aagagagca ggtttactga taggtatcga gatcgacggc cttgaccact    7680
tccaccaggc acatgtgatc tctcctctca tcgcggtctt tggagagctt agtgtgataa    7740
```

```
gtgatatgat ggtagcgcgg aatgtggaca gccgctgaac cggccagtgg ccgattcatc  7800
tggctacact tggtcaccag cttctccgtc accccctcga tgtcgtaggc ttgattgaac  7860
tccacgcgga ttccgttgtt cacagtgtcg gggagaatgt aaaggatgct ggggaggcac  7920
tggaaggcga cattcttccg aagaaatatgc ccgtccttct taaagttttc tccagtcaga  7980
gtcaccggt tgtagataga tcccctctca taggtgacca tcgcgcgggt ctttgtacact  8040
ccatctccct caaaagaaat ggtgcgctct tgggtataac cttccggcat ggcggatttg  8100
aagaagtcct taatgtggct agggtactta gcaaaacact gcactccata cgagagggtt  8160
gacacaaggg tggcccaagg cactggcaga tctccagtgg tacagatata cttggcctta  8220
atggttccag tcgtagcgtc cccggttcct tctcccttga tgatgaactt cattccttcg  8280
acgtcccctt ccagctcggt gatgtacgga atctccttct caaacagctt agcaccttcg  8340
gtcagggcag tcatggtggc ggccttctg caaaaagaac aagcaagctc ttgtctatga  8400
gaagaggctg cgggagaaga aagtcagatt agcgtggcca gtccctccc cccacccgcc  8460
tccattcccg ccgcatgccc catcacgtcc tctaccatcc tctgcaatgc ggagcctggg  8520
ctcggcttcc ggacctcgca ccagcgcccc taaacccgta cagcgtcctt cccccattc  8580
ctaatttcca ttcctctccg gcctcctgcg gcccagtcct ttttttttctt ttctttttca  8640
cctggcactg cacaagaaga tgcggctgtc tctagaacag ggaggagcag agagcaccag  8700
ggagggctgc agtccgtatt tataggaact ggatggtggg gggagctgat gacgcgcgc  8760
ccgcctcccg ctcggctcat ccagtcccag cccaagggcg cagaggcctg agctacgtgc  8820
acccgtaaag ccgcgagtag ctgggcctct ctcattcccc cctccctct tttttggaccc  8880
gcctcgtttt tgaaatgtgc acgcaccaag cgtgtgggct ccgacctgag aggggaggg  8940
gagctgagat tgtcccgccg aggaagtgac cggatgaggg ttcccaggat aggactcagg  9000
gaatacagac tatggattaa ggacgaggga tccttggact gtgcaccaag gacatccagg  9060
acccagaaac cagaaagctg cttcccgaat aaaatgggag aatctgagag ctgcaggaac  9120
cagggaaatg gagcagaagt gtgggtctgc ccaaggctgc cccatcgaac ttctccctat  9180
tagtgaaaag gcttaggaga agttgaggat cttctcgttg ttcttcggaa gactactctg  9240
gagacgtcta ccgggtaggg gaggcgcttt tcccaaggca gtctggagca tgcgctttag  9300
cagccccgct gggcacttgg cgctacacaa gtgcctctg gcctcgcaca cattccacat  9360
ccaccggtag gcgccaaccg gctccgttct tggtggccc cttcgcgcca ccttctactc  9420
ctccctagt caggaagttc ccccccgccc cgcagctcgc gtcgtgcagg acgtgacaaa  9480
tggaagtagc acgactcact agtctcgtgc agatggacag caccgctgag caatggaagc  9540
gggtaggcct ttggggcagc ggccaatagc agctttgctc cttcgctttc tgagagcagc  9600
ggccgggaag gggcggtgcg ggaggcgggg tgtggggcgg tagtgtgggc cctgttcctg  9660
cccgcgcggt gttccgcatt ctgcaagcct ccggagcgca cgtccgtctc aggggcagct  9720
tgcttgttct ttttgcagaa gctcagaata aacgctcaac tttggccgcc acc            9773
```

| SEQ ID NO: 255 | moltype = DNA   length = 11286 |
| --- | --- |
| FEATURE | Location/Qualifiers |
| misc_feature | 1..11286 |
|  | note = Synthetic |
| source | 1..11286 |
|  | mol_type = other DNA |
|  | organism = synthetic construct |

SEQUENCE: 255
```
atggcactcc ctgtcaccgc cctcctcctc ccactcgccc tcttgctgca cgccgctcgc   60
ccggatattc agatgacgca gaccacctca agtctgtcgg cctcccttgg tgatcgggtc  120
accatttcct gccgagccag ccaggacatc tccaagtacc tgaactggta ccagcagaag  180
cccgacggga ccgtgaagct gctgatctac catacctccc ggggtgccg                240
tcaaggttta gcggatcggg atccggcacc gactactcgc tgactatctc aacttggaa   300
caagaggaca tcgccaccta cttctgtcaa caagggaata tctgcccta cactttcggc   360
ggggaacca agctcgagat cactggcgg ggcggctcgg gcgtggtgg atccggggc     420
ggtggctccg aggtcaagct tcaggaatcc ggacccggcc tggtggcacc gtcacaatcc   480
ctatccgtga catgcaccgt cagcggagtg tcgctgcccg attacggagt gtcttggatt   540
aggcagcccc cgcgcaaagg tcttgagtgg ctgggagtga tctggggatc agagactacc   600
tactacaaca gcgccctcaa gtcgaggctc accatcatca ggacaactc caagtcccaa   660
gtgtttctga agatgaactc cctgcaaact gacgacaccg ccatctacta ctgcgcgaag   720
cactactact acggggaag ctacgctatg gactattggg gacagggaac ttccgtgact   780
gtgtccagca ccacgacacc agcccgcgcc ccgccgaccc ccgccccgac cattgcgagc   840
cagccgctga gccttcggcc ggaagcctgc aggcccgcgg ccggcggagc cgtgcacacc   900
agaggactgg acttcgcctg cgatatctat atctgggcgc ctctggccgg aacctgtgga   960
gtcctgctgc tgtcactcgt gattactctg tactgcaagc gcggtcggaa gaagctgctc  1020
tacatttca gcaacctttt catgcggcca gtgcagacca ctcaggagaa gatggctgt   1080
tcctgccggt tccctgaaga agaagagggc ggctgcgaat tgagagtgaa gttctcccgc  1140
tcggctgacg ctcccgccta caacagggg cagaaccagc tgtataacga actgaacctc  1200
gggcgcgcg aggaatacga cgtgctggac aagcgggacg gccgatcc tgagatgggg  1260
ggaaagcccc ggagaaagaa ccctcaggag ggcctgtaca atgagctgca gaaagacaaa  1320
atggccgagc gtacagcga gatcggcatg aagggcgaac gccggagagg aaagggacac  1380
gacggactgt accagggact gtccaccgcg accaaggata cctacgacgc cctgcacatg  1440
caggcactgc cacctcggtg ataaaaatta atggctaata aggaaattt attttcattg  1500
caatagtgtg ttggaattt ttgtgtctct cactcggaaa aacatatgag agggcaaatc  1560
atttaaaaca tcagaatgag tatttggttt agagtttggc aacatatgcc catatgctgg  1620
ctgccatgaa caaggttgg ctataaagag gtcatcagta tatgaaacag ccccctgctg  1680
tccattcctt attccataga aaagccttga cttgaggtta gatttttttt atattttgtt  1740
ttgtgttatt ttttcttta acatccctaa aattttcctt acatgtttta ctagccagat  1800
ttttcctcct ctgactact ctcccagtca tagctgtccc tcttctctta tggagatcag  1860
aaaatttgt gtcgccctc gctgaacacc aggtgggccg cctactgcgc acgcgcgggt  1920
ttgcgggcag ccgcctgggc tgtgggagca gcccgggcag agctcctg cctctccacc  1980
agcccacccc gccgctgac cgcccctcc caccccca ccccaccc cggaaaacg    2040
cgtcgtcccc tgggctgggt ggtgacccc gtcccgcgaa acaccgggcc ccgcgcagcg  2100
tccgggcctg acaccgctcc ggcggctcgc ctcctatgcg ccccgcgcc accgtcgccc  2160
```

```
gcccgcccgg gccctgcag ccgcccaggt gccagcacgg agcgcctggc ggcggaacgc  2220
agacccagg cccggcgcac accggggacg ctgagcgttc caggcgggag ggaaggcggg  2280
cagagatgga gagaggaacg ggagtcctag aggggcggaa ggacgggcgg agggacgtta  2340
ggagggaggg agggaggcag ggaggcaggg aggaacggag ggaaagacag agcgacgcag  2400
ggactggggg cgggcgggag gaaggggggg aacgggggga gaaggcaggg gaggaaaagc  2460
ggtcctcggc ctccgggagt agcgggaccc ccgccctccg ggaaaacggt cagcgtccgg  2520
cgcgggctga gggctgggcc cacagccgcc gcgccggccg gcggggcacc acccattcgc  2580
cccggttccg tggcccaggg agtgggcggt ttcctccggg acaaaagacc gggactcggg  2640
ttgccgtcgg gtgttcaccc gcgcggttca cagaccgcac atccccaggc tgagccctgc  2700
aacgcggcgc gaggccgaca gccccggcca cggaggagcc acacgcagga cgacggaggc  2760
gtgattttgg tttccgcgtg gctttgccct ccgcaaggcg gcctgttgct caagtctctc  2820
cggcccccga aaggctggcc atgccgactg tttgctcccg gagctctgcg ggcacccgga  2880
aacatgcagg gaagggtgca agcccggcac ggtgccttcg ctctccttgc caggttccaa  2940
accggccaca ctgcagactc cccacgttgc cgcacgcggg aatccatcgt caggccatca  3000
cgccggggag gcatctcctc tctgggggtgt cgctctggac ttctacgtgg aaatgaacga  3060
gagccacacg cctgcgtgtg ccagaccgtc ccggcaacgg cgacgcccac aggcattgcc  3120
tccttcacgg agagagggcc tggcacactc aagactccca cggaggttca gttccacact  3180
ccacctaggt catatttta gttaaaaaaa ataattatat gttttataat gaaaagaatc  3240
tcattatctt tcagtattag gttgatttat attccaaaga ataatatttt tgttaaattg  3300
ttgattttg taaacctcta aatgtttgtt gctaaaatta ctgtgtttaa gaaaaagatt  3360
aataaataat aataatttca taattaaaaa cttctttcat tgaatgccat taaataaacc  3420
attattttac aaaataagat caacataatt gagtaaataa taataagaac aatattatag  3480
tacaacaaaa tatgggtatg tcataccctg ccacattctt gatgtaactt ttttcacct  3540
catgctcgcc gggttaaggg ctacaatgaa ctcgaaacga ccgtttgca ttttttagaca  3600
tttagaagcc tatatcttgt tacagaattg gaattcacaca aaaattctac catatttga  3660
aagcttaggt tgttctgaaa aaaacaatat attgtttttcc tgggtaaact aaaagtcccc  3720
tcgaggaaag gcccctaaag tgaaacagtg caaaacgttc aaaaactgtc tggcaataca  3780
agttccactt tgaccaaaac ggctggcagt aaaagggtta agcggccgct cagccttgag  3840
cggtatcagc tcactcaaag gcggtaatac ggttatccac agaatcaggg gataacgcag  3900
gaaagaacat gtgagcaaaa ggccagcaaa aggccagga ccgtaaaaag gccgcgttgc  3960
tggcgttttt ccataggctc cgcccccctg acgagcatca caaaaatcga cgctcaagtc  4020
agaggtggcg aaacccgaca ggactataaa gataccaggc gtttccccct ggaagctccc  4080
tcgtgcgctc tcctgttccg accctgccgc ttaccggata cctgtccgcc tttctccctt  4140
cgggaagcgt ggcgctttct catagctcac gctgtaggta tctcagttcg gtgtaggtcg  4200
ttcgctccaa gctgggctgt gtgcacgaac ccccgttca gcccgaccgc tgcgccttat  4260
ccgtaacta tcgtcttgag tccaacccgg taagacacga cttatcgcca ctggcagcag  4320
ccactggtaa caggattagc agagcgaggt atgtaggcgg tgctacagag ttcttgaagt  4380
ggtgggctaa ctacggctac actagaagaa cagtatttgg tatctgcgct ctgctgaagc  4440
cagttacctt cggaaaaaga gttggtagct cttgatccgg caaacaaacc accgctggta  4500
gcggtggttt ttttgtttgc aagcagcaga ttacgcgcag aaaaaaagga tctcaagaag  4560
atccttgat cttttctacg gggtctgacg ctcagtggaa cgacgcgcgc gtaactcacg  4620
ttaagggatt ttggtcatga gttagaaaaa ctcatcgagc atcaaatgaa actgcaattt  4680
attcatatca ggattatcaa taccatattt ttgaaaaagc cgtttctgta atgaaggaga  4740
aaactcaccg aggcagttcc ataggatggc aagatcctgg tatcggtctg cgattccgac  4800
tcgtccaaca tcaatacaac ctattaattt ccccctcgtca aaaataaggt tatcaagtga  4860
gaaatcacca tgagtgacga ctgaatccgg tgagaatggc aaaagtttat gcatttcttt  4920
ccagacttgt tcaacaggcc agccattacg ctcgtcatca aaatcactcg catcaaccaa  4980
accgttattc attcgtgatt gcgcctgagc gaggcgaaat acgcgatcgc tgttaaaaggg  5040
acaattacaa acaggaatcg agtgcaaccg gcgcaggaac actgccagcg catcaacaat  5100
attttcacct gaatcaggat attcttctaa tacctgaac gctgttttc cggggatcgc  5160
agtggtgagt aaccatgcat catcaggagt acggataaaa tgcttgatgg tcggaagtgg  5220
cataaattcc gtcagccagt ttagtctgac catctcatct gtaacatcat tggcaacgct  5280
acctttgcca tgtttcagaa acaactctgg cgcatcgggc ttcccataca agcgatagat  5340
tgtcgcacct gattgcccga cattatcgcg agcccattta tacccatata aatcagcatc  5400
catgttggaa tttaatgcg gcctcgacgt ttcccgttgg atatgctca ttttttactt  5460
cctcaccttg tcgtattata ctatgccgat atactatgcc gatgattaat tgtcgacact  5520
gcggggggctc tggcgcgcct taaccttttt actgccaatg acgcatggga tacgtcgtgg  5580
cagtaaaagg gcttaaatgc caacgacgcg tcccatacgt tgttggcatt ttaattcttc  5640
tctctgcagc ggcagcatgt gccgccgctg cagagagttt ctagccgatga cagcccctct  5700
gggcaacgag ccgggggggc tgtcccatga cgcggctaga catgcacgac cattaacccg  5760
gcgagcatga ggcagggtat ctcatacct ggtaaaattt taaagttgtg tatttatataa  5820
aattttcgtc tgacaacact agcgcgctca gtagctggag gcaggagcgt gcgggagggg  5880
atagtggcgt gatcgcagtg tggcacggga caccggcgag atattcgtgt gcaaacctgt  5940
ttcgggtatg ttataccctg cctcattgtt gacgtatttt tttatgtaa tttttccgat  6000
tattaatttc aactgtttta ttggtatttt tatgttatcc attgttcttt ttttatgatt  6060
tactgtatcg gttgtctttc gttcctttag ttgagttttt tttattatt ttcagttttt  6120
gatcaaagct agcgcgagct cacgggggaca gcccccccc aaagccccca gggatgtaat  6180
tacgtccctc cccccgctagg gggcagcagc gagccgcccc gggctccgcc ccggtccggc  6240
gctccccccg catcccgag ccggcagcgt gcggggacag cccgggacg gggaaggtgg  6300
cacgggatcg cttcctctg aacgcttctc gctgctcttt gagcctgcag acacctgggg  6360
ggatacgggg aaaaagcttt aggctgaaag agagatttag aatgacagaa tcatagaacg  6420
gcctggggttg caaaggagca cagtgctcat ccagatccaa ccccctgcta tgtgcagggt  6480
catcaaccag cagcccaggc tgcccagagc cacatccagc ctggccttga atgcctgcag  6540
ggatggggca tccacagcct ccttgggcaa cctgttcagt cgtcaccac cctctgggg  6600
aaaaactgcc tcctcatatc caacccaaac ctccccctgtc tcagttctaaa gccattccc  6660
cttgtcctat caagggggag tttgctgtga cattgttggt ctgggtgac acatgtttgc  6720
caattcagtg catcacggag aggcagatct tggggataag gaagtgcagg acagcatgga  6780
cgtgggacat gctggtgttg aggggctctgg gacactctcc aagtcacagc gttcagaaca  6840
gccttaagga taagaagata ggatagaagg acaaagagca agttaaaacc cagcatggag  6900
```

```
aggagcacaa aaaggccaca gacactgctg gtccctgtgt ctgagcctgc atgtttgatg   6960
gtgtctggat gcaagcagaa gggtggaag tgcttgcctg gagagataca gctgggtcag    7020
taggactggg acaggcagct ggagaattgc catgtagatg ttcatacaat cgtcaaatca   7080
tgaaggctga aaaagccctc caagatcccc aagaccaacc ccaacccacc caccgtgccc   7140
actggccatg tccctcagtg ccacatcccc acagttcttc atcacctcca gggacggtga   7200
cccccccacc tccgtgggca gctgtgccac tgcagcaccg ctctttggag aaggtaaatc   7260
ttgctaaatc cagcccgacc ctcccctggc acaacgtaag gccattatct ctcatccaac   7320
tccaggacgg agtcagtgag aatattggta ccggggtgtg gtgtcttctt aacctcaccc   7380
aggaggaacc gggtcaattc ttcagcacct gggtacccat agagcccacc gcatcccag    7440
catgcctgct attgtattcc caatcctccc ccttgctgtc ctgcccacc ccacccccca   7500
gaatagaatg acacctactc agacaatgcg atgcaatttc ctcattttat taggaaagga   7560
cagtgggagt ggcaccttcc agggtcaagg aaggcacggg ggaggggcaa acaacagatg   7620
gctggcaaga gagcaggttt actgataggt atcgagatcg acggccttga ccacttccac   7680
caggcacatg tgatctctcc tctcatcgcg gtctttgagg agcttagtgt gataagtgat   7740
atgatggtag cgcggaatgt ggacagccgc tgaaccggcc agtggccgat tcatctggct   7800
acacttggtc accagcttct ccgtcacccc ctcgatgtcg taggcttgat tgaactccac   7860
gcggattccg ttgttcacag tgtcgggag aatgtaaagg atgctgggag ggcactggaa    7920
ggcacattc ttccgaagaa tatgcccgtc cttcttaaag ttttctccaa tcagagtcac    7980
ccggttgtag atagatcccc tctcataggt gaccatcgcg cgggtcttgt acactccatc   8040
tccctcaaaa gaaatggtgc gctcttgggt ataaccttcc ggcatggcgg atttgaagaa   8100
gtccttaatg tggctagggt acttagcaaa acactgcact ccatacgaga gggttgacac   8160
aagggtggcc caaggcactg gcagatctcc agtggtacag atatacttgg ccttaatggt   8220
tccagtcgta gcgtcccgg ttccttctcc cttgatgatg aacttcattc cttcgacgtc    8280
ccccttccagc tcgtgatgt acggaatctc cttctcaaac agcttagcac cttcggtcag   8340
ggcagtcatg gtggcggccc ttctgcaaaa agaacaagca agctcttgtc tatgagaaga   8400
ggctgcggga gaagaaagtc agattagcgt ggccagtccc ctccccccac ccgcctccat   8460
tcccgccgca tgcccatca cgtcctctac catcctctgc aatgcggagc ctgggctcgg    8520
cttccggacc tcgcaccagc gcccctaaac ccgtacagcg tccttccccc cattcctaat   8580
ttccattcct ctccggcctc ctgcggccca gtcctttttt ttcttttctt tttcacctgg   8640
cactgcacaa gaagatgcgg ctgtctctag aacagggagg agcagagagc accagggagg   8700
gctgcagtcc gtatttatag gaactggatg gtggggggag ctgatgacgc gcgccccgcc   8760
tcccgctcgg ctcatccagt cccagctcaa gggcgcagag gcctgagcta cgtgcacccg   8820
taaagccgcg agtagctggg cctctctcat tcccccctc cctcttttg gacccgcctc     8880
gttttttgaaa tgtgcacgca ccaagcgtgt gggctccgac ctgagagggg gagggagct   8940
gagattgtcc cgccgaggaa gtgaccggat gaggttccc aggataggac tcagggaata   9000
cagactatgg attaaggacg aggagtcctc ggagtgtgca ccaaggacat ccaggaccca   9060
gaaaccagaa agctgcttcc cgaataaaat gggagaatct gagagctgca ggaaccaggg   9120
aaatggagca gaagtgtggg tctgcccaag gctgccccat cgaacttctc cctattagtg   9180
aaaaggctta ggagaagttg aggatcttct cgttgttctt cggaagacta ctctggagac   9240
gtctaccggg taggggaggc gcttttccca aggcagtctg gagcatgcgc tttagcagcc   9300
ccgctgggca cttggcgcta cacaagtggc ctctggcctc gcacacattc cacatccacc   9360
ggtaggcgcc aaccggctcc gttctttggt ggccccttcg cgccaccttc tactcctccc   9420
ctagtcagga agttccccc cgcccgcag ctcgcgtcgt caggagcagtg acaaatggaa    9480
gtagcacgac tcactagtct cgtgcagatg gacagcaccg ctgagcaatg gaagcgggta   9540
ggcctttggg gcagcggcca atagcagctt tgctccttcg ctttctgaga gcagcggccg   9600
ggaagggcg gtgcggagg cgggggtgtgg ggcggtagtg tgggccctgt tcctgcccgc    9660
gcggtgttcc gcattctgca agcctccgga gcgcacgtcc gtctcagggg cagcttgctt   9720
gttctttttg cagaagctca gaataaacgc tcaactttgg ccgccaccat gggagcaccc   9780
accctgcctc ccgcttggca accgttcctg aaagaccacc ggatttcgac cttcaagaat   9840
tggccgttcc tcgagggctg tgcctgcact cctgagcgga tggccgaggc cgggttcatc   9900
cactgtccaa ccgagaacga acctgacctg gcccagtgct tcttctgctt taaggaactt   9960
gagggttggg agccggacga tgaccccatc gaagaacaca agaagcattc ctccggctgc  10020
gccttcctga gcgtgaagaa acagttcgaa gaactgactc tgggagagtt cttgaagctc  10080
gacagagagc gcgccaagaa caagatcgcg aaggaaacca caacaagaa gaaagaattt   10140
gaggaaaccg cgaagaaggt ccgcagggcg attgaacagc tggctgccat ggattgataa   10200
aagcttaatg ctggagcctc ggtagccgtt cctcctgccc gctgggcctc ccaacgggcc  10260
ctcctccct ccttgcaccg gcccttcctg gtctttgaat aaagtttacc tgactcatgg    10320
tcctttcact ttcacatggg atttcccagt tatgaaatta ataaaaatca gtgatttcca  10380
catctgtgtg tgcctgtgcc aggctgggtg gggaacagga ggccgagatg attccgggaa  10440
ctgtcagaag gaatcaatga tttccacatc ctgtctgtct tatgtcttgg gggtggggga  10500
ggccaggaag attccaggaa ggtcagagtc aatcaatggt ttccacatct ctcagtgcct  10560
ctatctggag gccaggtagg gctggccttg ggggaggggg aggccagaat gactccaaga  10620
gctacaggaa gggggaggg ggaaaaaggc cagaataatt ccaggaaccg ccaagaagat   10680
gacgtcggaa ggaagttccc caactttccc gcctctcagc ctttgaaaga aagaaagggg  10740
aggggcagg ccgcgtgcag ccgcgagcgg tgctgggctc cggctccaat tcccatctc    10800
agtcgttccc aaagtcctcc tgtttcatcc aagcgtgtaa gggtcccgt ccttgactcc   10860
ctagtgtcct gctgcccaca gtccagtcct gggaaccagc accgatcacc tcccatcggg  10920
ccaatctcag tcccttcccc cctacgtcgg ggcccacacg ctcggtgcgt gcccagttga  10980
accaggcggc tgcggaaaaa aaaagcggg gagaaagtag ggcccggcta ctagcggttt   11040
tacgggcgca cgtagctcag gcctcaagac cttgggctgg gactggctga gcctggcggg  11100
aggcggggtc cgagtcaccg cctgccgccg cgccccggt ttctataaat tgagcccgca   11160
gcctcccgct tcgctctctg ctcctcctgt tcgacagtca gccgcatctt cttttgcgtc  11220
gccagggga gcttgcttgt tcttttttgca gaagctcaga ataaacgctc aactttggcc  11280
gccacc                                                             11286

SEQ ID NO: 256        moltype = DNA   length = 11520
FEATURE               Location/Qualifiers
misc_feature          1..11520
                      note = Synthetic
```

| source | 1..11520 |
| | mol_type = other DNA |
| | organism = synthetic construct |

SEQUENCE: 256

```
atggcactcc ctgtcaccgc cctcctcctc ccactcgccc tcttgctgca cgccgctcgc   60
ccggatattc agatgacgca gaccacctca agtctgtcgg cctcccttgg tgatcgggtc  120
accatttcct gccgagccag ccaggacatc tccaagtacc tgaactggta ccagcagaag  180
cccgacggga ccgtgaagct gctgatctac atacctcccc ggctgcatag cggggtgccg  240
tcaaggttta gcggatcggg atccggcacc gactactcgc tgactatctc caacttggaa  300
caagaggaca tcgccaccta cttctgtcaa caagggaata ctctgcccta cactttcggc  360
gggggaacca agctcgagat cactggcggc ggcggctcgg gcggtggtgg atccgggggc  420
ggtggctccg aggtcaagct tcaggaatcc ggacccggcc tggtggcacc gtcacaatcc  480
ctatccgtga catgcaccgt cagcggagtg tcgctgcccg attacggagt gtcttggatt  540
aggcagcccc cgcgcaaagg tcttgagtgg ctgggaggag tctgggatc agagactacc  600
tactacaaca gcgccctcaa gtcgaggctc accatcatca aggacaactc caagtcccaa  660
gtgtttctga gatgaactcc cctgcaaact gacgacaccg ccatctacta ctgcgcgaag  720
cactactact acggggaag ctacgctatg gactattggg gacagggaac ttccgtgact  780
gtgtccagca ccacgacacc agcccgcgc ccgcgaccc ccgcccgac cattgcgagc  840
cagccgctga gccttcggcc ggaagcctgc aggcccgcgg ccggcggagc cgtgcacacc  900
agaggactgg acttcgcctg cgatatctat atctgggcgc ctctggccgg aacctgtgga  960
gtcctgctgc tgtcactcgt gattactctg tactgcaagc gcggtcggaa gaagctgctc 1020
tacattttca gcaacctttt catgcggcca gtgcagacca ctcaggaaga agatggctgt 1080
tcctgccggt tccctgaaga agaagagggc ggctgcgaat tgagagtgaa gttctcccgc 1140
tcggctgacg ctcccgccta caaacagggg cagaaccagc tgtataacga actgaacctc 1200
gggcgccgcg aggaatacga cgtgctggac aagcggagag ccgcgatcc tgagatgggg 1260
ggaaagcccc ggagaaagaa ccctcaggag ggcctgtaca atgagctgca gaaagacaaa 1320
atggccgagg cgtacagcga gatcggcatg aagggcgaac gccggagagg aaagggcac 1380
gacgactgt accagggact gtccaccgcg accaaggata cctacgacgc cctgcacatg 1440
caggcactgc cacctcggtg ataaaaatta atggctaata aaggaaattt attttcattg 1500
caatagtgtg ttgaatttt ttgtgtctct cactcggaag aacatatggg agggcaaatc 1560
atttaaaaca tcagaatgag tatttggttt agagtttggc aacatatgcc catatgctgt 1620
ctgccatgaa caaggttgg ctataaagag gtcatcagta tatgaaacag cccctgctg 1680
tccattcctt attccataga aaagccttga cttgaggtta gatttttttt atattttgtt 1740
ttgtgttatt ttttcttta acatcctaa aatttcctt acatgttttta ctagccagat 1800
ttttcctcct ctcctgacta ctcccagtca tagctgtccc tcttctctta tggagatcag 1860
aaaatttgt gtcgccttc gctgaacacc aggtgggccg cctactgcgc acgcgcgggt 1920
ttgcgggcag ccgcctgggc tgtgggagca gcccgggcag agctctcctg cctctccacc 1980
agcccacccc gccgctgac cgcccctcc cacccccca cccccaccc ccggaaaacg 2040
cgtcgtcccc tgggctgggt ggtgacccc gtcccgcgaa acaccgggcc ccgcgcaggg 2100
tccgggcctg acaccgctcc ggcggctcgc ctcctatgcg ccccccgcgcc accgtcgccc 2160
gcccgccgg gcccctgcag ccgcccaggt gccagcacgg agcgcctggc ggcggaacgc 2220
agaccccagg cccggcgcac accggggacg ctgagcgttc caggcgggag ggaaggcggg 2280
cagagatgga gagggaacg ggagtcctag aggggcggaa ggacgggcgg agggacgtta 2340
ggagggaggg agggaggcag ggaggcaggg aggaacggag ggaaagacag agcgacgcag 2400
ggactgggg cgggcgggag ggagccgggg aacgggggga ggaaggcagg gaggaaaagc 2460
ggtcctcggc ctccggagt agcgggaccc ccgcctccg ggaaacggt cagcgtccgg 2520
cgcgggctga gggctgggcc cacagccgcc gcgccgggcc gcgggaccc acccattcgc 2580
cccggttccg tggcccaggg agtgggcggt ttcctccggg acaaaagacc gggactcggg 2640
ttgccgtcgg gtgttcaccc gcgcggttca cagaccgcac atccccaggc tgagccctgc 2700
aacgcggcgc gaggccgaca gccccggcca cggaggagcc acacgcagga cgacggaggc 2760
gtgattttgg tttccgcgtg gctttgccct ccgcaaggcg gcctgttgct caagtctctc 2820
cggccccga aaggctggcc atgccgactg tttgctcccg gagctctgcg ggcacccgga 2880
aacatgcagg gaagggtgca agccggcac ggtgccttcg ctctccttgc caggttccaa 2940
accgccaca ctgcagactc ccacgttgc cgcacgcggg aatccatcgt caggccatca 3000
cgccgggag gcatctcctc tctgggtgt cgctctgaca ttctacgtgg aaatgaacga 3060
gagccacacg cctgcgtgtg ccagaccgtc ccggcaacgg cgacgcccac aggcattgcc 3120
tccttcacgg agagagggcc tggcacactc aagactccca cggaggttca gttccacact 3180
ccacctaggt catattttta gtttaaaaaa ataattatat gttttataat gaaaagaatc 3240
tcattatctt tcagtattag gttgatttat attccaaaga ataatttttt tgttaaattg 3300
ttgattttttg taaacctcta aatgtttgtt gctaaaatta ctgtgtttaa gaaaaagatt 3360
aataaataat aataatttca taattaaaaa cttctttcat tgaatgccat taaataaacc 3420
attattttac aaaataagat caacataatt gagtaaataa taataagaac aatattatag 3480
tacaacaaaa tatgggtatg tcatacctg ccacattctt gatgtaactt ttttcacct 3540
catgctcgcc gggttaaggg ctacaatgaa ctcgaaaca ccggtttgca ttttagaca 3600
tttagaagcc tatatcttgt tacagaattg gaattacaca aaaattctac catattttga 3660
aagcttaggt tgttctgaaa aaacaatat attgttttcc tgggtaaact aaaagtcccc 3720
tcgaggaaag gcccctaaag tgaaacagtg caaaacgttc aaaaactgtc tggcaataca 3780
agttccactt tgaccaaaac ggctggcagt aaaagggtta agcggccgtc cagccttgag 3840
cggtatcagc tcactcaaag gcggtaatac ggttatccac agaatcaggg gataacgcag 3900
gaaagaacat gtgagcaaaa ggccagcaaa aggccaggaa ccgtaaaaag gccgcgttgc 3960
tggcgttttt ccataggctc cgcccccctg acgagcatca aaaaatcga cgctcaagtc 4020
agaggtggcg aaacccgaca ggactataaa gataccaggc gtttccccct ggaagctccc 4080
tcgtgcgctc tcctgttccg accctgccgc ttaccggata cctgtccgcc tttctccctt 4140
cgggaagcgt ggcgctttct catagctcac gctgtaggta tctcagttcg gtgtaggtca 4200
ttcgctccaa gctgggctgt gtgcacgaac ccccgttca gcccgaccgc tgcgccttat 4260
ccggtaacta tcgtcttgag tccaacccgg taagacacga cttatcgcca ctggcagcag 4320
ccactggtaa caggattagc agagcgaggt atgtaggcgg tgctacagag ttcttgaagt 4380
ggtgggctaa ctacgctac actagaagaa cagtatttgg tatctgcgct ctgctgaagc 4440
cagttacctt cggaaaaaga gttggtagct cttgatccgg caaacaaacc accgctggta 4500
```

```
gcggtggttt ttttgtttgc aagcagcaga ttacgcgcag aaaaaaagga tctcaagaag  4560
atcctttgat cttttctacg gggtctgacg ctcagtggaa cgacgcgcgc gtaactcacg  4620
ttaagggatt ttggtcatga gttagaaaaa ctcatcgagc atcaaatgaa actgcaattt  4680
attcatatca ggattatcaa taccatattt ttgaaaaagc cgtttctgta atgaaggaga  4740
aaactcaccg aggcagttcc ataggatggc aagatcctgg tatcggtctg cgattccgac  4800
tcgtccaaca tcaatacaac ctattaattt cccctcgtca aaaataaggt tatcaagtga  4860
gaaatcacca tgagtgacga ctgaatccgg tgagaatggc aaaagtttat gcatttcttt  4920
ccagacttgt tcaacaggcc agccattacg ctcgtcatca aaatcactcg catcaaccaa  4980
accgttattc attcgtgatt gcgcctgagc gaggcgaaat acgcgatcgc tgttaaaagg  5040
acaattacaa acaggaatcg agtgcaaccg gcgcaggaac actgccagcg catcaacagt  5100
attttcacct gaatcaggat attcttctaa tacctggaac gctgttttc cggggatcgc  5160
agtggtgagt aaccatgcat catcaggagt acggataaaa tgcttgatgg tcggaagtgg  5220
cataaattcc gtcagccagt ttagtctgac catctcatct gtaacatcat tggcaacgct  5280
acctttgcca tgtttcagaa acaactctgg cgcatcgggc ttcccataca agcgatagat  5340
tgtcgcacct gattgcccga cattatcgcg agcccattta tacccatata aatcagcatc  5400
catgttggaa tttaatcgcg gcctcgacgt ttccgttgg atatggctca tttttttactt  5460
cctcaccttg tcgtattata ctatgccgat atactatgcc gatgattaat tgtcgacact  5520
gcggggggctc tggcgcgcct taacctttt actgccaatg acgcatggga tacgtcgtgg  5580
cagtaaaagg gcttaaatgc caacgacgcg tcccatacgt tgttggcatt ttaattcttc  5640
tctctgcagc ggcagcatgt gccgccgctg cagagagttt ctagcgatga cagccctct  5700
gggcaacgag ccgggggggc tgtcccatga cgcggctaga catgcacgac cattaacccg  5760
gcgagcatga ggcagggtat ctcataccct ggtaaaattt taaagttgtg tattttataa  5820
aattttcgtc tgacaacact agcgcgctca gtagctggag gcaggagcgt gcgggagggg  5880
atagtggcgt gatcgcagtg tggcacggga caccggcgag atattcgtgt gcaaacctgt  5940
ttcgggtatg ttatacctg cctcattgtt gacgtatttt ttttatgtaa ttttccgat  6000
tattaatttc aactgtttta ttggtatttt tatgttatcc attgttcttt ttttatgatt  6060
tactgtatcg gttgtcttc gttccttag ttgagttttt ttttattatt ttcagttttt  6120
gatcaaagct agcgcgagct cacggggaca gcccccccc aaagccccca gggatgtaat  6180
tacgtccctc ccccgctagg gggcagcagc gagccgcccg gggctccgct ccggtccggc  6240
gctccccccg catcccgag ccggcagcgt gcggggacag cccgggcacg gggaaggtgg  6300
cacgggatcg ctttcctctg aacgcttctc gctgctcttt gagcctgcag acacctgggg  6360
ggatacgggg aaaagctttt aggctgaaag agagatttag aatgacagaa tcatagaacg  6420
gcctgggttg caaggagca cagtgctcat ccagatccaa cccctgcta tgtgcagggt  6480
catcaaccag cagcccaggc tgcccagagc cacatccagc ctggccttga atgcctgcag  6540
ggatggggca tccacagcct ccttgggcaa cctgttcagt gcgtcaccac cctctgggg  6600
aaaaactgcc tcctcatatc caacccaaac ctcccctgtc tcagtgtaaa gccattcccc  6660
cttgtcctat caaggggag tttgctgtga cattgttggt ctggggtgac acatgtttgc  6720
caattcagtg catcacggag aggcagatct tggggataag gaagtgcagg acagcatgga  6780
cgtggacat gctggtgttg agggctctgg gacactctcc aagtcacagc gttcagaaca  6840
gccttaagga taagaagata ggatagaagg acaaagagca agttaaaacc cagcatggag  6900
aggagcacaa aaaggccaca gacactgctg gtccctgtgt ctgagcctgc atgtttgatg  6960
gtgtctggat gcaagcagaa ggggtggaag tgcttgcctg gagagataca gctgggtcag  7020
taggacatgg acaggcagct ggagaattgc catgtagatg ttcatacaat cgtcaaatca  7080
tgaaggctgg aaaagccctc caagatcccc aagaccaacc ccaacccacc caccgtgccc  7140
actggccatg tccctcagtg ccacatcccc acagttcttc atcacctcca gggacggtga  7200
cccccccacc tccgtgggca gctgtgccac tgcagcaccg ctctttggag aaggtaaatc  7260
ttgctaaatc cagcccgacc ctcccctggc acaacgtaag gccattatct ctcatccaac  7320
tccaggacgg agtcagtgag aatattggta ccggggtgtg gtgtcttctt aacctcaccg  7380
aggaggaacc gggtcaattc ttcagcacct gggtaccat agagcccacc gcatcccag  7440
catgcctgct attgtattcc caatcctccc ccttgctgtc ctgccccacc ccacccccca  7500
gaatagaatg acacctactc agacaatgcg atgcaatttc ctcatttttat taggaaagga  7560
cagtgggagt ggcaccttcc agggtcaagg aaggcacggg ggaggggcaa acaacagatg  7620
gctggcaaga gagcaggttt actgataggc atcgagatcg acggcttga ccacttccac  7680
caggcacatg tgatctctcc tctcatcgcg gtctttggag agcttagtgt gataagtgat  7740
atgatggtag cgcggaatgt ggacagccgc tgaaccggcc agtggccgat tcatctggct  7800
acacttggtc accagcttct ccgtcacccc ctcgatgtcg taggcttgat tgaactccac  7860
gcggattccg ttgttcacag tgtcgggag aatgtaaagg atgctgggag ggcactggaa  7920
ggcgacattc ttccgaagaa tatgcccgtc cttcttaaag ttttctccag tcagtcac  7980
ccggttgtag atagatcccc tctcataggt gaccatcgcg cgggtcttgt acactccatc  8040
tccctcaaaa gaaatggtgc gctcttgggt ataaccttcc ggcatggcgg atttgaagaa  8100
gtccttaatg tggctagggt acttagcaaa acactgcact ccatacgaga gggttgacac  8160
aagggtggcc caaggcactg gcagatctcc agtggtacag atatacttgg ccttaatggt  8220
tccagtcgta gcgtccccgg ttccttctcc cttgatgatg aacttcattc cttcgacgtc  8280
ccctttccagc tcggtgatgt acggaatctc ctttctcaaac agcttagcac cttcggtcag  8340
ggcagtcatg gtggcggccc ttctgcaaaa agaacaagca agctcttgtc tatgagaaga  8400
ggctgcggga gaagaaagtc agattagcgt ggccagtccc ctcccccac ccgcctccat  8460
tccgccgca tgcccatca cgtcctctac catcctctgc aatgcgggagc ctgggctcgg  8520
cttccggacg tcgcaccagc gcccctaaac ccgtacagcg tccttccccc cattcctaat  8580
ttccattcct ctccggcctc ctgcggccca gtcctttctt ttctttttctt tttcacctg  8640
cactgcacaa gaagatgcgg ctgtctctag aacagggagg agcagagagc accagggagg  8700
gctgcagtcc gtatttatag gaactggatg gtgggggag ctgatgacgc gcgcccgcc  8760
tcccgctcgg ctcatccagt cccagctcaa gggcgcagag gcctgagcta cgtgcacccg  8820
taaagccgcg agtagctggg cctctctcat tccccccctc cctcttttg gacccgctc  8880
gttttgtgaaa tgtgcacgca caagcgtgt gggctccgac tggggagct gaggggagct  8940
gagattgtcc cgccgaggaa gtgaccggat gagggtccc aggataggac tcagggaata  9000
cagactatgg attaaggacg aggagtcctc ggagtgtgca ccaaggacat ccaggaccca  9060
gaaccagaa agctgcttcc cgaataaaat gggagaatct gagagctgca ggaaccaggg  9120
aaatggagca gaagtgtggg tctgcccaag gctgccccat cgaacttctc cctattagtg  9180
aaaaggctta ggagaagttg aggatcttct cgttgttctt cggaagacta ctctggagac  9240
```

```
gtctaccggg tagggaggc gcttttccca aggcagtctg gagcatgcgc tttagcagcc   9300
ccgctgggca cttggcgcta cacaagtggc ctctggcctc gcacacattc cacatccacc   9360
ggtaggcgcc aaccggctcc gttctttggt ggcccttcg cgccaccttc tactcctccc   9420
ctagtcagga agttccccc cgccccgcag ctcgcgtcgt gcaggacgtg acaaatggaa   9480
gtagcacgac tcactagtct cgtgcagatg dacagcaccg ctgagcaatg gaagcgggta   9540
ggcctttggg gcagcggcca atagcagctt tgctccttcg ctttctgaga gcagcggccg   9600
ggaaggggcg gtgcgggagg cggggtgtgg ggcggtagtg tgggcccgt tcctgcccgc   9660
gcggtgttcc gcattctgca agcctccgga gcgcacgtcc gtctcagggg cagcttgctt   9720
gttctttttg cagaagctca gaataaacgc tcaactttgg ccgccaccat gctgaggctg   9780
ctgctggctc tgaacttgtt tccatcaatt caagtcaccg gcaacaagat ccttgtgaag   9840
cagagcccca tgctcgtggc gtacgataat gccgtgaacc tgagctgcaa atattcgtac   9900
aacctgttct cgcgcgagtt ccgggcctcg ctgcacaagg gctgactc cgccgtggaa   9960
gtctgcgtgt tgtacgggaa ctacagccag cagctccaag tgtacagcaa gaccggattc   10020
aactgtgacg gaaagctcgg gaacgaatcc gtgactttct acctccaaaa ccttcacgtg   10080
aatcagaccg acatctactt ctgcaagatt gaagtcatgt accctcctcc ctacctggag   10140
aacgagaagt ccaacggtac catcatccac gtgaagggca acacctgtg cccgtccct   10200
ctgttccccgg gaccgtccaa gcccttctgg gtgctcgtgt cgtcggtgg cgtgctggcc   10260
tgttactcct tgctcgtgac tgtggcattc attatctttt gggtccggtc caagagatct   10320
cggctgctgc actccgatta catgaacatg cccccgagc gcccgggacc gaccagaaag   10380
cattatcagc catacgcgcc ccctcgcgac ttcgccgcct accggtcatg ataaaagctt   10440
aatgctggag cctcggtagc cgttcctcct gcccgctggg cctcccaacg ggccctcctc   10500
ccctccttgc accggcctt cctggtcttt gaataaagtt tacctgactc atggtccttt   10560
cactttcaca tgggatttcc cagttatgaa attaataaaa atcagtgatt ccacatcctg   10620
tgtgtgcctg tgccaggctg ggtgggaac aggaggccga gatgattccg ggaactgtca   10680
gaaggaatca atgatttcca catcctgtct gtcttatgtc ttggggggtg gggaggccag   10740
gaagattcca ggaaggtcag agtcaatcaa tggtttccaa atctctcagt gcctctatct   10800
ggaggccagg tagggctggc cttggggag gggaggcca gaatgactcc aagagctaca   10860
ggaagggggg aggggaaaa aggccagaat aattccagga accgcaaga agatgacgtc   10920
gaggagaagt tccccaactt tcccgcctct cagcctttga aagaagaaa ggggagggg   10980
caggccgcgt gcagccgcga gcggtgctgg gctccggctc caattcccca tctcagtcgt   11040
tcccaaagtc ctcctgtttc atccaagcgt gtaagggtcc ccgtccttga ctccctagtg   11100
tcctgctgcc cacagtccag tcctgggaac cagcaccgat cacctccat cgggccaatc   11160
tcagtccctt cccccctacg tcggggccca cacgctcgt gcgtgcccag ttgaaccagg   11220
cggctgcgga aaaaaaaaag cggggagaaa gtagggcccg gctactagcg gttttacggg   11280
cgcacgtagc tcaggcctca agaccttggg ctgggactgg ctgagcctgg cgggaggcgg   11340
ggtccgagtc accgcctgcc gccgcgcccc cggtttctat aaattgagcc cgcagcctcc   11400
cgcttcgctc tctgctcctc ctgttcgaca gtcagccgca tcttcttttg cgtcgccagg   11460
gggagcttgc ttgttctttt tgcagaagct cagaataaac gctcaacttt ggccgccacc   11520
```

SEQ ID NO: 257         moltype = DNA  length = 11552
FEATURE                Location/Qualifiers
misc_feature       1..11552
                      note = Synthetic
source                  1..11552
                      mol_type = other DNA
                      organism = synthetic construct
SEQUENCE: 257

```
atgtcacagt ccaaccgcga gctcgtggtg gacttcctga gctataagct gtcccagaag     60
ggctactcgt ggagccagtt cagcgacgtg aagagaaca ggactgaagc acctgaaggg    120
accgagagcg agatgaaac cccgtcggcc atcaacggaa acccttcttg gcaccttgcc    180
gactcccgga ccgtgaacgg cgcgaccgga cattcatcct ccctgaatgc ccgcgaactt    240
attccaatgg ccgctgtgaa gcaggccctt cgcgaggccg ggacgaatt cgagctgaga    300
tacagacggg cgttctccga cttgacctcg caactccaca tcaccccgg aaccgcgtac    360
cagtcgtttg aacaagtcgt caacgaactc ttccgggatg gcgtgaactg ggacggatc    420
gtggccttct tctcctttgg tggcgctctg tgcgtcgagt ccgtgacaa agagatgcaa    480
gtgctggtgt ccagaatcgc agcctggatg gccacctacc tcaacgatca cctggagccc    540
tggattcagg aaaacggcgg atgggacact tccgtggagc tgtacggaaa caatgccgct    600
gccgaatccc ggaagggcca ggaaaggttc aatcgctggt tcttgacggg gatgactgtg    660
gccggagtgg tcctgctggg tagcctgttc tcacggaagt gataaaagct taattaatgg    720
ctaataaagg aaatttattt tcattgcaat agtgtgttgg aattttttgt gtctctcact    780
cggaagaaca tatgggaggg caaatcattt aaaacatcag aatgagtatt tggtttagag    840
tttggcaaca tatgcccata tgctggctgc catgaacaaa ggttggctat aaagaggtca    900
tcagtatatg aaacagcccc ctgctgtcca ttccttattc catagaaaag ccttgacttg    960
aggttagatt tttttatat tttgttttgt gttattttt tcttaacat ccctaaaatt   1020
ttccttacat gttttactag ccagattttt cctcctctcc tgactactcc cagtcatagc   1080
tgtccctctt ctcttatgga gatcagaaaa ttttgtgtcg cccttcgctg aacaccaggt   1140
gggccgccta ctgcgcacgc gcgggttgc gggcagccgc ctgggctgtg ggagcagccc   1200
gggcagagct ctcctgcctc tccaccagcc accccgccg cctgaccgcc cctccccac   1260
ccccaccccc ccaccccgg aaaacgcgtc gtccctcggc ctgggtggtg accccgtctc   1320
cgcgaaacac cgggccccgc gcagcgtccg gcctgacac cgctccgcg gctcgcctcc   1380
tatgcgcccc cgcgccaccg tcgcccgccc gcccgggcc ctgcagcgc caggtgcca   1440
gcacggagcg cctggcggcg aacgcagac cccaggcccg gcgcacaccg ggacgctga   1500
gcgttccagg cggagggaa ggcgggcaga gatggagaga ggaacgggag tcctagaggg   1560
gcggaaggac gggcggaggg acgttaggag ggaggagga cgccaggagga cgcagggagga   1620
acggagggaa agacagagcg acgcaggac tggggcggg cggagggag ccgggaacgg   1680
gggggaggaa ggcagggagg aaaagcgtc ctcggcctcc gggagtagcg ggaccccgc   1740
cctccggaa acggtcagc gtccggcgcg ggctgagggc tgggcccaca gccgccgcgc   1800
cggcggcgg ggcaccaccc attcgccccg gttccgtggc ccaggagtg gcggtttcc   1860
tccgggacaa aagaccggga ctcggggttgc cgtcgggtgt tcaccgcgc ggttcacaga   1920
```

```
ccgcacatcc ccaggctgag ccctgcaacg cggcgcgagg ccgacagccc cggccacgga   1980
ggagccacac gcaggacgac ggaggcgtga ttttggtttc cgcgtggctt tgccctccgc   2040
aaggcggcct gttgctcaag tctctccggc ccccgaaagg ctggccatgc cgactgtttg   2100
ctcccggagc tctgcgggca cccggaaaca tgcaggaagg ggtgcaagcc cggcacggtg   2160
ccttcgctct ccttgccagg ttccaaaccg gccacactgc agactcccca cgttgccgca   2220
cgcgggaatc catcgtcagg ccatcacgcc ggggaggcat ctcctctctg gggtgtcgct   2280
ctggacttct acgtggaaat gaacgagagc cacacgcctg cgtgtgccag accgtcccgg   2340
caacggcgac gcccacaggc attgcctcct tcacggagag agggcctggc acactcaaga   2400
ctcccacgga ggttcagttc cacactccac ctaggtcata tttttagttt aaaaaaataa   2460
ttatatgttt tataatgaaa agaatctcat tatctttcag tattaggttg atttatattc   2520
caaagaataa tatttttgtt aaattgttga tttttgtaaa cctctaaatg tttgttgcta   2580
aaattactgt gtttaagaaa aagattaata aataataata atttcataat taaaaacttc   2640
tttcattgaa tgccattaaa taaaccatta ttttacaaaa taagatcaac ataattgagt   2700
aaataataat aagaacaata ttatagtaca acaaaatatg ggtatgtcat accctgccac   2760
attcttgatg taactttttt tcacctcatg ctcgccgggt taagggctac aatgaactcg   2820
aaacgaccgg tttgcatttt tagacattta gaagcctata tcttgttaca gaattggaat   2880
tacacaaaaa ttctaccata ttttgaaagc ttaggttgtt ctgaaaaaaa caatatattg   2940
ttttcctggg taaactaaaa gtcccctcga ggaaaggccc ctaaagtgaa acagtgcaaa   3000
acgttcaaaa actgtctggc aatacaagtt ccactttgac caaaacggct ggcagtaaaa   3060
gggttaagcg gccgctcagc cttgagcggt atcagctcac tcaaaggcgg taatacggtt   3120
atccacagaa tcaggggata acgcaggaaa gaacatgtga gcaaaaggcc agcaaaaggc   3180
caggaaccgt aaaaaggccg cgttgctggc gtttttccat aggctccgcc ccctgacga   3240
gcatcacaaa aatcgacgct caagtcagag gtggcgaaac ccgacaggac tataaagata   3300
ccaggcgttt ccccctggaa gctccctcgt gcgctctcct gttccgaccc tgccgcttac   3360
cggatacctg tccgcctttc tcccttcggg aagcgtggcg ctttctcata gctcacgctg   3420
taggtatctc agttcggtgt aggtcgttcg ctccaagctg ggctgtgtgc acgaaccccc   3480
cgttcagccc gaccgctgcg ccttatccgg taactatcgt cttgagtcca acccggtaag   3540
acacgactta tcgccactgg cagcagccac tggtaacagg attagcagag cgaggtatgt   3600
aggcggtgct acagagttct tgaagtggtg gcctaactac ggctacacta agaacagt    3660
atttggtatc tgcgctctgc tgaagccagt taccttcgga aaaagagttg gtagctcttg   3720
atccggcaaa caaccaccg ctggtagcgg tggtttttt gtttgcaagc agcagattac    3780
gcgcagaaaa aaaggatctc aagaagatcc tttgatcttt tctacggggt ctgacgctca   3840
gtggaacgac gcgcgcgtaa ctcacgttaa gggattttgg tcatgagtta gaaaaactca   3900
tcgagcataa aatgaaactg caatttattc atatcaggat tatcaatacc atattttga   3960
aaaagccgtt tctgtaatga aggagaaaac tcaccgaggc agttccatag gatggcaaga   4020
tcctggtatc ggtctgcgat tccgactcgt ccaacatcaa tacaacctat taatttcccc   4080
tcgtcaaaaa taaggttatc aagtgagaaa tcaccatgag tgacgactga atccggtgag   4140
aatggcaaaa gtttatgcat ttcttccag acttgttcaa caggccagcc attacgctcg    4200
tcatcaaaat cactcgcatc aaccaaaccg ttattcattc gtgattgcgc ctgagcgaga   4260
cgaaatacgc gatcgctgtt aaaaggacaa ttacaaacag gaatcgagtg caaccggcgc   4320
aggaacactg ccagcgcatc aacaatattt tcacctgaat caggatattc ttctaatacc   4380
tggaacgctg ttttttccggg gatcgcagtg gtgagtaacc atgcatcatc aggagtacgg   4440
ataaaatgct tgatggtcgg aagtggcata aattccgtca gccagtttag tctgaccatc   4500
tcatctgtaa catcattggc aacgctacct ttgccatgtt tcagaaacaa ctctggcgca   4560
tcgggcttcc catacaagcg atagattgtc gcacctgatt gcccgacatt atcgcgagcc   4620
catttatacc catataaatc agcatccatg ttggaattta atcgcggcct cgacgtttcc   4680
cgttggatat ggctcatttt ttacttcctc accttgtcgt attatactat gccgatatac   4740
tatgccgatg attaattgtc gacactgcgg gggctctggc gcgccttaac ctttttactg   4800
ccaatgacgc atgggatacg tcgtggcagt aaaagggctt aaatgccaac gacgcgtccc   4860
atacgttgtt ggcattttaa ttcttctctc tgcagcggca gcatgtgccg ccgctgcaga   4920
gagtttctag cgatgacagc ccctctgggc aacgagccgg ggggctgtc ccatgacgcg    4980
gctagacatg cacgaccatt aacccggcga gcatgaggcg gggtatctca taccctggta   5040
aaattttaaa gttgtgtatt ttataaaatt ttcgtctgac aacactagcg cgctcagtag   5100
ctggaggcag gagcgtgcgg gagggataq tggcgtgatc gcagtgtggc acgggacacc   5160
ggcgagatat tcgtgtgcaa acctgtttcg ggtatgttat accctgcctc attgttgacg   5220
tattttttt atgtaatttt tccgattatt aatttcaact gttttattgg tatttttatg   5280
ttatccattg ttcttttttt atgatttact gtatcggttg tctttcgttc ctttagttga   5340
gtttttttt attattttca gttttgatc aaagctagcg cgagctcacg gggacagccc     5400
ccccccaaag ccccccaggga tgtaattacg tccctccccc gctaggggc agcagcgagc   5460
cgccgggggc tccgctccgg tccggcgctc cccccgcatc cccgagccgc cagcgtgcgg   5520
ggacagcccg ggcacgggga aggtggcacg ggatcgcttt cctctgaacg cttctcgctg   5580
ctctttgagc ctgcagacac ctgggggat acgggaaaa agcttaggc tgaaagagag     5640
atttagaatg acagaatcat agaacggcct gggttgcaaa ggagcacagt gctcatccag   5700
atccaacccc ctgctatgtg caggggtcatc aaccagcagc ccaggctgcc cagagccaaa   5760
tccagcctgg ccttgaatgc ctgcaggat ggggcatcca cagcctcctt gggcaacctg    5820
ttcagtgcgt caccaccctc tgggggaaaa actgcctcct catatccaac ccaaacctcc   5880
cctgtctcag tgtaaagcca ttccccttg tcctatcaag gggagtttg ctgtgacatt     5940
gttggtctgg ggtgacacat gtttgccaat tcagtgcatc acggagaggc agatcttggg   6000
gataaggaag tgcaggacag catgacgtg ggacatgctg gtgttgaggg ctctgggaca    6060
ctctccaagt cacagcgttc agaacagcct taaggataag aagataggat agaaggacaa   6120
agagcaagtt aaaacccagc atggagagga gcacaaaaag gccacagaca ctgctggtcc   6180
ctgtgtctga gcctgcatgt ttgatggtgt ctggatgcaa gcagaagggg tggaagtgct   6240
tgcctggaga gatacagctg ggtcagtagg actgggacag gcagctggag aattgccatg   6300
tagatgttca tacaatcgta aaatcatgaa ggctgaaaa gccctccaag atccccagca    6360
ccaacccccaa cccacccacc gtgcccactg gccatgtccc tcagtgccac atccccacag   6420
ttcttcatca cctccaggga cggtgaccec cccacctccg tgggcagctg tgccactgca   6480
gcaccgctct ttgagaaggg taatcttgc taaatccagc ccgaccctcc cctggcacaa    6540
cgtaaggcca ttatctctca tccaactcca ggacggagtc agtgagaata ttggtaccgg   6600
ggtgtggtgt cttcttaacc tcacccagga ggaacccggg caattcttca gcacctgggt   6660
```

```
acccatagag cccaccgcat ccccagcatg cctgctattg tattcccaat cctcccctt    6720
gctgtcctgc cccaccccac cccccagaat agaatgacac ctactcagac aatgcgatgc    6780
aatttcctca tttttattagg aaaggacagt gggagtggca ccttccaggg tcaaggaagg    6840
cacgggggag gggcaaacaa cagatggctg gcaagagagc aggtttactg ataggtatcg    6900
agatcgacgg ccttgaccac ttccaccagg cacatgtgat ctctcctctc atcgcggtct    6960
ttggagagct tagtgtgata agtgatatga tggtagcgcg gaatgtggac agccgctgaa    7020
ccggccagtg gccgattcat ctggctacac ttggtcacca gcttctccgt caccccctcg    7080
atgtcgtagg cttgattgaa ctccacgcgg attccgttgt tcacagtgtc ggggagaatg    7140
taaaggatgc tgggagggca ctggaaggcg acattcttcc gaagaatatg cccgtccttc    7200
ttaaagttttt ctccagtcag agtcacccgg ttgtagatag atcccctctc ataggtgacc    7260
atcgcgcggg tcttgtacac tccatctccc tcaaaagaaa tggtgcgctc ttgggtataa    7320
ccttccggca tggcggattt gaagaagtcc ttaatgtggc tagggtactt agcaaaacac    7380
tgcactccat acgagagggt tgacacaagg gtggcccaag gcactggcag atctccagtg    7440
gtacagatat acttggcctt aatggttcca gtcgtagcgt ccccggttcc ttctccccttg    7500
atgatgaact tcattccttc gacgtccct tccagctcgg tgatgtacgg aatctccttc    7560
tcaaacagct tagcaccttc ggtcagggca gtcatggtgg cggcccttct gcaaaaagaa    7620
caagcaagct cttgtctatg agaagaggct gcgggagaag aaagtcagat tagcgtggcc    7680
agtccccctcc ccccaccccgc ctccattccc gccgcatgcc ccatcacgtc ctctaccatc    7740
ctctgcaatg cggagcctgg gctcggcttc cggacctcgc accagcgccc ctaaacccgt    7800
acagcgtcct tcccccccatt cctaatttcc attcctctcc ggcctcctgc ggcccagtcc    7860
ttttttttct tttcttttttc acctggcact gcacaagaag atgcggctgt ctctagaaca    7920
gggaggacga gagagcacca gggaggggctg cagtccgtat ttataggaac tggatggtgg    7980
ggggagctga tgacgcgcgc cccgcctccc gctcggctca tccagtccca gctcaagggc    8040
gcagaggcct gagctacgtg caccccgtaaa gccgcgagta gctgggcctc tctcattccc    8100
cccctccctc ttttttggacc cgcctcgttt ttgaaatgtg cacgcaccaa gcgtgtgggc    8160
tccgacctga gagggggagg ggagctgaga ttgtcccgcc gaggaagtga ccggatgagg    8220
gttcccagga taggactcag ggaatacaga ctatggatta aggacgagga gtccttggag    8280
tgtgcaccaa ggacatccag gacccagaaa ccagaaagct gcttcccgaa taaaatggga    8340
gaatctgaga gctgcaggaa ccaggggaaat ggagcagaag tgtgggtctg cccaaggctg    8400
ccccatcgaa ctttctccctta ttagtgaaaa ggcttaggag aagttgagga tcttctcgtt    8460
gttcttcgga agactactct ggagacgtct accgggtagg ggaggcgctt ttcccaaggc    8520
agtctggagc atgcgcttta gcagcccccgc tgggcacttg gcgctacaca agtgcctct    8580
ggcctcgcac acattccaca tccaccggta ggcgccaacc ggctccgttc tttggtggcc    8640
ccttcgcgcc acccttctact cctccccctag tcaggaagtt cccccccgcc ccgcagctcg    8700
cgtcgtgcag gacgtgacaa atgaagtag cacgactcac tagtctccgtg cagatggaca    8760
gcaccgctga gcaatggaag cgggtaggcc tttgggggcag cggccaatag cagctttgct    8820
ccttcgcttt ctgagagcag cggccgggaa ggggcggtgc gggaggcggg gtgtggggcg    8880
gtagtgtggg ccctgttcct gcccgcgcgg tgttccgcat tctgcaagcc tccggagcgc    8940
acgtccgtct caggggcagc ttgcttgttc tttttgcaga agctcagaat aaacgctcaa    9000
ctttggccgc caccatggca ctccctgtca ccgcccctcct cctcccactc gccctcttgc    9060
tgcacgccgc tcgcccggat attcagatga cgcagaccac ctcaagtctg tcggcctccc    9120
ttggtgatcg ggtcaccatt tcctgccgag ccagccagga catctccaag tacctgaact    9180
ggtaccagca gaagcccgac gggaccttgca agctgctgat ctaccatacc tcccggctgg    9240
atagcggggt gccgtcaagg tttagcggat cgggatccgc caccgactac tcgctgacta    9300
tctccaactt ggaacaagag gacatcgcca cctacttctg tcaacaaggg aatactctgc    9360
cctacacttt cggcgggggga accaagctcg agatcactgg cggcggcggc tcgggcggtg    9420
gtggatccgg gggcggttgc tccgggtca agcttcagga agccgaccc ggcctggtgg    9480
caccgtcaca atccctatcc gtgacatgca ccgtcagcgg agtgtcgctg cccgattacg    9540
gagtgtcttg gattaggcag ccccccgcgca aaggtcttga gtggctggga gtgatctggg    9600
gatcagagac tacctactac aacagcgccc tcaagtcgag gctcaccatc atcaaggaca    9660
actccaagtc ccaagtgttt ctgaagatga actccctgca aactgacgac accgccatct    9720
actactgcgc gaagcactac tactacgggg gaagctacgc tatggactat tggggacagg    9780
gaacttccgt gactgtgtcc agcaccacga caccagcccc gcgccgcc acccccgccc    9840
cgaccattgc gagccagccg ctgagccttc ggccggaagc ctgcaggccc gcggccggcg    9900
gagccgtgca caccagagga ctggacttcg cctgcgatat ctatatctgg gcgcctctgg    9960
ccggaacctg tggagtcctg ctgctgtcac tcgtgattac tctgtactgc aagcgcggtc    10020
ggaagaagct gctctacatt ttcaagcaac ctttcatgcg gccagtgcag accactcagg    10080
aagaagatgg ctgttcctgc cggttccctg aagaagaaga gggcggctgc gaattgagag    10140
tgaagtttctc ccgctcggct gacgctcccg cctacaaaca ggggcagaac cagctgtata    10200
acgaactgaa cctcggccgc cgcgaggaat acgacgtgct ggacaagcgg agaggccgca    10260
atcctgagat gggggggaaag ccccggagaa agaaccctca ggagggcctg tacaatgagc    10320
tgcagaaaga caaaatggcc gaggcgtaca gcgagatcgg catgaagggc gaacgccgga    10380
gaggaaaggg acacgacgga ctgtaccagg gactgtccac cgcgaccaag gatacctacg    10440
acgccctgca catgcaggca ctgccacctc ggtgagctgg agcctcggta gccgttcctc    10500
ctgcccgctg ggcctcccaa cgggccctcc tccctccttt gcaccggccc ttcctggtct    10560
ttgaataaag tttacctgac tcatggtcct ttcacttttca catgggattt cccagttatg    10620
aaattaataa aaatcagtga tttccacatc tgtgtgtgcc tgtgccaggc tgggtgggga    10680
acaggaggcc gagatgattc cgggaactgt cagaaggaat caatgatttc cacatcctgt    10740
ctgtcttatg tcttgggggg tggggaggcc aggaagattc caggaaggtc agagtcaatc    10800
aatggttttcc acatctctca gtgcctctat ctggaggcca ggtaggctg gccttggggg    10860
aggggggaggc cagaatgact ccaagagcta caggaagggg ggaggggaa aaaggccaga    10920
ataattccag gaaccgccaa gaagatgacg tcgaggagaa gttccccaac tttcccgcct    10980
ctcagccttt gaaagaaaga aagggagggg ggcaggccgc gtgcagccgc gagcggtgct    11040
gggctcggga tccaattccc catctcagtc gttccaaag tcctcctgtt tcatccaagc    11100
gtgtaagggt cccccgtcctt gactcccctag tgtcctgctg cccacagtcc agtcctggaa    11160
accagcaccg atcacctccc atcggggcaa tctcagtccc ttcccccta cgtcgggcc    11220
cacacgctcg gtgcgtgccc agttgaacca ggcggctgcg gaaaaaaaaa agcggggaga    11280
aagtagggcc cggctactag cggttttacg ggcgcacgta gctcaggcct caagaccttg    11340
ggctgggact ggctgagcct ggcggggaggc ggggtccgag tcaccgcctg ccgccgcgcc    11400
```

```
cccggtttct ataaattgag cccgcagcct cccgcttcgc tctctgctcc tcctgttcga   11460
cagtcagccg catcttcttt tgcgtcgcca gggggagctt gcttgttctt tttgcagaag   11520
ctcagaataa acgctcaact ttggccgcca cc                                 11552

SEQ ID NO: 258          moltype = DNA   length = 4980
FEATURE                 Location/Qualifiers
misc_feature            1..4980
                        note = Synthetic
source                  1..4980
                        mol_type = other DNA
                        organism = synthetic construct
SEQUENCE: 258
gagtctctct ggttagacca gatctgagcc tgggagctct ctggctaact agggaaccca   60
ctgcttaagc ctcaataaag cttgccttga gtgcttcaag tagtgtgtgc ccgtctgttg   120
tgtgactctg gtaactagag atccctcaga ccctttagt cagtgtggaa aatctctagc    180
agtggcgccc gaacagggac ttgaaagcga aagggaaacc agaggagctc tctcgacgca   240
ggactcggct tgctgaagcg cgcacggcaa gaggcgaggg gcggcgactg gtgagtacgc   300
caaaaatttt gactagcgga ggctagaagg agagagatgg gtgcgagagc gtcagtatta   360
agcgggggag aattagatcg cgatgggaaa aaattcggtt aaggccaggg ggaaagaaaa   420
aatataaatt aaaacatata gtatgggcaa gcagggagct agaacgattc gcagttaatc   480
ctggcctgtt agaaacatca gaaggctgta gacaaatact gggacagcta caaccatccc   540
ttcagacagg atcagaagaa cttagatcat tatataatac agtagcaacc ctctattgtg   600
tgcatcaaag gatagagata aaagacacca aggaagcttt agacaagata gaggaacagc   660
aaaacaaaag taagaccacc gcacagcaag cggccgctga tcttcagacc tggaggagga   720
gatatgaggg acaattggag aagtgaatta tataaatata agtagtaaaa aattgaacca   780
ttaggagtag cacccaccaa ggcaaagaga agagtggttgc agagagaaaa aagagcagtg   840
ggaataggag ctttgttcct tgggttcttg ggagcagcag gaagcactat gggcgcagcg   900
tcaatgacgc tgacggtaca ggccagacaa ttattgtctg gtatagtgca gcagcagaac   960
aatttgctga gggctattga ggcgcaacag catctgttgc aactcacagt ctggggcatc   1020
aagcagctcc aggcaagaat cctggctgtg gaaagatacc taaaggatca acagctcctg   1080
gggatttggg gttgctctgg aaaactcatt tgcaccactg ctgtgccttg aatgctagt    1140
tggagtaata aatctctgga acagatttgg aatcacacga cctggatgga gtgggacaga   1200
gaaattaaca attacacaag cttaatacac tccttaattg aagaatcgca aaaccagcaa   1260
gaaaagaatg aacaagaatt attggaatta gataaatggg caagtttgtg gaattggttt   1320
aacataacaa attggctgtg gtatataaaa ttattcataa tgatagtagg aggcttggta   1380
ggtttaagaa tagttttgc tgtactttct atagtgaata gagttaggca gggatattca   1440
ccattatcgt ttcagaccca cctcccaacc ccgaggggac ccgacaggcc cgaaggaata   1500
gaagaagaag gtggagagag agacagagac agatccattc gattagtgaa cggatctcga   1560
cggtatcggt taacttttaa aagaaaaggg gggattgggg ggtacagtgc aggggaaaga   1620
atagtagaca taatagcaac agacatacaa actaaagaat tacaaaaaca aattacaaaa   1680
attcaaaatt tttgtggtaa gcaggtatcg atcacgagac tagcctcgag atcgaaactt   1740
gatctgtcgc cgcaattcaa acttcgtgag gctccggtgc ccgtcagtga cctgctatac   1800
tctggaacg gctccggtgc ccgtcagtgg gcagagcgca catcgcccac agtccccgag   1860
aagttggggg gaggggtcgg caattgaacg ggtgcctaga aaggtggcg cggggtaaac   1920
tgggaaagtg atgtcgtgta ctggctccgc cttttttccg agggtggggg agaaccgtat   1980
ataagtgcag tagtcgccgt gaacgttctt tttcgcaacg ggtttgccgc cagaacacag   2040
ctgaagcttc gaggggctcg catctctcct tcacgcgccc gccgccctac ctgaggccgc   2100
catccacgcc ggttgagtcg cgttctgccg cctcccgcct gtggtgcctc ctgaactgcg   2160
tccgccgtct aggtaagttt aaagctcagg tcgtgaccgg gcctttgtcc ggcgctccct   2220
tggagcctac ctagactcag ccggctctcc acgctttgcc tgaccctgct tgctcaactc   2280
tacgtctttg tttcgttttc tgttctgcgc cgttacagat ccaagctgtg accggcgcct   2340
acgctagacg ccaccgtct caggggagct tgcttgttct ttttgcagaa gctcagaata   2400
aacgctcaac tttggccgcc accatggcac tcctgtcac cgccctcctc ctcccactcg   2460
ccctcttgct gcacgccgct cgcccggata ttcagatgac gcagaccacc tcaagtctgt   2520
cggcctccct tggtgatcgg gtcaccattt cctgccgagc cagccaggac atctccaagt   2580
acctgaactg gtaccagcag aagcccgacg ggaccgtgaa gctgctgatc taccatacct   2640
cccggctgca tagcggggtg ccgtcaaggt ttagcggatc gggatccggc accgactact   2700
cgctgactat ctccaacttg gaacaagagg acatcgccac ctacttctgt caacaaggga   2760
atactctgcc ctacactttc ggcggggaa ccaagctcga aatcactggc ggcggcggct    2820
cgggcggtgg tggatccggg ggcggtggct ccgaggtgca gcttcaggaa tccggaccgg   2880
gcctggtggc accgtcacaa tccctatccg tgacatgcac cgtcagcgga gtgtcgctgc   2940
ccgattacgc agtgtcttgg attaggcagc cccgcgcaa aggtcttgag tggctgggag   3000
tgatctgggg atcagagact acctactaca acagcgccct caagtcgagg ctcaccatca   3060
tcaaggacaa ctccaagtcc caagtgtttc tgaagatgaa ctccctgcaa actgacgaca   3120
ccgccatcta ctactgcgcg aagcactact actacggggg aagctacgct atggactatt   3180
ggggacaggg aacttccgtg actgtgtcca gcaccacgac accagccccg cgccgccga   3240
cccccgcccc gaccattgcg agccagccgc tgagccttcg gccggaagcc tgcaggcccg   3300
cggccggcgg agccgtgcac accagaggac tggacttcgc ctgcgatatc tatatctggg   3360
cgcctctggc cggaacctgt ggagtcctgc tgctgtcact ggtgattact ctgtactgca   3420
agcgcggtcg gaagaagctg ctctacattt tcaagcaacc tttcatgcgg ccagtgcaga   3480
ccactcagga agaagatggc tgttcctgcc ggttccctga agaagaagag ggcggctgcg   3540
aattgagagt gaagttctcc cgctcggctg acgctcccgc ctacaaacag gggcagaacc   3600
agctgtataa cgaactgaac ctcgggcgcc gcgaggaata cgacgtgctg gacaagcgga   3660
gaggccgcga tcctgagatg gggggaaagc ccggagaaga gaacccagag gagggcctgt   3720
acaatgagct gcagaaagac aaaatggccg aggcgtacag cgagatcggc atgaagggcg   3780
aacgccggag aggaaaggga cacgacggac tgtaccaggg actgtccacc gcgaccaagg   3840
ataccctacga cgccctgcac atgcaggcac tgccacctcg gtgataaaag cgtcttcttc   3900
ctgttaatca acctctggat tacaaaattt gtgaaagatt gactggtatt cttaactatg   3960
ttgctccttt tacgctatgt ggatacgctg ctttaatgcc tttgtatcat gctattgctt   4020
```

```
cccgtatggc tttcattttc tcctccttgt ataaatcctg gttgctgtct ctttatgagg    4080
agttgtggcc cgttgtcagg caacgtggcg tggtgtgcac tgtgtttgct gacgcaaccc    4140
ccactggttg gggcattgcc accacctgtc agctcctttc cgggactttc gctttccccc    4200
tcccattgc cacggcggaa ctcatcgccg cctgccttgc ccgctgctgg acaggggctc     4260
ggctgttggg cactgacaat tccgtggtgt tgtcgggaa gctgacgtcc tttccgcggc    4320
tgctcgcctg tgttgccacc tggattctgc gcgggacgtc cttctgctac gtcccttcgg    4380
ccctcaatcc agcggacctt ccttcccgcg cctgctgcc ggctctgcgg cctcttccgc    4440
ctcttcgcct tcgccctcag acgagtcgga tctcccttg ggccgcctcc ccgcccatgt     4500
atctttttca cctgtgcctt gttttttgcct gtgttccgcg tcctactttt caagcctcca    4560
agctgtgcct tgggcggctt tggggcatgg acatagatcc ctataaagaa tttggttcat    4620
cttatcagtt gttgaatttt cttcctttgg actcagatcg ggaattgcgc acgcagtggt    4680
acctttaaga ccaatgactt acaaggcagc tgtagatctt agccacttt taaaagaaaa    4740
gggggactg aagggctaa ttcactccca acgaagaaaa gatctgcttt ttgcttgtac      4800
tgagtctctc tggttagacc agatctgagc ctgggagctc tctggctaac tagggaaccc    4860
actgcttaag cctcaataaa gcttgccttg agtgcttcaa gtagtgtgtg cccgtctgtt    4920
gtgtgactct ggtaactaga gatccctcag acccttttag tcagtgtgga aaatctctag    4980

SEQ ID NO: 259         moltype = DNA  length = 6411
FEATURE                Location/Qualifiers
misc_feature           1..6411
                       note = Synthetic
source                 1..6411
                       mol_type = other DNA
                       organism = synthetic construct
SEQUENCE: 259
gagtctctct ggttagacca gatctgagcc tgggagctct ctggctaact agggaaccca     60
ctgcttaagc ctcaataaag cttgccttga gtgcttcaag tagtgtgtgc ccgtctgttg    120
tgtgactctg gtaactagag atccctcaga ccctttagt cagtgtggaa aatctctagc     180
agtggcgccc gaacagggac ttgaaagcga agggaaaacc agaggagctc tctcgacgca    240
ggactcggct tgctgaagcg cgcacggcaa gaggcgaggg gcggcgactg gtgagtacgc    300
caaaaatttt gactagcgga ggctagaagg agagagatgg gtgcgagagc gtcagtatta    360
agcgggggag aattagatcg cgatgggaaa aaattcggtt aaggccaggg ggaaagaaaa    420
aatataaatt aaaacatata gtatgggcaa gcagggagct agaacgattc gcagttaatc    480
ctggcctgtt agaaacatca gaaggctgta gacaaatact gggacagcta caaccatccc    540
ttcagacagg atcagaagaa cttagatcat tatataatac agtagcaacc ctctattgtg    600
tgcatcaaag gatagagata aaagacacca aggaagcttt agacaagata gaggaacagc    660
aaaacaaaag taagaccacc gcacagcaag cggccgctga tcttcagacc tggaggagga    720
gatatgaggg acaattggag aagtgaatta tataatata aagtagtaaa aattgaacca    780
ttaggagtag cacccaccaa ggcaaagaga agagtggtgc agagagaaaa aagagcagtg    840
ggaataggag ctttgttcct tgggttcttg ggagcagcag gaagcactat gggcgcagcg    900
tcaatgacgc tgacggtaca ggccagacaa ttattgtctg gtatagtgca gcagcagaac    960
aatttgctga gggctattga ggcgcaacag catctgttgc aactcacagt ctggggcatc   1020
aagcagctcc aggcaagaat cctggctgtg gaaagatacc taaaggatca acagctcctg   1080
gggatttggg gttgctctgg aaaactcatt tgcaccactg ctgtgccttg gaatgctagt   1140
tggagtaata aatctctgga acagatttgg aatcacacga cctggatgga gtgggacaga   1200
gaaattaaca attacacaag cttaatacac tccttaattg aagaatcgca aaaccagcaa   1260
gaaaagaatg aacaagaatt attggaatta gataaatggg caagtttgtg gaattggttt   1320
aacataacaa attggctgtg gtatataaaa ttattcataa tgatagtagg aggcttggta   1380
ggtttaagaa tagtttttgc tgtactttct atagtgaata gagttaggca gggatattca   1440
ccattatcgt ttcagaccca cctcccaacc ccgaggggac ccgacaggcc cgaaggaata   1500
gaagaagaag gtggagagag agacagagac agatccattc gattagtgaa cggatctcga   1560
cggtatcggt taactttta agaaaaaggg gggattgggg ggtacagtgc agggggaaaga   1620
atagtagaca taatagcaac agacatacaa actaaagaat tacaaaaaca aattacaaaa   1680
attcaaaatt tttgtggtaa gcaggtatcg atcacgagac tagcctcgag gcctgctatt   1740
gtcttgccaa tcctccccct tgctgtcctg ccccacccca ccccccagaa tagaatgaca   1800
cctactcaga caatgcgatg caatttcctc attttattag gaaaggacag tgggagtggc   1860
accttccagg gtcaaggaag gcacggggga ggggcaaaca acagatggct ggcaatcact   1920
tccgtgagaa caggctaccc agcaggacca ctccggccac agtcatcccc gtcaagaacc   1980
agcgattgaa ccttttctgg cccttccggg attcggcagc ggcattgttt ccgtacagct   2040
ccacgaaagt gtcccatccg ccgttttcct gaatcaggg ctccaggtga tcgttgaggt    2100
aggtggccat ccaggctgcg attctggaca ccagcacttg catctctttg tccacggact   2160
cgacgcacag agcgccacca aggagaagaa aggccacgat ccgtcccag ttcacgccat    2220
cccggaagag ttcgttgacg acttgttcaa acgactggta cgcggttccg ggggtgatgt   2280
ggagttgcga ggtcaagtcg gagaacgccc gtctgtatct cagctcgaat tcgtcccgcg   2340
cctcgcgaag ggcctgcttc acagcggcca ttgaatgac ttcgcgggca tccagggagg    2400
atgaatgtcc ggtcgcgccg ttcacggcg gggagtcggc aagtgccaa gaagggtttc     2460
cgttgatggc cgacgggtt tccatctcgc tctcggtccc ttcaggtgct tcagtcctgt   2520
tctcttccac gtcgctgaac tggctccacg agtagccctt ctgggacagc ttatagctt    2580
ggaagtccac cacgagctcg cggttggact tgacatggt ggcggccaa gttgagcgtt    2640
tattctgagc ttctaggaaa aagaagaagg aagctcccct gagacggacg tgcgctccgg   2700
aggcttgcag aatgcggaac accgcgcggg caggaacagg gcccacacta ccgcccaca    2760
ccccgcctcc cgcaccgccc cttcccggcc gctgctctca gaaagcgaag gagcaaagct   2820
gctattggcc gctgccccaa aggcctaccc gcttccattg ctcagcggtg ctgtccatct   2880
gcacgaact agtgagtcgt gctacttcca tttgtcactg cctgcagctg gcgagctgcg   2940
gggcgggggg gaacttcctg actagggag gagtagaagg tggcgacgaa gggccaccaa   3000
agaacggagc cggttggcgc ctaccggtgg atgtggaatg tgtgcgaggc cagaggccac   3060
ttgtgtagcg ccaagtgccc agcggggctg ctaaagcgca tgctcagac tgccttggga    3120
aaagcgcctc ccctacccgg tagacgtctc cagagggatc catcgaaact tgatctgtcg   3180
ccgcaattca aacttcgtga ggctccggtg cccgtcagtg acctgctata tctctggagac  3240
```

-continued

```
ggctccggtg cccgtcagtg ggcagagcgc acatcgccca cagtcccga gaagttgggg 3300
ggaggggtcg gcaattgaac gggtgcctag agaaggtggc gcggggtaaa ctgggaaagt 3360
gatgtcgtgt actggctccg ccttttccc gagggtgggg gagaaccgta tataagtgca 3420
gtagtcgccg tgaacgttct ttttcgcaac gggtttgccg ccagaacaca gctgaagctt 3480
cgaggggctc gcatctctcc ttcacgcgcc cgccgcccta cctgaggccg ccatccacgc 3540
cggttgagtc gcgttctgcc gcctcccgcc tgtggtgcct cctgaactgc gtccgccgtc 3600
taggtaagtt taaagctcag gtcgtgaccg ggcctttgtc cggcgctccc ttggagccta 3660
cctagactca gccggctctc cacgctttgc ctgaccctgc ttgctcaact ctacgtcttt 3720
gtttcgtttt ctgttctgcg ccgttacaga tccaagctgt gaccggcgcc tacgctagac 3780
gccaccgtc tcaggggagc ttgcttgttc tttttgcaga agctcagaat aaacgctcaa 3840
ctttggccgc caccatggca ctccctgtca ccgccctcct cctcccactc gccctcttgc 3900
tgcacgccgc tcgcccggat attcagatga cgcagaccac ctcaagtctg tcggcctccc 3960
ttggtgatcg ggtcaccatt tcctgccgag ccagccagga catctccaag tacctgaact 4020
ggtaccagca gaagcccgac gggaccgtga agctgctgat ctaccatacc tcccggctgc 4080
atagcgggt gccgtcaagg tttagcggat cgggatccgg caccgactac tcgctgacta 4140
tctccaacttt ggaacaagag gacatcgcca cctacttctg tcaacaaggg aatactctgc 4200
cctacacttt cggcggggga accaagctcg aaatcactgg cggcggcggc tcgggcggtg 4260
gtggatccgg gggcggtggc tccgagtca agcttcagga atccggaccc ggcctggtgg 4320
caccgtcaca atccctatcc gtgacatgca ccgtcagcgg agtgtcgctg cccgattacg 4380
gagtgtcttg gattaggcag ccccgcgca aaggtcttga gtggctggga gtgatctggg 4440
gatcagagac tacctactac aacagcgccc tcaagtcgag gctcaccatc atcaaggaca 4500
actccaagtc ccaagtgttt ctgaagatga actccctgca aactgacgac accgccatct 4560
actactgcgc gaagcactac tactacgggg gaagctacgc tatggactat tggggacagg 4620
gaacttccgt gactgtgtcc agcaccacga caccagcccc gcgcccgccg accccgccc 4680
cgaccattgc gagccagccg ctgagccttc ggccggaagc ctgcaggccc gcggccggcg 4740
gagccgtgca caccagagga ctggacttcg cctgcgatat ctatatctgg gcgcctctgg 4800
ccggaacctg tggagtcctg ctgctgtcac tcgtgattac tctgtactgc aagcgcggtc 4860
ggaagaagct gctctacatt ttcaagcaac ctttcatgcg gccagtgcag accactcagg 4920
aagaagatgg ctgttcctgc cggttccctg aagaagaaga gggcggctgc gaattgagag 4980
tgaagttctc ccgctcggct gacgctcccg cctacaaaca ggggcagaac cagctgtata 5040
acgaactgaa cctcgggcgc cgcgaggaat acgacgtgct ggacaagcgg agaggccgcg 5100
atcctgagat gggggggaaag cccggagaa agaaccctca ggagggcctg tacaatgagc 5160
tgcagaaaga caaaatggcc gaggcgtaca gcgagatcgg catgaagggc gaacgccgga 5220
gaggaaaggg acacgacgga ctgtaccagg gactgtccac cgcgaccaag gatacctacg 5280
acgccctgca catgcaggca ctgccacctc ggtgataaaa gcgtcttctt cctgttaatc 5340
aacctctgga ttacaaaatt tgtgaaagat tgactggtat tcttaactat gttgctcctt 5400
ttacgctatg tggatacgct gctttaatgc ctttgtatca tgctattgct tcccgtatgg 5460
ctttcatttt ctcctccttg tataaatcct ggttgctgtc tctttatgag gagttgtggc 5520
ccgttgtcag gcaacgtggc gtggtgtgca ctgtgtttgc tgacgcaacc cccactggtt 5580
ggggcattgc caccacctgt cagctccttt ccgggacttt cgctttcccc ctccctattg 5640
ccacggcgga actcatcgcc gcctgccttg cccgctgctg gacaggggct cggctgttgg 5700
gcactgacaa ttccgtggtg ttgtcgggga agctgacgtc ctttccgcgg ctgctcgcct 5760
gtgttgccac ctggattctg cgcgggacgt ccttctgcta ctcccttcg gcctcaatc 5820
cagcggacct tccttcccgc ggcctgctgc cggctctgcg gcctcttccg cctcttcgcc 5880
ttcgccctca gacgagtcgg atctcccttt gggccgcctc cccgcccatg tatctttttc 5940
acctgtgcct tgttttgcc tgtgttccgc gtcctacttt tcaagcctcc aagctgtgcc 6000
ttgggcggct ttggggcatg gacatagatc cctataaaga atttggttca tcttatcagt 6060
tgttgaattt tcttcctttg gactcagatc gggaattgcg cacgcagtgg tacctttaag 6120
accaatgact tacaaggcag ctgtagatct tagccacttt ttaaaagaaa aggggggact 6180
ggaagggcta attcactccc aacgaagaaa agatctgctt tttgcttgta ctgagtctct 6240
ctggttagac cagatctgag cctgggagct ctctggctaa ctagggaacc cactgcttaa 6300
gcctcaataa agcttgcctt gagtgcttca agtagtgtgt gcccgtctgt tgtgtgactc 6360
tggtaactag agatccctca gacccttta gtcagtgtgg aaaatctcta g 6411
```

```
SEQ ID NO: 260       moltype = DNA   length = 458
FEATURE              Location/Qualifiers
misc_feature         1..458
                     note = Synthetic
source               1..458
                     mol_type = other DNA
                     organism = synthetic construct
SEQUENCE: 260
tctaccgggt aggggaggcg ctttcccaa ggcagtctgg agcatgcgct ttagcagccc  60
cgctgggcac ttggcgctac acaagtggcc tctggcctcg cacacattcc acatccaccg 120
gtaggcgcca accggctccg ttctttggtg gcccctttcg gccaccttct actcctcccc 180
tagtcaggaa gttccccccc gccccgcagc tcgcgtcgtg caggacgtga caaatggaag 240
tagcacgact cactagtctc gtgcagatgg acagcaccgc tgagcaatgg aagcgggtag 300
gcctttgggg cagcggccaa tagcagcttt gctccttcgc tttctgagag cagcggccgg 360
gaaggggcgg tgcgggaggc ggggtgtggg gcggtagtgt gggccctgtt cctgcccgcg 420
cggtgttccg cattctgcaa gcctccggag cgcacgtc                          458
```

MODIFICATION OF CAR-T CELLS

CROSS-REFERENCE TO RELATED APPLICATIONS

This application claims the benefit of U.S. Provisional Application No. 63/491,171, filed on Mar. 20, 2023, and U.S. Provisional Application No. 63/321,262, filed on Mar. 18, 2022. This application is also a continuation-in-part of U.S. Nonprovisional patent application Ser. No. 17/429,342, filed on Aug. 8, 2021, which is a National Stage of International Application No. PCT/US2020/017283, filed on Feb. 7, 2020, which claims the benefit of U.S. Provisional Application No. 62/803,142, filed on Feb. 8, 2019. Each of these applications is incorporated by reference herein in its entirety.

SEQUENCE LISTING

A Sequence Listing has been submitted electronically in XML format and is hereby incorporated by reference in its entirety. The XML copy, created on Jun. 15, 2023, is named ATUM-BCL-USCIP final.xml and is 495,039 bytes in size.

BACKGROUND

Certain cells, including immune cells, can be modified genetically to provide modified immune cells with engineered therapeutic potential. Indeed, the introduction of DNA into the genomes of T cells is a technique that is core to cell therapy. It allows T cells to be re-programmed with genes encoding molecules including chimeric antigen receptors ("CAR"s), engineered T cell receptors, antibodies, including anti-checkpoint antibodies, and genes to reduce anergy and exhaustion.

T cells modified to express a CAR provide the basis for current FDA-approved CAR-T cell therapies. In such therapies, T cells are able to discriminate and kill tumor cells because of the CAR they have acquired by gene transfer. There is considerable interest in improving CAR-T cell therapies and using them for an expanded range of cancers. Similarly, there is interest in using other genetic approaches to redirect T cells and enhance T cell therapeutic efficacy and durability.

The genetic modification of T cells can be accomplished by a variety of methods. Introduction of heterologous (i.e., not naturally found in the target cell) DNA is often achieved using viral delivery. T cells can also be modified by electroporation (among other techniques) with mRNA or DNA. In the latter case, transposons provide an attractive vehicle for efficiently delivering large genetic payloads into T cells. See, e.g., U.S. Pat. No. 10,041,077, which is incorporated by reference herein in its entirety. Electroporation can, however, be an inefficient process, especially when large DNA molecules are involved, when the transferred gene(s) compromises viability, or when cellular fitness/viability prior to electroporation is low. Regardless of the means for genetic modification, for immune cells to respond adequately to threats to the body, they must be able to survive or persist for long enough to attack their targets.

For therapies and research that require the ex vivo manipulation of immune cells, it is advantageous for the immune cells to proliferate. However, a variety of factors could become obstacles to improving the persistence and efficacy of CAR-T cells during production, pre-infusion processing, and in vivo interactions, and eventually lead to tumor relapse or undesired tumor control. For example, neither ex vivo culture conditions nor certain in vivo environments (for example, the environment within a solid tumor) are optimal for growth of immune cells. In another example, T cells from heavily pre-treated lymphoma patients show lower rates of ex vivo expansion and clinical response when engineered with anti-CD19 CAR than T cells from untreated patients. Early CD19+ relapse owing to low in vivo persistence and impaired efficacy accounts for a large proportion of the high relapse rate.

A need exists for methods that controllably enhance the function, persistence, and proliferation of human T cells, particularly under conditions that are naturally hostile to the T cells.

SUMMARY

Modified cells of this disclosure include, but are not limited to, those T cells that express an antigen receptor comprising a protein scaffold of the disclosure. Modified T cells of the disclosure include, but are not limited to, those T cells that express a CAR. Modified cells of the disclosure may be further subjected to genomic editing. A genomic editing construct, such as a function (e.g., persistence, proliferation, or cytotoxicity)-improving expression cassette (function-booster gene) that offers survival advantages to the conventional T cell, may be introduced into the modified cells and may be allowed to integrate into the genome of the cell during a subsequent incubation phase. The genome-edited cell is a modified cell that retains at least one of a persistence-, a proliferation-, or a cytotoxicity-improved property. Alternatively, or in addition, modified cells of the disclosure may be subjected to a first expression of a CAR and a second expression of one or more genome editing constructs.

In one aspect, a modified T cell is provided, the modified T cell expressing a heterologous polynucleotide comprising a nucleotide sequence encoding a function (e.g., at least one of persistence, proliferation, or cytotoxicity) booster, e.g., an apoptosis inhibitor. In one aspect, the modified T cell further comprises a CAR.

In one aspect, a modified T cell is provided, the modified T cell expressing: (A) a first heterologous polynucleotide comprising a first nucleotide sequence encoding a CAR; and (B) a second heterologous polynucleotide comprising a second nucleotide sequence encoding a function booster. Alternatively, the first heterologous polynucleotide comprises the first nucleotide sequence encoding the CAR and the second nucleotide sequence encoding the function booster. In either case, at least one of a persistence, a proliferation, or a cytotoxicity of the modified T cell is increased relative to a persistence, a proliferation, or a cytotoxicity of a T cell that does not comprise the first nucleotide sequence and the second nucleotide sequence.

In one aspect, a modified T cell is provided, the modified T cell expressing a first heterologous polynucleotide comprising a first nucleotide sequence encoding a CAR and either: (A) the modified T cell expresses a second heterologous polynucleotide comprising a second nucleotide sequence encoding a function booster; or (B) the first heterologous polynucleotide further comprises a second nucleotide sequence encoding a function booster, the modified T cell characterized by at least one of a persistence, a proliferation, or a cytotoxicity of the modified T cell that is increased relative to a persistence, a proliferation, or a cytotoxicity of a T cell that does not comprise the first nucleotide sequence and either of (A) or (B).

In one aspect, a method is provided, the method comprising: introducing into a primary human T cell: (A) a transposon composition, the transposon composition comprising a transposon, the transposon comprising an antigen receptor, a therapeutic protein, or a sequence encoding the same; and (B) a transposase composition comprising a transposase or a sequence encoding the transposase, to produce modified T cells that express a protein selected from the group consisting of SEQ ID NOs: 239, 240, and 241.

In another aspect, a method is provided for preparing a modified T cell expressing a first heterologous polynucleotide comprising a first nucleotide sequence encoding a CAR and either: (A) the modified T cell expresses a second heterologous polynucleotide comprising a second nucleotide sequence encoding a function booster; or (B) the first heterologous polynucleotide further comprises a second nucleotide sequence encoding a function booster, the modified T cell characterized by at least one of a persistence, a proliferation, or a cytotoxicity of the modified T cell that is increased relative to a persistence, a proliferation, or a cytotoxicity of a T cell that does not comprise the first nucleotide sequence and either of (A) or (B), wherein the method comprises introducing the first heterologous polynucleotide and, where the modified immune cell further expresses a second heterologous polynucleotide comprising a second nucleotide sequence encoding a function-boosting protein, the second heterologous polynucleotide, into a T cell ex-vivo.

In one aspect, a method for producing modified T cells is provided, the method comprising: (A) introducing into a primary human T cell a composition comprising an antigen receptor, a therapeutic protein, or a sequence encoding the same, to produce a modified T cell, wherein the antigen receptor or therapeutic protein is not contained in a transposon, and (B) contacting the modified T cell and a T cell activator composition comprising one or more of an anti-human CD3 monospecific antibody complex, an anti-human CD28 monospecific antibody complex, or a feeder cell engaging the same and an activation supplement to produce a modified T cell, wherein the modified T cell expresses a protein selected from the group consisting of SEQ ID NOs: 239, 240, and 241.

In another aspect, a method is provided for treating a subject having cancer, the method comprising administering a therapeutically effective amount of a modified T cell expressing a first heterologous polynucleotide comprising a first nucleotide sequence encoding a CAR and either: (A) the modified T cell expresses a second heterologous polynucleotide comprising a second nucleotide sequence encoding a function booster; or (B) the first heterologous polynucleotide further comprises a second nucleotide sequence encoding a function booster, wherein at least one of a persistence or a proliferation of the modified T cell is increased relative to a persistence or a proliferation of an otherwise biologically equivalent T cell that does not comprise the first nucleotide sequence and either of (A) or (B), and whereby the modified T cell induces antigen-specific killing of cancer cells in the subject to an extent greater than an otherwise biologically equivalent T cell that does not comprise the first nucleotide sequence and either of (A) or (B).

In one aspect, a polynucleotide is provided, the polynucleotide comprising a first nucleotide sequence encoding a CAR and a second nucleotide sequence encoding a function booster, the polynucleotide comprising a transposon. In one aspect, the CAR comprises an extracellular domain that specifically binds to a CD19 antigen. In one aspect, the function booster is selected from the group consisting of SEQ ID NOs: 239, 240, and 241.

In one aspect, a polynucleotide is provided, the polynucleotide comprising a first nucleotide sequence encoding a CAR and a second nucleotide sequence encoding a function booster, the polynucleotide comprising a lentivirus. In one aspect, the CAR comprises an extracellular domain that specifically binds to a CD19 antigen. In one aspect, the function booster is selected from the group consisting of SEQ ID NOs: 239, 240, and 241.

In one aspect, a polynucleotide is provided, the polynucleotide comprising: a first nucleotide sequence encoding a CAR, a second nucleotide sequence encoding a function-boosting protein, and a third nucleotide sequence encoding firefly luciferase, the polynucleotide comprising a transposon, wherein the CAR comprises an extracellular domain that specifically binds to a CD19 antigen, and wherein the function boosting protein is selected from the group consisting of SEQ ID NOs: 239, 240, and 241.

In one aspect, a kit is provided, the kit comprising: (A) a polynucleotide, the polynucleotide comprising: (1) a first nucleotide sequence encoding a CAR; and (2) a second nucleotide sequence encoding a function booster, the polynucleotide comprising a transposon; (B) a transposase capable of transposing the transposon; and, optionally, (C) an anti-hCD19-CD3 bispecific T cell engager (a "BiTE").

BRIEF DESCRIPTION OF THE FIGURES

FIG. 11, row B, represents the overexpression of genes encoding for Bcl-xL, Survivin, and CD28-D124E/T195P protein in the conventional CAR-T and in CAR-Bcl-xL, CAR-Survivin, and CAR-CD28-D124E/T195P T cells, respectively.

FIG. 28, row B, shows a Kaplan-Meier survival curve of all of the mice referred to in FIG. 27 at 124 days.

DETAILED DESCRIPTION

Figure 1:
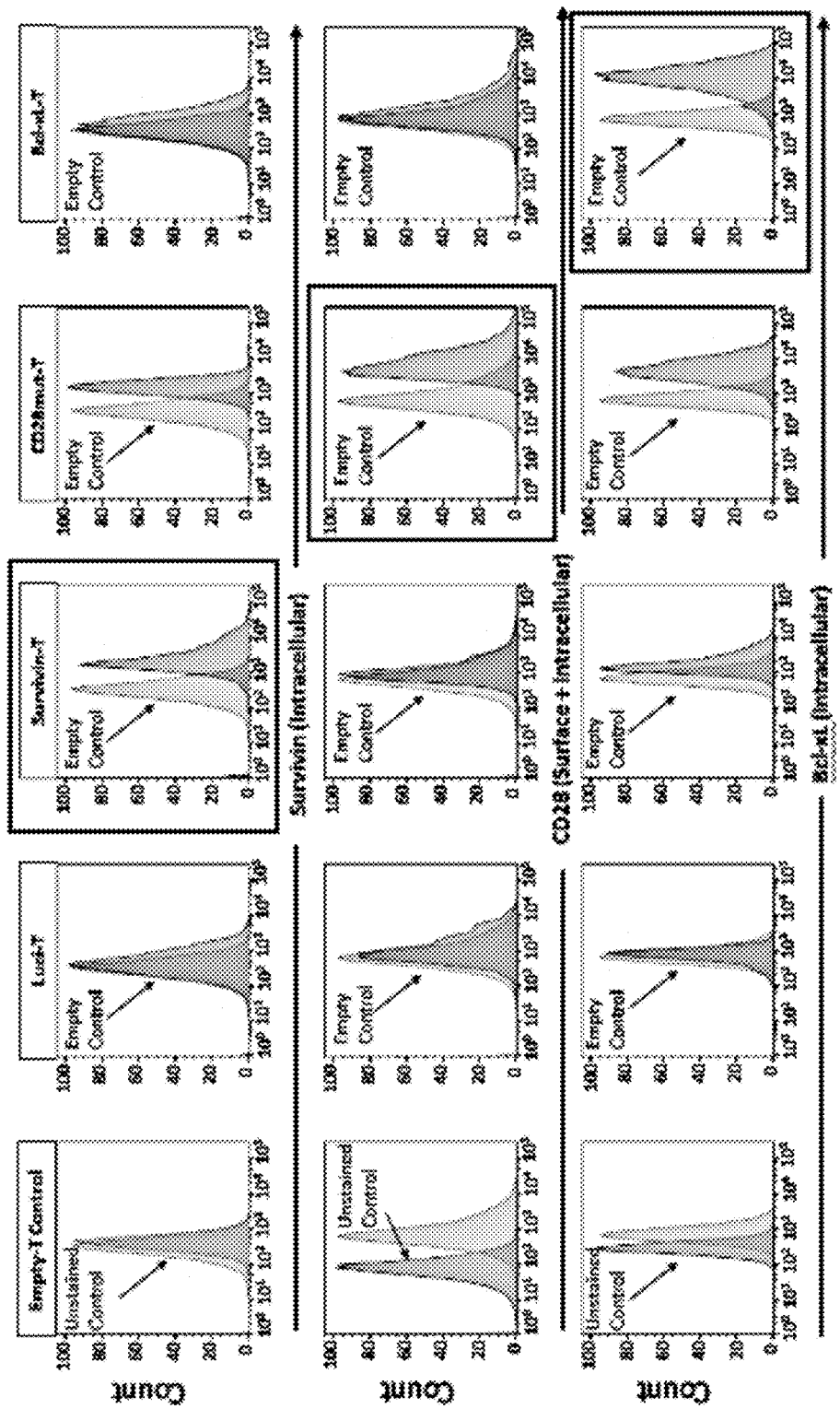
FIG. 1 is a set of FACS data showing the expression of function (persistence)-booster genes encoding Bcl-xL, Survivin, or CD28-D124E/T195P in T cells into which transposons have been transfected ("Gene-T cells"). Luci-T cells and untransfected T cells ("Empty T cells") were included as controls. "Luci-T cells" are T cells expressing genes encoding for firefly luciferase ("ffLuc") and green fluorescent protein ("GFP") but not Bcl-xL, Survivin, or CD28-D124E/T195P.

Viral and non-viral primary human CD8$^+$ T cell genetic manipulation approaches are provided for enhancing CD8$^+$ T cell survival and prolonging a durable CAR-T tumor response. Bcl-xL (BCL2L1) (SEQ ID NO: 239), Survivin (BIRC5) (SEQ ID NO: 240) CD28-D124E/T195P (SEQ ID NO: 241), were identified as potential genetic regulators that result in long-term CD8$^+$ T cell persistence. Bcl-xL, Survivin, or CD28-D124E/T195P, along with a CAR, showed significantly enhanced CD8$^+$ T cell persistence and sustained anti-tumor response in vitro and in vivo.

In one aspect, the Leap-In Transposase® system (DNA TWOPOINTO, Inc. dba ATUM) may be used as a delivery approach to produce stable transgene expression with low genotoxicity and minimal disruption to other essential genes. In another aspect, lentiviral particles may be used as the delivery approach.

Reprogramming CD8$^+$ T Cells for Enhanced Survival Ex Vivo

Several distinct gene candidates were identified that showed a highly concordant, progressive pro-survival effect. Three genes, encoding for Bcl-xL, Survivin, and CD28-D124E/T195P, respectively, reached 99.57% DasherGFP expression after 56 days and maintained above 99% for a 340 day ex vivo culture. The expression of the genes encoding for Bcl-xL, Survivin, and CD28-D124E/T195P were evaluated in long-term cultured cells and were compared to Luci-T cells and/or Empty T cells. Using flow cytometric analysis, increased expression of the genes encoding for Bcl-xL, Survivin, and CD28-D124E/T195P (surface-bound and intracellular) was demonstrated in their gene edited cell lines. Moreover, increased expression of the genes encoding for Bcl-xL and Survivin was observed in a CD28-D124E/T195P gene edited cell line, which again highlighted the importance of these genes in promoting CD8$^+$ T cell survival.

Whether and to what extent the pro-survival effect of Bcl-xL, Survivin, and CD28-D124E/T195P on primary human CD8$^+$ T cells depends on the cytokine-driving effect on resting T cell homeostasis was investigated. The IL-7 and IL-15 provided by the TSF-K562-aAPCs are known to play important roles in memory T progenitors for maintaining the quality and quantity of memory T cells. Here, Gene-T cells were re-stimulated with aCD3/aCD28 Dynabeads, and their proliferation and persistence were determined in the presence or absence of IL-2. In the presence of IL-2, long-term cultured Gene-T cells can still respond to recall expansion and demonstrated superior survival compared to freshly isolated CD8$^+$ T cells from a paired donor. In the absence of IL-2, where freshly isolated normal CD8$^+$ showed a poor fitness leading to drastic cell death, Gene-T cells still demonstrated maintenance of a live cell population. In summary, the functional screen provided insights into reprogramming CD8$^+$ T cells by overexpressing exogenous genes that govern the T cell fitness independently and identified several genetic regulators that play a significant role in promoting CD8$^+$ T cell persistence and survival.

Functional Characterization Revealed that Genes Encoding for Bcl-xL, Survivin, and CD28-D124E/T195P Sustained CD8$^+$ T Cytotoxicity Upon Re-Challenge The effect of increased protein expression in Gene-T cells on T cell function in response to antigenic stimulation was investigated. How each gene affected activation, cytokine release, and cytotoxicity after 6 hours of stimulation with aCD3/aCD28 microbeads in freshly transfected CD8$^+$ T cells was characterized and compared with control Luci-T cells and Empty T cells. Cell surface expression of the early activation marker CD69 and the late activation marker HLA-DR were characterized, while also assaying the secretion of IFN-γ in the supernatant. In comparison with the control Luci-T cells, the transposon-delivered genes did not significantly impact the expression of either of the activation markers CD69 or HLA-DR. Furthermore, there was no significant increase or decrease in the secretion of IFN-γ post-activation in the Gene-T cells.

Having established that the transposon-delivered genes improve T cell survival without affecting normal T cell function, the cytotoxic capabilities of the Gene-T cells were tested using long-term repeated tumor antigen stimulation conditions. Compared to a short-term killing, this evaluation can better reveal if the survival enhancement persists and potentially show a benefit in the recursive killing. The antiCD19/anti-CD3 bi-specific T cell engager, Blinatumomab, was used in a co-culture system to engage T cells and the CD19+ luciferase expressing cell line NALM-6 (NALM-6-Luc). Using this model, the cytotoxic function of the Gene-T cells was evaluated using a luciferase-based tumor cell killing readout, flow cytometry-based T cell quantification, and cytokine secretion. On days 1 and 3, there was no observable difference in BiTE-mediated NALM-6 tumor killing in all tested T cell lines. Upon repeated stimulation over the course of 12 days, Bcl-xL, Survivin, and CD28-D124E/T195P-transfected T cells showed sustained long-term cytotoxicity compared to the normal CD8+ T cell control. The strongest effect was seen with the Bcl-xL-transfected T cells, which sustained >95% killing after seven tumor re-challenges. Analysis of T cell quantification also demonstrated a similar number of T cells up to day 3 followed by a decrease in normal T cells in comparison to the Gene-T cell lines. Cytokine secretion was similar in all cell lines until day 3 before following a similar pattern as that seen in the cytotoxicity and T cell quantification.

Functional and Phenotypical Characterization of Bcl-xL, Survivin, and CD28-D124E/T195P in CAR-T Cells A pro-survival effect of Bcl-xL, Survivin, and CD28-D124E/T195P gene overexpression exists in CD8+ T cells, which leads to a potential benefit in sustaining antigen-specific cytotoxicity upon repetitive tumor challenge. One potential therapeutic use of these long-term survival Gene-T cells that can potentially benefit the clinical outcome is to sustain CAR-T cell killing against relapsed tumors. Bcl-xL, Survivin, and CD28-D124E/T195P, along with Kymriah, a CAR-T cell therapy for B cell lymphomas that targets CD19 and has the 4-1BB co-stimulation gene and CD3 zeta ($\zeta$) activation gene, was transfected into primary human CD8+ T cells to assess the potential long-term survival benefits of these genes in CAR-T cells. Luci-T cells were also generated as a no-effect control. Introducing both the CD19-41BB$\zeta$ CAR and one of the survival genes does not significantly affect the CAR expression in comparison with introducing the CD19-41BB$\zeta$ CAR individually. Similar to genes introduced into CD8+ T cells alone, introduction of these genes in combination with the gene encoding for the CAR increased production of Bcl-xL, Survivin, and CD28-D124E/T195P protein compared with the control T cells. Consistent with the results in Gene-T cells, the overexpression of genes encoding for Bcl-xL, Survivin, and CD28-D124E/T195P also occurred in the CAR-Gene-T cells. The functional performances in activation, cytokine production, and proliferation between CAR-Gene-T cells and conventional CAR-T cells were evaluated. Integration of Bcl-xL, Survivin, and CD28-D124E/T195P genes does not contribute to significant differences in T cell activation compared to CAR-T cells without added survival genes, as assessed by increased CD69 or HLA-DR expression against non-specific stimulus (aCD3/aCD28 beads) or through CAR binding to CD19 on NALM-6 tumor cells. Similar results were observed when cells were assayed for the production of IFN-$\gamma$ after the same stimuli. During two weeks of expansion with TSF-K562 post-CAR-T generation, an improved expansion of CAR-Gene-T cells was observed compared to the conventional CAR-T cells.

The effect of Bcl-xL, Survivin, and CD28-D124E/T195P expression on CAR-T differentiation and long-term memory preservation post-antigen-specific stimulation was investigated. Freshly transfected CAR-Ts and Luci-T cells along with untreated empty-T cells were first stimulated with TSF aAPC for 2 weeks and resting in IL-2 only culture for another 2 weeks before sorting. All sorted CAR-T cells, Luci-T controls, and Empty-T controls were characterized for baseline phenotypes before being co-cultured with NALM-6-Luc at a 1:1 ratio. Periodic phenotyping was performed on D1, 7, 14, 21, and 28. As expected, all CAR-Ts containing a BB$\zeta$ showed a preserved CD45RA−CD62L+ CCR7+ central memory-like population on day 0, whereas Empty-T and Luci-T demonstrated mostly a CD45RA−CD62L+CCR7+ after TSF aAPC stimulation. CAR-Bcl-xL, CAR-Survivin, and CAR-CD28-D124E/T195P T cells showed elevated enrichment of CD45RA−CD62L+ population compared with conventional CAR-T on day 0. Over time, CAR-T failed to preserve the CD45RA-CD62L+ population and demonstrated a gradual shift into CD45RA−CD62L− effector memory-like, and eventually accumulated in the CD45RA+CD62L− terminally differentiated population. In contrast, CAR-Gene-T cells continued to demonstrate populations of central memory-like T cells that expressed CD45RA−CD62L+ or effector-memory like T cells that expressed CD45RA−CD62L for up to 28 days. Greater than 85% of CAR-Bcl-xL-T cells were less differentiated effector-memory like T cells on day 28.

CAR-GEN-T Cells Sustained Cytotoxicity by Persistence Retention and Exhibited a Benefit in Low Dose Administration In Vitro As described herein, Bcl-xL, Survivin, and CD28-D124E/T195P over-expression in CD8+ T cells sustained BiTE mediated cytotoxicity against NALM-6. The ability of these genes to sustain CAR mediated T cell anti-tumor activity by promoting CAR-T persistence was tested. A long-term re-challenge assay was conducted involving co-culturing Nalm-6-Luc with either the CAR-Gene-T cells, conventional CAR-T cells, or mock transfected T cells. The CAR-T cells were evaluated for prolonged cytotoxic capabilities, IFN-$\gamma$ release, and T cell expansion at various time points. Over-expression of Bcl-xL, Survivin, and CD28-D124E/T195P promoted the maintenance of CAR-T cytotoxicity and IFN-$\gamma$ release upon seven re-challenges. In contrast, the conventional CAR-T demonstrated continually decreasing cytotoxic capability and IFN-$\gamma$ secretion. This preservation of cytotoxicity and cytokine release was found to be mainly contributed to by the retention of T cell numbers in Car-Gene-T cells where the population doublings increased over 14 days compared to a significant decrease in conventional 19BBCAR-T cells. Upon normalizing the cytokine production per cell demonstrated that compared to conventional CAR-T, Bcl-xL over-expression contributed to a slightly enhanced impact on cytokine production per cell. CD28-D124E/T195P editing led to increased expansion over the first five days and increased IFN-$\gamma$ production.

Survivin, CD28-D124E/T195P, and Bcl-xL over-expression demonstrated a superior survival benefit in controlling repetitively challenged tumor burden. The ability of these pro-survival genes to retain their benefits in an effector-to-target dilution system was tested, whereby an excessive number of CAR-Gene-T cells were cultured with a single challenge of increasing numbers of tumor cells, on Day 0, and the cytotoxic capacity at each effector-to-target ratio was measured over the course of 15 days. Consistently, CAR-T failed to preserve long-term tumor control, with tumor growth seen after day 5. However, CAR-Gene-T cells over-expressing Survivin, CD28-D124E/T195P, and Bcl-xL demonstrated continual cytotoxic function over the 15 days, with the challenge at an E:T ratio of 1:10 demonstrating almost complete tumor cell killing. At the lowest E:T ratios (1:25 and 1:50), the CAR-Gene-T cells showed continual T cell killing. CAR-Bcl-xL-T cells reached around 40% killing on D15 at the lowest E:T ratio (1:50). Together, these findings indicate that CAR-Gene-T cells may have a therapeutic potential in sustaining long-term tumor control through prolonged survival and functional capabilities with the potential added benefit of being administrated at a lower dose than is currently being used.

CAR-Gene-T Cells Sustained Restored Memory-Like Phenotype Post Tumor Clearance The ability of Bcl-xL, Survivin, and CD28-D124E/T195P over-expression to contribute to CAR T cell differentiation and long-term memory preservation post-antigen-specific stimulation was studied. Freshly transfected CAR T cells, Luci-T cells, and untreated empty T cells were stimulated before undergoing fluorescence activated cell sorting using GFP expression. All sorted CAR-T cell, Luci-T cell, and empty T cell controls were characterized for baseline phenotypes, using expression of surface markers CD45RA, CD62L, and CCR7, before being co-cultured with NALM-6-Luc either bound or unbound, respectively, at a 1:1 ratio on Day 0. Periodical phenotyping was performed on D2, 7, 14, 21, and 28. As expected, all CAR-T cells containing a 4-1BBζ CAR showed a preserved CD45RA−CD62L+ CCR7+ central memory-like population on day 0, whereas Empty-T and Luci-T cells demonstrated mostly CD45RA−CD62L+CCR7+ effector memory-like T cells after the pre-experiment stimulation. CAR-Gene-T cells showed elevated enrichment of CD45RA−CD62L+ population compared with the conventional 19BBCAR T on day 0. Over time, CAR-T cells failed to preserve the CD45RA−CD62L+ population and gradually shifted into CD45RA−CD62L− effector memory-like, eventually accumulating in the CD45RA+CD62L− terminally differentiated population. In contrast, post tumor clearance, the CAR-Gene-T cells all demonstrated significant CD45RA−CD62L+ central memory-like populations on day 28 with >85% of the Bcl-xL over-expressing cells demonstrating the central-memory-like phenotype.

CAR-Gene-T Cells Sustained Persistence In Vivo

The CAR-Gene-T cells were evaluated in vivo. Their roles were first evaluated in an antigen-independent xenograft NSG model. To permit tracking of the T cells and following growth kinetics, all CAR constructs were engineered to include firefly luciferase for BLI based long-term monitoring. CD8$^+$ T cells transfected with CAR constructs or mock transfected were intravenously injected into 6 week old female NSG mice at $5\times10^6$ T cells per mouse (n=5), followed by two administrations of recombinant human interleukin-2 (rhIL-2) to boost the initial in vivo expansion. T cell growth was quantified by periodic BLI and by flow cytometric analysis of T cell numbers from blood samples drawn at predetermined timepoints. During the course of this study, two mice died, one from the Luci-T cells control group on d105 and one from the conventional CAR-T cells group on D108. However, all CAR-Gene-T cell injected mice were healthy by the end of the study (D182). No pathological indications were observed in the mice bearing long-lived CAR-T cells, suggesting that over-expression of Bcl-xL, Survivin, and CD28-D124E/T195P did not induce any T cell lymphoma or leukemia within the duration of this study. Injected T cells expanded equally over the first seven days, likely responding to the injection of rhIL-2. Thereafter, the Luci-T cells and CAR-T cells demonstrated an arrest in their proliferation by d14 followed by a contraction whereby they were both not detectable on d42. However, although CAR-Gene-T cells all showed arrested proliferation by d16, these T cells were still detectable in mice up to 182 days and therefore demonstrated significantly improved persistence compared with the control T cells (P<0.001). The CAR-Bcl-xL-T cells remained remarkably consistent for the duration of the experiment even though there was no antigen present in the mice for the T cells to recognize. Using anti-CD19 CAR and GFP dual expression, flow cytometric quantitation of T cells from mouse blood demonstrated very similar results when compared with the BLI data. Control T cells were undetectable by d56, whereas CAR-Gene-T cells were still detectable by flow cytometry on d182 with the CAR-Bcl-xL-T cells demonstrating the largest population of T cells. Consistent with the in vitro findings, the long-lived CAR-Gene-T cells in the mouse blood expressed CD62L+ CCR7+ while lacking expression of CD45RA, suggesting these cells were central-memory-like T cells. No control T cells were able to be detected in order to assess their expression of the surface markers. To further assess the differentiation status of the CAR-Gene-T cells, the protein expression of the transcriptional factors TCF-1, Bcl-6, TOX, and T-bet were evaluated in comparison with naïve, central memory, effector memory, and effector subset from freshly isolated paired-donor PBMCs. The expression pattern in the CAR-Gene-T cells presented a notable intracellular enrichment of TCF-1 and Bcl-6, a low expression of T-bet, and medium expression of TOX, which is similar to the expression pattern of the PBMC central memory-like subset

CAR-Gene-T Cells Sustained a Complete Tumor Clearance In Vivo

CAR-Gene-T cells, especially CAR-Bcl-xL-T cells, show a superior persistence in vitro and in vivo using a non-tumor bearing NSG model. A tumor burden xenograft model was used to determine the effect of over-expressing the pro-survival genes in CAR T cells on cytotoxicity over time in comparison with conventional CAR-T cells. The CAR-T cells were added at a range of doses in NALM-6 bearing mice. CAR T cells can achieve almost complete tumor clearance below the detection threshold of the assay at a dose of $2\times10^6$, yet still fail to maintain protection in the longer term. At the lower dose of $1\times10^6$, CAR T cells initially reduce the tumor burden, but the tumor burden begins to increase after d8 and subsequently leads to death (medium survival: 22.6 d). However, injection of $1\times10^6$ CAR-Bcl-xL-T cells over-achieved efficient tumor clearance within 48 hours, and mice survived longer (n=3). One CAR-Bcl-xL-T cell treated mouse died 165 days post-treatment without signs of tumor relapse. Blood samples from the CAR-Bcl-xL-T cell treated mice on day 70 post-treatment consistently revealed the presence of GFP and CAR expressing T cells and no observable population of CD19/CD21+ tumor cells in circulation. To further investigate whether complete tumor clearance had been achieved, or whether there were residual tumor cells in the bone marrow or tissues that were being consistently controlled by CAR-Bcl-xL-T cells, T cell depletion was performed using anti-CD8 antibody. CD8 depletion was confirmed by flow cytometric analysis of blood samples on day 8 post antibody injection, and tumor growth was measured over the following weeks. There was no re-emergence of residual NALM-6 tumor cells measured by BLI, suggesting that the tumor was completely cleared by the CAR-Bcl-xL-T cells. Furthermore, neither of the T cell depleted mice died up to 32 days after T cell depletion, further suggesting that mice were completely cleared of the tumor resulting in long-term tumor-free survival.

CAR-Gen-T Cells Provide Long-Term Tumor Protection Upon Rechallenge In Vivo

Finally, the potential for prolonged cytotoxic function of CAR-Gene-T cells was evaluated, and it was determined whether this translates into controlling relapsing CD19+ lymphoma in vivo. It was first tested whether CAR-Gene-T cells can clear the tumor at a low dose (previously shown to decrease the tumor burden but not clear all tumor cells when using the conventional CAR-T cells). NALM-6 tumor bearing mice were intravenously injected with $1\times10^6$ CAR-Survivin, CAR-CD28-D124E/T195P, and CAR-Bcl-xL-T cells with mock T cells and conventional CAR-T cells acting as control. In the event of tumor clearance, mice were re-challenged with NALM-6 cells on day 28 and day 76 to assess long term tumor protection by CAR-Gene-T cells. Consistent with previous results, $1\times10^6$ CAR T cells led to a decrease in the tumor burden but ultimately resulted in a lack of sustained tumor control and eventually death (median survival=33.2 d). However, the CAR-Gene-T cells all demonstrated a more efficient killing and sustainable tumor control with complete tumor clearance apparent between day 4 and 6. All of the CAR-Gene-T cell treated mice remained tumor-free at 28 days post-CAR-T infusion. The ability of the circulating CAR T cells to recognize and kill further tumors was tested. Thus, a second dose ($1\times10^6$) of NALM-6 was intravenously injected into surviving mice alongside an untreated control group of age-matched mice (n=5). As it was unclear how quickly these tumor cells would be killed by the CAR-T cells, tumor engraftment was confirmed 2 h post injection. In comparison with the death of control mice within 22 days, mice with circulating CAR-Gene-T cells killed the re-challenged tumor and maintained tumor-free survival for more than 40 days. The surviving mice were re-challenged a third time at a late time point (76 days post-CAR T cell infusion). Again, mice with circulating CAR-Gene-T cells maintained tumor control compared with a third group of control mice receiving tumor only, resulting in a significant survival advantage with mice remaining healthy and having no observable tumors at 125 days. To determine if the increased tumor clearance after initial and subsequent tumor challenges was due to prolonged survival of CAR-Gene-T cells, blood samples were taken from all mice for quantitation of CAR-T cells. The number of conventional CAR-T cells began decreasing between day 7 and 14 with no detectable CAR-T cells present in the blood on day 28. Similar to previous data, mice with circulating CAR-Gene-T cells demonstrated the presence of these T cells at all timepoints assayed. To investigate whether superior tumor control correlated with the memory preservation and potential transcriptional drivers, the phenotype and expression of transcriptional factors TCF-1, Bcl-6, Tox, and T-bet were characterized in the circulating CAR-T cells in the surviving mice. Circulating CAR T cells presented a central memory-like phenotype demonstrated by the expression of CD45RA-CD62L+ and a TCF-1+, Bcl-6+, Toxlow, T-bet-expression pattern resembling the central memory subset in PBMC. The long-term persistent CAR-Gene-T cells expressed very low levels of exhaustion markers PD-1, Tim-3, LAG-3, and TIGIT, in comparison with control fresh $CD8^+$ T cells stimulated with aCD3/aCD28 beads and cultured for 8 days, which demonstrated high expression of the same markers. The expression of these markers on untreated or conventional CAR-T cells were unable to be assessed, as there were no surviving mice in these groups. Low expression of exhaustion markers is consistent with T cells found in the blood with a central memory-like phenotype.

In aggregate, the findings reported herein support the hypothesis that optimized engagement of Bcl-xL, Survivin, and CD28-D124E/T195P can significantly improve the $CD8^+$ T cell survival and provide further benefit on top of the sustenance afforded by 4-1BB-based CARs, thereby resulting in enhanced CAR-T cell potency and durable anti-tumor protection.

Definitions

Use of the singular forms "a," "an," and "the" include plural references unless the context clearly dictates otherwise. For example, reference to "a polynucleotide" may include a plurality of polynucleotides.

Terms such as "connected," "attached," "linked," and "conjugated" are used interchangeably herein and encompass direct as well as indirect connection, attachment, linkage, or conjugation unless the context clearly dictates otherwise. Where a range of values is recited, each intervening integer value, and each fraction thereof, between the recited upper and lower limits of that range is also specifically disclosed, along with each subrange between such values. The upper and lower limits of any range can independently be included in or excluded from the range, and each range where either, neither, or both limits are included is also encompassed. Where a value being discussed has inherent limits, for example where a component can be present at a concentration of from 0 to 100%, or where the pH of an aqueous solution can range from 1 to 14, those inherent limits are specifically disclosed. Where a value is explicitly recited, values that are "about" (that is, within ±10%) the same quantity or amount as the recited value are also within the scope. Where a combination is disclosed, each sub-combination of the elements of that combination is also specifically disclosed. Conversely, where different elements or groups of elements are individually disclosed, combinations thereof are also disclosed. Where any element is disclosed as having a plurality of alternatives, examples in which each alternative is excluded singly or in any combination with the other alternatives are also hereby disclosed; more than one element can have such exclusions, and all combinations of elements having such exclusions are hereby disclosed.

Unless defined otherwise herein, all technical and scientific terms have the same meaning as commonly understood by one of ordinary skill in the relevant art. Singleton, et al., Dictionary of Microbiology and Molecular Biology, 2nd Ed., John Wiley and Sons, New York (1994), and Hale & Marham, The Harper Collins Dictionary of Biology, Harper Perennial, N Y, 1991, provide one of skill with a general dictionary of many of the terms used herein. Unless otherwise indicated, nucleic acids are written left to right in 5' to 3' orientation; and amino acid sequences are written left to right in amino to carboxy orientation. The terms defined immediately below are more fully defined by reference to the specification as a whole.

The "configuration" of a polynucleotide means the functional sequence elements within the polynucleotide and the order and direction of those elements.

The terms "corresponding transposon" and "corresponding transposase" are used to indicate an activity relationship between a transposase and a transposon. A transposase transposases its corresponding transposon.

The term "coupling element" or "translational coupling element" means a DNA sequence that allows the expression of a first polypeptide to be linked to the expression of a second polypeptide. Internal ribosome entry site elements ("IRES elements") and cis-acting hydrolase elements ("CHYSEL elements") are examples of coupling elements.

The terms "DNA sequence," "RNA sequence," and "polynucleotide sequence" refer to a contiguous nucleic acid sequence. The sequence can be an oligonucleotide of 2 to 20 nucleotides in length to a full-length genomic sequence of thousands or hundreds of thousands of base pairs.

The term "expression construct" means any polynucleotide designed to transcribe an RNA, such as, for example, a construct that contains at least one promoter that is or may be operably linked to a downstream gene, coding region, or polynucleotide sequence (for example, a cDNA or genomic DNA fragment that encodes a polypeptide or protein, or an RNA effector molecule, for example, an antisense RNA, triplex-forming RNA, ribozyme, an artificially selected high affinity RNA ligand (aptamer), a double-stranded RNA, for example, an RNA molecule comprising a stem-loop or hairpin dsRNA, or a bi-finger or multi-finger dsRNA or a microRNA, or any RNA). An "expression vector" is a polynucleotide comprising a promoter that can be operably linked to a second polynucleotide. Transfection or transformation of the expression construct into a recipient cell allows the cell to express an RNA effector molecule, polypeptide, or protein encoded by the expression construct. An expression construct may be a genetically engineered plasmid, virus, recombinant virus, or an artificial chromosome derived from, for example, a bacteriophage, adenovirus, adeno-associated virus, retrovirus, lentivirus, poxvirus, or herpesvirus. Such expression vectors can include sequences from bacteria, viruses, or phages. Such vectors include chromosomal, episomal, and virus-derived vectors, for example, vectors derived from bacterial plasmids, bacteriophages, yeast episomes, yeast chromosomal elements, and viruses, vectors derived from combinations thereof, such as those derived from plasmid and bacteriophage genetic elements, cosmids, and phagemids. An expression construct can be replicated in a living cell, or it can be made synthetically. The terms "expression construct," "expression vector," "vector," and "plasmid" are used interchangeably herein to demonstrate the application of the invention in a general, illustrative sense, and are not intended to limit the invention to a particular type of expression construct.

The term "expression polypeptide" means a polypeptide encoded by a gene on an expression construct.

The term "expression system" means any in vivo or in vitro biological system that is used to produce one or more gene product encoded by a polynucleotide.

A "gene transfer system" refers to a vector or gene transfer vector, i.e., a polynucleotide comprising the gene to be transferred which is cloned into a vector (a "gene transfer polynucleotide" or "gene transfer construct"). A gene transfer system may also comprise other features to facilitate the process of gene transfer. For example, a gene transfer system may comprise a vector and a lipid or viral packaging mix for enabling a first polynucleotide to enter a cell, or it may comprise a polynucleotide that includes a transposon and a second polynucleotide sequence encoding a corresponding transposase to enhance productive genomic integration of the transposon. The transposases and transposons of a gene transfer system may be on the same nucleic acid molecule or on different nucleic acid molecules. The transposase of a gene transfer system may be provided as a polynucleotide or as a polypeptide.

Two elements are "heterologous" to one another if not naturally associated. For example, a nucleic acid sequence encoding a protein linked to a heterologous promoter means a promoter other than that which naturally drives expression of the protein. A heterologous nucleic acid flanked by transposon ends or inverted terminal repeats ("ITR"s) means a heterologous nucleic acid not naturally flanked by those transposon ends or ITRs, such as a nucleic acid encoding a polypeptide other than a transposase, including an antibody heavy or light chain. A nucleic acid is heterologous to a cell if not naturally found in the cell or if naturally found in the cell but in a different location (e.g., episomal or different genomic location) than the location described.

The term "host" means any prokaryotic or eukaryotic organism that can be a recipient of a nucleic acid. A "host" includes prokaryotic or eukaryotic organisms that can be genetically engineered. For examples of such hosts, see Maniatis et al., Molecular Cloning. A Laboratory Manual, Cold Spring Harbor Laboratory, Cold Spring Harbor, N.Y. (1982). As used herein, the terms "host," "host cell," "host system," and "expression host" can be used interchangeably.

As used throughout the disclosure, the term "introducing" refers to delivering the polynucleotide construct into a host cell. Methods for introducing polynucleotide constructs into host cells may include, for example, stable transfection transformation (e.g., transposons, CRISPR/Cas9, etc.), transient transfection transformation (e.g., Ionizable Lipid Nanoparticles), virus-mediated transduction (e.g., lentivirus, retrovirus, etc.), nanoparticle-mediated endocytosis, or pinocytosis methods.

An "intron" is a segment of a DNA or RNA molecule that does not code for proteins and interrupts the sequence of genes.

An "IRES" or "internal ribosome entry site" means a specialized sequence that directly promotes ribosome binding, independent of a cap structure.

An "isolated" polypeptide or polynucleotide means a polypeptide or polynucleotide that has been either removed from its natural environment, produced using recombinant techniques, or chemically or enzymatically synthesized. Polypeptides or polynucleotides may be purified, that is, essentially free from any other polypeptide or polynucleotide and associated cellular products or other impurities.

The terms "nucleoside" and "nucleotide" include those moieties that contain not only the known purine and pyrimidine bases, but also other heterocyclic bases that have been modified. Such modifications include methylated purines or pyrimidines, acylated purines or pyrimidines, or other heterocycles. Modified nucleosides or nucleotides can also include modifications on the sugar moiety, for example, where one or more of the hydroxyl groups are replaced with halogen, aliphatic groups, or are functionalized as ethers, amines, or the like. The term "nucleotidic unit" is intended to encompass nucleosides and nucleotides.

An "Open Reading Frame" or "ORF" means a portion of a polynucleotide that, when translated into amino acids, contains no stop codons. The genetic code reads DNA sequences in groups of three base pairs, which means that a double-stranded DNA molecule can read in any of six possible reading frames-three in the forward direction and three in the reverse. An ORF typically also includes an initiation codon at which translation may start.

The term "operably linked" refers to functional linkage between two sequences such that one sequence modifies the behavior of the other. For example, a first polynucleotide comprising a nucleic acid expression control sequence (such as a promoter, IRES sequence, enhancer, or array of transcription factor binding sites) and a second polynucleotide are operably linked if the first polynucleotide affects transcription and/or translation of the second polynucleotide. Similarly, a first amino acid sequence comprising a secretion signal, i.e., a subcellular localization signal, and a second amino acid sequence are operably linked if the first amino acid sequence causes the second amino acid sequence to be secreted or localized to a subcellular location.

A "piggyBac-like transposase" means a transposase with at least 20% sequence identity as identified using the TBLASTN algorithm to the piggyBac transposase from *Trichoplusia ni* (SEQ ID NO: 79), and as more fully described in Sakar, A. et. Al., (2003). Mol. Gen. Genomics 270: 173-180. "Molecular evolutionary analysis of the widespread piggyBac transposon family and related 'domesticated' species," incorporated herein by reference in its entirety and further characterized by a DDE-like DDD motif, with aspartate residues at positions corresponding to D268, D346, and D447 of *Trichoplusia ni* piggyBac transposase on maximal alignment. PiggyBac-like transposases are also characterized by their ability to excise their transposons precisely with a high frequency. A "piggyBac-like transposon" means a transposon having transposon ends that are the same or at least 80%, including at least 90, 95, 96, 97, 98 or 99% identical to the transposon ends of a naturally occurring transposon that encodes a piggyBac-like transposase. A piggyBac-like transposon includes an ITR sequence of approximately 12-16 bases at each end. These repeats may be identical at the two ends, or the repeats at the two ends may differ at 1 or 2 or 3 or 4 positions in the two ITRs. The transposon is flanked on each side by a 4 base sequence corresponding to the integration target sequence that is duplicated on transposon integration (the "Target Site Duplication" or "Target Sequence Duplication" or "TSD").

The terms "polynucleotide," "oligonucleotide," "nucleic acid," "nucleic acid molecule," and "gene" are used interchangeably to refer to a polymeric form of nucleotides of any length, and may comprise ribonucleotides, deoxyribonucleotides, analogs thereof, or mixtures thereof. These terms refer only to the primary structure of the molecule. Thus, the terms include triple-, double-, and single-stranded DNA, as well as triple-, double-, and single-stranded RNA. The terms also encompass modified, for example by alkylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, siRNA, and mRNA, whether spliced or unspliced, any other type of polynucleotide that is an N- or C-glycoside of a purine or pyrimidine base, and other polymers containing non-nucleotidic backbones, for example, polyamide (for example, peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration that allows for base pairing and base stacking, such as is found in DNA and RNA. There is no intended distinction in length between the terms "polynucleotide," "oligonucleotide," "nucleic acid," and "nucleic acid molecule," and these terms are used interchangeably herein. These terms include, for example, 3'-deoxy-2', 5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, inter-nucleotide modifications such as, for example, those with uncharged linkages (for example, methyl phosphonates, phosphotriesters, phosphoramidates, carbamates, or the like) with negatively charged linkages (for example, phosphorothioates, phosphorodithioates, or the like), and with positively charged linkages (for example, aminoalkylphosphoramidates, aminoalkylphosphotriesters), those containing pendant moieties, such as, for example, proteins (including enzymes (for example, nucleases), toxins, antibodies, signal peptides, poly-L-lysine, or the like), those with intercalators (for example, acridine, psoralen, or the like), those containing chelates (of, for example, metals, radioactive metals, boron, oxidative metals, or the like), those containing alkylators, those with modified linkages (for example, alpha anomeric nucleic acids or the like), as well as unmodified forms of the polynucleotide or oligonucleotide.

A "promoter" means a nucleic acid sequence sufficient to direct transcription of an operably linked nucleic acid molecule. A promoter can be used together with other transcription control elements (for example, enhancers) that are sufficient to render promoter-dependent gene expression controllable in a cell type-specific, tissue-specific, or temporal-specific manner, or that are inducible by external signals or agents; such elements, may be within the 3' region of a gene or within an intron. In one aspect, the promoter may be operably linked to a nucleic acid sequence, for example, a cDNA, a gene sequence, or an effector RNA coding sequence, in such a way as to enable expression of the nucleic acid sequence, or a promoter is provided in an expression cassette into which a selected nucleic acid sequence to be transcribed can be conveniently inserted.

Sequence identity can be determined by aligning sequences using algorithms, such as BESTFIT, FASTA, and TFASTA in the Wisconsin Genetics Software Package Release 7.0 (Genetics Computer Group, 575 Science Dr., Madison, Wis.), using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occur in both sequences to yield the number of matched positions, dividing the number of matched positions by the total number of matched and mismatched positions not counting gaps in the window of comparison (i.e., the window size), and multiplying the result by 100 to yield the percentage of sequence identity. Unless otherwise indicated, the window of comparison between two sequences is defined by the entire length of the shorter of the two sequences. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal, or internal extensions, deletions, or insertions into the peptide sequence shall not be construed as affecting homology.

The phrase "stable transfection/transformation" refers to introducing a polynucleotide construct into a host genome and permanently expressing the gene of interest through the integration of the transfected DNA into the nuclear genome, which will be passed on to the future generations of the cell.

A "target nucleic acid" is a nucleic acid into which a transposon is to be inserted. Such a target can be part of a chromosome, an episome, or a vector.

An "integration target sequence" or "target sequence" or "target site" for a transposase is a site or sequence in a target DNA molecule into which a transposon can be inserted by a transposase. The piggyBac transposase from *Trichoplusia ni* inserts its transposon predominantly into the target sequence 5'-TTAA-3'. PiggyBac-like transposases transpose their transposons using a cut-and-paste mechanism, which results in duplication of their 4 base pair target sequence on insertion into a DNA molecule. The target sequence is thus found on each side of an integrated piggyBac-like transposon.

The term "translation" refers to the process by which a polypeptide is synthesized by a ribosome "reading" the sequence of a polynucleotide.

A "transposase" is a polypeptide that catalyzes the excision of a corresponding transposon from a donor polynucleotide, for example a vector, and (providing the transposase is not integration-deficient) the subsequent integration of the transposon into a target nucleic acid. A transposase may be a piggyBac-like transposase. Other non-limiting, suitable transposases are disclosed in U.S. Pat. No. 10,041,077B2, which is incorporated herein by reference in its entirety.

The term "transposition" refers to the action of a transposase in excising a transposon from one polynucleotide and then integrating it, either into a different site in the same polynucleotide, or into a second polynucleotide.

The term "transposon" means a polynucleotide that can be excised from a first polynucleotide, for instance, a vector, and be integrated into a second position in the same polynucleotide, or into a second polynucleotide, for instance, the genomic or extrachromosomal DNA of a cell, by the action of a corresponding trans-acting transposase. A transposon comprises a first transposon end and a second transposon end, which are polynucleotide sequences recognized by and transposed by a transposase. A transposon usually further comprises a first polynucleotide sequence between the two transposon ends, such that the first polynucleotide sequence is transposed along with the two transposon ends by the action of the transposase. Natural transposons frequently comprise DNA encoding a transposase that acts on the transposon. Transposons as claimed herein are "synthetic transposons," comprising a heterologous polynucleotide sequence that is transposable by virtue of its juxtaposition between two transposon ends. A suitable transposon is a piggyBac-like transposon. Other non-limiting, suitable transposons are disclosed in U.S. Pat. No. 10,041,077B2.

The term "transposon end" means the cis-acting nucleotide sequences that are sufficient for recognition by and transposition by a corresponding transposase. Transposon ends of piggyBac-like transposons comprise perfect or imperfect repeats such that the respective repeats in the two transposon ends are reverse complements of each other. These are referred to as ITRs or terminal inverted repeats ("TIR"s). A transposon end may or may not include an additional sequence proximal to the ITR that promotes or augments transposition.

The term "vector," "DNA vector," or "gene transfer vector" refers to a polynucleotide that is used to perform a "carrying" function for another polynucleotide. For example, vectors are often used to allow a polynucleotide to be propagated within a living cell, to allow a polynucleotide to be packaged for delivery into a cell, or to allow a polynucleotide to be integrated into the genomic DNA of a cell. A vector may further comprise additional functional elements, such as, for example, a transposon or a lentivirus.

An "immune cell" can refer to any cell of an immune system including cells of adaptive and innate immune systems and including cells of myeloid or lymphoid origin. Examples of immune cells include leucocytes, lymphocytes, macrophages, neutrophils, dendritic cells, lymphoid cells, mast cells eosinophils basophils, and natural killer cells. Lymphocytes include B and T lymphocytes. T lymphocytes include killer T cells, helper T cells, and gamma delta T cells. Immune cells can be primary cells isolated from a subject or can be the result of further culturing including in the form of a cell line. Immune cells can be the subject of genetic engineering in addition to that described herein, e.g., expression of a CAR-T receptor.

The disclosure refers to several proteins for which it provides an example "SEQ ID NO:" representing the wild-type human sequence of the protein. Unless otherwise apparent from the context, reference to a protein should be understood as including the specific SEQ ID NO, as well as allelic, species, and induced variants thereof having at least 90, 95, or 99% identity thereto. Examples of allelic and species variants can be found in the SwissProt and other databases. Any such sequences for the protein can be modified to include one or more of the activating mutations described herein to confer enhanced survival of an immune cell expressing the protein as further described herein.

Mutations are sometimes referred to in the form XnY, wherein X is a wildtype amino acid, n is an amino acid position of X in a wildtype sequence, and Y is a replacement amino acid. If the mutation occurs in a sequence having a different number of amino acids than the wildtype sequence, it is present at the position in the sequence aligned with position n in the wildtype sequence when the respective sequences are maximally aligned.

If a nucleic acid is said to encode an activating mutant of a specified protein what is meant is that the nucleic acid encodes the protein including the activating mutation.

An apoptosis inhibitor is a substance that interferes with the process of programmed cell death (apoptosis). Apoptosis is a highly regulated process in which cell death is induced by activation of intracellular caspase proteases. Apoptosis inhibitors include proteins whose natural function is to oppose apoptosis and proteins whose natural function is to participate in apoptosis, but which comprise mutations that interfere with apoptosis.

An apoptosis assay detects and quantifies the cellular events associated with programmed cell death, including caspase activation, cell surface exposure of phosphatidylserine, and DNA fragmentation. The initiator and effector caspases are particularly good targets for detecting apoptosis in cells. Caspase activity assays either use peptide substrates, which are cleaved by caspases, or similar substrates that bind to activated caspases in live cells (McStay et al., 2014 Cold Spring Harbor Protocols, Measuring Apoptosis: Caspase Inhibitors and Activity assays; Niles et al, 2008, Methods Mol Biol., 414:137-50). An example assay to measure apoptosis inhibition is the bioluminescence assay that uses luciferase described herein. A number of caspase assay kits are commercially available that use either fluorescence or luminescence readouts. For example, the caspase-Glo® assays from Promega use the luminogenic caspase-8 tetrapeptide substrate (Z-LETD-aminoluciferin), the caspase-9 tetrapeptide substrate (Z-LEHD-aminoluciferin), the caspase-3/7 substrate (Z-DEVD-aminoluciferin), the caspase-6 substrate (Z-VEID-aminoluciferin), or the caspase-2 substrate (Z-VDVAD-aminoluciferin), and a stable luciferase in proprietary buffers. In the absence of active caspase or inhibition of caspase, the caspase substrates do not act as substrates for luciferase and, thus, produce no light. On cleavage of the substrates by the respective caspase, aminoluciferin is liberated and can contribute to the generation of light in a luminescence reaction. The resulting luminescent signal is directly proportional to the amount of caspase activity present in the sample. An example of a caspase activity assay kit that uses a fluorescence substrate N-AcetylAsp-Glu-Val-Asp-7-amino-4-methylcoumarin or Ac-DEVDAMC for caspase-3 is the Caspase-3 Activity assay kit from Cell Signaling Technology. Activated caspase-3 cleaves this substrate between DEVD and AMC, generating highly fluorescent AMC that can be detected using a fluorescence reader with excitation at 380 nm and emission between 420-460 nm. Cleavage of the substrate only occurs in lysates of apoptotic cells; therefore, the amount of AMC produced is proportional to the number of apoptotic cells in the sample.

Genetic Elements Useful for Expression in Immune Cells

Transposon Elements

The consistency of expression of a gene from a heterologous polynucleotide in an immune cell can be improved if the heterologous polynucleotide is integrated into the genome of the host cell. Integration of a polynucleotide into the genome of a host cell also generally makes it stably heritable, by subjecting it to the same mechanisms that ensure the replication and division of genomic DNA. Such stable heritability is desirable for achieving good and consistent expression over long growth periods. For stable modification of immune cells, particularly for therapeutic applications, the stability of the modification and consistency of expression levels are important.

Heterologous polynucleotides may be more efficiently integrated into a target genome if they are part of a transposon, for example so that they may be integrated by a transposase. A particular benefit of a transposon is that the entire polynucleotide between the transposon ITRs is integrated. This is in contrast with random integration, where a polynucleotide introduced into a eukaryotic cell is often fragmented at random in the cell, and only parts of the polynucleotide become incorporated into the target genome, usually at a low frequency. There are several different classes of transposon. piggyBac-like transposons include the piggyBac transposon from the looper moth *Trichoplusia ni*, *Xenopus* piggyBac-like transposons, *Bombyx* piggyBac-like transposons, *Heliothis* piggyBac-like transposons, *Helicoverpa* piggyBac-like transposons, *Agrotis* piggyBac-like transposons, *Amyelois* piggyBac-like transposons, piggyBat piggyBac-like transposons, and *Oryzias* piggyBac-like transposons. hAT transposons include TcBuster. Mariner transposons include Sleeping Beauty. Each of these transposons can be integrated into the genome of a mammalian cell by a corresponding transposase. Heterologous polynucleotides incorporated into transposons may be integrated into immune cells, as well as hepatocytes, neural cells, muscle cells, blood cells, embryonic stem cells, somatic stem cells, hematopoietic cells, embryos, zygotes, and sperm cells (some of which are open to being manipulated in an in vitro setting). Cells can also be pluripotent cells (cells whose descendants can differentiate into several restricted cell types, such as hematopoietic stem cells or other stem cells) or totipotent cells (i.e., a cell whose descendants can become any cell type in an organism, e.g., embryonic stem cells).

Gene transfer systems may comprise a transposon in combination with a corresponding transposase protein that transposases the transposon, or a nucleic acid that encodes the corresponding transposase protein and is expressible in the target cell. The nucleic acid encoding the transposase protein may be a DNA molecule or an mRNA molecule.

In certain aspects, piggyBac-like transposons may be advantageous as gene transfer systems for the applications described herein compared with lentiviral vectors. Lentiviruses may not be packaged efficiently if they exceed a certain size, and a significant amount of their DNA may already be occupied with sequences required for viral synthesis, assembly, and packaging. Genes integrated through lentiviral vectors can show highly variable expression due to promoter silencing (Antoniou et al., 2013. Hum Gene Ther 24, 363-374. "Optimizing retroviral gene expression for effective therapies"): silencing can be reduced either by increasing copy number or by incorporating insulators into the integrating polynucleotide (Emery, 2011. Hum Gene Ther 22, 761-774. "The use of chromatin insulators to improve the expression and safety of integrating gene transfer vectors."). Including insulators in lentiviral constructs can be challenging because of size limitations and because of effects of including these sequences on viral packaging and titer. In contrast, the efficient integration of a piggyBac-like transposon into a target genome by its corresponding transposase is unperturbed by increasing the transposon size. It is therefore possible to include multiple genes for modification of the properties of an immune cell into a single transposon, together with flanking insulators, without compromising the ability of the corresponding transposase to integrate the transposon into the genome of an immune cell. Safety is also of significant concern when modifying the genome of a cell that is to be placed into a human. When making modifications of immune cells such as T cells to enhance their ability to kill tumor cells and to improve their ability to survive and proliferate, it is useful to be able to also incorporate into the genome of the cell a gene that provides a means of killing the modified immune cell. Examples of such "kill switches" include expression of an antigen that is efficiently recognized by an existing therapeutic agent (for example, a surface-expressed antigen such as CD20 that is normally found exclusively on B-cells and is recognized and treated by the drug rituximab or CD19 that is normally found exclusively on B-cells and is recognized and treated by the drug blinotumomab) and an inducible caspase 9 suicide switch (Straathof et. al., 2005. Blood 105, 4247-4254. "An inducible caspase 9 safety switch for T-cell therapy"). For kill switches to be useful, they must be present in the genome of every modified cell. This cargo, plus the regulatory elements for expression, may occupy essentially the entire capacity of the lentiviral vector, leaving no additional space for the addition of insulators or for other genes such as those for enhancing the survival or proliferation or function of the T-cell. Gene transfer systems comprising a piggyBac-like transposon and its corresponding transposase may thus be advantageous for integrating genes including genes encoding CARs into the genomes of immune cells including T-cells.

When there are multiple components of a gene transfer system, for example one or more polynucleotides comprising transposon ends flanking genes for expression in the target cell, and a transposase (which may be provided either as a protein or encoded by a nucleic acid), these components can be transfected into a cell at the same time, or sequentially. For example, a transposase protein or its encoding nucleic acid may be transfected into a cell prior to, at the same time, or after transfection of a corresponding transposon. Additionally, administration of either component of the gene transfer system may occur repeatedly, for example, by administering at least two doses of this component.

Transposase proteins may be encoded by polynucleotides including RNA or DNA. RNA molecules may include those with appropriate substitutions to reduce toxicity effects on the cell, for example substitution of uridine with pseudouridine and substitution of cytosine with 5-methyl cytosine. mRNA encoding the transposase may be prepared such that it has a 5'-cap structure to improve expression in a target cell. Example cap structures are a cap analog (G(5')ppp(5')G), an anti-reverse cap analog (3'-O-Me-m7G(5')ppp(5')G, a clean cap (m7G(5')ppp(5')(2'OmeA)pG), and an mCap (m7G(5')ppp(5')G). mRNA encoding the transposase may be prepared such that some bases are partially or fully substituted, for example uridine may be substituted with pseudo-uridine, and cytosine may be substituted with 5-methyl-cytosine. Any combinations of these caps and substitutions may be made. Similarly, the nucleic acid encoding the transposase protein or the transposon can be transfected into the cell as a linear fragment or as a circularized fragment, either as a plasmid or as recombinant viral DNA. If the transposase is introduced as a DNA sequence encoding the transposase, then the ORF encoding the transposase may be operably linked to a promoter that is active in the target mammalian cell.

A suitable piggyBac-like transposon for modifying the genome of a mammalian cell is a *Xenopus* transposon, which comprises, from 5' to 3', a first ITR with the nucleotide sequence SEQ ID NO: 1, a heterologous polynucleotide to be transposed, and a second ITR with the nucleotide sequence SEQ ID NO: 2. The transposon may further be flanked by a copy of the tetranucleotide 5'-TTAA-3' on each side, immediately adjacent to the ITRs and distal to the heterologous polynucleotide. The transposon may further comprise a first additional polynucleotide immediately adjacent to one ITR, e.g., the first ITR, and proximal to the heterologous polynucleotide, whose nucleotide sequence is at least 95% identical to SEQ ID NO: 5 or 6. The transposon may further comprise a second additional polynucleotide immediately adjacent to one ITR, e.g., the second ITR, and proximal to the heterologous polynucleotide, whose nucleotide sequence is at least 95% identical to SEQ ID NO: 7 or 8. This transposon may be transposed by a corresponding *Xenopus* transposase comprising a polypeptide sequence at least 90% identical to the polypeptide sequence of SEQ ID NO: 9 or 10, for example any of SEQ ID NOs: 9-41. The *Xenopus* transposase may optionally be fused to a heterologous nuclear localization signal. The transposase may be a hyperactive variant of a naturally occurring transposase. The hyperactive variant transposase may comprise one or more of the following amino acid changes, relative to the polypeptide sequence of SEQ ID NO: 9: Y6L, Y6H, Y6V, Y6I, Y6C, Y6G, Y6A, Y6S, Y6F, Y6R, Y6P, Y6D, Y6N, S7G, S7V, S7D, E9W, E9D, E9E, M16E, M16N, M16D, M16S, M16Q, M16T, M16A, M16L, M16H, M16F, M16I, S18C, S18Y, S18M, S18L, S18Q, S18G, S18P, S18A, S18W, S18H, S18K, S18I, S18V, S19C, S19V, S19L, S19F, S19K, S19E, S19D, S19G, S19N, S19A, S19M, S19P, S19Y, S19R, S19T, S19Q, S20G, S20M, S20L, S20V, S20H, S20W, S20A, S20C, S20Q, S20D, S20F, S20N, S20R, E21N, E21W, E21G, E21Q, E21L, E21D, E21A, E21P, E21T, E21S, E21Y, E21V, E21F, E21M, E22C, E22H, E22R, E22L, E22K, E22S, E22G, E22M, E22V, E22Q, E22A, E22Y, E22W, E22D, E22T, F23Q, F23A, F23D, F23W, F23K, F23T, F23V, F23M, F23N, F23P, F23H, F23E, F23C, F23R, F23Y, S24L, S24W, S24H, S24V, S24P, S24I, S24F, S24K, S24Y, S24D, S24C, S24N, S24G, S24A, S26F, S26H, S26V, S26Q, S26Y, S26W, S28K, S28Y, S28C, S28M, S28L, S28H, S28T, S28Q, V31L, V31T, V31I, V31Q, V31K, A34L, A34E, L67A, L67T, L67M, L67V, L67C, L67H, L67E, L67Y, G73H, G73N, G73K, G73F, G73V, G73D, G73S, G73W, G73L, A76L, A76R, A76E, A76I, A76V, D77N, D77Q, D77Y, D77L, D77T, P88A, P88E, P88N, P88H, P88D, P88L, N91D, N91R, N91A, N91L, N91H, N91V, Y141I, Y141M, Y141Q, Y141S, Y141E, Y141W, Y141V, Y141F, Y141A, Y141C, Y141K, Y141L, Y141H, Y141R, N145C, N145M, N145A, N145Q, N145I, N145F, N145G, N145D, N145E, N145V, N145H, N145W, N145Y, N145L, N145R, N145S, P146V, P146T, P146W, P146C, P146Q, P146L, P146Y, P146K, P146N, P146F, P146E, P148M, P148R, P148V, P148F, P148T, P148C, P148Q, P148H, Y150W, Y150A, Y150F, Y150H, Y150S, Y150V, Y150C, Y150M, Y150N, Y150D, Y150E, Y150Q, Y150K, H157F, H157I, H157T, H157S, H157W, A162L, A162A, A162C, A162K, A162T, A162G, A162M, A162S, A162I, A162Y, A162Q, A179T, A179K, A179S, A179V, A179R, L182V, L182I, L182Q, L182T, L182W, L182R, L182S, T189C, T189N, T189L, T189K, T189Q, T189V, T189A, T189W, T189Y, T189G, T189F, T189S, T189H, L192V, L192C, L192H, L192M, L192I, S193P, S193T, S193R, S193K, S193G, S193D, S193N, S193F, S193H, S193Q, S193Y, V196L, V196S, V196W, V196A, V196F, V196M, V196I, S198G, S198R, S198A, S198K, T200C, T200I, T200M, T200L, T200N, T200W, T200V, T200Q, T200Y, T200H, T200R, S202A, S202P, L210H, L210A, F212Y, F212N, F212M, F212C, F212A, N218V, N218R, N218T, N218C, N218G, N218I, N218P, N218D, N218E, A248S, A248L, A248H, A248C, A248N, A248I, A248Q, A248Y, A248M, A248D, L263V, L263A, L263M, L263R, L263D, Q270V, Q270K, Q270A, Q270C, Q270P, Q270L, Q270I, Q270E, Q270G, Q270Y, Q270N, Q270T, Q270W, Q270H, S294R, S294N, S294G, S294T, S294C, T297C, T297P, T297V, T297M, T297L, T297D, E304D, E304H, E304S, E304Q, E304C, S308R, S308G, L310R, L310I, L310V, L333M, L333W, L333F, Q336Y, Q336N, Q336M, Q336A, Q336T, Q336L, Q336I, Q336G, Q336F, Q336E, Q336V, Q336C, Q336H, A354V, A354W, A354D, A354C, A354R, A354E, A354K, A354H, A354G, C357Q, C357H, C357W, C357N, C357I, C357V, C357M, C357R, C357F, C357D, L358A, L358F, L358E, L358R, L358Q, L358V, L358H, L358C, L358M, L358Y, L358K, L358N, L358I, D359N, D359A, D359L, D359H, D359R, D359S, D359Q, D359E, D359M, L377V, L377I, V423N, V423P, V423T, V423F, V423H, V423C, V423S, V423G, V423A, V423R, V423L, P426L, P426K, P426Y, P426F, P426T, P426W, P426V, P426C, P426S, P426Q, P426H, P426N, K428R, K428Q, K428N, K428T, K428F, S434A, S434T, S438Q, S438A, S438M, T447S, T447A, T447C, T447Q, T447N, T447G, L450M, L450V, L450A, L450I, L450E, A462M, A462T, A462Y, A462F, A462K, A462R, A462Q, A462H, A462E, A462N, A462C, V467T, V467C, V467A, V467K, I469V, I469N, I472V, I472L, I472W, I472M, I472F, L476I, L476V, L476N, L476F, L476M, L476C, L476Q, P488E, P488H, P488K, P488Q, P488F, P488M, P488L, P488N, P488D, Q498V, Q498L, Q498G, Q498H, Q498T, Q498C, Q498E, Q498M, L502I, L502M, L502V, L502G, L502F, E517M, E517V, E517A, E517K, E517L, E517G, E517S, E517I, P520W, P520R, P520M, P520F, P520Q, P520V, P520G, P520D, P520K, P520Y, P520E, P520L, P520T, S521A, S521H, S521C, S521V, S521W, S521T, S521K, S521F, S521G, N523W, N523A, N523G, N523S, N523P, N523M, N523Q, N523L, N523K, N523D, N523H, N523F, N523C, I533M, I533V, I533T, I533S, I533F, I533G, I533E, D534E, D534Q, D534L, D534R, D534V, D534C, D534M, D534N, D534A, D534G, D534F, D534T, D534H, D534K, D534S, F576L, F576K, F576V, F576D, F576W, F576M, F576C, F576R, F576Q, F576A, F576Y, F576N, F576G, F576I, F576E, K577L, K577G, K577D, K577R, K577H, K577Y, K577I, K577E, K577V, K577N, I582V, I582K, I582R, I582M, I582G, I582N, I582E, I582A, I582Q, Y583L, Y583C, Y583F, Y583D, Y583Q, L587F, L587D, L587R, L587I, L587P, L587N, L587E, L587S, L587Y, L587M, L587Q, L587G, L587W, L587K or L587T.

A suitable piggyBac-like transposon for modifying the genome of a mammalian cell is a *Bombyx* transposon, which comprises, from 5' to 3', a first ITR with the nucleotide sequence SEQ ID NO: 42, a heterologous polynucleotide to be transposed, and a second ITR with the nucleotide sequence SEQ ID NO: 43. The transposon may further be flanked by a copy of the tetranucleotide 5'-TTAA-3' on each side, immediately adjacent to the ITRs and distal to the heterologous polynucleotide. The transposon may further comprise a first additional polynucleotide immediately adjacent to one ITR, e.g., the first ITR, and proximal to the heterologous polynucleotide, whose nucleotide sequence is at least 95% identical to SEQ ID NO: 44. The transposon may further comprise a second additional polynucleotide immediately adjacent to one ITR, e.g., the second ITR, and proximal to the heterologous polynucleotide, whose nucleotide sequence is at least 95% identical to SEQ ID NO: 45. This transposon may be transposed by a corresponding *Bombyx* transposase comprising a polypeptide sequence at least 90% identical to the polypeptide sequence of SEQ ID NO: 46 or 47, for example any of SEQ ID NOs: 46-69. The *Bombyx* transposase may optionally be fused to a heterologous nuclear localization signal. The transposase may be a hyperactive variant of a naturally occurring transposase. The hyperactive variant transposase may comprise one or more of the following amino acid changes, relative to the polypeptide sequence of SEQ ID NO: 46: Q85E, Q85M, Q85K, Q85H, Q85N, Q85T, Q85F, Q85L, Q92E, Q92A, Q92P, Q92N, Q92I, Q92Y, Q92H, Q92F, Q92R, Q92D, Q92M, Q92W, Q92C, Q92G, Q92L, Q92V, Q92T, V93P, V93K, V93M, V93F, V93W, V93L, V93A, V93I, V93Q, P96A, P96T, P96M, P96R, P96G, P96V, P96E, P96Q, P96C, F97Q, F97K, F97H, F97T, F97C, F97W, F97V, F97E, F97P, F97D, F97A, F97R, F97G, F97N, F97Y, H165E, H165G, H165Q, H165T, H165M, H165V, H165L, H165C, H165N, H165D, H165K, H165W, H165A, E178S, E178H, E178Y, E178F, E178C, E178A, E178Q, E178G, E178V, E178D, E178L, E178P, E178W, C189D, C189Y, C189I, C189W, C189T, C189K, C189M, C189F, C189P, C189Q, C189V, A196G, L200I, L200F, L200C, L200M, L200Y, A201Q, A201L, A201M, L203V, L203D, L203G, L203E, L203C, L203T, L203M, L203A, L203Y, N207G, N207A, L211G, L211M, L211C, L211T, L211V, L211A, W215Y, T217V, T217A, T217I, T217P, T217C, T217Q, T217M, T217F, T217D, T217K, G219S, G219A, G219C, G219H, G219Q, Q235C, Q235N, Q235H, Q235G, Q235W, Q235Y, Q235A, Q235T, Q235E, Q235M, Q235F, Q238C, Q238M, Q238H, Q238V, Q238L, Q238T, Q238I, R242Q, K246I, K253V, M258V, F261L, S263K, C271S, N303C, N303R, N303G, N303A, N303D, N303S, N303H, N303E, N303R, N303K, N303L, N303Q, I312F, I312C, I312A, I312L, I312T, I312V, I312G, I312M, F321H, F321R, F321N, F321Y, F321W, F321D, F321G, F321E, F321M, F321K, F321A, F321Q, V323I, V323L, V323T, V323M, V323A, V324N, V324A, V324C, V324I, V324L, V324T, V324K, V324Y, V324H, V324F, V324S, V324Q, V324M, V324G, A330K, A330V, A330P, A330S, A330C, A330T, A330L, Q333P, Q333T, Q333M, Q333H, Q333S, P337W, P337E, P337H, P337I, P337A, P337M, P337N, P337D, P337K, P337Q, P337G, P337S, P337C, P337L, P337V, F368Y, L373C, L373V, L373I, L373S, L373T, V389I, V389M, V389T, V389L, V389A, R394H, R394K, R394T, R394P, R394M, R394A, Q395P, Q395F, Q395E, Q395C, Q395V, Q395A, Q395H, Q395S, Q395Y, S399N, S399E, S399K, S399H, S399D, S399Y, S399G, S399Q, S399R, S399T, S399A, S399V, S399M, R402Y, R402K, R402D, R402F, R402G, R402N, R402E, R402M, R402S, R402Q, R402T, R402C, R402L, R402V, T403W, T403A, T403V, T403F, T403L, T403Y, T403N, T403G, T403C, T403I, T403S, T403M, T403Q, T403K, T403E, D404I, D404S, D404E, D404N, D404H, D404C, D404M, D404G, D404A, D404Q, D404L, D404P, D404V, D404W, D404F, N408F, N408I, N408A, N408E, N408M, N408S, N408D, N408Y, N408H, N408C, N408Q, N408V, N408W, N408L, N408P, N408K, S409H, S409Y, S409N, S409I, S409D, S409F, S409T, S409C, S409Q, N441F, N441R, N441M, N441G, N441C, N441D, N441L, N441A, N441V, N441W, G448W, G448Y, G448H, G448C, G448T, G448V, G448N, G448Q, E449A, E449P, E449T, E449L, E449H, E449G, E449C, E449I, V469T, V469A, V469H, V469C, V469L, L472K, L472Q, L472M, C473G, C473Q, C473T, C473I, C473M, R484H, R484K, T507R, T507D, T507S, T507G, T507K, T507I, T507M, T507E, T507C, T507L, T507V, G523Q, G523T, G523A, G523M, G523S, G523C, G523I, G523L, I527M, I527V, Y528N, Y528W, Y528M, Y528Q, Y528K, Y528V, Y528I, Y528G, Y528D, Y528A, Y528E, Y528R, Y543C, Y543W, Y543I, Y543M, Y543Q, Y543A, Y543R, Y543H, E549K, E549C, E549I, E549Q, E549A, E549H, E549C, E549M, E549S, E549F, E549L, K550R, K550M, K550Q, S556G, S556V, S556I, P557W, P557T, P557S, P557A, P557Q, P557K, P557D, P557G, P557N, P557L, P557V, H559K, H559S, H559C, H559I, H559W, V560F, V560P, V560I, V560H, V560Y, V560K, N561P, N561Q, N561G, N561A, V562Y, V562I, V562S, V562M, V567I, V567H, V567N, S583M, E601V, E601F, E601Q, E601W, E605R, E605W, E605K, E605M, E605P, E605Y, E605C, E605H, E605A, E605Q, E605S, E605V, E605I, E605G, D607V, D607Y, D607C, D607N, D607W, D607T, D607A, D607H, D607Q, D607E, D607L, D607K, D607G, S609R, S609W, S609H, S609V, S609Q, S609G, S609T, S609K, S609N, S609Y, L610T, L610I, L610K, L610G, L610A, L610W, L610D, L610Q, L610S, L610F or L610N.

A suitable piggyBac-like transposon for modifying the genome of a mammalian cell is a *Myotis* transposon, which comprises, from 5' to 3', a first ITR with the nucleotide sequence SEQ ID NO: 70, a heterologous polynucleotide to be transposed, and a second ITR with the nucleotide sequence SEQ ID NO: 71. The transposon may further be flanked by a copy of the tetranucleotide 5'-TTAA-3' on each side, immediately adjacent to the ITRs and distal to the heterologous polynucleotide. The transposon may further comprise a first additional polynucleotide immediately adjacent to one ITR, e.g., the first ITR, and proximal to the heterologous polynucleotide, whose nucleotide sequence is at least 95% identical to SEQ ID NO: 72. The transposon may further comprise a second additional polynucleotide immediately adjacent to one ITR, e.g., the second ITR, and proximal to the heterologous polynucleotide, whose nucleotide sequence is at least 95% identical to SEQ ID NO: 73. This transposon may be transposed by a corresponding *Myotis* transposase comprising a polypeptide sequence at least 90% identical to the polypeptide sequence of SEQ ID NO: 74. The *Myotis* transposase may optionally be fused to a heterologous nuclear localization signal. The transposase may be a hyperactive variant of a naturally occurring transposase. The hyperactive variant transposase may comprise one or more of the following amino acid changes, relative to the sequence of SEQ ID NO: 74: A14V, D475G, P491Q, A561T, T546T, T300A, T294A, A520T, G239S, S5P, S8F, S54N, D9N, D9G, I345 V, M481V, EI 1G, K130T, G9G, R427H, S8P, S36G, D1OG, S36G.

A suitable piggyBac-like transposon for modifying the genome of a mammalian cell is a *Trichoplusia* transposon, which comprises, from 5' to 3', a first ITR with the nucleotide sequence SEQ ID NO: 75, a heterologous polynucleotide to be transposed, and a second ITR with the nucleotide sequence SEQ ID NO: 76. The transposon may further be flanked by a copy of the tetranucleotide 5'-TTAA-3' on each side, immediately adjacent to the ITRs and distal to the heterologous polynucleotide. The transposon may further comprise a first additional polynucleotide immediately adjacent to one ITR, e.g., the first ITR, and proximal to the heterologous polynucleotide, whose nucleotide sequence is at least 95% identical to SEQ ID NO: 77. The transposon may further comprise a second additional polynucleotide immediately adjacent to one ITR, e.g., the second ITR, and proximal to the heterologous polynucleotide, whose nucleotide sequence is at least 95% identical to SEQ ID NO: 78. This transposon may be transposed by a corresponding *Trichoplusia* transposase comprising a polypeptide sequence at least 90% identical to the polypeptide sequence of SEQ ID NO: 79. The *Trichoplusia* transposase may optionally be fused to a heterologous nuclear localization signal. The transposase may be a hyperactive variant of a naturally occurring transposase. The hyperactive variant transposase may comprise one or more of the following amino acid changes, relative to the sequence of SEQ ID NO: 79: G2C, Q40R, I30V, G165S, T43A, S61R, S103P, S103T, M194V, R281G, M282V, G316E, I426V, Q497L, N505D, Q573L, S509G, N570S, N538K, Q591P, Q591R, F594L, M194V, I30V, S103P, G165S, M282V, S509G, N538K, N571S, C41T, A1424G, C1472A, G1681A, T150C, A351G, A279G, T1638C, A898G, A880G, G1558A, A687G, G715A, T13C, C23T, G161A, G25A, T1050C, A1356G, A26G, A1033G, A1441G, A32G, A389C, A32G, A389C, A32G, T1572A, G456A, T1641C, T1 155C, G1280A, T22C, A106G, A29G, C137T, A14V, D475G, P491Q, A561T, T546T, T300A, T294A, A520T, G239S, S5P, S8F, S54N, D9N, D9G, I345V, M481V, E11G, K130T, G9G, R427H, S8P, S36G, D10G, S36G, A51T, C153A, C277T, G201A, G202A, T236A, A103T, A104C, T140C, G138T, T118A, C74T, A179C, S3N, I30V, A46S, A46T, I82W, S103P, R119P, C125A, C125L, G165S, Y177K, Y177H, F180L, F180I, F180V, M185L, A187G, F200W, V207P, V209F, M226F, L235R, V240K, F241L, P243K, N258S, M282Q, L296W, L296Y, L296F, M298V, M298A, M298L, P311V, P311I, R315K, T319G, Y327R, Y328V, C340G, C340L, D421H, V436I, M456Y, L470F, S486K, M503I, M503L, V552K, A570T, Q591P, Q591R, R65A, R65E, R95A, R95E, R97A, R97E, R135A, R135E, R161A, R161E, R192A, R192E, R208A, R208E, K176A, K176E, K195A, K195E, S171E, M14V, D270N, I30V, G165S, M282L, M282I, M282V or M282A.

A suitable piggyBac-like transposon for modifying the genome of a mammalian cell is an *Amyelois* transposon, which comprises, from 5' to 3', a first ITR with the nucleotide sequence SEQ ID NO: 80, a heterologous polynucleotide to be transposed, and a second ITR with the nucleotide sequence SEQ ID NO: 81. The transposon may further be flanked by a copy of the tetranucleotide 5'-TTAA-3' on each side, immediately adjacent to the ITRs and distal to the heterologous polynucleotide. The transposon may further comprise a first additional polynucleotide immediately adjacent to one ITR, e.g., the first ITR, and proximal to the heterologous polynucleotide, whose nucleotide sequence is at least 95% identical to SEQ ID NO: 82. The transposon may further comprise a second additional polynucleotide immediately adjacent to one ITR, e.g., the second ITR, and proximal to the heterologous polynucleotide, whose nucleotide sequence is at least 95% identical to SEQ ID NO: 83. This transposon may be transposed by a corresponding *Amyelois* transposase comprising a polypeptide sequence at least 90% identical to the polypeptide sequence of SEQ ID NO: 84. The *Amyelois* transposase may optionally be fused to a heterologous nuclear localization signal. The transposase may be a hyperactive variant of a naturally occurring transposase. The hyperactive variant transposase may comprise one or more of the following amino acid changes, relative to the sequence of SEQ ID NO: 84: P65E, P65D, R95S, R95T, V100I, V100L, V100M, L115D, L115E, E116P, H121Q, H121N, K139E, K139D, T159N, T159Q, V166F, V166Y, V166W, G179N, G179Q, W187F, W187Y, P198R, P198K, L203R, L203K, I209L, I209V, I209M, N211R, N211K, E238D, L273I, L273V, L273M, D304K, D304R, I323L, I323M, I323V, Q329G, Q329R, Q329K, T345L, T345I, T345V, T345M, K362R, T366R, T366K, T380S, L408M, L408I, L408V, E413R, E413T, S416E, S416D, I426M, I426L, I426V, S435G, L458M, L458I, L458V, A472S, A472T, V475I, V475L, V475M, N483K, N483R, I491M, I491V, I491L, A529P, K540R, S560K, S560R, T562K, T562R, S563K, S563R.

A suitable piggyBac-like transposon for modifying the genome of a mammalian cell is a *Heliothis* transposon, which comprises, from 5' to 3', a first ITR with the nucleotide sequence SEQ ID NO: 85, a heterologous polynucleotide to be transposed, and a second ITR with the nucleotide sequence SEQ ID NO: 86. The transposon may further be flanked by a copy of the tetranucleotide 5'-TTAA-3' on each side, immediately adjacent to the ITRs and distal to the heterologous polynucleotide. The transposon may further comprise a first additional polynucleotide immediately adjacent to one ITR, e.g., the first ITR, and proximal to the heterologous polynucleotide, whose nucleotide sequence is at least 95% identical to SEQ ID NO: 87. The transposon may further comprise a second additional polynucleotide immediately adjacent to one ITR, e.g., the second ITR, and proximal to the heterologous polynucleotide, whose nucleotide sequence is at least 95% identical to SEQ ID NO: 88. This transposon may be transposed by a corresponding *Heliothis* transposase comprising a polypeptide sequence at least 90% identical to the polypeptide sequence of SEQ ID NO: 89. The *Heliothis* transposase may optionally be fused to a heterologous nuclear localization signal. The transposase may be a hyperactive variant of a naturally occurring transposase. The hyperactive variant transposase may comprise one or more of the following amino acid changes, relative to the sequence of SEQ ID NO: 89: S41V, S41I, S41L, L43S, L43T, V81E, V81D, D83S, D83T, V85L, V85I, V85M, P125S, P125T, Q126S, Q126T, Q131R, Q131K, Q131T, Q131S, S136V, S136I, S136L, S136M, E140C, E140A, N151Q, K169E, K169D, N212S, I239L, I239V, I239M, H241N, H241Q, T268D, T268E, T297C, M300R, M300K, M305N, M305Q, L312I, C316A, C316M, L321V, L321M, N322T, N322S, P351G, H357R, H357K, H357D, H357E, K360Q, K360N, E379P, K397S, K397T, Y421F, Y421W, V450I, V450L, V450M, Y495F, Y495W, A447N, A447D, A449S, A449V, K476L, V492A, I500M, L585K and T595K.

A suitable piggyBac-like transposon for modifying the genome of a mammalian cell is an Oryzias transposon which comprises, from 5' to 3', a first ITR with the nucleotide sequence SEQ ID NO: 90, a heterologous polynucleotide to be transposed, and a second ITR with the nucleotide sequence SEQ ID NO: 91. The transposon may further be flanked by a copy of the tetranucleotide 5'-TTAA-3' on each side, immediately adjacent to the ITRs and distal to the heterologous polynucleotide. The transposon may further comprise a first additional polynucleotide immediately adjacent to one ITR, e.g., the first ITR, and proximal to the heterologous polynucleotide, whose nucleotide sequence is at least 95% identical to SEQ ID NO: 94. The transposon may further comprise a second additional polynucleotide immediately adjacent to one ITR, e.g., the second ITR, and proximal to the heterologous polynucleotide, whose nucleotide sequence is at least 95% identical to SEQ ID NO: 95. This transposon may be transposed by a corresponding Oryzias transposase comprising a polypeptide sequence at least 90% identical to the polypeptide sequence of SEQ ID NO: 96. The Oryzias transposase may optionally be fused to a heterologous nuclear localization signal. The transposase may be a hyperactive variant of a naturally occurring transposase. The hyperactive variant transposase may comprise one or more of the following amino acid changes, relative to the sequence of SEQ ID NO: 96: E22D, A124C, Q131D, Q131E, L138V, L138I, L138M, D160E, Y164F, Y164W, I167L, I167V, I167M, T202R, T202K, I206L, I206V, I206M, I210L, I210V, I210M, N214D, N214E, V253I, V253L, V253M, V258L, V258I, V258M, A284L, A284I, A284M, A284V, V386I, V386M, V386L, M400L, M400I, M400V, S408E, S408D, L409I, L409V, L409M, V458L, V458M, V458I, V467I, V467M, V467L, L468I, L468V, L468M, A514R, A514K, V515I, V515M, V515L, R548K, D549K, D549R, D550R, D550K, S551K and S551R A suitable piggyBac-like transposon for modifying the genome of a mammalian cell is an *Agrotis* transposon, which comprises, from 5' to 3', a first ITR with the nucleotide sequence SEQ ID NO: 97, a heterologous polynucleotide to be transposed, and a second ITR with the nucleotide sequence SEQ ID NO: 98. The transposon may further be flanked by a copy of the tetranucleotide 5'-TTAA-3' on each side, immediately adjacent to the ITRs and distal to the heterologous polynucleotide. The transposon may further comprise a first additional polynucleotide immediately adjacent to one ITR, e.g., the first ITR, and proximal to the heterologous polynucleotide, whose nucleotide sequence is at least 95% identical to SEQ ID NO: 99. The transposon may further comprise a second additional polynucleotide immediately adjacent to one ITR, e.g., the second ITR, and proximal to the heterologous polynucleotide, whose nucleotide sequence is at least 95% identical to SEQ ID NO: 100. This transposon may be transposed by a corresponding *Agrotis* transposase comprising a polypeptide sequence at least 90% identical to the polypeptide sequence of SEQ ID NO: 101. The *Agrotis* transposase may optionally be fused to a heterologous nuclear localization signal. The transposase may be a hyperactive variant of a naturally occurring transposase.

A suitable piggyBac-like transposon for modifying the genome of a mammalian cell is a *Helicoverpa* transposon, which comprises, from 5' to 3', a first ITR with the nucleotide sequence SEQ ID NO: 102, a heterologous polynucleotide to be transposed, and a second ITR with the nucleotide sequence SEQ ID NO: 103. The transposon may further be flanked by a copy of the tetranucleotide 5'-TTAA-3' on each side, immediately adjacent to the ITRs and distal to the heterologous polynucleotide. The transposon may further comprise a first additional polynucleotide immediately adjacent to one ITR, e.g., the first ITR, and proximal to the heterologous polynucleotide, whose nucleotide sequence is at least 95% identical to SEQ ID NO: 104. The transposon may further comprise a second additional polynucleotide immediately adjacent to one ITR, e.g., the second ITR, and proximal to the heterologous polynucleotide, whose nucleotide sequence is at least 95% identical to SEQ ID NO: 105. This transposon may be transposed by a corresponding *Helicoverpa* transposase comprising a polypeptide sequence at least 90% identical to the polypeptide sequence of SEQ ID NO: 106. The *Helicoverpa* transposase may optionally be fused to a heterologous nuclear localization signal. The transposase may be a hyperactive variant of a naturally occurring transposase.

A suitable Mariner transposon for modifying the genome of a mammalian cell is a Sleeping Beauty transposon, which comprises, from 5' to 3', a first ITR with the with nucleotide sequence of SEQ ID NO: 107, a heterologous polynucleotide to be transposed, and a second ITR with nucleotide sequence of SEQ ID NO: 108. The transposon may further comprise a first additional polynucleotide immediately adjacent to one ITR, e.g., the first ITR, and proximal to the heterologous polynucleotide, whose nucleotide sequence is at least 95% identical to SEQ ID NO: 109. The transposon may further comprise a second additional polynucleotide immediately adjacent to one ITR, e.g., the second ITR, and proximal to the heterologous polynucleotide, whose nucleotide sequence is at least 95% identical to SEQ ID NO: 110. This transposon may be transposed by a corresponding Sleeping Beauty transposase comprising a polypeptide sequence at least 90% identical to the polypeptide sequence of SEQ ID NO: 111, including hyperactive variants thereof.

A suitable hAT transposon for modifying the genome of a mammalian cell is a TcBuster transposon, which comprises, from 5' to 3', a first ITR with the nucleotide sequence SEQ ID NO: 112, a heterologous polynucleotide to be transposed, and a second ITR with the nucleotide sequence SEQ ID NO: 113. The transposon may further comprise a first additional polynucleotide immediately adjacent to one ITR, e.g., the first ITR, and proximal to the heterologous polynucleotide, whose nucleotide sequence is at least 95% identical to SEQ ID NO: 114. The transposon may further comprise a second additional polynucleotide immediately adjacent to one ITR, e.g., the second ITR, and proximal to the heterologous polynucleotide, whose nucleotide sequence is at least 95% identical to SEQ ID NO: 115. This transposon may be transposed by a corresponding Sleeping Beauty transposase comprising a polypeptide sequence at least 90% identical to the polypeptide sequence of SEQ ID NO: 116, including hyperactive variants thereof.

A transposase protein can be introduced into a cell as a protein or as a nucleic acid encoding the transposase, for example as a ribonucleic acid, including mRNA or any polynucleotide recognized by the translational machinery of a cell; as DNA, e.g., as extrachromosomal DNA including episomal DNA; as plasmid DNA, or as viral nucleic acid. Furthermore, the nucleic acid encoding the transposase protein can be transfected into a cell as a nucleic acid vector such as a plasmid, or as a gene expression vector, including a viral vector. The nucleic acid can be circular or linear. DNA encoding the transposase protein can be stably inserted into the genome of the cell or into a vector for constitutive or inducible expression. Where the transposase protein is transfected into the cell or inserted into the vector as DNA, the transposase encoding sequence may be operably linked to a heterologous promoter. There are a variety of promoters that could be used, including constitutive promoters, tissue-specific promoters, inducible promoters, species-specific promoters, cell-type specific promoters, and the like. All DNA or RNA sequences encoding transposase proteins are expressly contemplated. Alternatively, the transposase may be introduced into the cell directly as protein, for example using cell-penetrating peptides (e.g., as described in Ramsey and Flynn, 2015. Pharmacol. Ther. 154: 78-86 "Cell-penetrating peptides transport therapeutics into cells"); using small molecules including salt plus propanebetaine (e.g., as described in Astolfo et. Al., 2015. Cell 161: 674-690); or electroporation (e.g., as described in Morgan and Day, 1995. Methods in Molecular Biology 48: 63-71 "The introduction of proteins into mammalian cells by electroporation").

Gene Transfer Systems

Gene transfer systems comprise a polynucleotide to be transferred to a host cell. The gene transfer system may comprise any of the transposons or transposases described herein, or it may comprise one or more polynucleotides that have other features that facilitate efficient gene transfer without the need for a transposase or transposon.

When there are multiple components of a gene transfer system, for example the one or more polynucleotides comprising genes for expression in the target cell and optionally comprising transposon ends, and a transposase (which may be provided either as a protein or encoded by a nucleic acid), these components can be transfected into a cell at the same time, or at different times. For example, a transposase protein or its encoding nucleic acid may be transfected into a cell prior to, simultaneously with, or subsequent to transfection of a corresponding transposon. Additionally, administration of either component of the gene transfer system may occur repeatedly, for example, by administering at least two doses of this component.

Transposase proteins may be encoded by polynucleotides including RNA or DNA. If the transposase is provided as a gene encoded in DNA, it may be operably linked to a promoter that is active in the target cell. RNA molecules may include those with appropriate substitutions to reduce toxicity effects on the cell, for example, substitution of uridine with pseudouridine and substitution of cytosine with 5-methyl cytosine. Similarly, the transposon or the nucleic acid encoding the transposases described herein can be transfected into the cell as a linear fragment or as a circularized fragment, either as a plasmid or as recombinant viral DNA.

The components of the gene transfer system may be transfected into one or more cells by techniques such as particle bombardment, electroporation, microinjection, combining the components with lipid nanoparticles or lipid-containing vesicles, such as cationic lipid vesicles, DNA condensing reagents (example, calcium phosphate, polylysine or polyethyleneimine), or inserting the components (that is the nucleic acids) thereof into a viral vector and contacting the viral vector with the cell. Where a viral vector is used, the viral vector can include any of a variety of viral vectors known in the art, including viral vectors selected from the group consisting of a retroviral vector, an adeno-virus vector, or an adeno-associated viral vector. The gene transfer system may be formulated in a suitable manner as known in the art, or as a pharmaceutical composition or kit.

Promoter Elements

Gene transfer systems for expression of polypeptides in immune cells may comprise a polynucleotide to be transferred to a host cell. The polynucleotide may comprise a promoter that is active in the immune cell. Examples include promoters from constitutively expressed genes, including mammalian glyceraldehyde 3-phosphate dehydrogenase ("GAPDH") genes (for example, sequences given by SEQ ID NOs: 117-127), mammalian phosphoglycerate kinase ("PGK") genes (for example, sequences given by SEQ ID NOs: 128-131), mammalian elongation factor 1a ("EF1a") genes (for example, sequences given by SEQ ID NOs: 132-152), mammalian elongation factor 2 ("EEF2") genes (for example sequences given by SEQ ID NOs: 153-163), and ubiquitin genes (for example, sequences given by SEQ ID NOs: 164-167). These genes may be used with or without intron sequences, including their natural intron sequences. Example intron sequences are given as SEQ ID NOs: 168-172.

Polyadenylation Elements

Gene transfer systems are useful for introducing genes for expression into eukaryotic cells. Many eukaryotic cells, including animal cells and higher plant cells, process the mRNA transcribed during gene expression. Protein-encoding genes are often polyadenylated, which stabilizes the mRNA within the cell. Polyadenylation signals may also help to terminate transcription. This can be particularly useful when more than one ORF is to be expressed from a polynucleotide, as it helps to reduce interference between two promoters. Polyadenylation sequences that are effective at terminating transcription from one promoter, thereby reducing interference with a second promoter located to the 3' of the first promoter, may be designed synthetically. Polyadenylation sequences SEQ ID NOs: 173-230 may all be useful for initiating polyadenylation of a transcribed sequence and in terminating transcription. Polyadenylation sequences SEQ ID NOs: 173-230 may be included in the polynucleotide of a gene transfer system for expression of genes in animal cells including vertebrate or invertebrate cells. Polyadenylation sequences SEQ ID NOs: 173-230 are useful for expressing genes in vertebrate cells, including cells from mammals including rodents such as rats, mice, and hamsters; ungulates, such as cows, goats, or sheep; swine; cells from human tissues and human stem cells. Polyadenylation sequences SEQ ID NOs: 173-230 are useful in different cell types including immune cells, lymphocytes, hepatocytes, neural cells, muscle cells, blood cells, embryonic stem cells, somatic stem cells, hematopoietic cells, embryos, zygotes, and sperm cells (some of which are open to be manipulated in an in vitro setting). Polyadenylation sequences SEQ ID NOs: 173-230 are useful for expressing genes in pluripotent cells or totipotent cells. Polyadenylation sequences SEQ ID NOs: 173-230 are useful for expressing genes in culture cells such as Chinese hamster ovary ("CHO") cells or Human embryonic kidney ("HEK293") cells.

Polyadenylation sequences SEQ ID NOs: 173-230 may be incorporated into a piggyBac-like transposon, or a Mariner transposon such as a Sleeping Beauty transposon, or an hAT transposon such as TcBuster, or in a non-transposon-based gene delivery polynucleotide. Polyadenylation sequences SEQ ID NOs: 173-230 may be incorporated into a polynucleotide to the 3' end of an open reading frame to be expressed. Polyadenylation sequences SEQ ID NOs: 173-230 are useful when placed between two genes to be expressed, to terminate transcription from a first promoter and reduce promoter interference. A suitable gene transfer system comprises a sequence at least 80% or 90% or 95% or 96% or 97% or 98% or 99% or 100% identical to any of SEQ ID NOs: 173-230.

Insulator Elements

When a heterologous polynucleotide is integrated into the genome of an immune cell, it is often desirable to prevent genetic elements within the heterologous polynucleotide from influencing expression of endogenous immune cell genes. Similarly, it is often desirable to prevent genes within the heterologous polynucleotide from being influenced by elements in the immune cell genome, for example from being silenced by incorporation into heterochromatin. Insulator elements are known to have enhancer-blocking activity (helping to prevent the genes in the heterologous polynucleotide from influencing the expression of endogenous immune cell genes) and barrier activity (helping to prevent genes within the heterologous polynucleotide from being silenced by incorporation into heterochromatin). Enhancer-blocking activity can result from binding of transcriptional repressor CTCF protein. Barrier activity can result from binding of vertebrate barrier proteins such as USF1 and VEZF1. Useful insulator sequences comprise binding sites for CTCF, USF1, or VEZF1. In one aspect, a gene transfer system comprises a polynucleotide comprising an insulator sequence comprising a binding site for CTCF, USF1, or VEZF1. In another aspect, a gene transfer system comprises a polynucleotide comprising two insulator sequences, each comprising a binding site for CTCF, USF1, or VEZF1, wherein the two insulator sequences flank any promoters or enhancers within the heterologous polynucleotide. Examples of insulator sequences are given as SEQ ID NOs: 231-237.

If a heterologous polynucleotide comprising a promoter or enhancer is integrated into the genome of an immune cell without insulator sequences, there is a risk that either the promoter or enhancer elements within the heterologous polynucleotide will influence expression of endogenous immune cell genes (for example oncogenes), or that promoter or enhancer elements within the heterologous polynucleotide will be silenced by incorporation into heterochromatin. When a heterologous polynucleotide is integrated into a target genome following random fragmentation, some genetic elements are often lost, and others may be rearranged. There is thus a significant risk that, if the heterologous polynucleotide comprises insulator elements flanking enhancer and promoter elements, the insulator elements may be rearranged or lost, and the enhancer and promoter elements may be able to influence and be influenced by the genomic environment into which they integrate. To mitigate this risk, in one aspect, the gene transfer system comprises a transposon gene transfer system, wherein the entire sequence between the two transposon ITRs is integrated, without rearrangement, into the immune cell genome. Thus, in some aspects, gene transfer systems for integration into immune cell genomes comprise a transposon in which elements are arranged in the following order: left transposon end; a first insulator sequence; sequences for expression within the immune cell; a second insulator sequence; right transposon end. The sequences for expression within the immune cell may include any number of regulatory sequences operably linked to any number of open reading frames. In some aspects, the transposon ends are those of a piggyBac-like transposon or a Mariner transposon such as a Sleeping Beauty transposon, or a hAT transposon such as TcBuster transposon.

Genetic Elements Useful for Enhancing Immune Cell Survival

T-Cell Transformation Elements

One approach to enhance the persistence and proliferation of human immune cells is to integrate genetic elements to increase growth and/or survival into the genome of the immune cell. Thus, in one aspect, polynucleotides were prepared, the polynucleotides comprising genes having a sequence encoding a naturally occurring mutant human protein including an activating mutation operably linked to a heterologous promoter effective for expression of the protein in an immune cell. These heterologous polynucleotides were integrated into the genomes of T-cells. Growth and survival of these T-cells were evaluated in ex vivo culture.

CD28

The CD28 (Cluster of Differentiation 28) gene is often found mutated in peripheral T-cell lymphomas. The most common activating mutations are D124E, D124V, T195I, and T195P. In one aspect, a heterologous polynucleotide encoding an activating mutant of a CD28 protein may be introduced into an immune cell to enhance its survival or its proliferation and to reduce restimulation-induced cell death. In one aspect, a polynucleotide encoding a protein comprising a modified version of CD28, whose sequence comprises one or more mutations selected from D124E, D124V, T195I, and T195P, is provided. The CD28 protein is given by SEQ ID NO: 238. An example mutated CD28 protein is given as CD28-D124E/T195P (SEQ ID NO: 241). The mutated CD28 may further comprise replacement of the secretion signal in the first 18 amino acids of SEQ ID NOs: 241 and 238 with another functionally active secretion signal. In one aspect, a polynucleotide comprising a nucleic acid encoding an activating mutant of CD28 is provided, wherein the nucleic acid is operably linked to a heterologous promoter. Example heterologous promoters that may be operably linked to the nucleic acid encoding mutated CD28 include an EF1 promoter, a PGK promoter, a GAPDH promoter, an EEF2 promoter, a ubiquitin promoter, an SV40 promoter, and an HSVTK promoter, for example a sequence selected from SEQ ID NOs: 117-172. In one aspect, a polynucleotide comprising a nucleic acid encoding an activating mutant of CD28 is provided, wherein the nucleic acid is operably linked to a heterologous polyadenylation signal, for example a polyadenylation signal from a virus that infects mammalian cells, a mammalian EF1 polyadenylation signal, a mammalian growth hormone polyadenylation signal, or a mammalian globin polyadenylation signal, for example a sequence selected from SEQ ID NOs: 173-230. In one aspect, a polynucleotide comprising a gene encoding an activating mutant of CD28 is provided, wherein the polynucleotide is part of a piggyBac-like transposon that further comprises sequences with SEQ ID NOs: 8 and 1, or sequences with SEQ ID NOs: 42 and 43, or sequences with SEQ ID NOs: 75 and 76, or sequences with SEQ ID NOs:

3 and 4. In one aspect, a polynucleotide comprising a gene encoding an activating mutant of CD28 is provided, wherein the polynucleotide is part of a Mariner transposon such as a Sleeping Beauty transposon that further comprises a sequence that is 90% identical to SEQ ID NO: 109 and a sequence that is 90% identical to SEQ ID NO: 110. In one aspect, a polynucleotide comprising a gene encoding an activating mutant of CD28 is provided, wherein the polynucleotide is part of an hAT transposon such as a TcBuster transposon that further comprises a sequence that is 90% identical to SEQ ID NO: 92 and a sequence that is 90% identical to SEQ ID NO: 93. The transposon comprising the polynucleotide encoding the activating mutant of CD28 may be introduced into the immune cell together with a corresponding transposase or a polynucleotide encoding a corresponding transposase. In one aspect, a polynucleotide comprising a gene encoding an activating mutant of CD28 is provided, wherein the polynucleotide is part of a lentiviral vector. The lentiviral vector comprising the polynucleotide encoding the activating mutant of CD28 may be packaged and used to infect the immune cell. The immune cell may be a T-cell.

In one aspect, an immune cell is provided whose genome comprises a heterologous polynucleotide comprising a gene encoding a CD28 protein with an activating mutation. In some aspects, the heterologous polynucleotide comprises a lentiviral vector, a piggyBac-like transposon, a Mariner transposon such as a Sleeping Beauty transposon, or an hAT transposon such as a TcBuster transposon. In some aspects, the immune cell genome comprises three copies of the CD28 gene: two endogenous copies and one heterologous mutant copy.

Survivin

The gene encoding Survivin (a member of the Inhibitor of Apoptosis family of proteins, also called baculoviral inhibitor of apoptosis repeat-containing 5 or BIRC5) is sometimes found to be upregulated in T-cell leukemias. In one aspect, a heterologous polynucleotide encoding a Survivin protein operably linked to a heterologous promoter may be introduced into an immune cell to enhance its survival or its proliferation, and to reduce restimulation-induced cell death. In one aspect, a polynucleotide encoding a protein comprising SEQ ID NO: 240 operably linked to a heterologous promoter is provided. Example heterologous promoters that may be operably linked to the gene encoding Survivin include an EF1 promoter, a PGK promoter, a GAPDH promoter, an EEF2 promoter, a ubiquitin promoter, an SV40 promoter, or an HSVTK promoter, for example a sequence selected from SEQ ID NOs: 117-172. In one aspect, a polynucleotide comprising a gene encoding Survivin is provided, wherein the gene is operably linked to a heterologous polyadenylation signal, for example a polyadenylation signal from a virus that infects mammalian cells, a mammalian EF1 polyadenylation signal, a mammalian growth hormone polyadenylation signal, or a mammalian globin polyadenylation signal, for example a sequence selected from SEQ ID NOs: 173-230. In one aspect, a polynucleotide comprising a gene encoding Survivin is provided, wherein the polynucleotide is part of a piggyBac-like transposon that further comprises sequences with SEQ ID NOs: 8 and 1, or sequences with SEQ ID NOs: 42 and 43, or sequences with SEQ ID NOs: 75 and 76, or sequences with SEQ ID NOs: 3 and 4. In one aspect, a polynucleotide comprising a gene encoding Survivin is provided, wherein the polynucleotide is part of a Mariner transposon such as a Sleeping Beauty transposon that further comprises a sequence that is 90% identical to SEQ ID NO: 109 and a sequence that is 90% identical to SEQ ID NO: 110. In one aspect, a polynucleotide comprising a gene encoding Survivin is provided, wherein the polynucleotide is part of an hAT transposon such as a TcBuster transposon that further comprises a sequence that is 90% identical to SEQ ID NO: 92 and a sequence that is 90% identical to SEQ ID NO: 93. The transposon comprising the polynucleotide encoding Survivin may be introduced into the immune cell together with a corresponding transposase or a polynucleotide encoding a corresponding transposase. In one aspect, a polynucleotide comprising a gene encoding Survivin is provided, wherein the polynucleotide is part of a lentiviral vector. The lentiviral vector comprising the polynucleotide encoding Survivin may be packaged and used to infect the immune cell. The immune cell may be a T-cell or a B-cell.

In one aspect, an immune cell is provided whose genome comprises a heterologous polynucleotide comprising a gene encoding Survivin and further comprising a lentiviral vector, a piggyBac-like transposon, a Mariner transposon such as a Sleeping Beauty transposon, or an hAT transposon such as a TcBuster transposon. In some aspects, the immune cell genome comprises three copies of the Survivin gene: two endogenous copies and one heterologous copy operably linked to a heterologous promoter.

Bcl-xL

The gene encoding Bcl-xL (an anti-apoptotic protein) is sometimes found to be upregulated in B-cell lymphomas. In one aspect, a heterologous polynucleotide encoding Bcl-xL protein operably linked to a heterologous promoter may be introduced into an immune cell to enhance its survival or its proliferation, and to reduce restimulation-induced cell death. In one aspect, a polynucleotide encoding a protein comprising SEQ ID NO: 239 operably linked to a heterologous promoter is provided. Example heterologous promoters that may be operably linked to a nucleic acid encoding Bcl-xL include an EF1 promoter, a PGK promoter, a GAPDH promoter, an EEF2 promoter, a ubiquitin promoter, an SV40 promoter, or an HSVTK promoter, for example a sequence selected from SEQ ID NOs: 117-172. In one aspect, a polynucleotide comprising a nucleic acid encoding Bcl-xL is provided, wherein the nucleic acid is operably linked to a heterologous polyadenylation signal, for example a polyadenylation signal from a virus that infects mammalian cells, a mammalian EF1 polyadenylation signal, a mammalian growth hormone polyadenylation signal, or a mammalian globin polyadenylation signal, for example a sequence selected from SEQ ID NOs: 173-230. In one aspect, a polynucleotide comprising a gene encoding Bcl-xL is provided, wherein the polynucleotide is part of a piggyBac-like transposon that further comprises sequences with SEQ ID NOs: 8 and 1, or sequences with SEQ ID NOs: 42 and 43, or sequences with SEQ ID NOs: 75 and 76, or sequences with SEQ ID NOs: 3 and 4. In one aspect, a polynucleotide comprising a gene encoding Bcl-xL is provided, wherein the polynucleotide is part of a Mariner transposon such as a Sleeping Beauty transposon that further comprises a sequence that is 90% identical to SEQ ID NO: 109 and a sequence that is 90% identical to SEQ ID NO: 110. In one aspect, a polynucleotide comprising a gene encoding Bcl-xL is provided, wherein the polynucleotide is part of an hAT transposon such as a TcBuster transposon that further comprises a sequence that is 90% identical to SEQ ID NO: 92 and a sequence that is 90% identical to SEQ ID NO: 93. The transposon comprising the polynucleotide encoding Bcl-xL may be introduced into the immune cell together with a polynucleotide encoding a corresponding transposase. In one aspect, a polynucleotide comprising a gene encoding Bcl-xL is provided, wherein the polynucleotide is part of a lentiviral vector. The lentiviral vector comprising the polynucleotide encoding Bcl-xL may be packaged and used to infect the immune cell. The immune cell may be a T-cell or a B-cell.

In one aspect, an immune cell is provided whose genome comprises a heterologous polynucleotide comprising a gene encoding Bcl-xL and further comprising a lentiviral vector, a piggyBac-like transposon, a Mariner transposon such as a Sleeping Beauty transposon, or an hAT transposon such as a TcBuster transposon. In some aspects, the immune cell genome comprises three copies of the Bcl-XL gene: two endogenous copies and one heterologous copy operably linked to a heterologous promoter.

Bcl2

The gene encoding Bcl2 (an anti-apoptotic protein) is sometimes found to be upregulated in B-cell lymphomas. In one aspect, a heterologous polynucleotide encoding a Bcl2 protein operably linked to a heterologous promoter may be introduced into an immune cell to enhance its survival or its proliferation. In one aspect, a polynucleotide encoding a protein comprising SEQ ID NO: 242 operably linked to a heterologous promoter is provided. Example heterologous promoters that may be operably linked to a nucleic acid encoding Bcl2 include an EF1 promoter, a PGK promoter, a GAPDH promoter, an EEF2 promoter, a ubiquitin promoter, an SV40 promoter, or an HSVTK promoter, for example a sequence selected from SEQ ID NOs 117-172. In one aspect, a polynucleotide comprising a nucleic acid encoding Bcl2 is provided, wherein the nucleic acid is operably linked to a heterologous polyadenylation signal, for example a polyadenylation signal from a virus that infects mammalian cells, a mammalian EF1 polyadenylation signal, a mammalian growth hormone polyadenylation signal, or a mammalian globin polyadenylation signal, for example a sequence selected from SEQ ID NOs 173-230. In one aspect, a polynucleotide comprising a gene encoding Bcl2 is provided, wherein the polynucleotide is part of a piggyBac-like transposon that further comprises sequences with SEQ ID NOs: 8 and 1, or sequences with SEQ ID NOs: 42 and 43, or sequences with SEQ ID NOs: 75 and 76, or sequences with SEQ ID NOs: 3 and 4. In one aspect, a polynucleotide comprising a gene encoding Bcl2 is provided, wherein the polynucleotide is part of a Mariner transposon such as a Sleeping Beauty transposon that further comprises a sequence that is 90% identical to SEQ ID NO: 109 and a sequence that is 90% identical to SEQ ID NO: 110. In one aspect, a polynucleotide comprising a gene encoding Bcl2 is provided, wherein the polynucleotide is part of an hAT transposon such as a TcBuster transposon that further comprises a sequence that is 90% identical to SEQ ID NO: 92 and a sequence that is 90% identical to SEQ ID NO: 93. The transposon comprising the polynucleotide encoding Bcl2 may be introduced into the immune cell together with a polynucleotide encoding a corresponding transposase. In one aspect, a polynucleotide comprising a gene encoding Bcl2 is provided, wherein the polynucleotide is part of a lentiviral vector. The lentiviral vector comprising the polynucleotide encoding Bcl2 may be packaged and used to infect the immune cell. The immune cell may be a T-cell or a B-cell.

In one aspect, an immune cell is provided whose genome comprises a heterologous polynucleotide comprising a gene encoding Bcl2 and further comprising a lentiviral vector, a piggyBac-like transposon, a Mariner transposon such as a Sleeping Beauty transposon, or an hAT transposon such as a TcBuster transposon. In some aspects, the immune cell genome comprises three copies of the Bcl2 gene: two endogenous copies and one heterologous copy operably linked to a heterologous promoter.

Bcl6

The gene encoding Bcl6 (an anti-apoptotic protein) is sometimes found to be upregulated in B-cell lymphomas. In one aspect, a heterologous polynucleotide encoding a Bcl6 protein operably linked to a heterologous promoter may be introduced into an immune cell to enhance its survival or its proliferation. A Bcl6 gene operably linked to a heterologous promoter is an immune cell survival-enhancing gene and an immune cell proliferation-enhancing gene. In one aspect, a polynucleotide encoding a protein comprising SEQ ID NO: 243 operably linked to a heterologous promoter is provided. Example heterologous promoters that may be operably linked to a nucleic acid encoding Bcl6 include an EF1 promoter, a PGK promoter, a GAPDH promoter, an EEF2 promoter, a ubiquitin promoter, an SV40 promoter, or an HSVTK promoter, for example a sequence selected from SEQ ID NOs 117-172. In one aspect, a polynucleotide comprising a nucleic acid encoding Bcl6 is provided, wherein the nucleic acid is operably linked to a heterologous polyadenylation signal, for example a polyadenylation signal from a virus that infects mammalian cells, a mammalian EF1 polyadenylation signal, a mammalian growth hormone polyadenylation signal, or a mammalian globin polyadenylation signal, for example a sequence selected from SEQ ID NOs 173-230. In one aspect, a polynucleotide comprising a gene encoding Bcl6 is provided, wherein the polynucleotide is part of a piggyBac-like transposon that further comprises sequences with SEQ ID NOs: 8 and 1, or sequences with SEQ ID NOs: 42 and 43, or sequences with SEQ ID NOs: 75 and 76, or sequences with SEQ ID NOs: 3 and 4. In one aspect, a polynucleotide comprising a gene encoding Bcl6 is provided, wherein the polynucleotide is part of a Mariner transposon such as a Sleeping Beauty transposon that further comprises a sequence that is 90% identical to SEQ ID NO: 109 and a sequence that is 90% identical to SEQ ID NO: 110. In one aspect, a polynucleotide comprising a gene encoding Bcl6 is provided, wherein the polynucleotide is part of an hAT transposon such as a TcBuster transposon that further comprises a sequence that is 90% identical to SEQ ID NO: 92 and a sequence that is 90% identical to SEQ ID NO: 93. The transposon comprising the polynucleotide encoding Bcl6 may be introduced into the immune cell together with a corresponding transposase or a polynucleotide encoding a corresponding transposase. In one aspect, a polynucleotide comprising a gene encoding Bcl6 is provided, wherein the polynucleotide is part of a lentiviral vector. The lentiviral vector comprising the polynucleotide encoding Bcl6 may be packaged and used to infect the immune cell. The immune cell may be a T-cell or a B-cell.

In one aspect, an immune cell is provided whose genome comprises a heterologous polynucleotide comprising a gene encoding Bcl6 and further comprising a lentiviral vector or a piggyBac-like transposon. In some aspects, the immune cell genome comprises three copies of the Bcl6 gene: two endogenous copies and one heterologous copy operably linked to a heterologous promoter.

Kits

In one aspect, kits are provided, the kits comprising a transposase as a protein or encoded by a nucleic acid, and/or a transposon; or a gene transfer system as described herein comprising a transposase as a protein or encoded by a nucleic acid, in combination with a transposon; optionally together with a pharmaceutically acceptable carrier, adjuvant, or vehicle, and optionally with instructions for use, including as an internet address, e.g., on packaging, where instructions are provided. In one aspect, any of the components of the kit may be administered and/or transfected into cells in a subsequent order or in parallel, e.g., a transposase protein or its encoding nucleic acid may be administered and/or transfected into a cell as defined above prior to, simultaneously with, or subsequent to administration and/or transfection of a transposon. Alternatively, a transposon may be transfected into a cell as defined above prior to, simultaneously with, or subsequent to transfection of a transposase protein or its encoding nucleic acid. If transfected in parallel, both components may be provided in a separated formulation and/or mixed with each other directly prior to administration to avoid transposition prior to transfection. Additionally, administration and/or transfection of at least one component of the kit may occur in a time staggered mode, e.g., by administering multiple doses of such component.

EXAMPLES

The following examples illustrate the methods, compositions, and kits disclosed herein and should not be construed as limiting in any way. Various equivalents will be apparent from the following examples; such equivalents are also contemplated to be part of the invention disclosed and claimed herein.

Example 1: Construction of Gene Transfer Polynucleotides Encoding Bcl-xL, Survivin, or CD28-D124E/T195P Gene transfer polynucleotide 335791 (with nucleotide sequence SEQ ID NO: 244) comprised an ORF encoding Bcl-xL (with polypeptide sequence SEQ ID NO: 239). Gene transfer polynucleotide 335797 (with nucleotide sequence SEQ ID NO: 245) comprised an ORF encoding Survivin (with polypeptide sequence SEQ ID NO: 240). Gene transfer polynucleotide 335823 (with nucleotide sequence SEQ ID NO: 246) comprised an ORF encoding CD28-D124E/T195P (with polypeptide sequence SEQ ID NO: 241). In each case, the ORF was operably linked to a PGK promoter with nucleotide sequence SEQ ID NO: 128 and a rabbit globin polyadenylation signal with nucleotide sequence SEQ ID NO: 195. Each gene transfer polynucleotide further comprised a GFP reporter (with nucleotide sequence SEQ ID NO: 247) comprising an ORF encoding DasherGFP operably linked to a GAPDH promoter and a BGH polyadenylation signal sequence. The two ORFs in each gene transfer polynucleotide were configured to be divergently transcribed. The two ORFs in each gene transfer polynucleotide were flanked on one side by an HS4 insulator (nucleotide sequence SEQ ID NO: 236), and on the other by a D4Z4 insulator (nucleotide sequence SEQ ID NO: 232). Each gene transfer polynucleotide further comprised, on the distal side of one insulator, a target sequence 5'-TTAA-3', immediately followed by a piggyBac-like transposon inverted terminal repeat nucleotide sequence SEQ ID NO: 248 (which is an embodiment of SEQ ID NO: 1), immediately followed by additional transposon end nucleotide sequence SEQ ID NO: 249 (which is >95% identical to SEQ ID NO: 5). Each gene transfer polynucleotide further comprised, on the distal side of the other insulator, additional transposon end nucleotide sequence SEQ ID NO: 8 (which is >95% identical to SEQ ID NO: 7), immediately followed by a piggyBac-like transposon inverted terminal repeat nucleotide sequence SEQ ID NO: 250 (which is an embodiment of SEQ ID NO: 2), immediately followed by a target sequence 5'-TTAA-3'. All of the described elements of each gene transfer polynucleotide were transposable as a single transposon by a corresponding transposase, for example a transposase with polypeptide sequence selected from SEQ ID NOs: 9-41.

Example 2: Transfection of CD8+ T Cells with Gene Transfer Polynucleotides Encoding Bcl-xL, Survivin, or CD28-D124E/T195P Primary human CD8+ T cells were isolated from consented healthy donor PBMCs by magnetic bead separation using an EasySep™ Human CD8 Selection Kit II (STEMCELL) according to the manufacturer's protocol or by using negative selection sorting on a BD FACSAria cell sorter (BD Biosciences) on a large amount of cells (up to $10^{11}$). For T cell priming and stimulation, a TSF feeder cell was used. A lentivirus was used to generate a TSF (K562-aAPC-IL2-IL7-IL15) feeder cell line with additional hIL-2, hIL-7, and hIL-15 genes in K562-based artificial antigen-presenting cells (K56-aAPCs). The parent feeder cells, described in international patent application publication number WO2018132508, were generously provided by Dr. Marcela V Maus (MGH). K562-aAPCs were modified with two chimeric stimulatory receptors, α-CD3-GFP and α-CD28-mCherry, which were initially generated from wild-type K562 cells by lentiviral introduction of an α-CD3 single-chain variable fragment (scFv) derived from the OKT3 clone and an α-CD28 scFv derived from the 9.3 clone, respectively.

Before transfection, CD8+ T cells were activated for 3 days using pre-irradiated rhIL-2-, rhIL-7-, and rhIL-15-secreting TSF feeder cells at a 1:10 T:TSF ratio or aCD3/aCD28 coupled Dynabeads (Life Technologies) at a 1:1 ratio, and the cells were cultured in complete RMPI media (RPMI-1640 media supplemented with 2-5% human serum, 1% non-essential amino acids, 1%, sodium pyruvate, 1% glutamine, penicillin, streptomycin, and 50 M β-mercaptoethanol) with rhIL2 (200-500 IU, PeproTech). Pre-irradiated TSF feeder cells were pre-determined to die out after 3 days in the co-culture as confirmed by flow cytometry.

Each gene transfer polynucleotide described in Example 1 (with nucleotide sequences SEQ ID NOs: 244-246 encoding Bcl-xL, Survivin, or CD28-D124E/T195P, respectively) was electroporated, together with mRNA (with nucleotide sequence SEQ ID NO: 251, encoding a transposase with polypeptide sequence SEQ ID NO: 15), into primed CD8+ T cells using a Neon transfection kit and device (ThermoFisher).

A low-transfection efficiency system was used for a survival competition assay. Specifically, a mixture of resuspended cells (2 $e^5$ cells at 2 $e^7$/ml in R-10 buffer), gene transfer polynucleotide (1 µg, 1 µg/µl), and transposase mRNA (0.1 ug, 0.1 ug/ul) was made prior to electroporation. A 10 µL Neon transfection kit and Neon device were used for electroporation at 1600 v, 10 ms, 3 pulses. A high-transfection efficiency system was used in CAR-Gene-T constructions. Specifically, upon each transfection (10 μL/test), 0.6 ug transposase mRNA was complexed with $2 e^5$ cells resuspended in R-10 buffer at $2 e^7$/ml. 6 ug gene transfer polynucleotide DNA was added prior to electroporation at 1600 v, 10 ms, 3 pulses.

After transfection, cells were passed to pre-warmed T Cell Transfection media, that is, an antibiotic-free complete RMPI media supplemented with rhIL-2 (500 IU, PeproTech), rhIL-7, and rhIL-15 (10 ng/ml, PeproTech). Transfection efficiency was determined 24 h post electroporation by flow cytometry. 30% of the total transfection reaction was plated into a different well for monitoring transfection efficiency on day 1. The rest (70%) of the reaction was left unmixed during most of the cell culture period post-electroporation.

The optimal time point to collect the transfected cells for further downstream analysis, such as flow analysis and sorting, is between 7-14 days, depending on the plate used, the donor, and the transfection efficiency. Transfected cells were collected all at once to prevent further disruptions.

TSF activated transgene transfected CD8$^+$ T cells ("Gene-T cells") were cultured for 2 weeks with pre-irradiated TSF feeder cells, which were supplemented by changing the media twice per week, followed by resting in R-10 media for 2-48 weeks prior to sorting and/or other downstream functional assays.

In certain aspects, Gene-T cells were pre-activated by Dynabeads and were supplemented with rhIL-7 and rhIL-15 (5 ng/ml; PeproTech). T cells were cultured in rhIL-7/rhIL-15-depleted media for 2 d before being used in in vitro functional assays.

Example 3: Persistent Over-Expression of Genes Encoding for Survivin, CD28-D124E/T195P, or Bcl-xL in CD8$^+$ T Cells Gene transfer polynucleotides encoding Bcl-xL, Survivin, or CD28-D124E/T195P were constructed according to Example 1, and the constructs were transfected into CD8$^+$ T cells according to Example 2 to provide Gene-T cells.

Gene-T cells were stimulated with irradiated TSF feeder cells at a 1:1 ratio for 2 weeks post transfection in R10 media. The culture was continued in RPMI complete media supplemented with hIL-2 200-500 IU for up to 140 days. As a negative control, Empty T cells were isolated and cultured for 2 weeks under the same conditions.

Approximately $1 \times 10^6$ cells were harvested and washed twice before FACS staining. For surface staining, the cells were resuspended in 200 μl FACS buffer, stained with surface antibodies (Anti-human CD8-PerCp 5.5 (BD Biosciences, #560662); Survivin: Rabbit mAb, AF647 conjugated, Cell signaling #716487; Bcl-xL: Rabbit mAb, PE-conjugated, Cell signaling #54H6; and CD28: Syrian hamster IgG, PE/Cy7 conjugated, BioLegend #102125), and incubated for 40 min at rt in the dark. The cells were washed twice by centrifugation at 1600 rpm for 5 min, resuspended in 200 μl of ice-cold FACS buffer, filtered, and run on a BD Fortessa.

For intracellular staining, 500 μl of Fixation Buffer was added to the cells, and the cells were incubated at rt for 20 min. The cells were washed in FACS buffer, and the supernatant was discarded. 100 μl of 0.5% Triton X-100 was added, followed by gentle mixing, and incubation for 15 min at rt. 2 ml of FACS buffer was added, followed by centrifugation at 350 g for 5 min, and the supernatant was discarded. The antibodies for Survivin, CD28-D124E/T195P, and Bcl-xL for intracellular protein were added to the tubes (normally 1/50 or 1/100 dilution), followed by incubation for 60 min at rt in the dark. The cells were wash with 2 ml of FACS buffer, centrifuged at 350 g for 5 min, and the supernatant was discarded. Another 1 mL of FACS buffer was added, followed by centrifugation at 350 g for 5 min, and the supernatant was discarded. The cells were resuspended in 200 ul of fresh FACS buffer, filtered, and run on a BD Fortessa.

Figure 2:
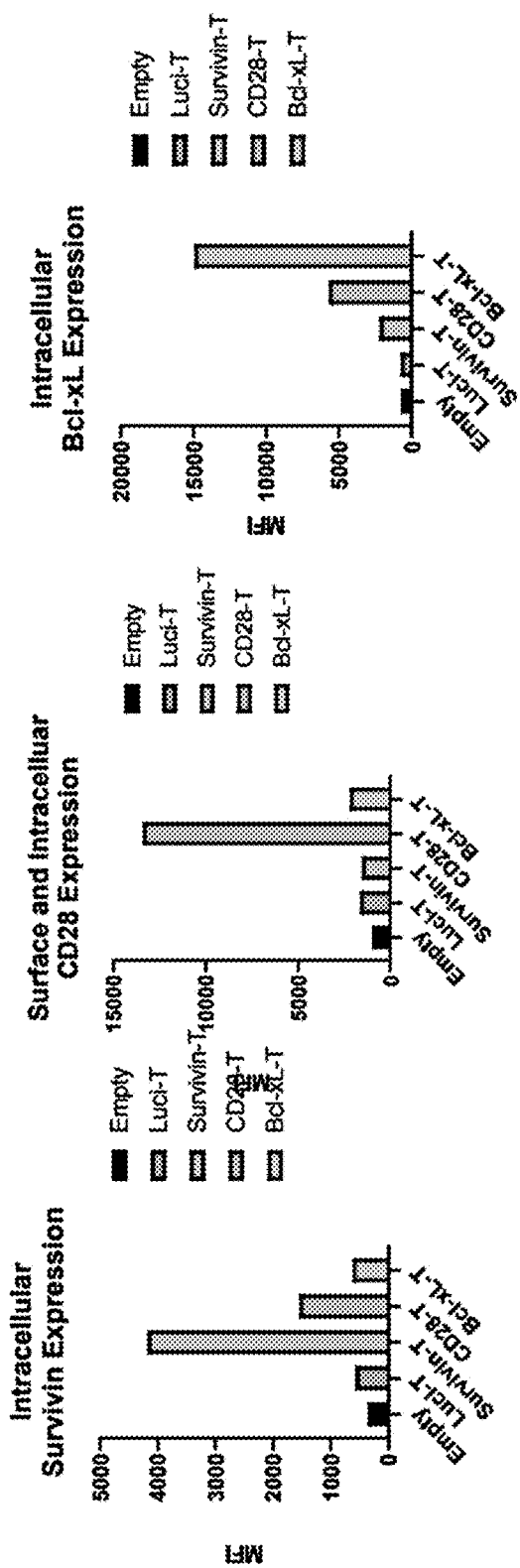
FIG. 2 quantifies the over-expression in the Gene-T cells described in FIG. 1, where "MFI" (on the y-axis) is the mean fluorescence index, and shows that the genes encoding for Bcl-xL, Survivin, and CD28-D124E/T195P are overexpressed in their respective Gene-T cells.

FIG. 1 is a set of FACS data showing the expression of function (persistence)-booster genes encoding Bcl-xL, Survivin, or CD28-D124E/T195P in Gene-T cells. FIG. 2 quantifies the protein over-expression in the Gene-T cells described in FIG. 1 and shows that Bcl-xL, Survivin, and CD28-D124E/T195P are overexpressed in their respective Gene-T cells.

Example 4: Preservation of T Cell Function in Gene-T Cells

Gene transfer polynucleotides encoding Bcl-xL, Survivin, or CD28-D124E/T195P were constructed according to Example 1, and the constructs were transfected into CD8$^+$ T cells according to Example 2.

Gene-T cells were stimulated with irradiated TSF feeder cells at a 1:1 ratio for 2 weeks post-transfection in R-10 media. The culture was continued in RPMI Complete media supplemented with rhIL-2 200-500 IU for 4 weeks.

Approximately $1 \times 10^6$ cells were resuspended at $1 \times 10^6$ cells/mL in AIM-V media. The cells were separated evenly into treated and untreated groups. Pre-washed and resuspended aCD3/aCD28 Dyna Dynabeads Human T-Activator CD3/CD28 (Invitrogen, #11161D) were added to obtain a bead-to-cell ratio of 1:1. The treated and untreated cells were incubated in a humidified CO$_2$ incubator at 37° C. for 6 h. Activation of the T cells was assessed by testing for upregulation of the CD69 or HLA-DR molecules by FACS analysis. The cells were harvested, washed twice in FACS buffer, resuspended in FACS buffer, and stained with surface antibody (Anti-human CD3-APC/Cy7 (BioLegend, #100221), Anti-human CD8-PerCP (BioLegend, #980916), and Anti-human CD69-BV510 (BioLegend, #310935) or Anti-human HLA-DR (BioLegend, #307635)) for 2 h. The cells were washed three times by centrifugation at 1600 rpm for 5 min and resuspended in 200 μl of ice-cold FACS buffer, filtered, and run on BD fortessa. The experiment included Luci-T cells and "Normal T" (Empty T) cells as negative controls.

Figure 3:
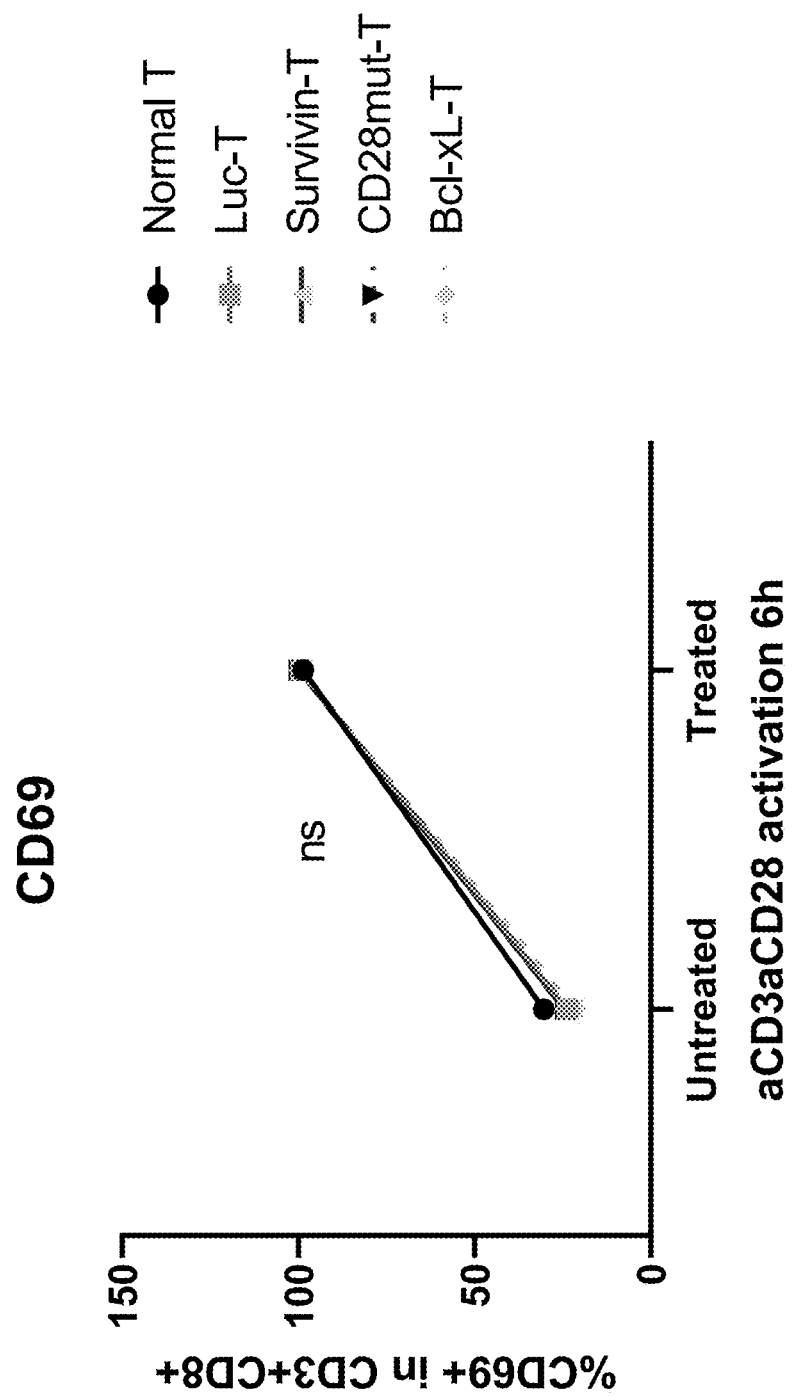
FIG. 3 shows a nonsignificant difference in the expression of CD69 (% of CD69+ in $CD3^+CD8^+$ cells) between Gene-T cells and Empty T cells after 6 h of aCD3/aCD28 activation, indicating that Gene-T cells are activated normally.
Figure 4:
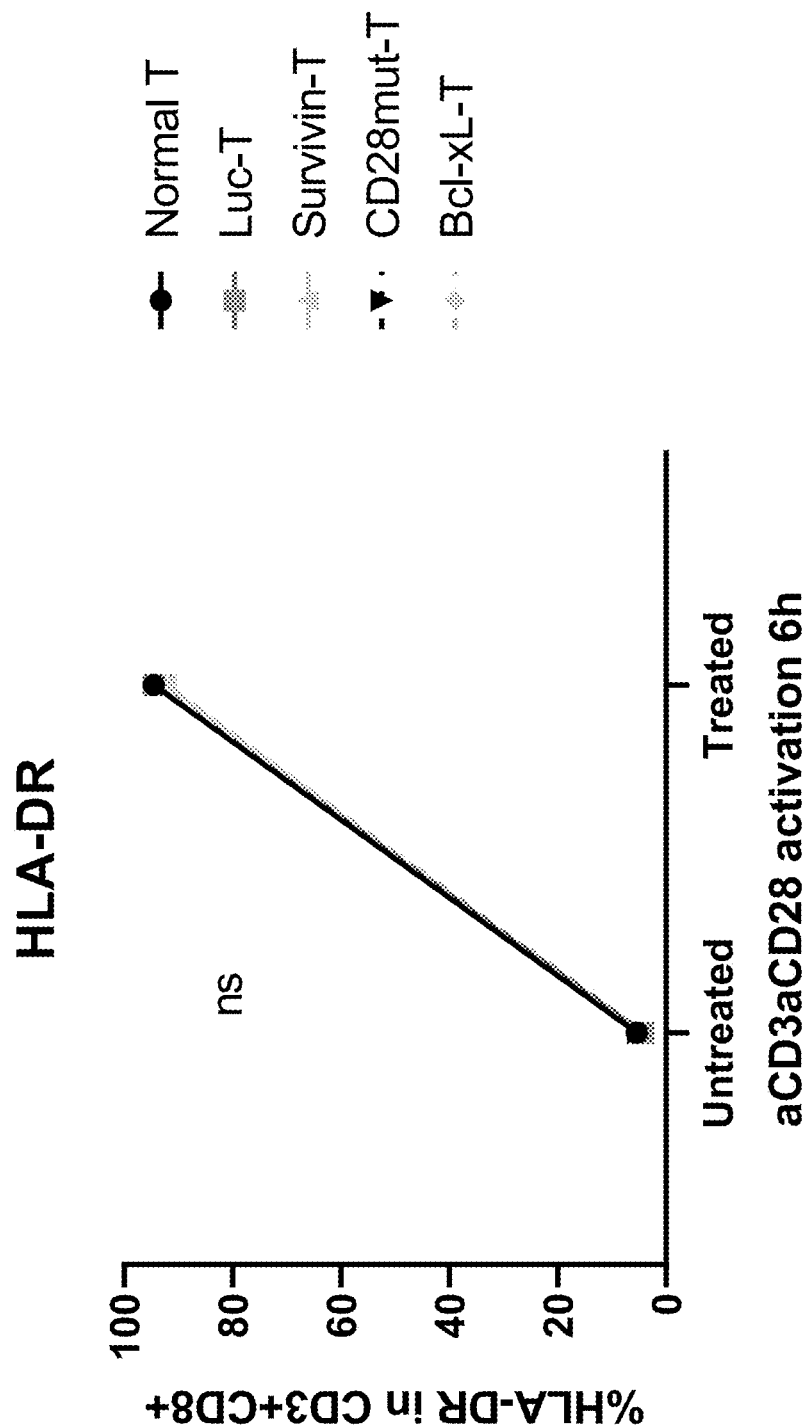
FIG. 4 shows a nonsignificant difference in the expression of HLA-DR (% of HLA-DR+ in $CD3^+CD8^+$ cells) between Gene-T cells and Empty T cells after 6 h of aCD3/aCD28 activation, again indicating that Gene-T cells are activated normally.

FIG. 3 shows a nonsignificant difference in the expression of CD69 (% of CD69+ in CD3$^+$CD8$^+$ cells) between Gene-T cells and Empty T cells after 6 h of aCD3/aCD28 activation, indicating that Gene-T cells are activated normally. FIG. 4 shows a nonsignificant difference in the expression of HLA-DR (% of HLA-DR+ in CD3$^+$CD8$^+$ cells) between Gene-T cells and Empty T cells after 6 h of aCD3/aCD28 activation, again indicating that Gene-T cells are activated normally.

Supernatants from the stimulated cells were tested for the presence of IFN-γ. The supernatant was harvested, and IFN-γ production was quantified by ELISA according to the manufacturer's protocol. IFN-γ production was analyzed by absorbance readings at 450 nm within 30 min using a BD bio-luminometer and quantified by a standard control curve according to the manufacturer's protocol. The experiment included Luci-T and Empty T cells as negative controls.

Figure 5:
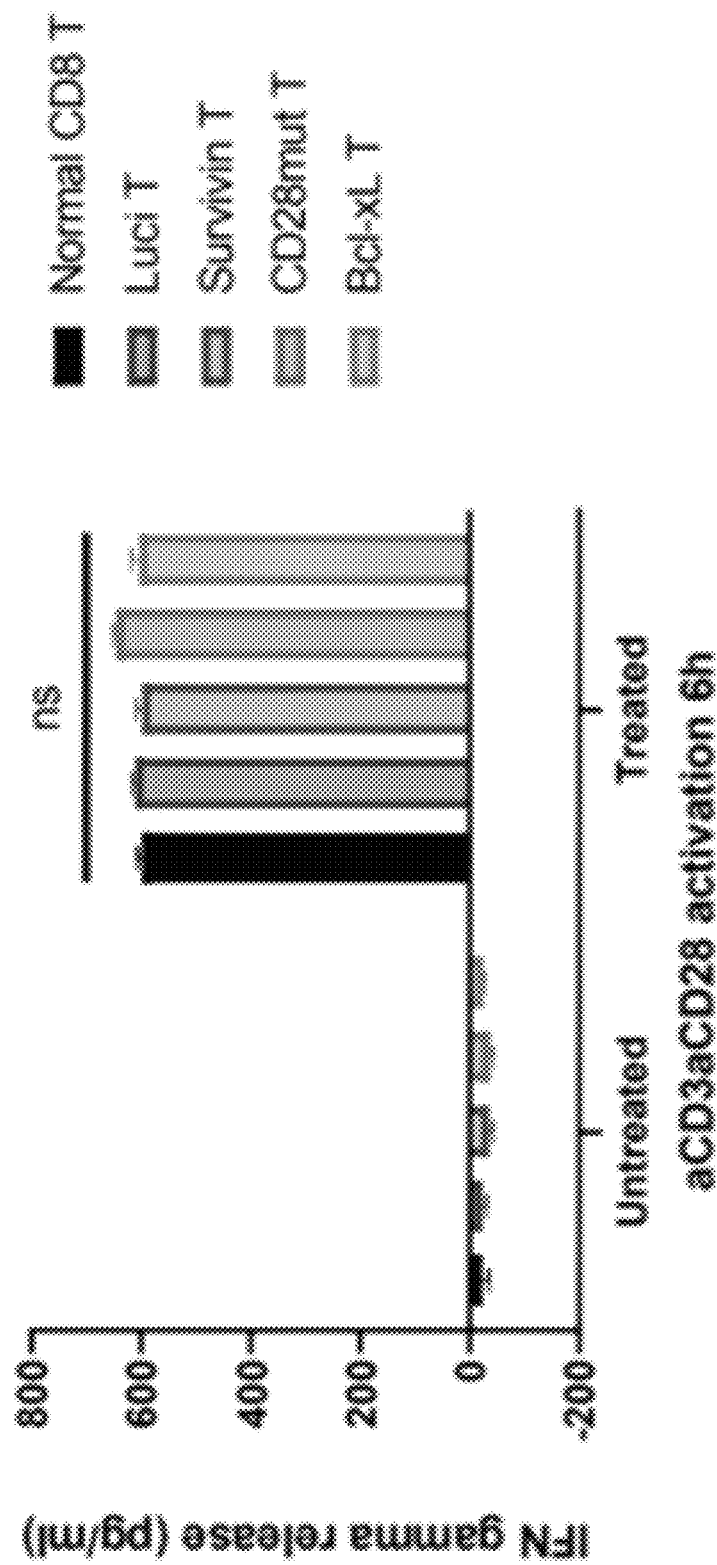
FIG. 5 shows a nonsignificant difference in cytokine production in the supernatant between Gene-T cells and Empty T cells after 6 h of aCD3/aCD28 activation (shown in FIG. 3 and FIG. 4), indicating that Gene-T cells produce cytokines normally. The bar depicts Interferon-γ (IFN-γ) release levels in the supernatant (n=3).

FIG. 5 shows a nonsignificant difference in cytokine production in the supernatant between Gene-T cells and Empty T cells after 6 h of aCD3/aCD28 activation (shown in FIG. 3 and FIG. 4), indicating that Gene-T cells produce cytokines normally. The bar depicts IFN-γ release levels in the supernatant (n=3).

Taken together, FIGS. 3, 4, and 5 demonstrate that the transfection of T cells with gene transfer polynucleotides encoding Bcl-xL, Survivin, or CD28-D124E/T195P does not change the normal function of the T cells.

Example 5: Re-Expansion and IL-2-Independent Persistence of Gene-T Cells Post Long-Term Ex Vivo Culture Gene transfer polynucleotides encoding Bcl-xL, Survivin, or CD28-D124E/T195P were constructed according to Example 1, and the constructs were transfected into CD8$^+$ T cells according to Example 2.

Gene-T cells were primed by irradiated TSF feeder cells at a 10:1 T cell:TSF ratio. After two weeks, transposon-positive cells were purified using a FACS-based sorting on CD8, CAR, and GFP expression. The purified cells were cultured in RPMI Complete Media supplemented with recombinant rhIL-2 (PeproTech, #200-02) 200-500 IU for at least 340 days.

The re-expansion ability of long-term ex vivo cultured Gene-T cells was investigated using CD8$^+$ T cell activation Dynabeads (Life Technologies, #11161D). Gene-T cells were harvested after at least 340 days ex vivo culture. Fresh CD8$^+$ T cells were isolated as an experimental control. The T cells were re-stimulated with aCD3/aCD28 Dynabeads (Life Technologies) at a 1:1 ratio for 24 h at a density of 0.5-1×10$^6$ cells/ml in the complete RPMI media with or without 500 IU rhIL-2 for 24h.

The activated T cells were harvested, and the beads were removed. The cells were counted using a hemocytometer. Cells were continually cultured and counted with viability dye every other day after thorough resuspension. Viable cell numbers were recorded, and population doublings were calculated as $\log^2$ (Increase factors day 0 to day n), where increase factor=(total # cells day n/total # of cells day 0).

Figure 6:
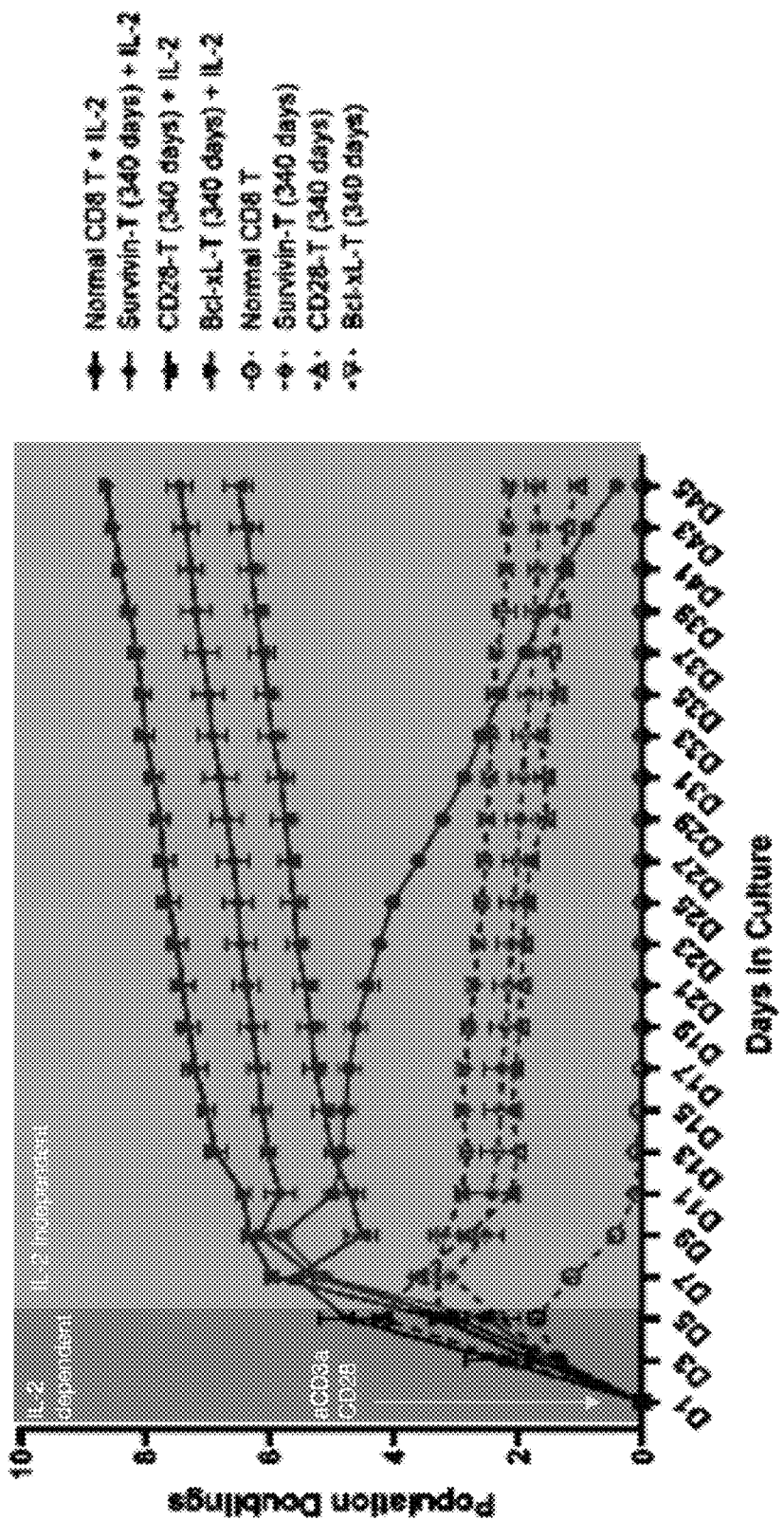
FIG. 6 shows the relative recall expansion (population doublings) of long-term ex vivo cultured Gene-T cells and Empty T cells after aCD3/aCD28 stimulation (n=3), where the culturing environment was compared both with the existence of rhIL-2 and without. The graph identifies an inferred period of time in which the recalled expansion of the cells exhibited an IL-2-dependent phase versus an IL-2-independent phase. Bcl-xL, Survivin, and CD28-D124E/T195P Gene-T cells persist longer and have a survival advantage (but not uncontrolled expansion) with IL-2 and retain the survival advantage without IL-2.

FIG. 6 shows the relative recall expansion (population doublings) of long-term ex vivo cultured Gene-T cells and Empty T cells after aCD3/aCD28 stimulation. The graph identifies an inferred period of time in which the expansion of the cells was IL-2-dependent versus IL-2-independent. Normal T cells will not survive for 340 days, so for the control it was necessary to use fresh unmodified T cells. In the absence of added IL-2, the fresh control cultures fail to expand and die off after 5 days. The fresh control cultures survive for much longer in the presence of IL-2, but they do not expand beyond 9 days. As shown in FIG. 6, Gene-T cells first showed a similar level of recalled expansion at the beginning of 5 days (without rhIL-2) or 9 days (with rhIL-2) compared to the fresh T cell control, indicating the Gene-T cells' normal response to rhIL-2 and aCD3/aCD28 stimulation. However, instead of undergoing a population contraction like the fresh T cells, Gene-T cells continued to expand for 45 days in the presence of IL-2. Gene-T cells also showed an rhIL-2 independent persistence, which led to a prolonged survival (without expansion) for 45 days in the absence of rhIL-2.

Figure 7:
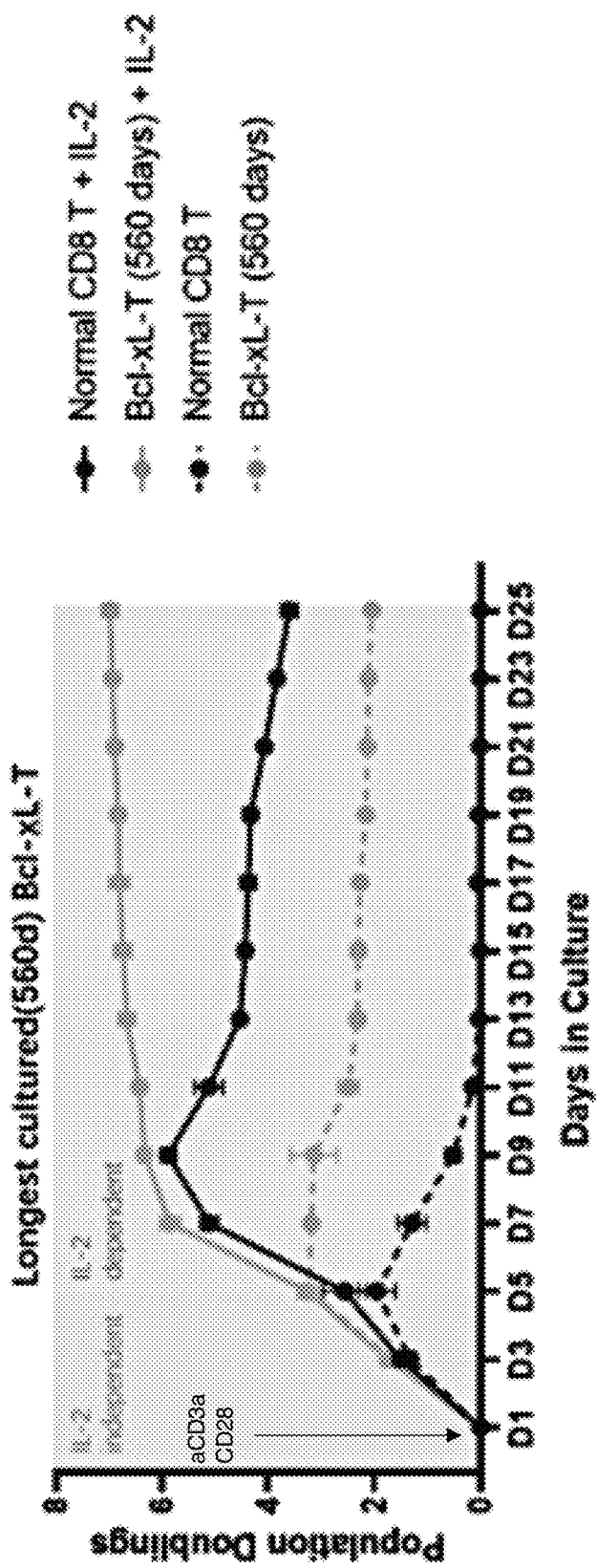
FIG. 7 shows that 560 days long-term ex vivo cultured T cells transfected with a gene encoding for Bcl-xL exhibited a recalled expansion response to aCD3/aCD28 stimulation with and without the presence of IL-2, which indicates that Bcl-xL-T can respond to recall stimulation and shows a prolonged survival (without uncontrolled expansion) compared to Empty T cells with or without IL-2, even after 560 days in ex vivo culture.

FIG. 7 shows that after 560 days in ex vivo culture, Bcl-xL-T cells still exhibited a recalled expansion response to aCD3/aCD28 stimulation and continued expansion in the presence of rhIL-2, as well as prolonged survival (without expansion) in the absence of rhIL-2.

Example 6: BiTE Re-Challenge Assay Demonstrating Preservation of T Cell Function in Gene-T Cells Gene transfer polynucleotides encoding Bcl-xL, Survivin, or CD28-D124E/T195P were constructed according to Example 1, and the constructs were transfected into CD8$^+$ T cells according to Example 2.

Gene-T cells were stimulated with feeder cells (iK562 cells transfected to express IL-2, IL-15, and IL-7) at a 1:1 ratio for 2 weeks post-transfection in R-10 media. The culture was continued in RPMI Complete media supplemented with iL-2 200-500 IU for one more week.

The NALM-6 target cells used in this assay expressed a cytosolic luciferase that was released into the culture media when they were lysed. The experiment involved mixing the T cells and target cells initially (on day 0) at a 1:1 ratio in a 96-well plate in the presence of a BiTE. A small amount of supernatant fluid was removed on day 1 and tested for the presence of luciferase by luminometry (after adding the luciferase substrate D-luciferin). The admixture of NALM-6 cells and the subsequent analysis for the presence of released luciferase were repeated on a two-day interval for a total of seven times.

Starting with 1×10$^5$ NALM-6-Luc (NALM-6-Luciferase tumor cell line (pre-B cell leukemia)) in 180 μl AIM-V media, 0.2 μg BiTE (Anti-hCD19-CD3 bispecific T cell engager (BiTE) (InvivoGen, #bimab-hcd19cd3)) dilutions in 20 μl were added for labeling, followed by incubation at rt for 30 min. 14 mL of AIM-V media was added, and the cells were spun at 500 g for 10 min. The supernatant was removed, and the cells were resuspended in the residual volume (~100 μl). 1×10$^5$ Labeled-NALM-6-Luc cells were resuspended in 100 μL RPMI complete media.

On Day 0, labeled-NALM-6/unlabeled-NALM-6 and T cells were co-cultured. Unlabeled-NALM-6-Luc were calculated and collected at 1×10$^5$/test, and each type of T cell was calculated and collected at 1×10$^5$/test. For 96-well plate assays, in each test well, BiTE labeled-NALM-6-Luc or unlabeled-NALM-6 were seeded at 1×10$^5$/test in 100 μl RPMI complete media. Each type of T cell was resuspended at 1×10$^5$/test in 100 μL. Each type of T cell was added at different time points to each well at a final effector-to-target ratio of 1:1. Tests of T cells only and NALM-6-Luc only were seeded at 1×10$^5$/test in 200 μl at each timepoint. The cells were incubated in a humidified CO$_2$ incubator at 37° C. for 24 h.

On Day 1, post-co-culture, cells were harvested and analyzed for cytokine production, cytotoxicity, and T cell quantification. For cytokine production, supernatant from the co-culture well was harvested, and IFN-γ production was quantified by ELISA (IFN gamma Human ELISA Kit (Invitrogen, #KHC4021) according to the manufacturer's protocol. IFN-γ production was analyzed by absorbance readings at 450 nm within 30 min using a BD bio-luminometer and quantified by a standard control curve according to the manufacturer's protocol.

For cytotoxicity, cells from the co-culture well were harvested and washed. A 150 μg/mL working solution of D-Luciferin (XenoLight D-Luciferin (Perkin Elmer, #122799)) was prepared in a pre-warmed tissue culture media. A 200× stock solution of Luciferin was quick-thawed and diluted 1:200 in complete media (150 μg/mL final concentration). 1× Luciferin solution was added to the cells just prior to reading bioluminescence on a bio-luminometer. Percentage of killing was normalized by accumulated live NALM-6 cell only (0%), dead NALM-6 tumor cells being treated by cell lysis solution (100%).

For T cell quantification, after the cytotoxicity assay, the cells were wash 3 times in PBS and resuspended in 200 µl FACS buffer. For surface staining, the cells were resuspended in 200 µl FACS buffer and stained with surface antibodies (Anti-human CD3-APC/Cy7 (BioLegend, #100221), Anti-human CD8-PerCP (BioLegend, #980916), Anti-human CD19-PE (BioLegend, #302254)), followed by incubation for 40 min at rt in the dark. The cells were washed with 2 ml of FACS buffer, centrifuged at 350 g for 5 min, and the supernatant was discarded. 1 ml of FACS buffer was added, the mixture was centrifuged at 350 g for 5 min, and the supernatant was discarded. The cells were resuspended in 200 µl of fresh buffer and filtered. Flow cytometry counting beads (CountBright Absolute Counting Beads (ThermoFisher, #C36950) were added before running on BD Fortessa x-20. T cell and NALM-6 absolute cell number were quantified as below:

Calculation of cell concentration:

$$\frac{A}{B} \times \frac{C}{D} = \text{concentration of sample as cells}/\mu L$$

Where:

$A$ = number of cell events $B$ = number of bead events $C$ = assigned bead count of the lot (beads/50 $\mu L$)

$D$ = volume of sample ($\mu L$)

For the following 2 weeks, the NALM-6-Luc rechallenge step was applied to every co-culture well and the NALM-6-only well. On Day 2, all T cells underwent two tumor challenges, and on Day 12, all T cells underwent six tumor challenges. To perform the challenges, 100 µl of supernatant from each well was aspirated. The same amount of tumor at $1\times10^5$/test in 100 µL was applied to the repetitive challenge assay every other day (D2, D4, D6, D8, D10, D12). 24 h after tumor re-challenge, cells from each column at the indicated timepoint were collected for cytotoxicity, cytokine production, and T cell quantification analysis.

Figure 8:
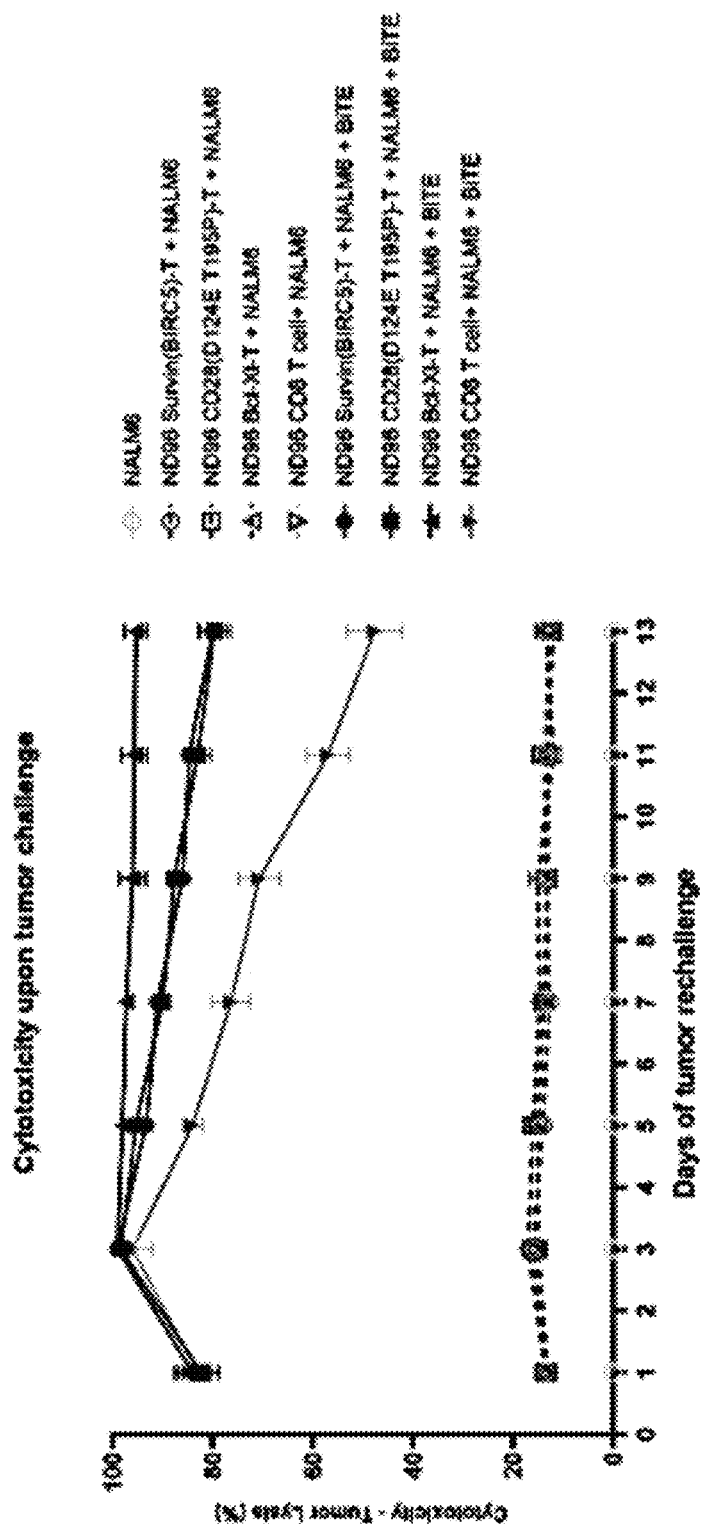
FIG. 8 shows the T cell cytotoxicity results of a BiTE-mediated NALM-6 tumor re-challenge model (designed to mimic a B cell tumor relapse), where an anti-CD3/CD19 BiTE was introduced to engage the T cell and the tumor. The killing ability of the normal T cells decreased upon repetitive challenge, whereas the Gene-T cells sustained cytotoxicity.

FIG. 8 shows the cytotoxicity results of the assay. Normal T cells (ND96 CD8+ T cell+NALM-6+BiTE) gradually lost their cytotoxic efficacy in this assay, such that after the last admixture, tumor cell killing was reduced by 50%. By contrast, cytotoxic efficacy decreased at a much slower rate in the cultures of T cells expressing either Survivin or CD28-D124E/T195P, and it persisted nearly completely in the cultures containing the Bcl-xL-expressing cells.

Figure 9:
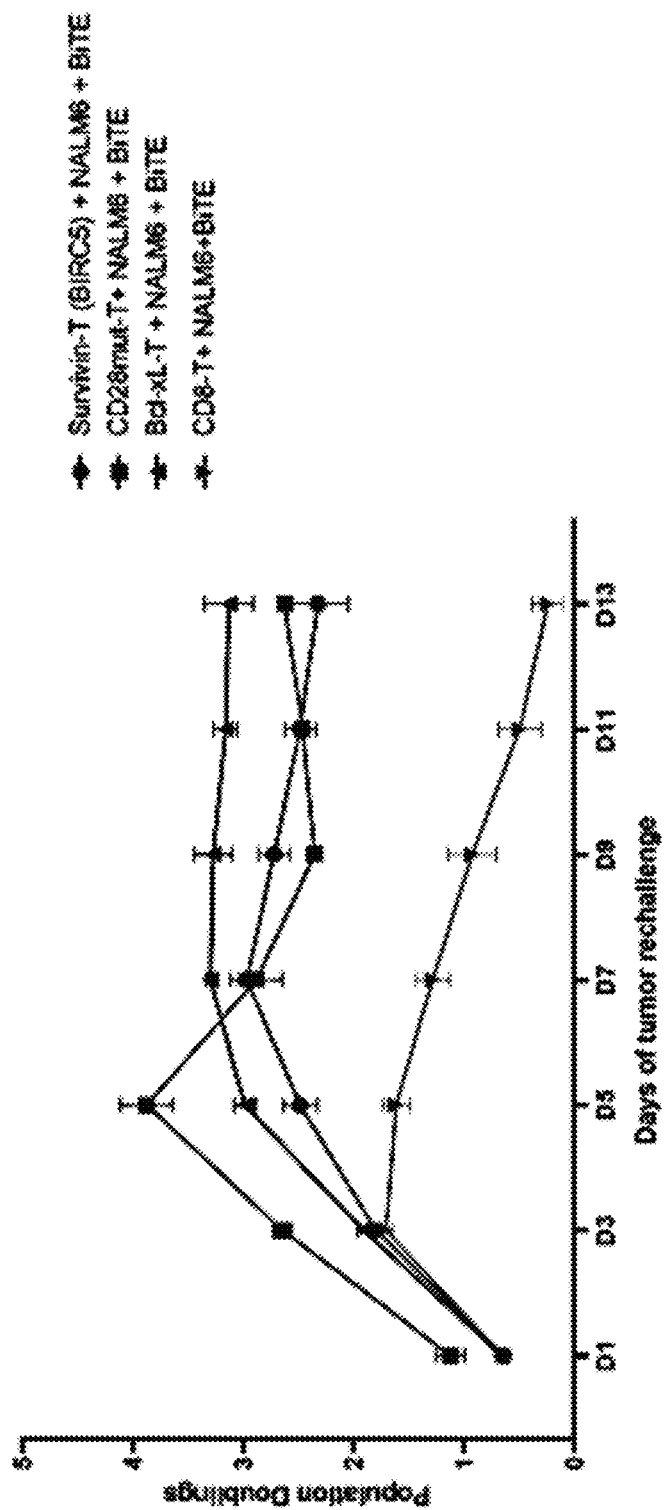
FIG. 9 shows the expansion and persistence of T cells during the in vitro BiTE-mediated re-challenge assay referred to in FIG. 8.

In some aspects, the changes in cytotoxic efficacy may be at least partially a consequence of differences in the relative persistence of T cells in the different cultures. FIG. 9 shows the expansion and persistence of T cells during the in vitro challenge assay. Normal T cells proliferated initially, but became progressively less numerous, whereas all three genes of interest promoted greater expansion and persistence of T cells in the cultures, with the superior apparent persistence of the Bcl-xL-expressing cells correlating with the stronger cytotoxic efficacy present in cultures of these cells.

IFN-γ production in the cells was quantified by ELISA according to the manufacturer's protocol. IFN-γ production was analyzed by absorbance readings at 450 nm within 30 min using a BD bio-luminometer and quantified by a standard control curve according to the manufacturer's protocol. All three transgenes promoted significantly higher and more persistent cytokine production than normal T cells, as shown in FIG. 10.

Figure 10:
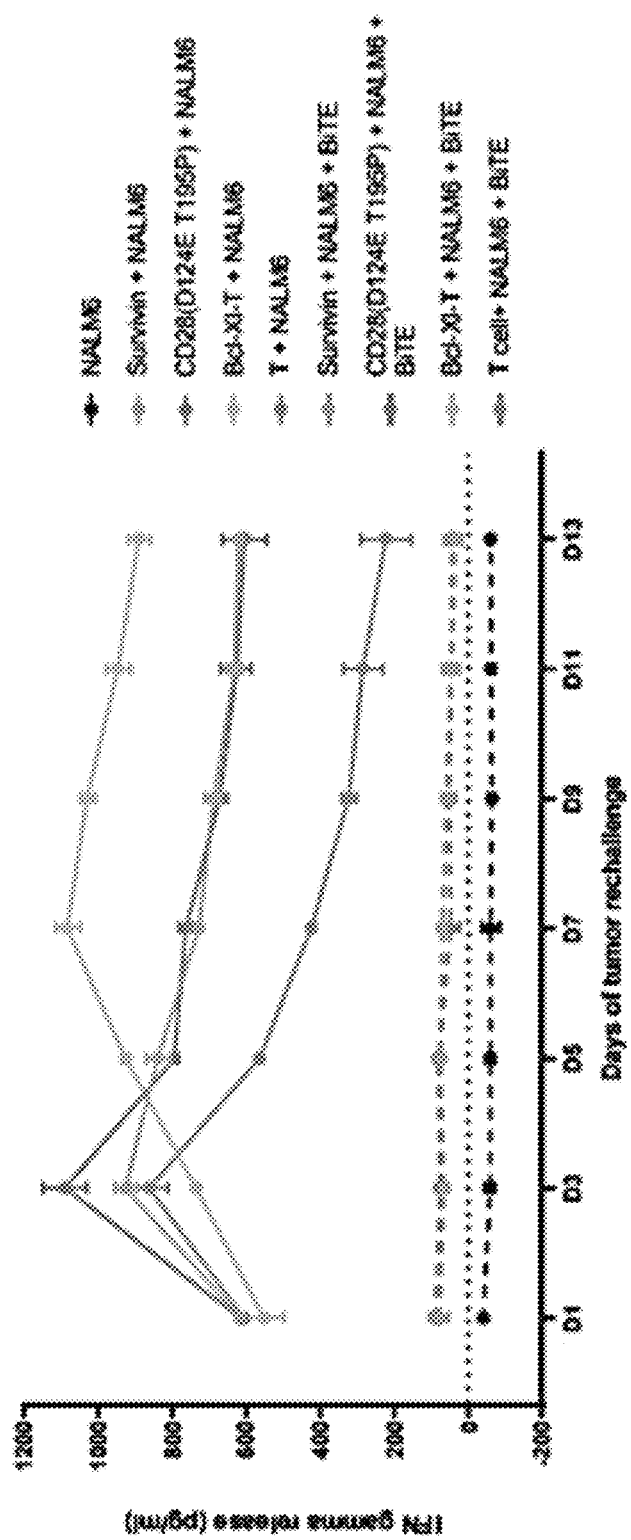
FIG. 10 shows the relative IFN-γ production, as quantified by ELISA, in Gene-T cells during the in vitro BiTE re-challenge assay referred to in FIGS. 8 and 9.

FIGS. 8, 9, and 10 show that T cell function is preserved in Gene-T cells.

Example 7: Construction of Gene Transfer Polynucleotides Encoding a CAR and Bcl-xL, Survivin, or CD28-D124E/T195P The disclosure provides, among other things, a method for producing human CAR-Gene-expressing T cells using the Leap-In® transposase system under conditions that preserve the stable expression of Survivin, CD28-D124E/T195P, and Bcl-xL with potent CAR expression and activity ("CAR-Gene-T cells"). In certain aspects of the method, the Leap-In® transposase system may be used for stable integration of an antigen-specific CAR and a function-boosting gene into primary human T cells, whereby the transposon is co-delivered along with an mRNA transposase in a single electroporation reaction. Delivery of a transposon encoding a CAR and function-boosting gene results in 30%-70% of cells with stable integration and a survival advantage. To confirm that the survival advantage does not diminish the CAR expression, the CAR-Gene-T cells were measured for CAR and each gene expression simultaneously. To confirm that the survival advantage does not impact normal T cell function, the sorted CAR-Gene-T cells were activated and assessed for expansion, activation marker expression, cytokine production, and immunophenotyping. Additionally, these CAR-Gene-T cells, which harbor a survival advantage, exhibit potent anti-tumor activity even after multiple tumor challenges.

In one aspect, the disclosure provides a transposon comprising the CAR of the disclosure. In one aspect, the disclosure provides a composition comprising the CAR and at least one pharmaceutically acceptable carrier. Transposons of the disclosure are episomally maintained or are integrated into the genome of the modified cell. The transposon may be part of a two-component Leap-In® transposase system that uses a transposon and transposase for enhanced non-viral gene transfer.

Four gene transfer polynucleotides were constructed. Each comprised: (i) a target sequence 5'-TTAA-3', immediately followed by a piggyBac-like transposon inverted terminal repeat nucleotide sequence SEQ ID NO: 248 (which is an embodiment of SEQ ID NO: 1), immediately followed by additional transposon end nucleotide sequence SEQ ID NO: 249 (which is >95% identical to SEQ ID NO: 5); (ii) an HS4 insulator (nucleotide sequence SEQ ID NO: 236); (iii) a GFP reporter (sequence SEQ ID NO: 247) comprising a gene encoding DasherGFP operably linked to a GAPDH promoter and a BGH polyadenylation signal sequence; (iv) an ORF encoding a CD19-binding chimeric antigen receptor with polypeptide sequence SEQ ID NO: 252, operably linked to a PGK promoter with nucleotide sequence SEQ ID NO: 128 and a polyadenylation signal sequence with nucleotide sequence SEQ ID NO: 253; (v) (where applicable) an ORF encoding a function-boosting protein operably linked to a GAPDH promoter with nucleotide sequence SEQ ID NO: 117 and a globin polyadenylation signal sequence with nucleotide sequence Seq ID NO: 195; (vi) a D4Z4 insulator with nucleotide sequence SEQ ID NO: 232; and (vii) additional transposon end nucleotide sequence SEQ ID NO: 8 (which is >95% identical to SEQ ID NO: 7), immediately followed by a piggyBac-like transposon inverted terminal repeat nucleotide sequence SEQ ID NO: 250 (which is an embodiment of SEQ ID NO: 2), immediately followed by a target sequence 5'-TTAA-3'.

All of the elements of the gene transfer polynucleotides are transposable as a single transposon by corresponding transposases, for example a transposase with polypeptide sequence selected from SEQ ID NOs: 13-30. The first gene transfer polynucleotide (346463 with nucleotide sequence SEQ ID NO: 254) did not comprise an ORF encoding a function boosting protein. The second gene transfer polynucleotide (346776 with nucleotide sequence SEQ ID NO: 255) comprised an ORF encoding the function boosting protein Survivin with polypeptide SEQ ID NO: 2. The third gene transfer polynucleotide (346777 with nucleotide sequence SEQ ID NO: 256) comprised an ORF encoding the function boosting protein CD28-D124E/T195P with polypeptide sequence SEQ ID NO: 241. The fourth gene transfer polynucleotide (381703 with nucleotide sequence 257) comprised an ORF encoding the function boosting protein Bcl-xL with polypeptide sequence SEQ ID NO: 239.

Example 8: Transfection of CD8$^+$ T Cells with Gene Transfer Polynucleotides Encoding a CAR and Bcl-xL, Survivin, or CD28-D124E/T195P Primary human CD8$^+$ T cells were isolated according to Example 1. Before transfection, the CD8$^+$ T cells were primed with pre-irradiated hIL-2-, hIL-7-, and hIL-15-secreting TSF feeder cells for 3 days at a 1:10 ratio in complete RPMI media. Upon transfection (day 0), each gene transfer polynucleotide described in Example 7 (with nucleotide sequences SEQ ID NOs: 254, 257, 255, or 256 encoding CAR alone, CAR+Bcl-xL, CAR+ Survivin, or CAR+CD28-D124E/T195P, respectively) was electroporated, together with mRNA (with nucleotide sequence SEQ ID NO: 251, encoding a transposase with polypeptide sequence SEQ ID NO: 15), into primed CD8$^+$ T cells.

In certain aspects, the method of generating modified CAR-Gene-T cells may be optimized for better yields (greater number or greater proportion of transfected T cells) at a high-transfection efficiency. Specifically, upon each transfection (10 µL/test), 0.6 ug mRNA encoding transposase with polypeptide sequence SEQ ID NO: 15 was complexed with 2 e$^5$ cells resuspended in R-10 buffer at 2 e$^7$/ml. Gene transfer polynucleotide DNA (6 ug) was added prior to electroporation at 1600 v, 10 ms, 3 pulses. Two electroporation reactions were pooled in one well of a 48-well tissue culture-treated plate containing antibiotic-free complete RPMI media supplemented with 200 IU rhIL-2, rhIL-7, and rhIL-15 at 5 ng/ml for 24 h. The media was switched to complete RPMI with antibiotics, 2% human serum, and pre-irradiated TSF feeder cells as indicated above for 2-4 weeks. The transfected CD8$^+$ T cells and mock T cells were washed, stained, and sorted for CAR$^+$GFP$^+$CD8$^+$ cells and CD8$^+$ T cells (as a control).

CAR-Gene-T cell expansion ability was assessed after aCD3/aCD28 stimulation through TSF feeder cell stimulation. Sorted CAR-Gene-T cells were co-cultured and stimulated with TSF feeder cells at a 1:10 ratio on day 0 and day 7. T cell population doublings were measured every other day for 2 weeks.

Example 9: CAR Expression is Preserved in CAR-Gene-T Cells

Gene transfer polynucleotides encoding a CAR with or without Bcl-xL, Survivin, or CD28-D124E/T195P were constructed according to Example 7, and the constructs were transfected into CD8$^+$ T cells according to Example 8.

CAR-Gene-T cells were stimulated with irradiated TSF feeder cells at a 1:10 ratio for 2 weeks post-transfection in R10 media. The culture was continued in RPMI complete media supplemented with hIL-2 500 IU for 140 days.

The experiment included three controls: "19BBCAR-T" or simply "CAR-T," which were T cells expressing the CAR and GFP but without Bcl-xL, Survivin, or CD28-D124E/T195P; "Luci-T"; and "Empty T."

Approximately 1×10$^6$ cells were harvested and washed twice before FACS staining. For CD19 CAR staining, cells were resuspended in 200 µl FACS buffer, stained with Biotinylated Human CD19, and incubated for 30 min at rt in the dark. The cells were washed twice by centrifugation at 1600 rpm for 5 min.

For surface staining, the cells were resuspended in 200 µl FACS buffer, stained with surface antibodies (Anti-human CD8-PerCp 5.5 (BD Biosciences, #560662), Biotinylated Human CD19, Fc Tag (Acro Biosystems, #CD9-H8259-25 ug), Brilliant Violet 711™ Streptavidin (BioLegend, #405241)), and incubated for 40 min at rt in the dark. The cells were washed twice by centrifugation at 1600 rpm for 5 min and resuspended in 200 µl of ice cold FACS buffer.

For intracellular staining, 500 µl Fixation Buffer (BioLegend) was added to the cells, followed by incubation at rt for 20 min, and washing in FACS buffer. The supernatant was discarded. 100 µl of 0.5% Triton X-100 was added, followed by incubation for 15 min at rt 2 ml of FACS buffer was added, the mixture was centrifuged at 350 g for 5 min, and the supernatant was discarded.

The intracellular staining antibodies (Survivin: Rabbit mAb, AF647 conjugated, Cell signaling #716487, Bcl-xL: Rabbit mAb, PE conjugated, Cell signaling #54H6, CD28: syrian hamster IgG, PE/Cy7 conjugated, BioLegend #102125) were added to tubes (normally ⅟50 or ⅟100 dilution), followed by incubation for 60 min at rt in the dark. The cells were washed with 2 ml of FACS buffer, the solution was centrifuged at 350 g for 5 min, and the supernatant discarded. 1 mL of FACS buffer was added, the solution was centrifuged at 350 g for 5 min, and the supernatant discarded. The cells were resuspended in 200 µl of fresh buffer, filtered, and run on BD fortessa.

Figure 11:
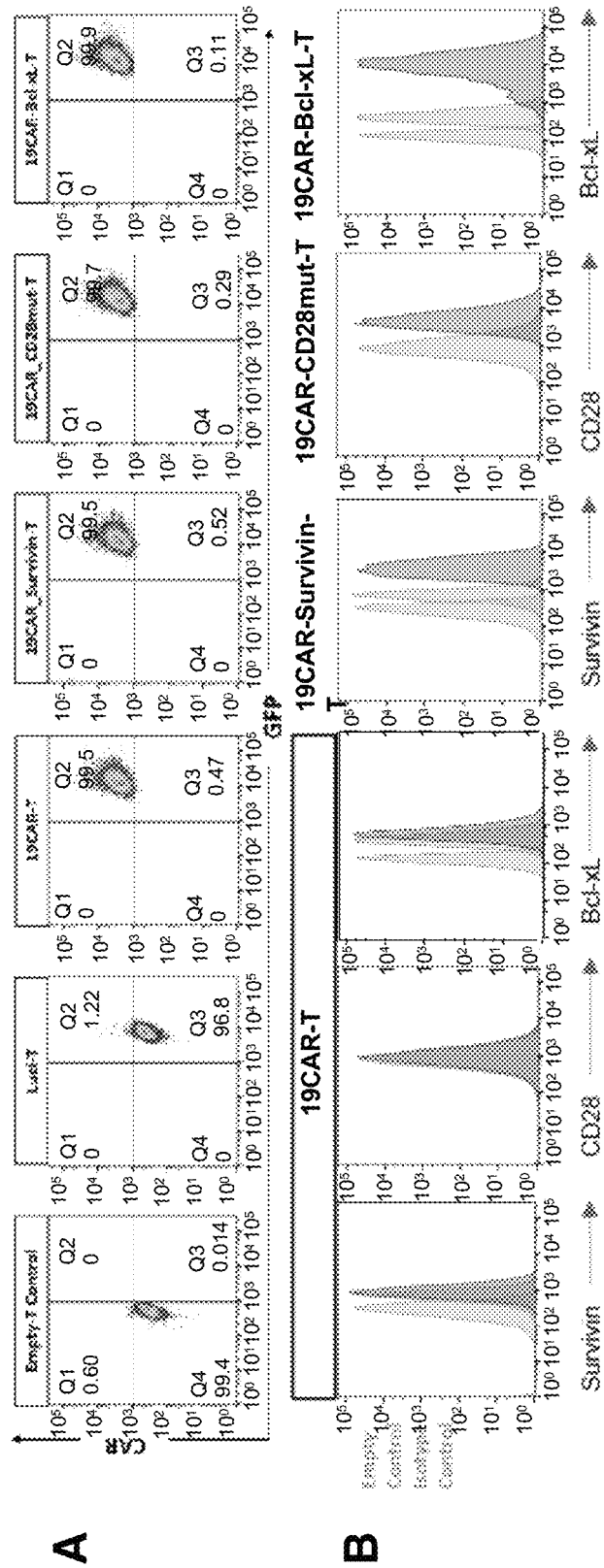
FIG. 11, row A, shows FACS data showing CAR expression and Gene (GFP) expression in CAR-Gene-T cells.

FIG. 11, row A, shows FACS data showing CAR expression and Gene (GFP) expression in CAR-Gene-T cells. FIG. 11, row B, shows the expression of genes encoding for Bcl-xL, Survivin, and CD28-D124E/T195P protein in the conventional CAR-T and in CAR-Bcl-xL, CAR-Survivin, and CAR-CD28-D124E/T195P cells, respectively.

Example 10: Preservation of T Cell Function in CAR-Gene-T Cells

Gene transfer polynucleotides encoding a CAR with or without Bcl-xL, Survivin, or CD28-D124E/T195P were constructed according to Example 7, and the constructs were transfected into CD8$^+$ T cells according to Example 8.

CAR-Gene-T cells were stimulated with feeder cells (iK562) at a 1:1 ratio for 1 week post transfection in R-10 media. The culture was continued in RPMI Complete media supplemented with iL-2 500 IU for four weeks.

The experiment included three controls: CAR-T, Luci-T, and Empty T. The T cells were activated in one of two ways: either with a stimulatory cocktail of antibodies specific for CD3 and CD28 or with tumor cells expressing the CD19 antigen recognized by the CAR.

Approximately 1×10⁶ cells were resuspended at 1×10⁶ cells/mL in AIM-V media. The cells were separated evenly into treated and untreated groups. For the aCD3/aCD28 group, prewashed and resuspended aCD3/aCD28 Dyna Dynabeads Human T-Activator CD3/CD28 (Invitrogen, #11161D) were added to obtain a bead-to-cell ratio of 1:1. For the NALM-6 culture group, NALM-6 tumor cell line (pre-B cell leukemia) cells were added at a T cell-to-NALM-6 cell ratio of 1:1. The treated and untreated cells were incubated in a humidified $CO_2$ incubator at 37° C. for 6 h.

Activation of the T cells was assessed by testing for upregulation of the CD69 or HLA-DR molecules by FACS analysis. Exposure to NALM-6 cells caused robust upregulation of both molecules in cells that expressed the CAR, while the antibody cocktail induced activation of all six kinds of T cells. The cells were harvested, washed twice in FACS buffer, resuspended in FACS buffer, and stained with surface antibody (Anti-human CD3-APC/Cy7 (BioLegend, #100221), Anti-human CD8-PerCP (BioLegend, #980916), Anti-human CD69-BV510 (BioLegend, #310935), or Anti-human HLA-DR (BioLegend, #307635)) for 2 h. The cells were washed three times by centrifugation at 1600 rpm for 5 min and resuspended in 200 μl of ice-cold FACS buffer, filtered, and run on BD Fortessa x-20.

Figure 12:
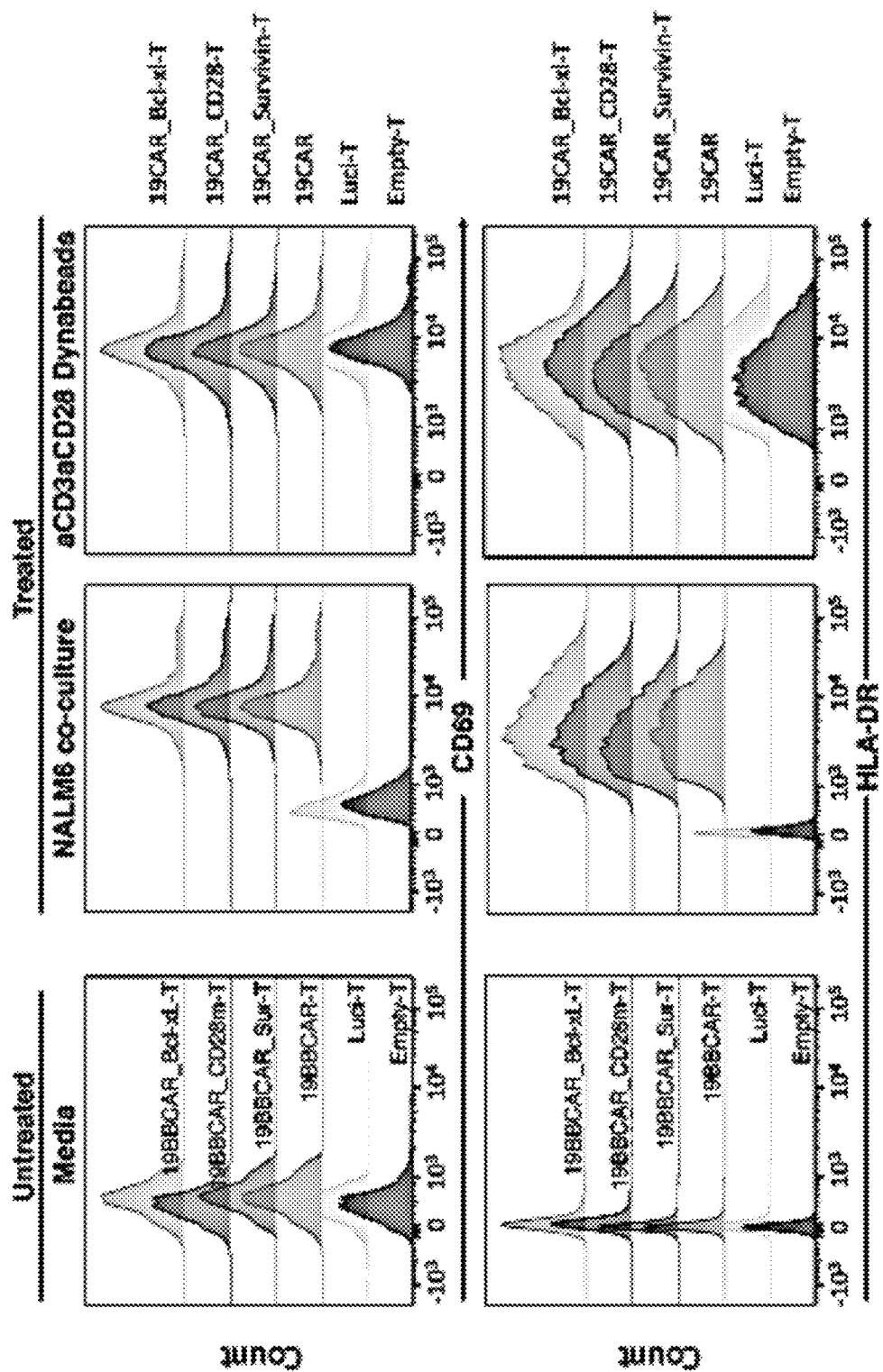
FIG. 12 show the FACS data of CD69 and HLA-DR expression in the conventional CAR-T cells and in CAR-Bcl-xL, CAR-Survivin, or CAR-CD28-D124E/T195P T cells, respectively, upon aCD3/aCD28 non-specific stimulation and antigen-specific stimulation from $CD19^+$ NALM-6 co-culture. Luci-T and Empty T were included as controls.
Figure 13:
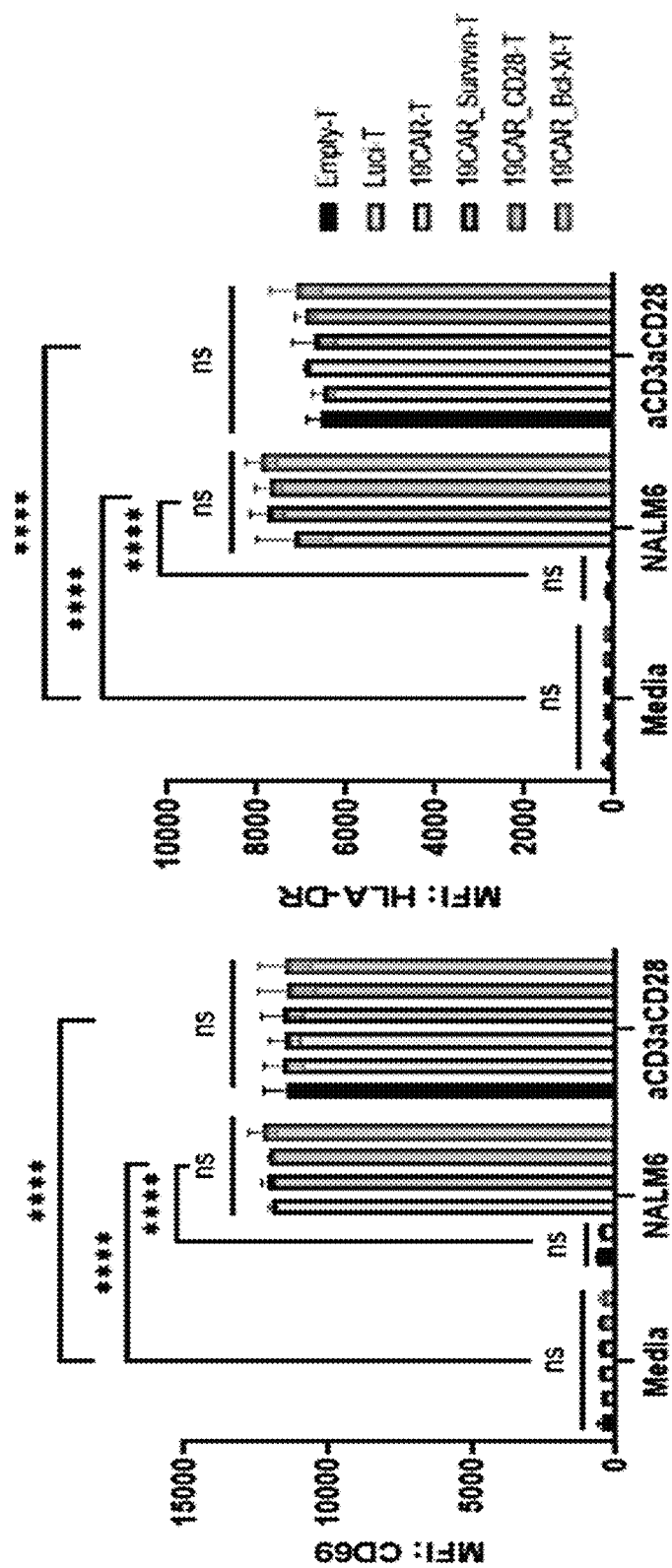
FIG. 13 quantifies the CD69 and HLA-DR expression in the CAR-Gene-T cells referred to in FIG. 12 and indicates a nonsignificant difference in activation function between CAR-Gene-T cells and conventional CAR-T cells.

FIGS. 12 and 13 show the effect of additional expression of survival genes encoding Bcl-xL, Survivin, or CD28-D124E/T195P on the activation phenotype of T cells expressing an anti-CD19 CAR. The CAR-containing cells show expression of CD69 and HLA-DR following exposure to tumor cells carrying the CD19 antigen. The same markers are induced when the T cells were stimulated with aCD3aCD28. The CAR-Gene-T cells exhibited normal activation via CD3 and CD28 and normal antigen specific activation via CD19.

Supernatants from the stimulated cells were tested for the presence of IFN-γ. The supernatant was harvested, and IFN-γ production was quantified by ELISA according to the manufacturer's protocol. IFN-γ production was analyzed by absorbance readings at 450 nm within 30 min using a BD bio-luminometer and quantified by a standard control curve according to the manufacturer's protocol.

Figure 14:
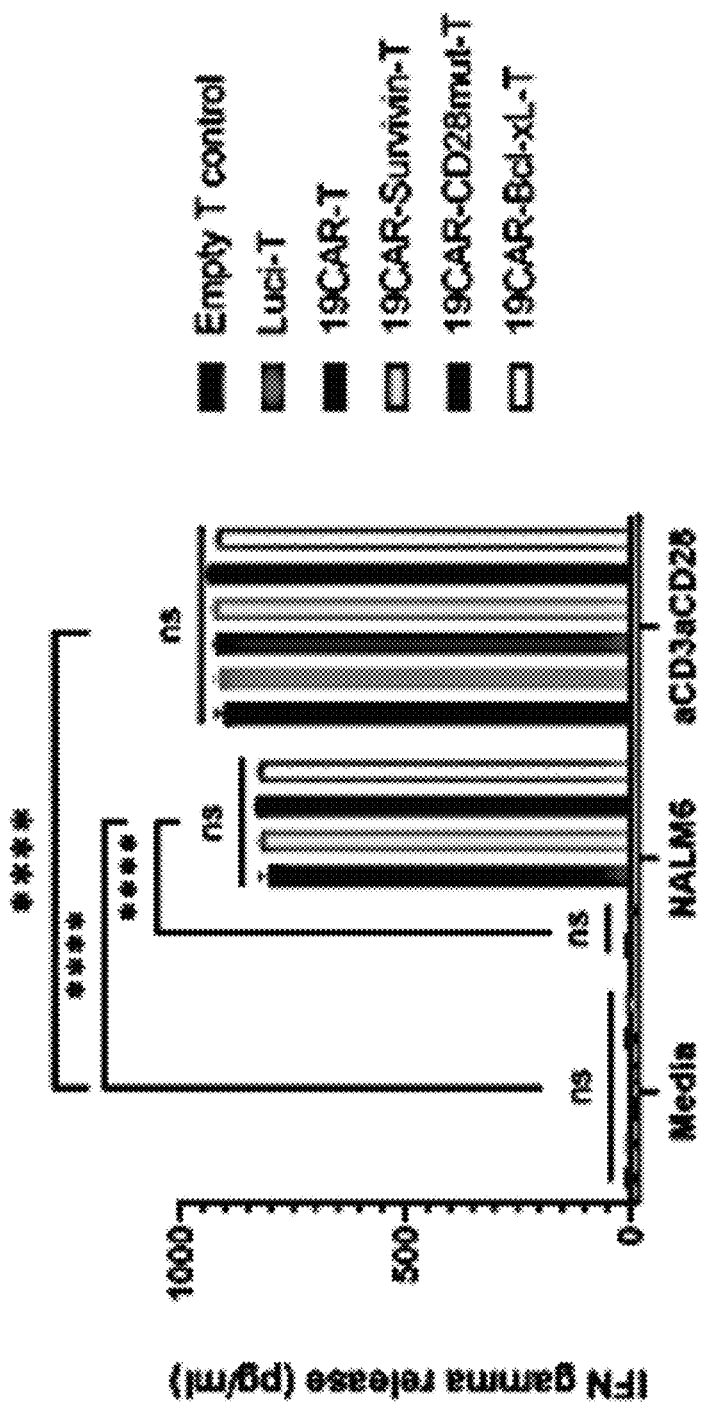
FIG. 14 shows the results when the supernatants from the stimulated cells referred to in FIGS. 12 and 13 were tested for the presence of IFN-γ, and indicates a nonsignificant difference in cytokine production function between CAR-Gene-T cells and conventional CAR-T cells.

FIG. 14 shows the results when the supernatants from the stimulated cells described in FIGS. 12 and 13 were tested for the presence of Interferon-γ. The cytokine was present in all cases where there was also CD69 or HLA-DR upregulation.

Example 11—Long-Lived CAR-Gene-T Cells Restored a CD45RA–CD62L+ Population Post Antigen Clearance Gene transfer polynucleotides encoding a CAR with or without Bcl-xL, Survivin, or CD28-D124E/T195P were constructed according to Example 7, and the constructs were transfected into CD8⁺ T cells according to Example 8.

Transfected CAR-Gene-T cells were stimulated with feeder cells (iK562) at a 1:1 ratio for 2 weeks post-transfection in R-10 media. The culture was continued in R-10 media supplemented with hIL-2 for one more week. Feeder cells were confirmed dead with a fluorescence microscope and FACS.

The experiment included three controls: CAR-T, Luci-T, and Empty T.

Cells were seeded at a density of 5×10⁶ cells/mL in AIM-V media in a 96-well plate in different columns. Baseline FACS Surface antibody staining was established by harvesting and washing the cells twice before FACS staining. The cells were resuspended in 200 μl FACS buffer, stained with surface antibodies (Anti-human CD8-PerCp 5.5 (BD Biosciences, #560662), Anti-human CD3-APC (BioLegend, #317318), Anti-human CD45RA-BUV737 (BD Biosciences, #612846), Anti-human CCR7-APC/Cy7 (BioLegend, #353212), Anti-human CD62L-PE/Cy7 (BioLegend, #304822)), and incubated for 2 h at rt in the dark. The cells were washed three times by centrifugation at 1600 rpm for 5 min and resuspended in 200 μl of ice cold FACS buffer, filtered, and run on BD Fortessa.

Baseline CD45RA, CCR7, and CD62L were determined. Baseline percentage of Tc Naive (CD45RA+CD62L+CCR7+), Tc Central Memory (CD45RA–CD62L+CCR7+), Tc Effector Memory (CD45RA–CD62L–CCR7–), and Tc Effector (CD45RA+CD62L–CCR7–) of each kind of transfected cells were analyzed for further comparative analysis. The results are shown in the top panel of FIG. 15.

The T cells were co-cultured with NALM-6 cells. NALM-6 cells were resuspended in AIM-V media, and 100 μl aliquots were added to each well in the 96-well plate at a T cell-to-NALM-6 cell ratio of 1:1 in each well. The NALM-6 co-cultured T cells were incubated in a humidified $CO_2$ incubator at 37° C.

Figure 15:
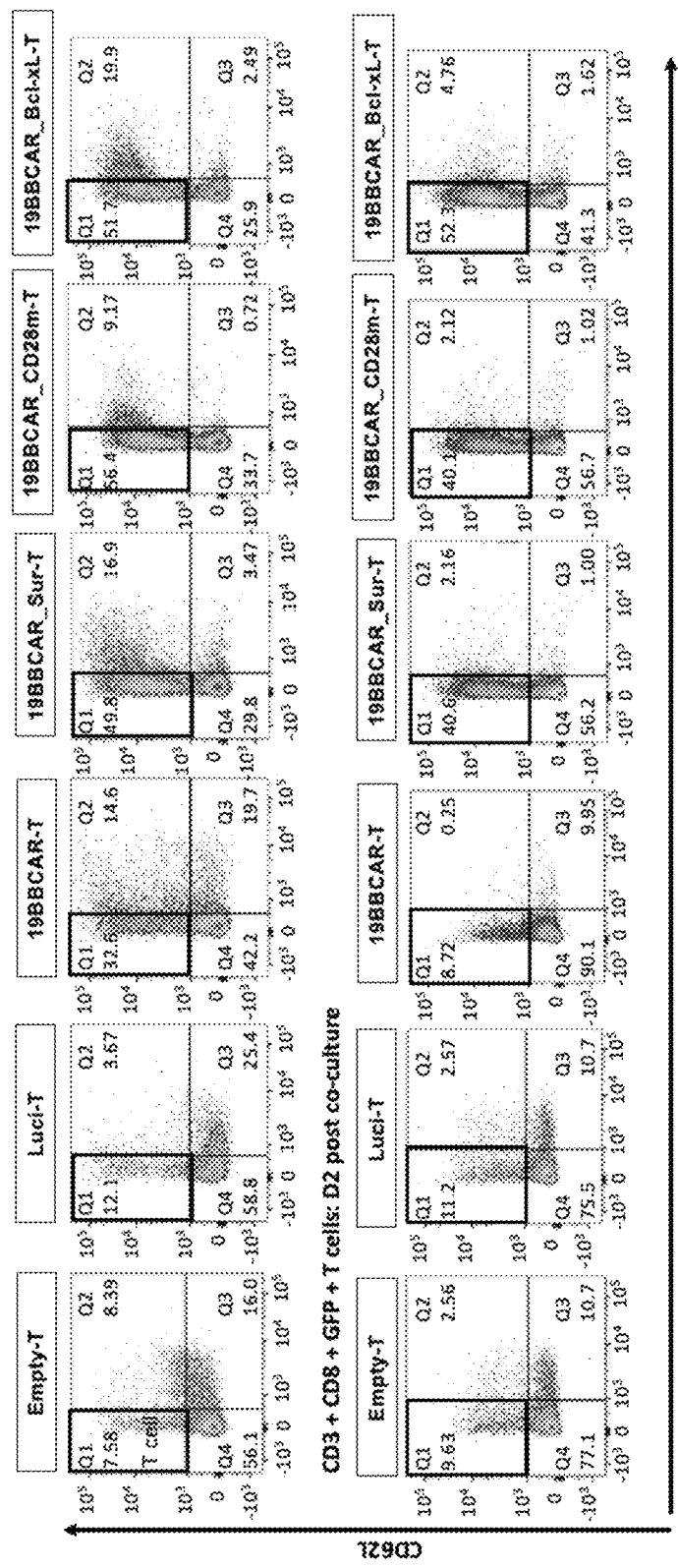
FIGS. 15 and 16 show that CAR-Gene-T cells expressing a survival gene encoding Bcl-xL, Survivin, or CD28-D124E/T195P restored and retained a CD45RA–CD62L+ population post antigen (NALM-6 cells) clearance compared to conventional CAR-T. Luci-T and Empty T were included as controls.
Figure 16:
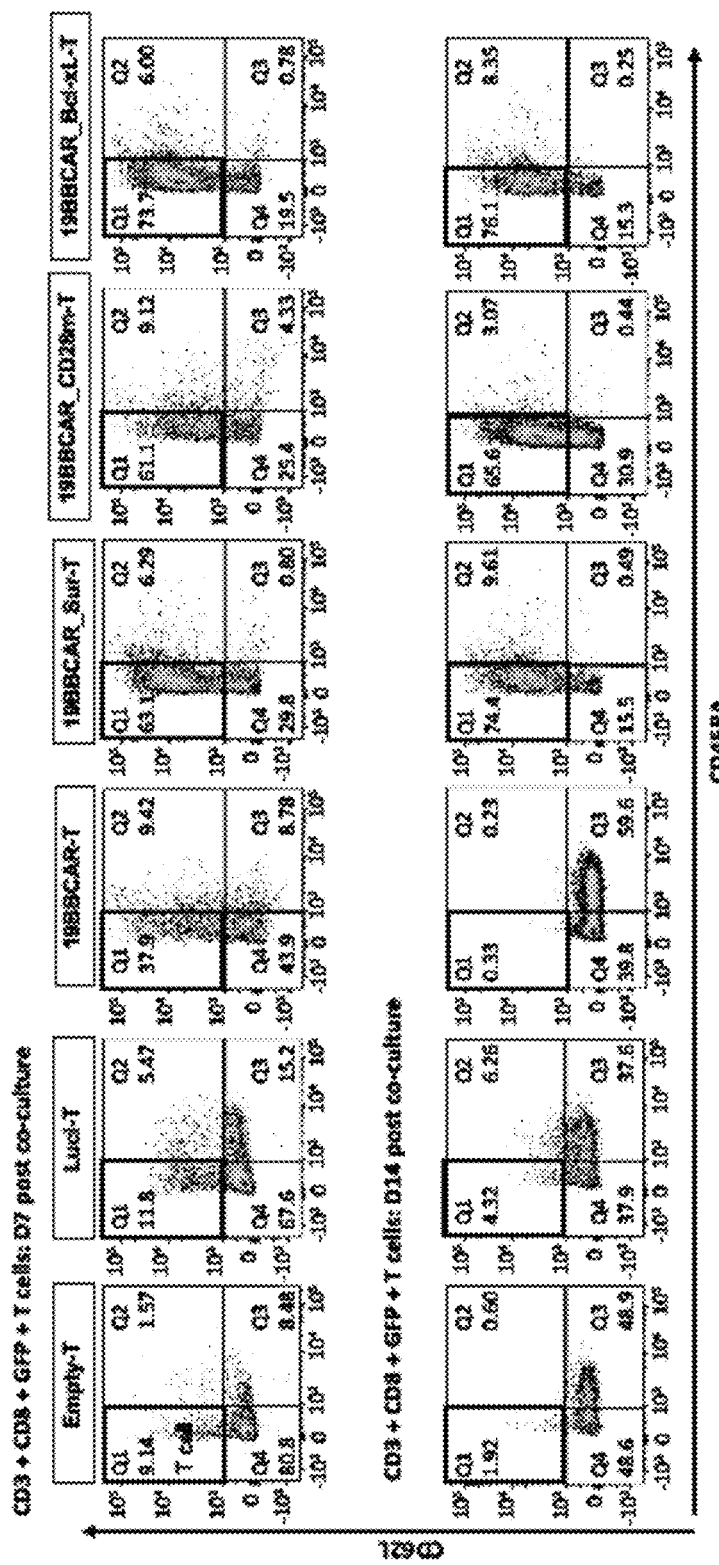

On days 2, 7, and 14, cells were harvested for FACS surface antibody staining and analysis. The percentage of Tc Naive ($CD45RA^+CD62L^+CCR7^+$), Tc Central Memory ($CD45RA^-CD62L^+CCR7^+$), Tc Effector Memory ($CD45RA^-CD62L^-CCR7^-$), and Tc Effector ($CD45RA^+CD62L^-CCR7^-$) of each kind of transfected cells at each timepoint were analyzed. FIGS. 15 and 16 show that T cells expressing an anti-CD19 CAR and a survival gene encoding Bcl-xL, Survivin, or CD28-D124E/T195P restored a $CD45RA^-CD62L^+$ population post antigen (NALM-6 cells) clearance. At 14 days after antigen exposure, the control CAR-T cells are low for expression of CD62L, and many of them are also $CD45RA^+$. By contrast, most of the cells in the transgene-expressing cultures are $CD62L^+$. The data suggest that cells with an apparent effector phenotype predominate in the control CAR-T cultures, while cells with a phenotype that is central memory-like predominate in the transgene-positive cultures. Enrichment for cells with a central memory phenotype is expected to correlate with improved outcomes in preclinical models.

Example 12—CAR-Gene-T Re-Challenge Assay

Gene transfer polynucleotides encoding a CAR with or without Bcl-xL, Survivin, or CD28-D124E/T195P were constructed according to Example 7, and the constructs were transfected into CD8⁺ T cells according to Example 8.

CAR-Gene-T cells were stimulated with feeder cells (iK562) at a 1:1 ratio for one week post transfection in R10 media. The culture was continued in RPMI complete media supplemented with iL-2 500 IU for one more week.

On Day 0, NALM-6 (NALM-6-Luciferase tumor cell line (pre-B cell leukemia)) and CAR-T cells were co-cultured. NALM-6-Luc cells were calculated and collected at 1×10⁵/test, and each type of CAR-T cell was calculated and collected at 1×10⁵/test. For 96-well plate assays, in each test well, NALM-6-Luc at 1×10⁵/test was seeded in 100 μl RPMI complete media. Each type of CAR-T cell was resuspended at 1×10⁵/test in 100 μl RPMI complete media. Each type of CAR-T cell was added at different timepoints to each well at a final effector-to-target ratio of 1:1. Tests of CAR-T cells only and NALM-6-Luc only were seeded at 1×10⁵/test in 200 μl at each timepoint. Cells were incubated in a humidified $CO_2$ incubator at 37° C. for 24 h.

On Day 1, cells were harvested for cytotoxicity, cytokine production, and T cell quantification analysis. For cytokine production, supernatant from the co-culture well was harvested, and IFN-γ production was quantified by ELISA (IFN gamma Human ELISA Kit (Invitrogen, #KHC4021) according to the manufacturer's protocol. IFN-γ production was analyzed by absorbance readings at 450 nm within 30 min using a BD bio-luminometer and was quantified by a standard control curve according to the manufacturer's protocol.

For the cytotoxicity assay, cells from the co-culture well were harvested and washed. A 150 µg/mL working solution of D-Luciferin (XenoLight D-Luciferin (Perkin Elmer, #122799) in pre-warmed tissue culture media was prepared. A 200× stock solution of Luciferin was quick-thawed and diluted 1:200 in complete media (150 µg/mL final concentration). A 1× Luciferin solution was added to cells just prior to reading bioluminescence on a bio-luminometer. The percentage of killing was normalized by accumulated live NALM-6 cells only (0%), dead NALM-6 tumor cells being treated by cell lysis solution (100%).

For T cell quantification, after the cytotoxicity assay, the cells were washed three times in PBS and resuspended in 200 µl FACS buffer. For surface staining, the cells were resuspended in 200 µl FACS buffer, stained with surface antibodies (Anti-human CD3-APC/Cy7 (BioLegend, #100221), Anti-human CD8-PerCP (BioLegend, #980916), Anti-human CD19-PE (BioLegend, #302254)), and incubated for 40 min at rt in the dark. The cells were washed with 2 ml of FACS buffer, centrifuged at 350 g for 5 min, and the supernatant was discarded. 1 ml of FACS buffer was added, the mixture was centrifuged at 350 g for 5 min, and the supernatant was discarded. The cells were resuspended in 200 µl of fresh buffer and filtered. Flow cytometry counting beads were added before running on a BD Fortessa.

For the following two weeks, the NALM-6-Luc rechallenge step was applied to every co-culture well and the NALM-6 only well. On Day 2, all T cells underwent two tumor challenges, and on Day 12, all T cells underwent six tumor challenges. To perform the challenges, 100 µl of supernatant from each well was aspirated. The same amount of tumor at $1\times10^5$/test in 100 µl was applied to the repetitive challenge assay every other day (D2, D4, D6, D8, D10, D12). 24 h after tumor re-challenge, cells from each column at the indicated timepoint were collected for cytotoxicity, cytokine production, and T cell quantification analysis.

Figure 17:
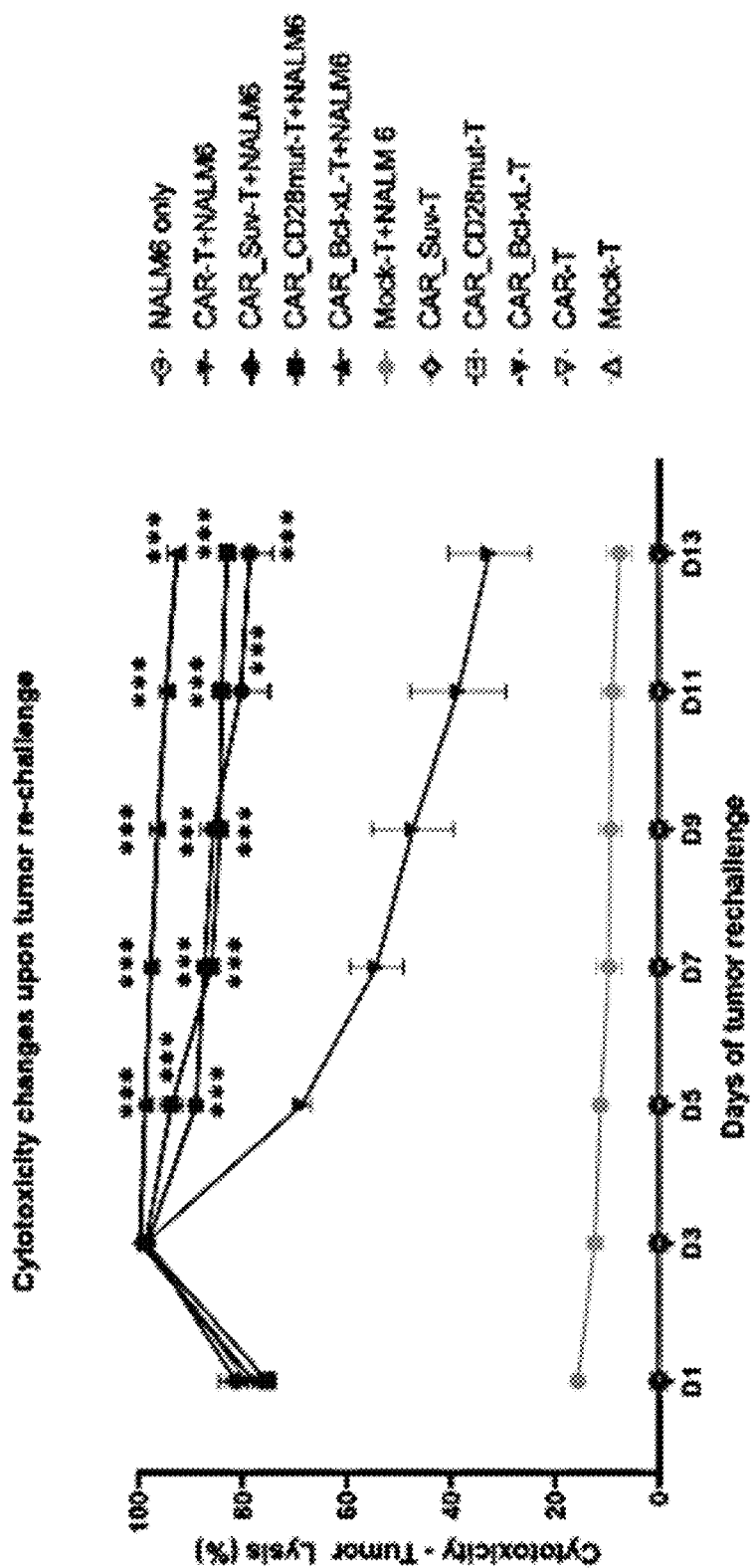
FIG. 17 shows the cytotoxicity results of an in vitro CAR-Gene-T cell NALM-6 tumor re-challenge assay (designed to mimic a B cell tumor relapse).

FIG. 17 shows the cytotoxicity results of the assay. Normal T cells (ND96 CD8+ T cell+NALM-6+CAR) gradually lost their cytotoxic efficacy in this assay, such that after the last admixture, tumor cell killing was reduced by over 60%. By contrast, cytotoxic efficacy decreased at a much slower rate in the cultures of T cells expressing either Survivin or CD28-D124E/T195P, and it decreased hardly at all in the cultures containing the Bcl-xL-expressing cells.

Figure 18:
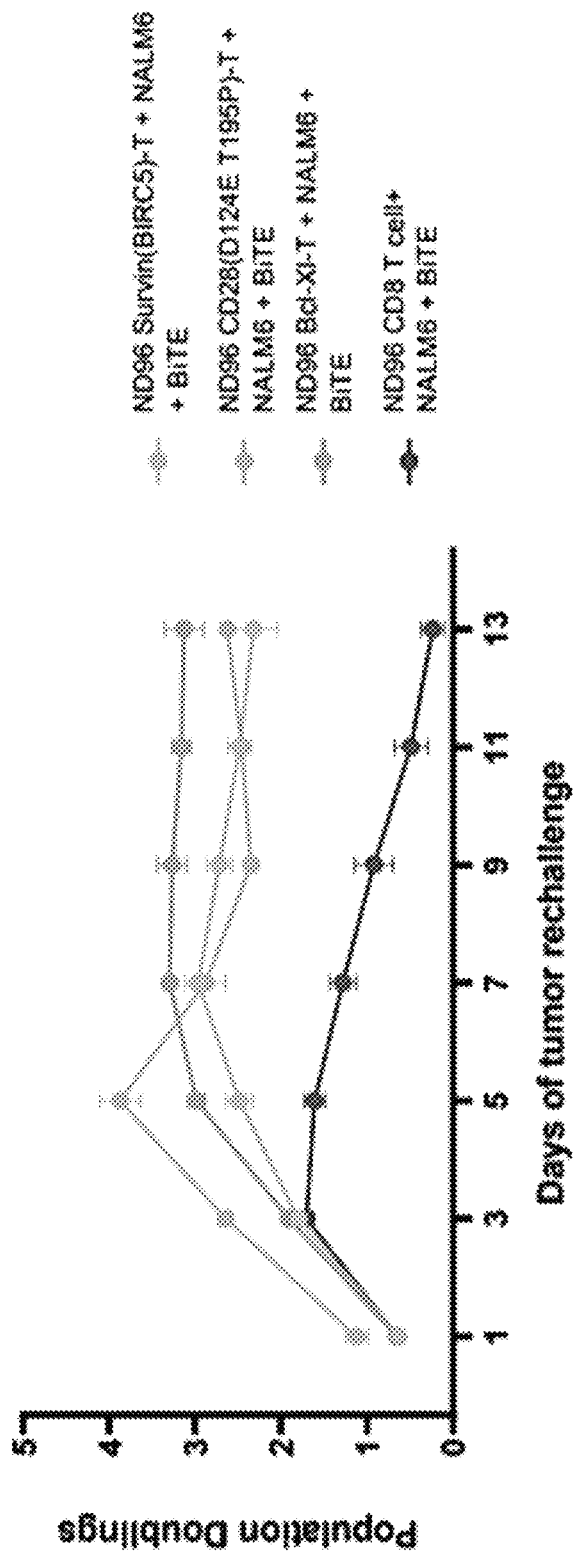
FIG. 18 shows the expansion and persistence of T cells during the in vitro CAR-Gene-T cell NALM-6 rechallenge assay referred to in FIG. 17.
Figure 19:
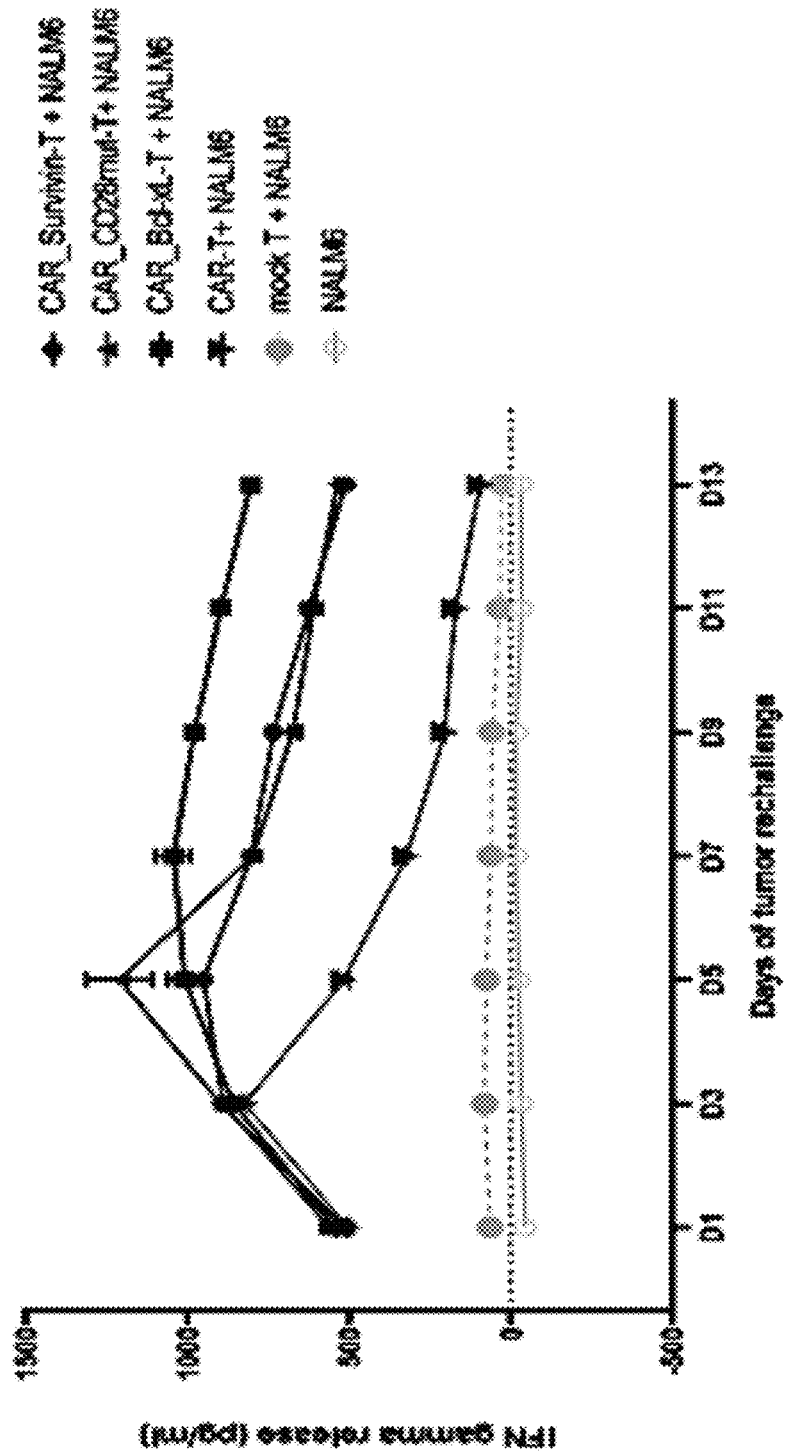
FIG. 19 shows the cytokine release data for the in vitro CAR-Gene-T cell NALM-6 rechallenge assay referred to in FIGS. 17 and 18.
Figure 20:
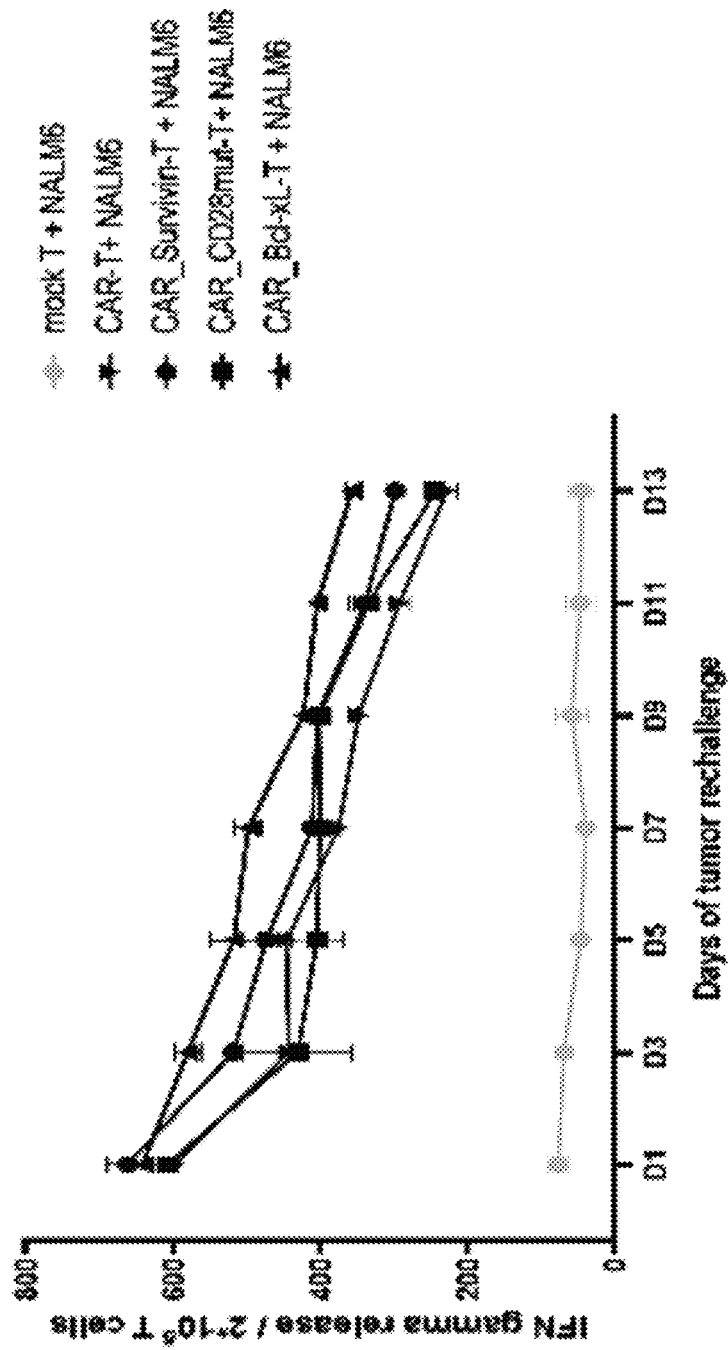
FIG. 20 shows the per cell cytokine release data for the in vitro CAR-Gene-T cell NALM-6 rechallenge assay referred to in FIGS. 17-19.

FIG. 18 shows the expansion and persistence of T cells during the in vitro challenge assay. Normal T cells proliferated initially, but then became progressively less numerous, whereas all three transgenes promoted greater expansion and persistence of T cells in the cultures, with the superior apparent persistence of the Bcl-xL-expressing cells correlating with the stronger cytotoxic efficacy present in cultures of these cells. FIG. 19 shows the cytokine release data for the in vitro challenge assay. FIG. 20 shows the per cell cytokine release data for the in vitro challenge assay.

Example 13—In Vivo T Cell Dose Study

Xenograft Mouse Models
NSG Mice

All animal procedures were reviewed and implemented in accordance with protocols approved by the Institutional Animal Care and Use Committee (IACUC) at Massachusetts General Hospital (MGH). NOD. Cg-Prkdcscid Il2rgtm1Wjl/SzJ (NSG) female mice (stock #005557) were obtained from the Jackson Laboratory (Bar Harbor, ME) at six weeks of age (if not specified), used for all tumor transplantation studies, and maintained under pathogen-free BL2 conditions in-house. NOD. Cg-Prkdcscid Il2rgtm1Wjl/SzJ (NSG) benefits from a longer lifespan than NOD SCID, which should support long-term engraftment studies and the ability to have a median life of >89 weeks.

NALM-6 Acute Lymphoblastic Leukemia (ALL) Models

Mice engrafted NALM-6 B cell precursor leukemia line will experience systematic B-lineage acute lymphoblastic leukemia. To establish the NALM-6 ALL models, $1\times10^6$ NALM-6-Luc tumor cells were harvested in the logarithmic growth phase and washed twice in PBS before engrafting into each mouse by intravenous injection on day 6. NALM-6-Luc cells (NALM-6 transduced via lentivirus with click beetle green luciferase gene (CBG-Luc)) tumor cell lines were obtained from Dr. Marcela V Maus (MGH). All tumor-bearing models were allowed to grow for approximately one week before therapy. Tumor progression was longitudinally evaluated by BLI every other day. Anesthetized mice received i.p. injections of D-luciferin at 10 uL/g body weight (PerkinElmer). 10 min post-injection, mice were imaged using a Xenogen IVIS Spectrum system (Caliper Life Science) to assess tumor bioluminescence. Total bioluminescent flux and average radiance were quantified using Living Image 4.4 (PerkinElmer). At the time of T cell injection (day 0), once tumor engraftment was confirmed, mice were randomized based on the tumor BLI to ensure a similar tumor burden among experimental groups. All CAR-Ts for in vivo experiments were transfected and activated for two weeks, stained, and pre-sorted for 19BBCAR+GFP+ using a FACSAria sorter (BD Biosciences) or MA900 sorter (Sony). The dose-finding and rechallenge models specified below were adapted from the NALM-6 leukemia model.

Survival Endpoints

Observational clinical symptoms for the NALM-6 tumor-bearing mice may include varying degrees of hind limb paralysis, weight loss, and possibly urinary dysfunction. The clinical signs justifying euthanasia include severe hind limb paralysis and sustained weight loss of 20%. Any mouse exhibiting abnormal signs of paralysis and/or significant weight loss (>20%) (severity=moderate-severe, score=2-3) will be euthanized on the same day. Since an autopsy will be performed, the corpses of the mice will be preserved for organ collection. According to MGH IACUC regulations, these are regarded as the endpoints of survival experiments.

In Vivo T Cell Analysis

All mouse blood and tissue samples collected and harvested at the indicated time were first lysed to remove the red blood cells using ACK Lysing Buffer (Thermo Fisher, #A1049201). Following RBC lysis, samples were stained for anti-NSG mouse MHC-I H2Kd antibody (PE-Cy7, BioLegend, #368522), anti-human antibodies hCD45 (BV421, BioLegend, #116622, #368256), hCD8 (PE, BioLegend, #344706), hCD19 (APC, BioLegend, #302212)/hCD21 (APC, BioLegend, #354905), and aqua fixable viability dye (BV510, Thermo Fisher, #L34957). CD19CAR expression was detected via biotinylated human CD19 protein (AcroBioscience, CD9-H8259) and stained with BV711 Streptavidin (BioLegend, #563262). Gene modifications were detected via GFP expression. For cell counting, absolute counting beads were added (Thermo Fisher, #C36950) according to the manufacturer's instructions. Engrafted adoptive CAR-T cells in the mouse peripheral blood were evaluated by flow cytometry for the ratio of % $CD19^+$ $CD21^+$/% $CD8^+$, % $hCD45^+hCD8^+CAR^+GFP^+$. For phenotypic characterization, hCD45RA (BD Bioscience, #564442, #304122), hCD62L (BioLegend, 304822), and hCCR7 (BioLegend, #353212) antibodies were used to characterize $T_{Naive}$-like ($CCR7^+CD62L^+CD45RA^+$), $T_{Central\ Memory}$-like ($CCR7^+CD62L^+CD45RA^-$), $T_{Effector\ Memory}$-like ($CCR7^-CD62L^+CD45RA^-$), and $T_{EMRA}$-like ($CCR7^-CD62L^+CD45RA^+$) subsets. Unstained and fluorochrome-missing-one cells were used as controls to provide accurate compensation and data analysis. Data were analyzed with the FlowJo software v.10.1 (FlowJo LLC). For exhaustion analysis, anti-human antibodies Tim3 (BioLegend, 345027), PD-1 (BioLegend, 329937), LAG3 (BioLegend, 3369304), and TIGIT (BioLegend, 372704) were used to determine the expression level in CAR-Gene-T cells.

Xenograft NALM-6 Dose-Finding Model

In the NALM-6 leukemia dose-finding model, six days post tumor engraftment, three doses ($0.5 \times 10^6$, $1 \times 10^6$, and $2 \times 10^6$) of the 19BBCAR-T treatment group (n=5) were tested via intravenous injection compared to an untreated group (day 0). BLI was performed every other day, demonstrating NALM-6 tumor growth. 100 μl of survival blood samplings were performed by cheek bleed procedure on day 7. For the endpoint analysis, non-survival blood samplings were performed by cardiac puncture, and multiple organs (spleen, bone marrow) were harvested for T cell analysis.

Xenograft NALM-6 Efficacy-Rechallenge Model

In the NALM-6 leukemia rechallenge model, six days post tumor engraftment, five treatment groups (n=5), including a diluted dose ($2 \times 10^5$) of CAR-Bcl-xL-T cells, a standard amount ($1 \times 10^6$) of three types of CAR-Gene (CAR-Survivin, CAR-CD28-D124E/T195P, and CAR-Bcl-xL) T cells, and CAR-T cells, along with a control group (n=5) of mock-T cells at the standard dose ($1 \times 10^6$), were injected into each mouse intravenously on day 0. To assess differences in response to additional exposure to tumor cells, tumor rechallenge experiments were performed on day 28 post-CAR-T treatment by intravenous administration of $1 \times 10^6$ NALM-6-Luc cells to another age-matched untreated group (n=5). BLI was performed every other day, demonstrating NALM-6 tumor growth. 100 μl of survival blood samplings were performed by cheek bleed procedure on days 7, 14, 28, 44, and 60. At the endpoint of the study, non-survival blood samplings were performed by cardiac puncture, and multiple organs (spleen, bone marrow) were harvested for T cell analysis.

Xenograft ffLucCAR-T Persistence-Safety Model

To investigate the long-term effect of Survivin, CD28-D124E/T195P, and Bcl-xL modification in T cell persistence and to determine whether a long-term persistence of these CAR-Gen-T cells will lead to a tumor transformation in mice, a xenograft ffLucCAR-T model was established. Mice were infused with $5 \times 10^6$ ffLuc tagged CAR-Ts, and T cell expansion was tracked by in vivo imaging of T cell BLI. Background BLI was measured prior to T cell injection. Imaging was performed every other day in the first two weeks post T cell infusion. Supplemental hIL-2 (diluted in PBS) was i.p. weekly administered at 5000 units/mouse to support T cell growth. IL-2 was withdrawn, and imaging was performed less frequently than once per week. 100 μl of survival blood samplings were performed by cheek bleed procedure on days 14, 28, and 56 for T cells analysis as indicated above. At the endpoint of the study, non-survival blood samplings were performed by cardiac puncture, and multiple organs (spleen, bone marrow) were also harvested for additional T cell tumor genetic analysis of % Aberrant $hCD3^+hCD4^+hCD8$. Potential disease on site was determined if the mice met two of the descriptions relating to unusual clinical observations, abnormal hematological changes and T cell phenotypes, an excessive T cell expansion, or a suspected small nodule was detected, as further detailed in Tables 1 and 2:

TABLE 1

Analysis & Pathological Indexes:

| Analysis | Description | Performing day |
|---|---|---|
| Clinical observations | Abnormal symptoms observed or informed by CCM veterinarian | Daily |
| Body mass | Weight loss (threshold: 20%) | Daily |
| In vivo imaging | IVIS BLI imaging, 10 min post i.p. substrate BLI intensity: T cell expansion; BLI dispersity: lymphoma | d7 or 14, *disease onsite day, weekly post decease onsite until euthanasia. |
| Blood sampling (survival) | Mice will be bled for 100 ul# via mandibular vein or retro-orbital vein collection for hematology and T cell analysis | d7 or 14, *disease onsite |
| Hematology | Cts. Leukocyte, lymphocyte, erythrocyte, and platelets | day, weekly post disease |
| T cell analysis | % $hCD45^+hCD8^+CAR^+GFP^+$; % $hCD45^+hCD19^+hCD21^+$; % $CD45RA^+CCR7-CD62L^-$, $CD45RA^+CCR7^+CD62L^+$, $CDRA^-CCR7^+CD62L^+$, $CD45RA^-CCR7^-CD62L^-$ %$TIM3^+$; $LAG3^+$; $PD-1^+$; $TIGIT^+$ Aberrant % $hCD3^+hCD8^+$ $hCD4^+$ | on site until euthanasia |
| Pathological examination (non-survival) | Non-survival Blood sampling (via Cardiac puncture or Abdominal/thoracic blood vessel); Necropsy; Bone marrow, spleen, thymus, liver sampling. (Diagnosis follow indices below) | Endpoint |

On average, mice have around 58.5 ml of blood per kg of bodyweight. A mouse weighing 22 g (6 wks old) would therefore have a total blood volume (TBV) of approximately 58.5 ml/kg × 0.020 kg = 1.29 ml. For a survival repeating mouse blood sampling, <10% TBV can be collect at maximum.

TABLE 2

| Indexes | T cell lymphoma pathological features | Methods |
|---|---|---|
| Symptoms | Abdominal swelling; Roach back; Reduced activity; Paralysis; Tremor; Narrowed eyes; Hypothermia; Tail fibrosis; Abdominal ascites | Observation, consulted by veterinarian |
| T cell lymphoma diagnosis | High-grade lymphoma with prominent tumor infiltration of the bone marrow, spleen, liver and thymus; | Tissue samples from necropsy: H&E (Hematoxylin and eosin) staining |

TABLE 2-continued

| Indexes | T cell lymphoma pathological features | Methods |
|---|---|---|
| Pathology | Splenomegaly; Lymphadenopathy; Enlarged LNs; Disorganized architecture of spleen and LNs; Skin ulcers. | Tissue samples from necropsy: measurement (potentially imaging) |
| Hematology | Anemia; Thrombocytopenia; Elevated white blood cell counts; | Survival and non-survival blood sampling: counting |
| Phenotyping | An aberrant hCD3+hCD8+hCD4+ population; A pronounced hCD3+Ki67+ population. | Survival and non-survival blood sampling + Tissue samples from necropsy: T cell analysis |
| Imaging | Excessive T cell expansion: suspected small nodule presumably accumulated at bone marrow, spleen, thymus and liver. | Live mouse IVIS BLI imaging |
| *Clonality | Oligoclonal T cells; | Vβ staining (*if spare PBMCs are available) |

Dose-Finding Study Results

The antitumor activity of different doses of conventional CAR-T and mock T controls were compared in an in vivo NALM-6 dose-finding model using NSG mice engrafted with a NALM-6-Luc B cell precursor leukemia cell line. An initial engraftment of $1 \times 10^6$ NALM-6 tumor grew rapidly in mice treated with mock T cells, similar to the untreated group.

Figure 21:
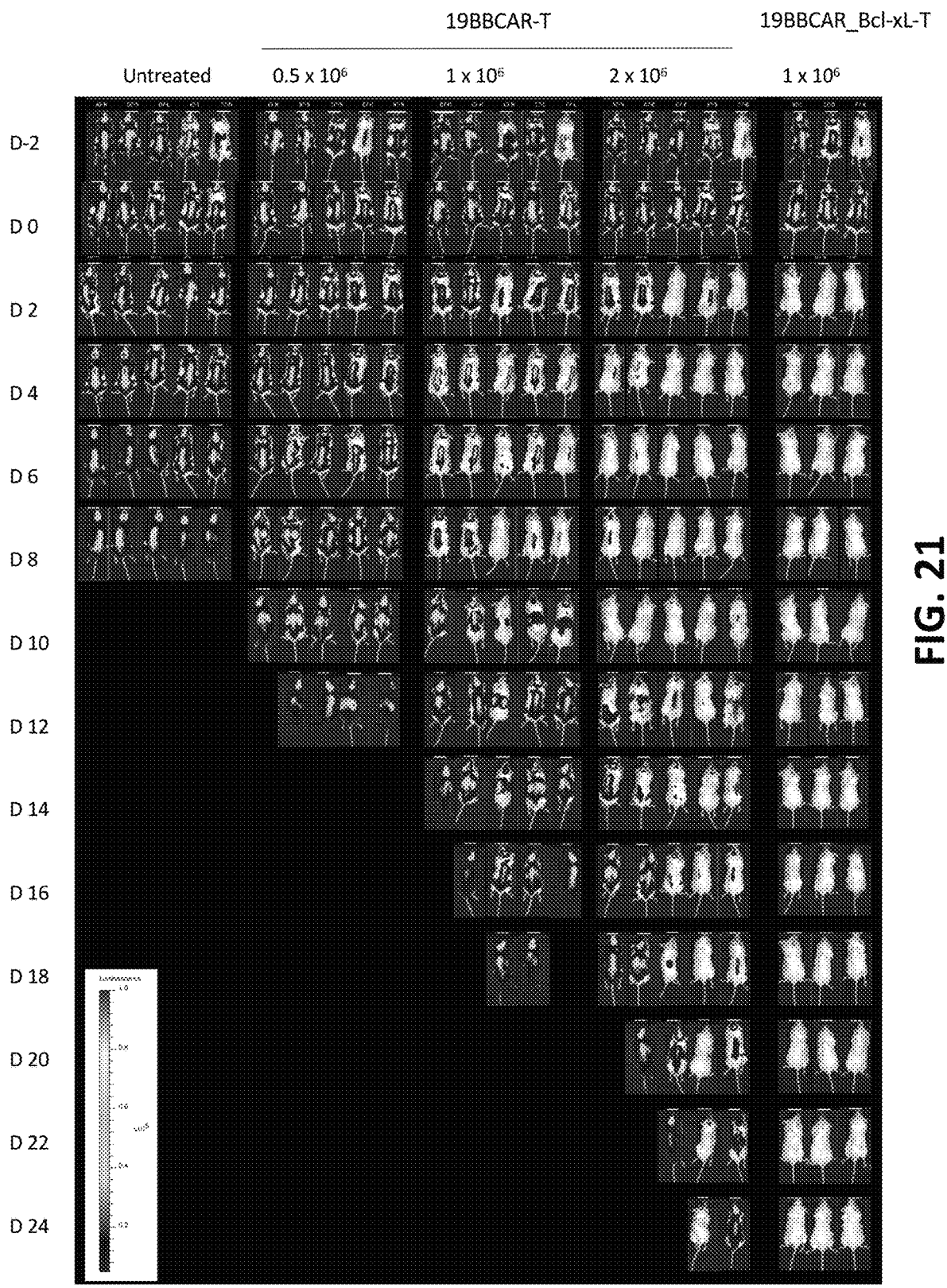
FIG. 21 shows bioluminescence images (BLI) of NSG mice bearing NALM-6 tumors, which were treated by intravenous injection with: (i) different doses of conventional CAR-T cells (n=5); or (ii) CAR-Bcl-xL T cells at a dose of $1\times10^6$ (n=3). An untreated group (n=5) was included as a control.
Figure 22:
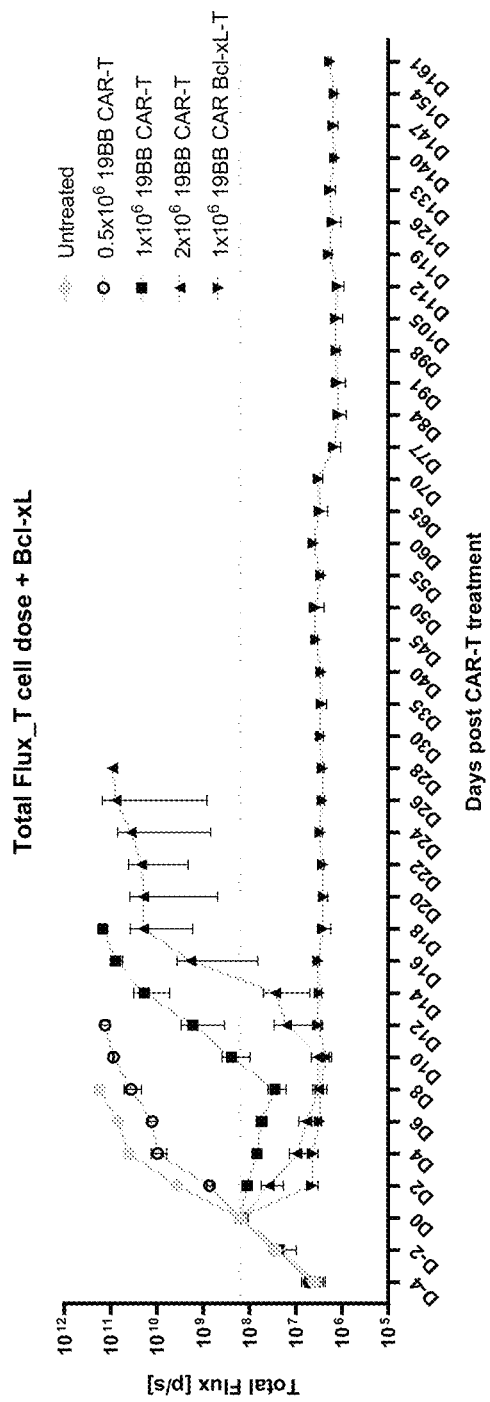
FIG. 22 shows BLI quantification results in total flux (p/s) of the NSG mice referred to in FIG. 21.

FIGS. 21 and 22 show the BLI imaging and quantification of total flux results, respectively, illustrating the tumor progression. The efficacy of CAR-T cells that do not express a survival gene is dose-dependent. CAR-Bcl-xL-T cells are significantly more effective at tumor control than CAR-T cells that do not express a survival gene, at half of the highest dosage.

Figure 23:
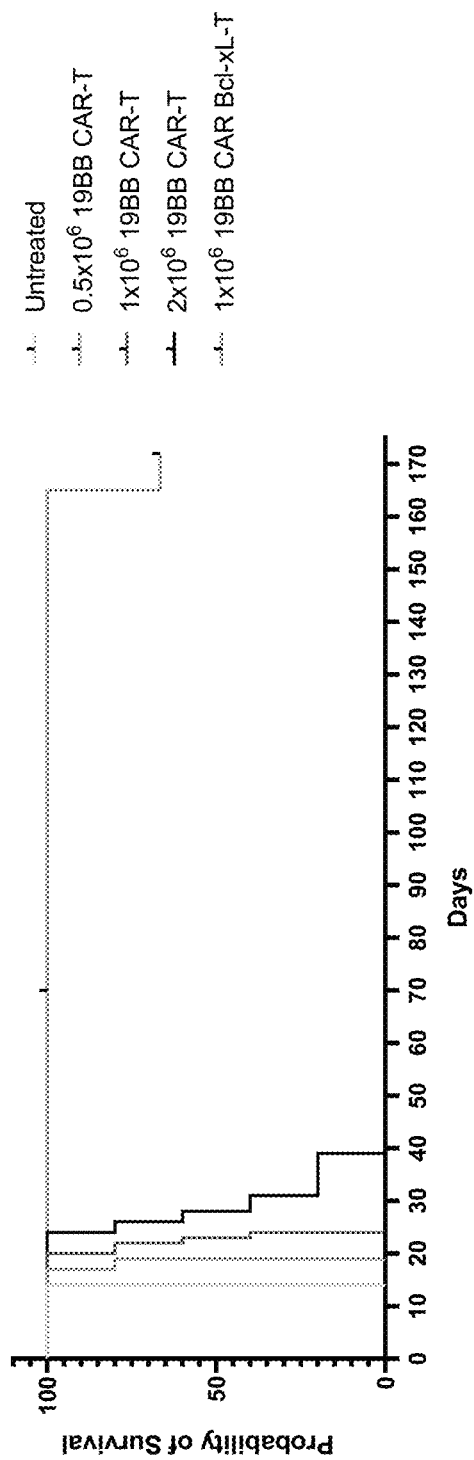
FIG. 23 shows a Kaplan-Meier survival curve of the mice referred to in FIGS. 21 and 22 at 161 days.

A $0.5 \times 10^6$ dose of CAR-T represented an ineffective dose, as no mice reported a complete response. The tumors expanded drastically and lead to death in 20 days (FIG. 23). A $2 \times 10^6$ dose of CAR-T cells demonstrates the strongest anti-tumor effect among the conventional CAR-T groups, as CAR-T cells effectively cleared the tumor on day 6. Mice remained tumor-free or maintained a low tumor burden after treatment for the longest time among the conventional CAR-T groups, but all 5 mice showed different levels of tumor relapse starting on day 12, and all mice died in 40 days (FIG. 23). A $1 \times 10^6$ dose of CAR-T cells represented a semi-optimal dose, as CAR-T established a semi-effective tumor control for a short time, but the relapse presented on day 12 in all mice and lead to death in 22 days (FIG. 23).

FIGS. 21 and 22 also demonstrate that compared to the conventional CAR-T, CAR-Bcl-xL at a $1 \times 10^6$ dose (n=3) established a long-lasting effective tumor control, as all mice presented a complete response quickly on day 2 and remained tumor-free for 161 days (FIG. 23).

Figure 24:
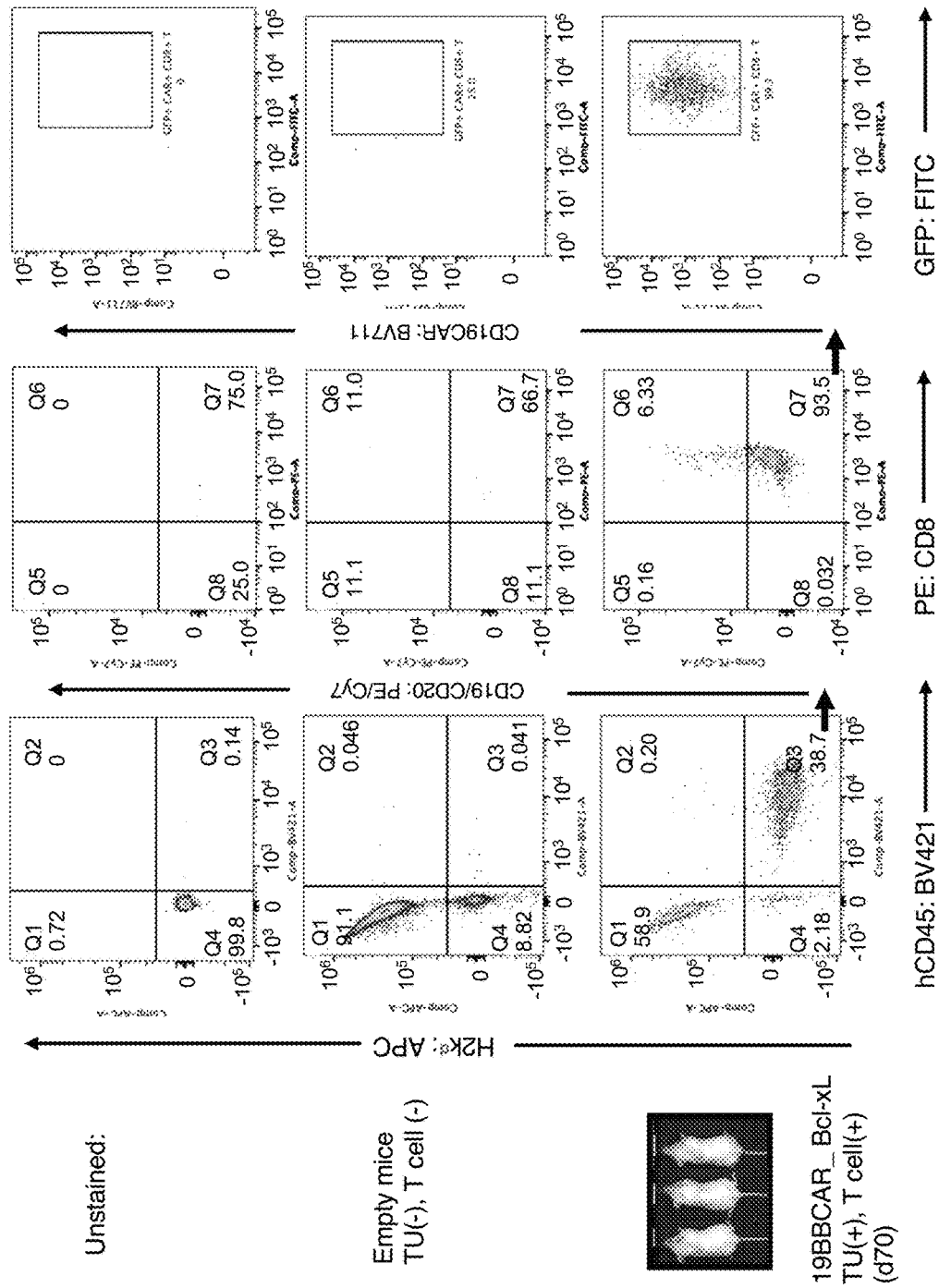
FIG. 24 shows mouse blood FACS analysis of: (i) $CD8^+$ T cells vs $CD19^+$ B cells in $hCD45^+$ cells; and (ii) $CAR^+$ $GFP^+$ cells in $CD8^+$ cells from mice treated with CAR-Bcl-xL-T cells. Unstained cells and blood from tumor-free empty NSG mice were included as controls.

FIG. 24 showed FACS analysis of blood from CAR-Bcl-xL-T treated mice, indicating that CD8+CAR+GFP+ persisted in the blood 70 days post-treatment.

Based on these results, to investigate the efficacy and anti-tumor cytotoxicity of different CAR-Gene-T cells against re-current tumors, a dose of $1 \times 10^6$ was used for an efficacy-rechallenge study.

Efficacy Re-Challenge Study Results

Figure 25:
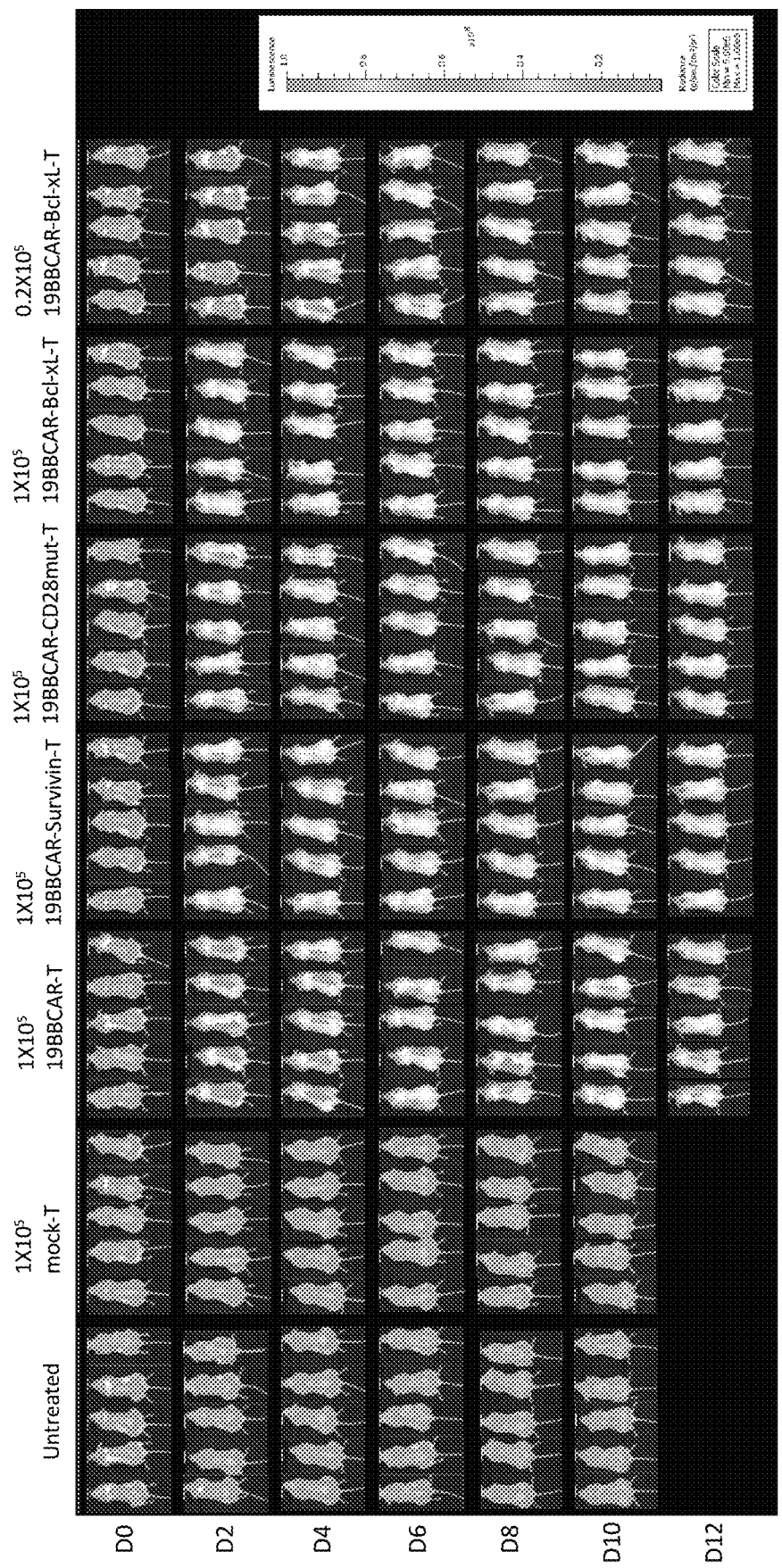
FIG. 25 shows BLI from an efficacy-rechallenge study, where NSG mice bearing NALM-6 tumors were treated (by intravenous injection) with CAR-T, CAR-Bcl-xL, CAR-Survivin, or CAR-CD28-D124E/T195P cells at a dose of $1\times10^6$ (n=5). A reduced dose ($2\times10^5$) group treated with CAR-Bcl-xL cells was also included (n=5). An untreated group and a mock-T cell treated group (n=5) were included as controls.
Figure 26:
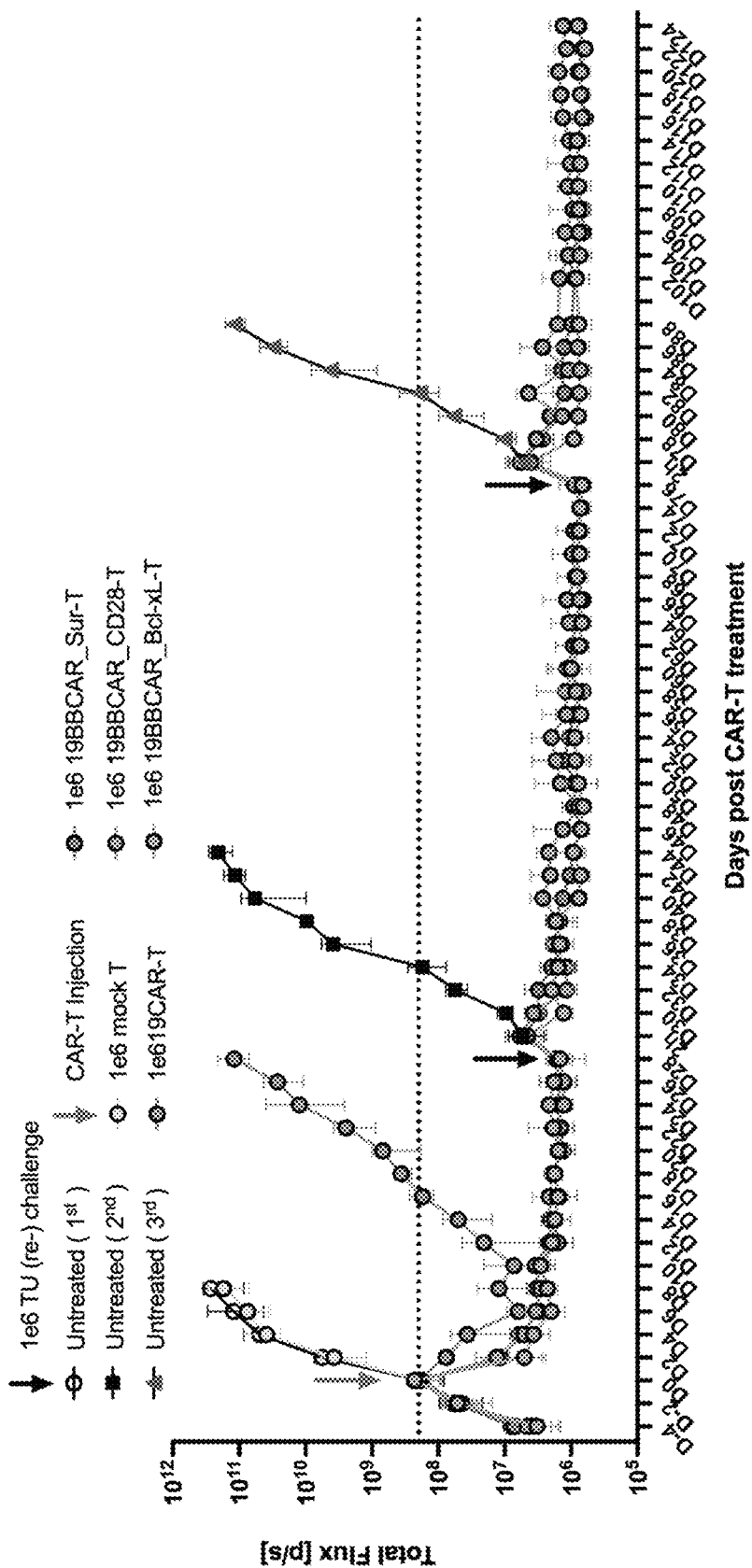
FIG. 26 shows BLI quantification results in total flux (p/s), after 124 days, of the mice referred to in FIG. 25 that were treated at a dose of $1\times10^6$. An untreated group and a mock-T cell treated group were included as controls.
Figure 27:
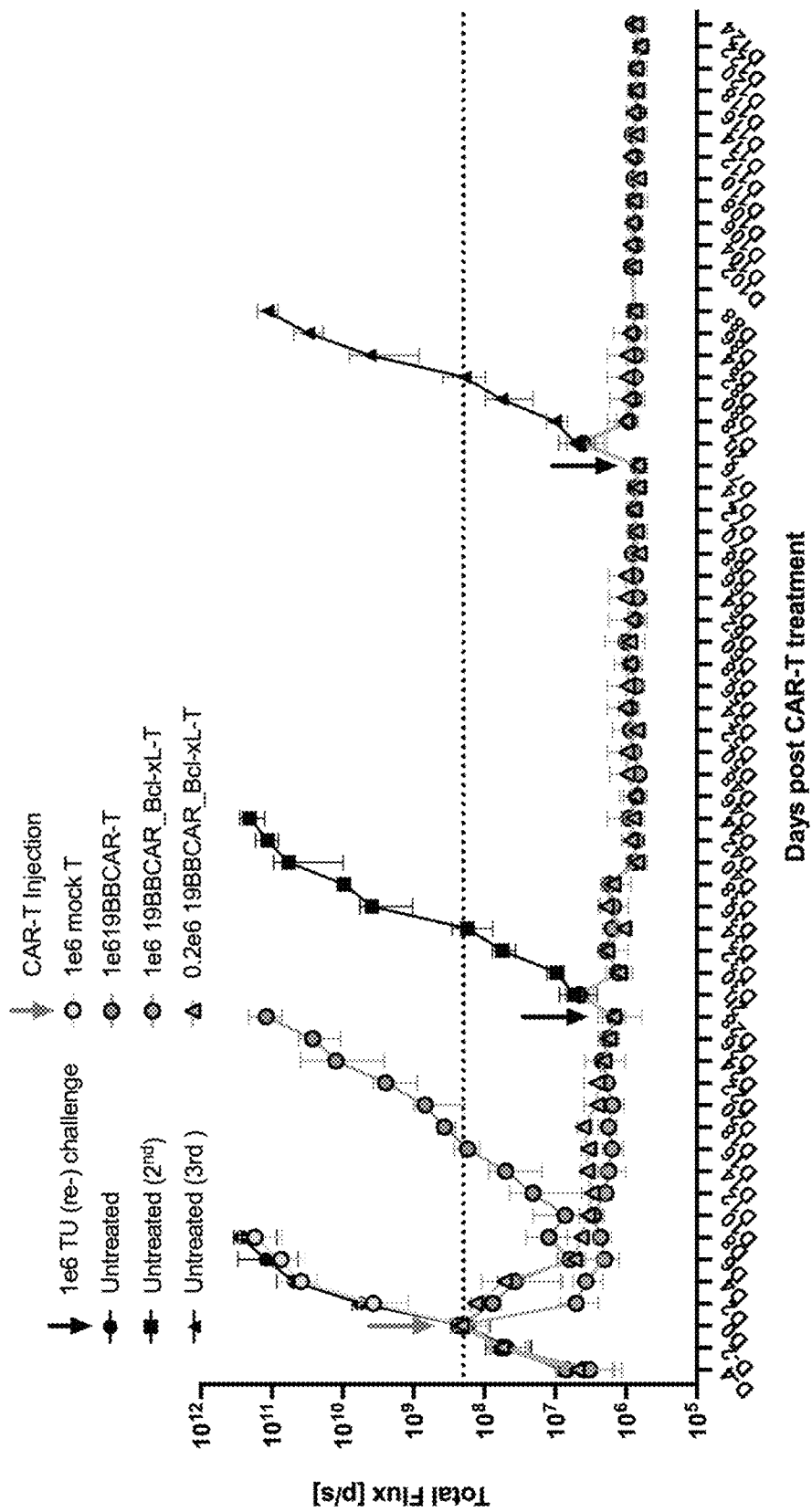
FIG. 27 shows BLI quantification results in total flux (p/s), after 124 days, of the mice referred to in FIG. 25 that were treated with CAR-Bcl-xL at a dose of $1\times10^6$ and a reduced dose at $2\times10^5$. An untreated group and a mock-T cell treated group were included as controls.
Figure 28:
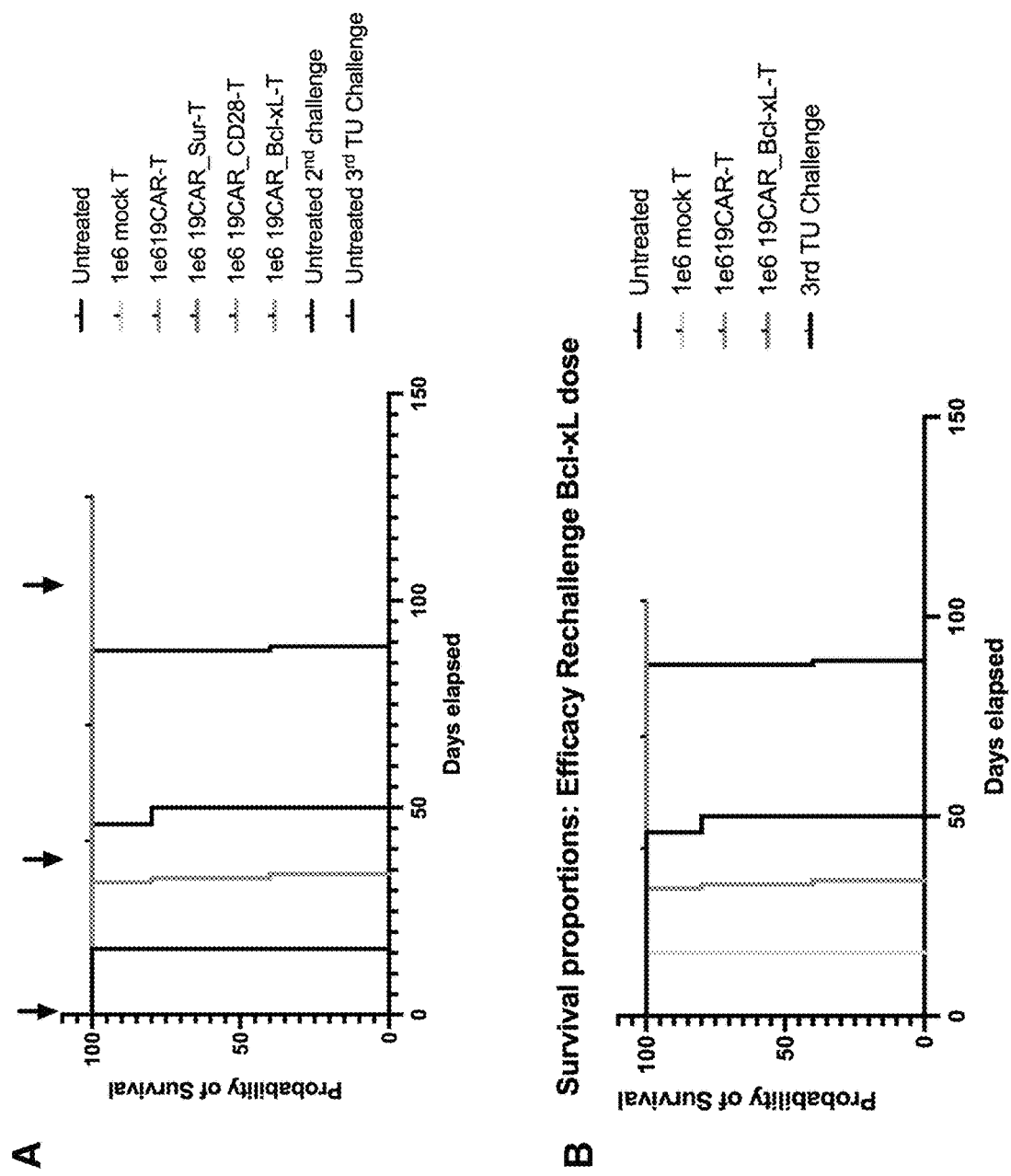
FIG. 28, row A, shows a Kaplan-Meier survival curve of all of the mice referred to in FIG. 26 at 124 days.

The antitumor activity of Survivin, CD28-D124E/T195P, and Bcl-xL-modified CAR-T, conventional CAR-T, and mock T controls were compared in an in vivo NALM-6 leukemia rechallenge model using NSG mice engrafted with a NALM-6-Luc B cell precursor leukemia cell line. An initial engraftment of $1 \times 10^6$ NALM-6 tumor grew rapidly in mice treated with mock T cells, similar to the untreated group. The CAR-Gene-T cells and the CAR-T cells demonstrated anti-tumor capabilities in 6 days at a dose of $1 \times 10^6$. FIGS. 25 and 26 show BLI imaging and representative BLI quantifications of total flux, respectively, illustrating NALM-6-Luc tumor progression among CAR-Gene T cell, CAR T cell, mock-T cell, and untreated groups (n=5). FIG. 27 shows BLI quantification results in total flux (p/s), after 124 days, of the mice that were treated with CAR-Bcl-xL at a dose of $1 \times 10^6$ and a reduced dose at $2 \times 10^5$. FIG. 28, row A, shows a Kaplan-Meier survival curve of all of the mice referred to in FIG. 26 after 124 days. FIG. 28, row B, shows a Kaplan-Meier survival curve of all of the mice referred to in FIG. 27 after 124 days.

All CAR-Gene-T cells, even dose-reduced CAR-Bcl-xL-T, exhibited effective tumor control upon the initial tumor engraftment and a long-lasting anti-tumor response for at least 124 days (FIGS. 27, 28).

The persistent protection of CAR-Gene-T cells was even more pronounced in the tumor rechallenge experiments, when mice received an additional $1 \times 10^6$ NALM-6 tumor challenge on day 28 and day 74. Upon the rechallenge, an additional age-matched untreated control group (n=5) was introduced to demonstrate the second tumor engraftment. The CAR-Gene-T cells demonstrated a fast recall response of re-challenged tumor within 2 days after a similar tumor engraftment (shown at 2 h post tumor injection). CAR-Gene-T cell treated mice were tumor-free for >124 days after $1 \times 10^6$ CAR-T treatment upon two $1 \times 10^6$ tumor challenges, with tumor BLI sustained at a background level of around $1 \times 10^6$ f/s (FIGS. 27, 28).

CAR-T, on the other hand, gradually failed to maintain the tumor control, resulting in rapid tumor relapse and death (median survival=33.2 d).

Figure 29:
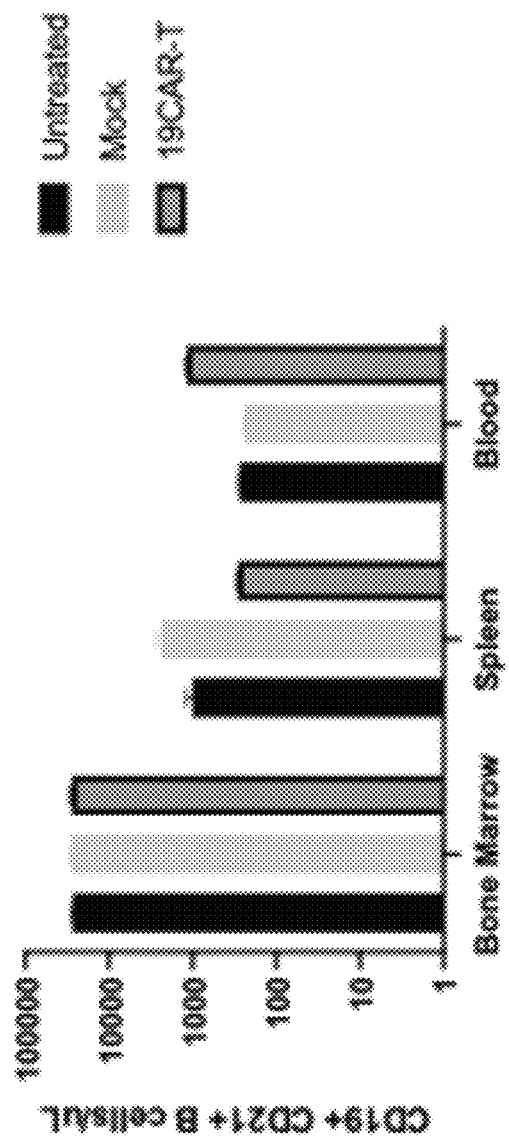
FIG. 29 shows quantifications of CD19+CD21+ B cells in bone marrow, spleen, and blood from untreated, mock-T, and conventional CAR-T cells at their endpoints (n=5).

FIG. 29 shows a quantification of CD19+CD21+ NALM-6 cells at the endpoint of the efficacy-rechallenge study. During necroscopy of CAR-T treated mice, CD19+CD21+ NALM-6 tumor cells were identifiable in bone marrow, spleen, and blood, as well as in the untreated and mock-treated groups, validating the results from BLI quantification.

Figure 30:
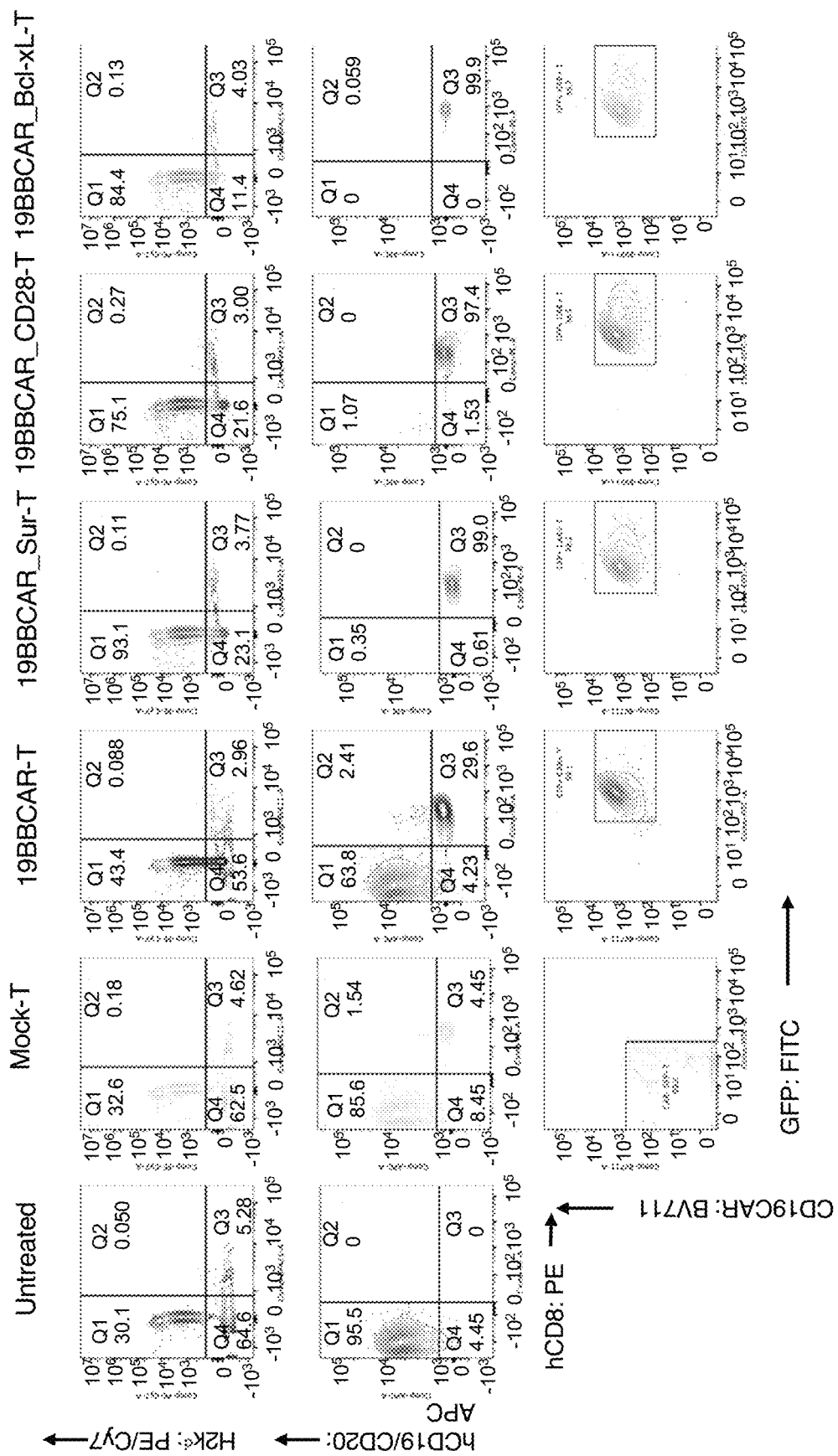
FIG. 30 shows a FACS analysis gating strategy for quantifying CAR-Gene-T ($hCD45^+CD19^-CD8^+CAR^+$ $GFP^+$) cells from mice in the efficacy-rechallenge study referred to in FIG. 25.

FIG. 30 is a set of representative flow charts showing CAR-T cells in mouse blood at day 7. CAR-Gene-T cells and CAR-T cells were detectable at their peak expansion on day 7 post-antigen stimulation. On day 14 post-CAR-T treatment, the CAR-T cell number decreased and became hard to detect at D28, while CAR-Gene-T cells were detectable in peripheral blood.

Figure 31:
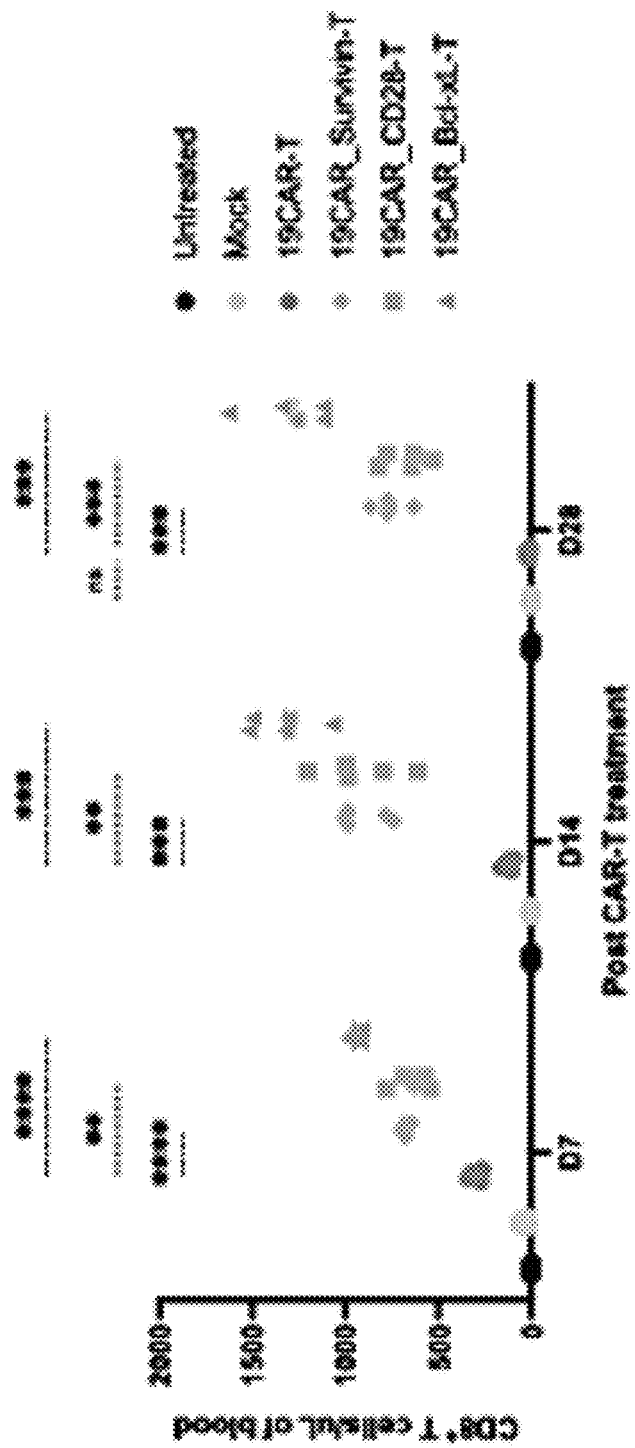
FIG. 31 shows quantification results of CAR-Gene-T cell numbers from mice in the efficacy-rechallenge study referred to in FIG. 25 on days 7, 14, and 28 by counting beads.

FIG. 31 is a quantification of CD8+ T cells in mouse blood at multiple timepoints post-CAR-T treatment (n=5, *, p<0.05, ***p<0.01 by two-way ANOVA test). Persistence of CAR-Gene-T cells after tumor clearance was better than the conventional CAR-T cells.

Figure 32:
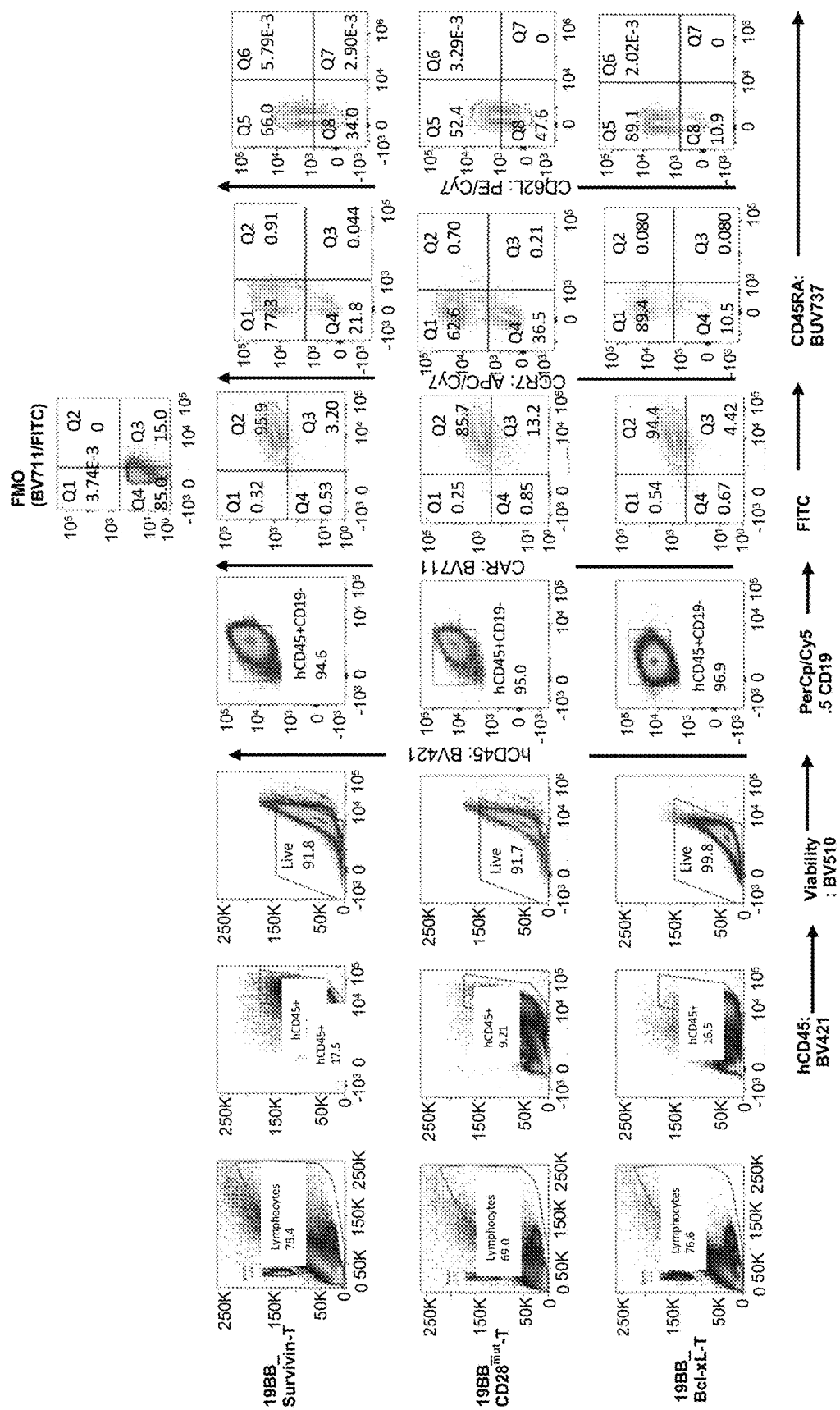
FIG. 32 shows T cell phenotyping analysis of CD45RA, CCR7, and CD62L expression from CAR-Bcl-xL, CAR-Survivin, or CAR-CD28-D124E/T195P (n=5) cell treated mice in the efficacy-rechallenge study referred to in FIG. 25 after 124 days.

FIG. 32 is a set of representative flow charts showing phenotype characterization of CAR-T cells in mouse blood samples at D124 post-CAR-T treatment. Consistent with the in vitro data, all CAR-Gene-T cells showed higher enrichment in the central memory-like (Tcm, defined as CD45RA− CCR7+CD62L+) subset.

Figure 33:
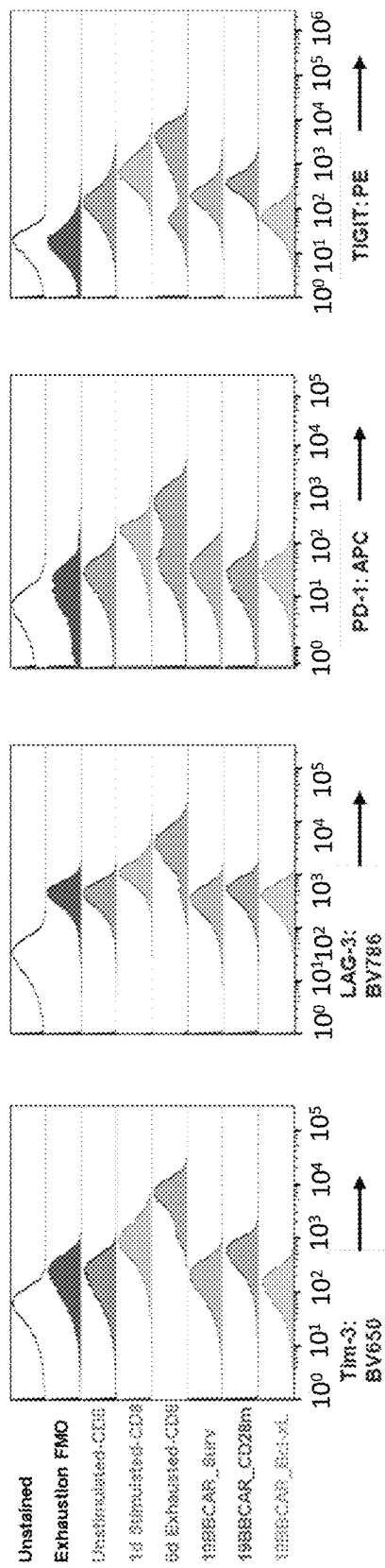
FIG. 33 shows T cell exhaustion analysis and quantification of Tim-3, LAG-3, PD-1, and TIGIT expression from CAR-Bcl-xL, CAR-Survivin, or CAR-CD28-D124E/T195P (n=5) cell treated mice in the efficacy-rechallenge study referred to in FIG. 25 after 124 days. An in vitro $CD8^+$ T cell exhaustion model (unstimulated, stimulated for 1 d, and stimulated for 6 d with aCD3/aCD28 stimulation) was used as positive and negative controls.

FIG. 33 represents the MFI quantifications of exhaustion marker expression on CAR-T cells from mouse blood samples at D124 post-CAR-T treatment. Unstimulated CD8 T cells that were subjected to a similar feeder cell priming process and resting for 2 weeks (but without further aCD3aCD28 stimulation) were used as an experimental control, replicating the pre-injection conditions of the CAR-T cells. An in vitro CD8+ T cell exhaustion model (unstimulated, stimulated for 1 d, and stimulated for 6 d with aCD3aCD28) has been used to establish positive controls for exhaustion markers. All of the CAR-Gene-T cells showed a low level of Tim-3, LAG-3, PD-1, and TIGIT expression, and exhibited no significant difference in exhaustion marker expression level compared to the resting CD8+ T cells pre-injection.

Persistence-Safety Study Results

To investigate the persistence and safety of CAR-Gene-T cells compared to conventional CAR-T, Luci-T controls, and an untreated group (n=5), a tumor-free T-cell-only ffLuc-CAR-T persistence-safety study was set up. NSG mice were infused with 5×10$^6$ ffLuc tagged CAR-T cells, and T cell expansion was tracked by in vivo BLI imaging.

Figure 34:
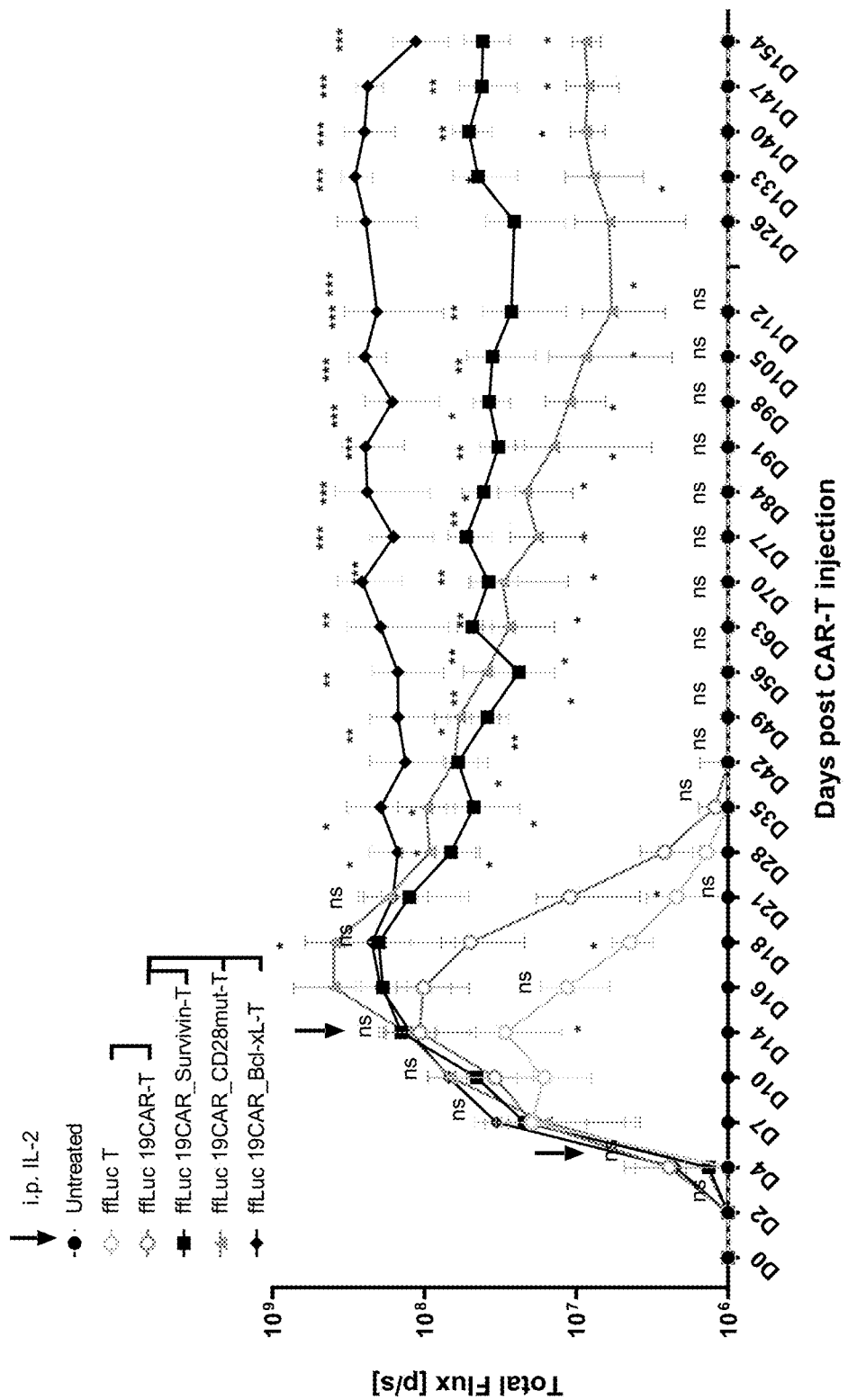
FIG. 34 shows BLI quantification results in total flux (p/s), after 147 days, of a persistence-safety study where tumor-free NSG mice were injected with CAR-T, CAR-Bcl-xL, CAR-Survivin, or CAR-CD28-D124E/T195P (n=5) cells at a dose of $5\times10^6$. An untreated group and a ffLuc-T cell injected group (n=5) were included as controls.

FIG. 34 shows representative BLI quantifications of total flux, illustrating T cell expansion and persistence among CAR-Gene-T cell, CAR-T cell, mock-T, and untreated groups (n=5). Compared to ffLuc-T cells, all ffLuc CAR-Gene-T cells demonstrated significantly superior persistence for 147 days post-injection. Consistent with the T cell quantification in vivo in a shorter period proliferation assay, among all the candidates, ffLuc CAR-Bcl-xL-T cells maintained the highest BLI signal and demonstrated the best survival advantage throughout the detection period, whereas ffLuc CAR-Survivin-T cells and ffLuc CAR-CD28-D124E/T195P-T cells decreased.

In contrast, conventional ffLuc CAR-T cells decreased quickly after the IL-2 withdrawal, and the BLI signal was hard to detect and showed no difference compared to Luci-T cells by day 35.

Figure 35:
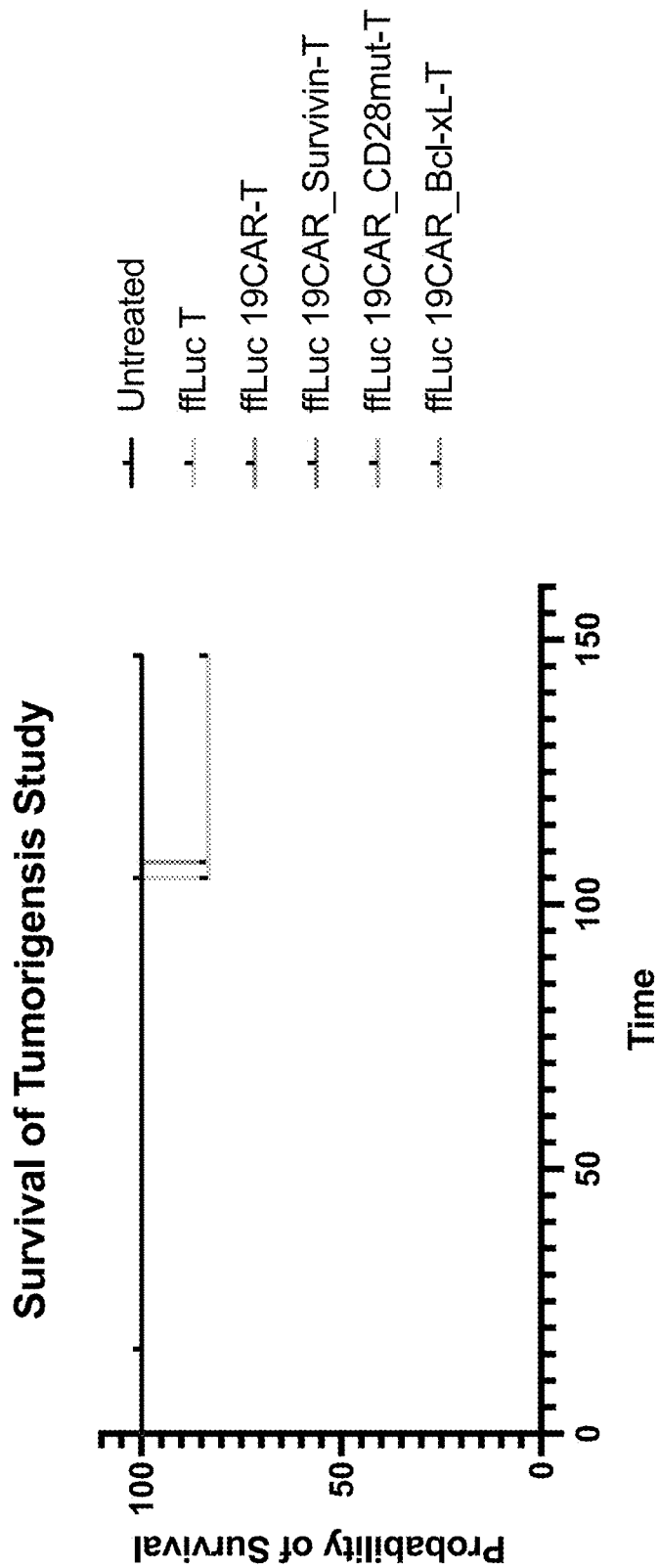
FIG. 35 shows a Kaplan-Meier survival curve of the mice in the persistence-safety study referred to FIG. 34 at 147 days.

FIG. 35 is a Kaplan-Meier survival curve showing T cell tumor-free survival. One mouse from the untreated group and one mouse from the ffLuc group died accidentally, mainly due to their age. No mice from the other groups died or presented any T cell leukemia or lymphoma-related disease.

Figure 36:
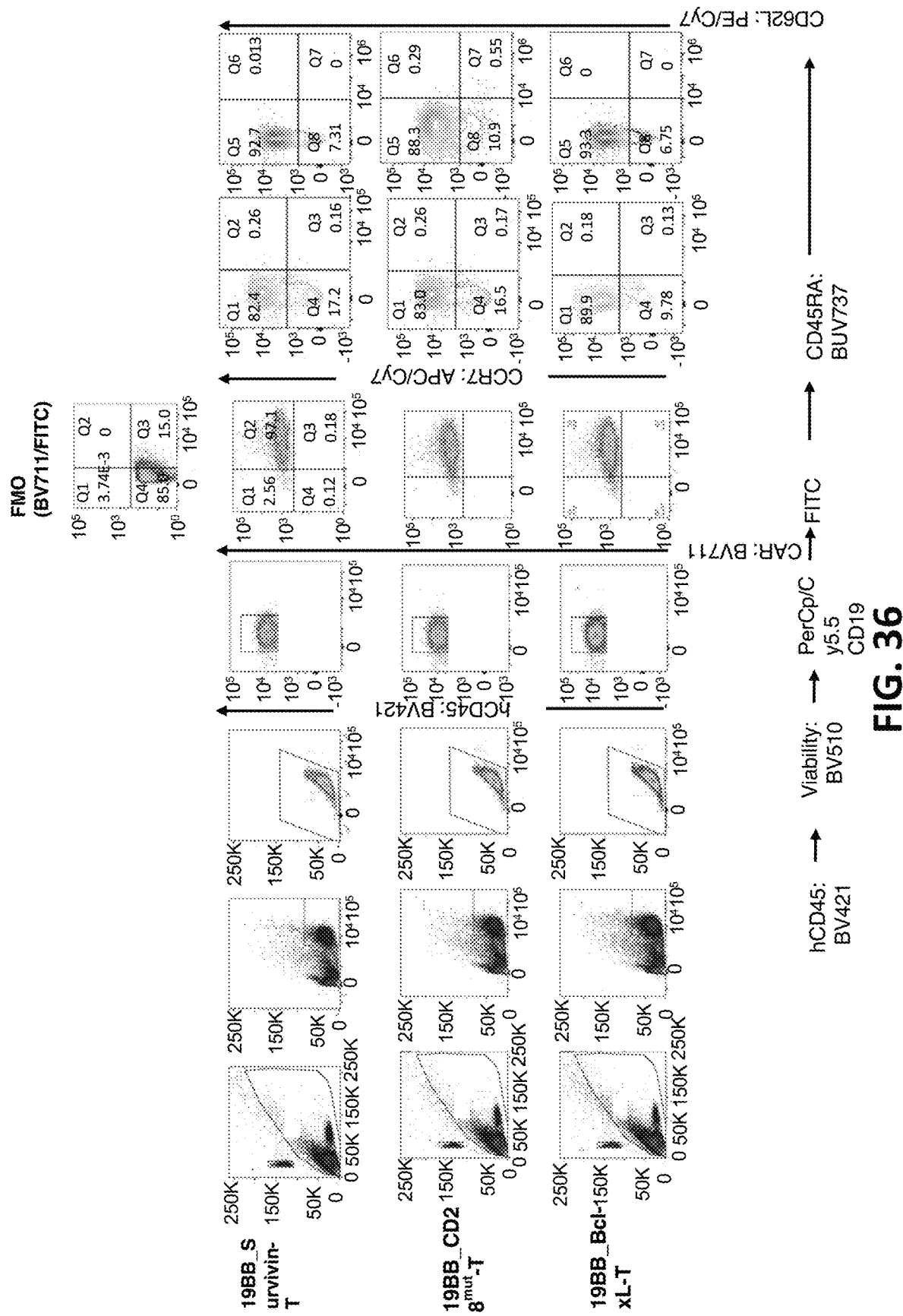
FIG. 36 shows T cell phenotyping analysis of CD45RA, CCR7, and CD62L expression from CAR-Bcl-xL, CAR-Survivin, or CAR-CD28-D124E/T195P (n=5) cell treated mice in the persistence-safety study referred to in FIGS. 34 and 35 at 147 days.

FIG. 36 is a set of representative flow charts showing phenotype characterization of ffLucCAR-T cells in the mouse blood samples at D147 post-CAR-T treatment. Consistent with in vitro data and efficacy-rechallenge group data, all CAR-Gene-T cells showed higher enrichment in the central memory-like (CD45RA$^-$CCR7$^+$CD62L$^+$) subset, and the CAR-Bcl-xL-T cells showed the highest expression.

Figure 37:
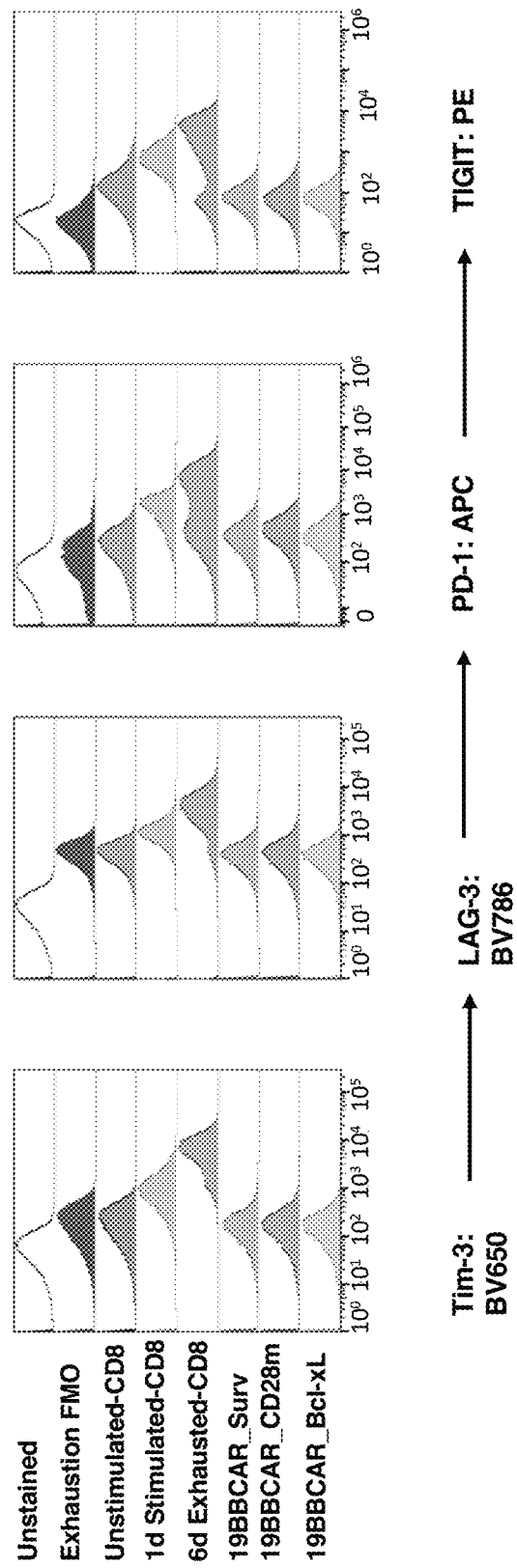
FIG. 37 shows T cell exhaustion analysis and quantification of Tim-3, LAG-3, PD-1, and TIGIT expression from CAR-Bcl-xL, CAR-Survivin, or CAR-CD28-D124E/T195P cell treated mice in the persistence-safety study referred to in FIGS. 34-36 at 124 days. An in vitro CD8$^+$ T cell exhaustion model (unstimulated, stimulated for 1 d, and stimulated for 6 d with aCD3/aCD28) was used as positive and negative controls.

FIG. 37 represents the MFI quantifications of exhaustion marker expression on the ffLuc CAR-T cells from the mouse blood samples at D147 post-CAR-T treatment. The analysis was performed in the same experiment with previously described efficacy-rechallenge study samples. Without seeing any antigens, all ffLuc CAR-Gene T cells showed a low level of Tim-3, LAG-3, PD-1, and TIGIT expression, which exhibit no significant difference compared to the resting CD8+ T cells pre-injection.

Figure 38:
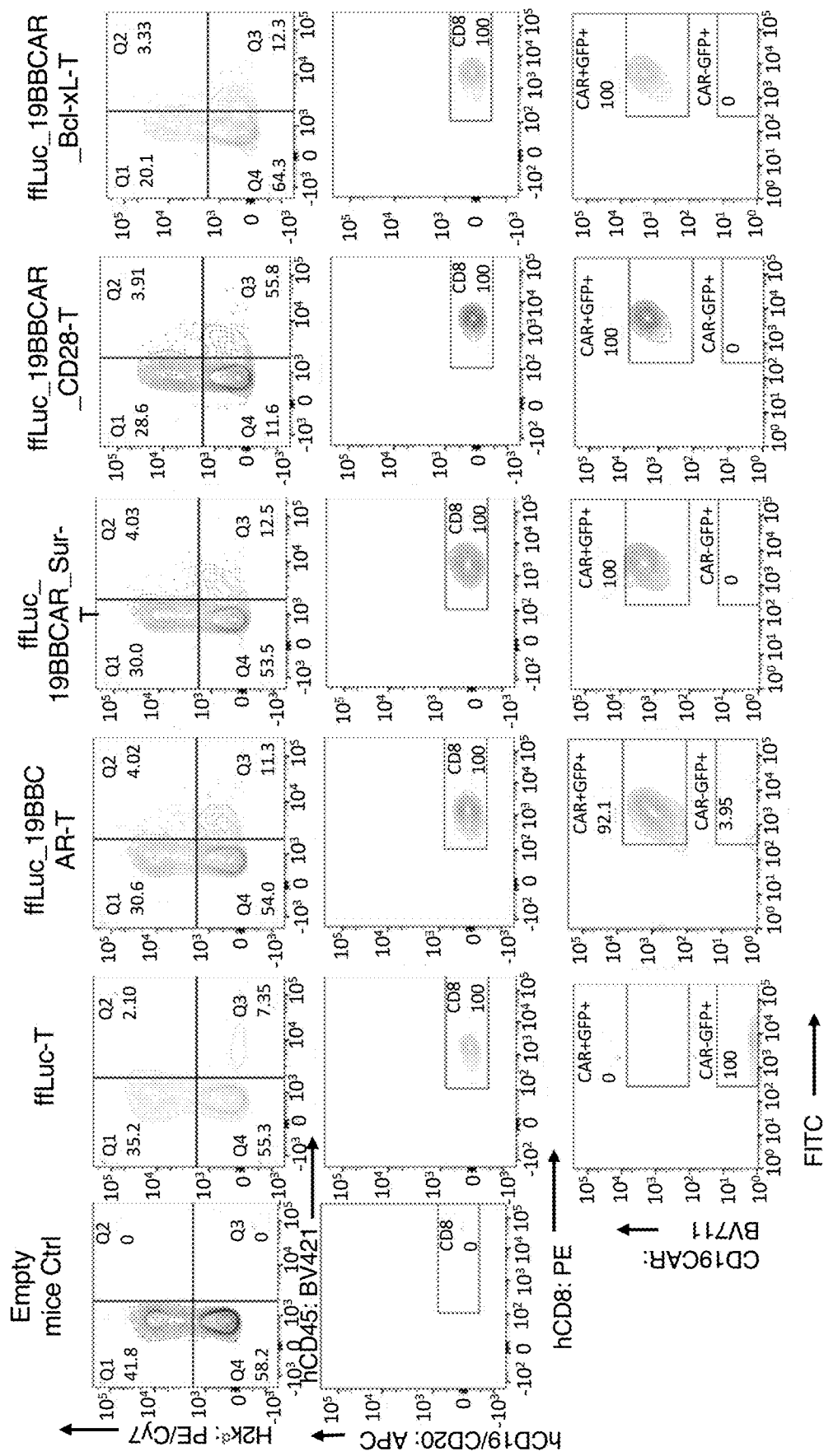
FIG. 38 shows a FACS analysis gating strategy for quantifying ffLuc-CAR-Gene-T (hCD45$^+$CD19$^-$CD8$^+$ CAR$^+$GFP$^+$) cells from mice in the persistence-safety study referred to in FIGS. 34-37.

FIG. 38 is a set of representative flow charts showing CAR-T cells in mouse blood from the persistence-safety study at day 14. All types of CAR-T cells were detectable at their peak expansion on day 14 after two rounds of IL-2 stimulation. The same strategy was applied to sample sets collected on day 28 and day 56.

Figure 39:
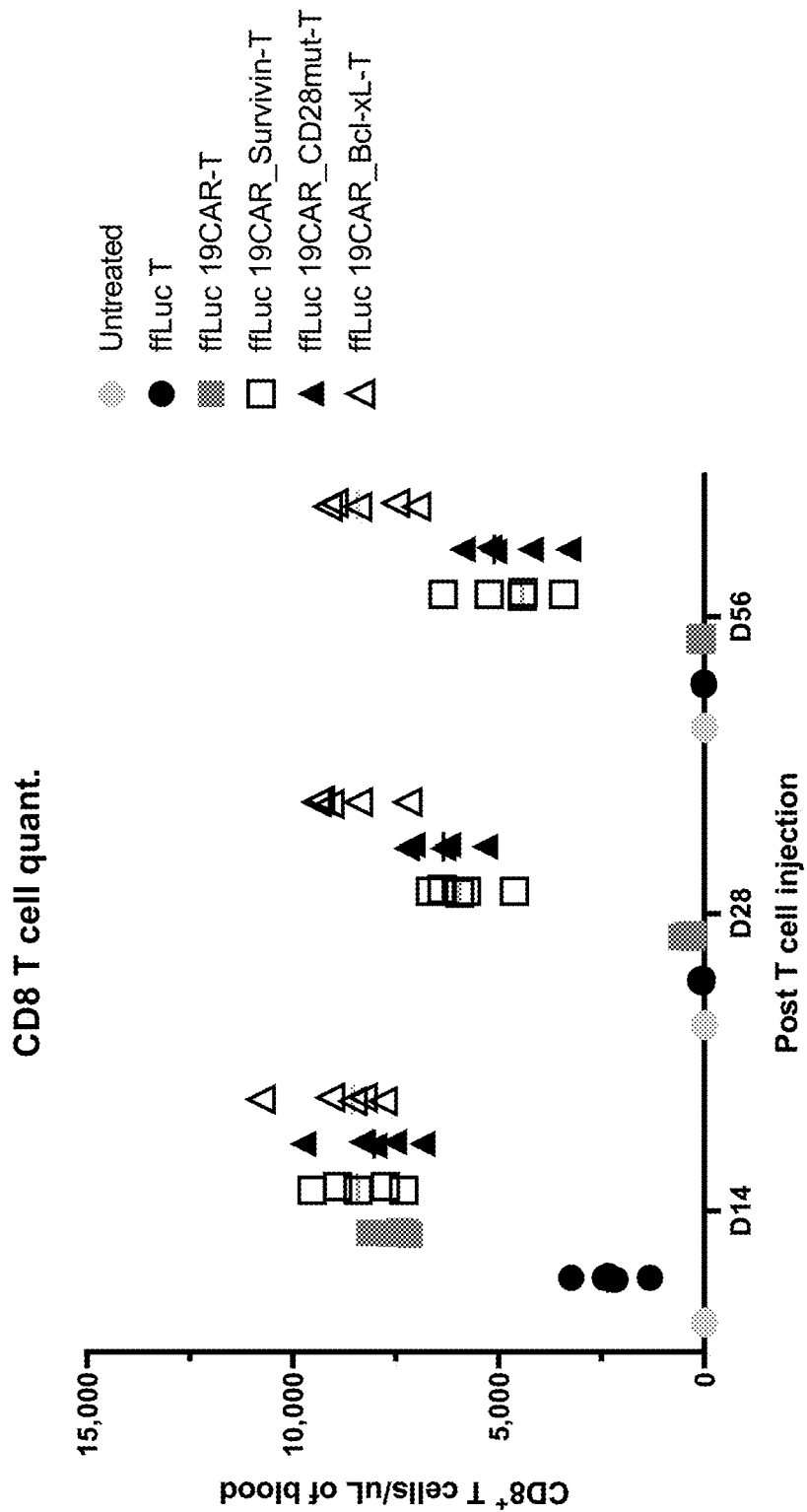
FIG. 39 shows quantification results of ffLuc-CAR-Gene-T cell numbers from mice in the persistence-safety study referred to in FIGS. 34-38 on days 14, 28, and 56 by counting beads.

FIG. 39 is a quantification of CD8+ T cells in mouse blood at multiple timepoints post-CAR-T treatment (n=5, *, $p<0.05$, ***$p<0.01$ by two-way ANOVA test). Persistence of CAR-Gene-T cells was higher even on day 56 post T cell injection, and IL-2 withdrawal did not significantly impact the T-cell survival. In contrast, the number of conventional ffLuc CAR-T cells drastically decreased post IL-2 withdrawal and became undetectable in the blood by day 28.

Figure 40:
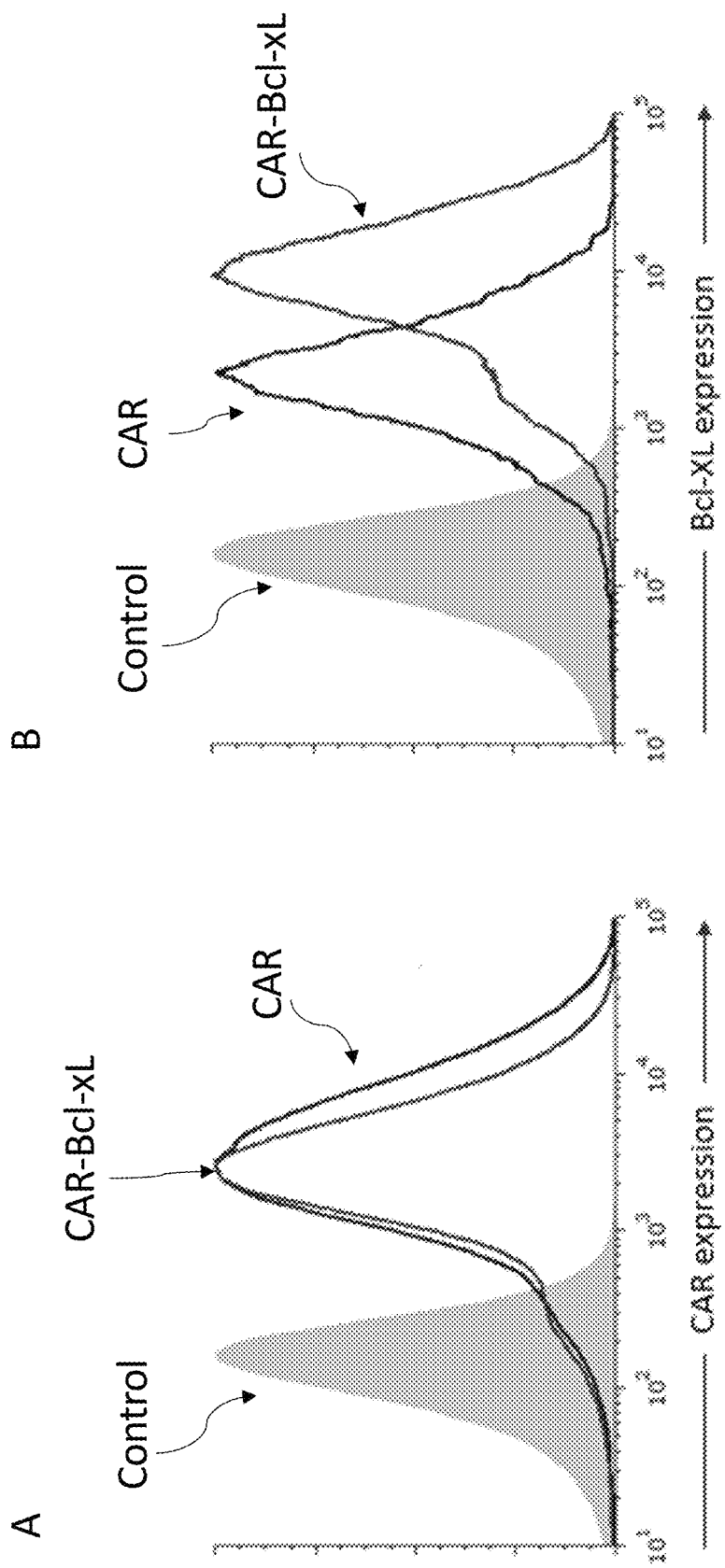
FIG. 40 shows the expression of CAR and Bcl-xL in human CD8$^+$ T cells transduced with lentiviruses expressing CD19 CAR alone or CD19 CAR and Bcl-xL. In "A," the CD8$^+$ T cells were stained with recombinant human CD19 protein labeled with PE. In "B," the CD8$^+$ T cells were stained intracellularly with monoclonal antibodies against human Bcl-xL.

Example 14—Generation of CAR-T Cells Expressing Ectopically Bcl-xL for In Vivo Studies Leukopak containing human primary leukocytes was purchased from StemCell Technologies. CD8+ T cells were purified from the Leukopak using a StemCell isolation kit #17953C and an Easy 250 EasySep magnet according to the manufacturer's instructions. Purified cells were frozen in a StemCell CryoStor CS10 and stored in a liquid nitrogen tank. Several vials of frozen cells were thawed, diluted with X-Vivo 15 complete media, spun, and reconstituted again in the media. Cells were set aside for 4 h in a tissue culture incubator to recover. Cells were stimulated with aCD3aCD28 Dynabeads for three days according to the manufacturer's instructions. On day 3, cells were spun down and resuspended in a solution containing concentrated lentiviruses obtained from VectorBuilder and polybrene. Two viral stocks were used separately, one containing the construct expressing CD19 CAR alone (Gene ID 470181 having SEQ ID NO: 258 and including an EF1a promoter having SEQ ID NO: 133 to express a CAR having SEQ ID NO: 252) and the other expressing CD19 CAR and Bcl-xL (Gene ID 470189 having SEQ ID NO: 259 and including an EF1a promoter having SEQ ID NO: 133 to express a CAR having SEQ ID NO: 252, as well as a PGK-chimeric promoter having SEQ ID NO: 260 to express Bcl-xL having SEQ ID NO: 239). Cells were transduced with lentiviral particles during spinfection at a multiplicity-of-infection equal to 10. Following transduction, cells were incubated for three days and then wash in PBS several times to reduce the original viral titer by 100,000 fold. After removal of free viruses, the spent aCD3aCD28 beads were removed using a magnet. Virus- and bead-free cells were stained with rhCD19-PE reagent obtained from ACRO Biosystems according to the manufacturer's instructions, and the transduction efficiency was evaluated by flow cytometry to be 30%. Populations of cells expressing CD19 CAR were sorted by FACS. Purified populations of cells were expanded in X-Vivo 15 complete media until the day of injections. On the day of injections, T cells were counted, spun down, and resuspended in sterile PBS at 0.25×10$^6$ cells per ml. FIG. 40 shows flow cytometry analysis of the expression of the CAR and Bcl-xL in transduced human CD8+ T cells.

Example 15: In Vivo Study for Efficacy of CAR-T in Raji-Luc Tumor Bearing NSG Mice with or without Bcl-xL The current study was designed to test CAR-T cells (+/−BclXL) generated by lentiviral (LV) transduction expressing the CD19-directed CAR with the 4-1BB costimulatory domain (Tisagenlecleucel, labeled as CAR1), as prepared in Example 14, as well as to test CAR-T cells (+/− BclXL) generated by transfection with transposons (Tn) expressing a CD19-directed CAR with the CD28 costimulatory domain (axicabtagene ciloleucel, labeled as CAR2), as prepared in Examples 7 and 8.

Mice were injected with a tumor cell line and subsequently treated with engineered CAR-T cells+/−Bcl-xL, and the tumor progression was monitored over time by assaying bioluminescence generated by the tumor cells after injection of the luciferase substrate. Table 3 shows a summary of treatment groups and experimental design:

TABLE 3

| Group No. | Group | N = | Dose CAR-T (cells) on d5 (I, V) | Bleeds for FACS | Imaging Days |
|---|---|---|---|---|---|
| 1 | Control | 5 | 0 | d7, 15, 23 | 5, 9, 13, 17, 21, 25, 29 |
| 2 | Tn-CAR1-T Control | 5 | 250,000 | d7, 15, 23 | 5, 9, 13, 17, 21, 25, 29 |
| 3 | Tn-CAR2-T | 5 | 250,000 | d7, 15, 23 | 5, 9, 13, 17, 21, 25, 29 |
| 4 | Tn-CAR2-T/Bcl-xL | 5 | 250,000 | d7, 15, 23 | 5, 9, 13, 17, 21, 25, 29 |
| 5 | LV-CAR1-T | 5 | 250,000 | d7, 15, 23 | 5, 9, 13, 17, 21, 25, 29 |
| 6 | LV-CAR1-T/Bcl-XL | 5 | 250,000 | d7, 15, 23 | 5, 9, 13, 17, 21, 25, 29 |

Six treatment groups, each with five mice, were injected with Raji-Luc tumor cells intravenously on day 0. On day 5, CAR-T cells specific to each treatment group (summarized in Table 3) were injected intravenously. Two control groups were included: a tumor-only group and a group treated with CAR1-T cells expressed from the transposon construct as described in Example 7.

All mice were monitored in the following respects: body weight (2×/week), bioluminescence (days 5, 9, 13, 17, 21, 25, 29), and bled for flow cytometry (FC) (days 7, 15, 23). FC analysis was performed for each of the blood samples using the following markers/panel: mTagBFP2 (CAR-T cells; PB); human CD4, CD8, CD3, CD45, CD20, CD25, and PD1. Counting beads were included to calibrate the accuracy of the data. The study was complete on day 29, and the mice were euthanized. Spleen and blood were harvested for FC analysis as described above. Any mice found moribund were euthanized.

Figure 41:
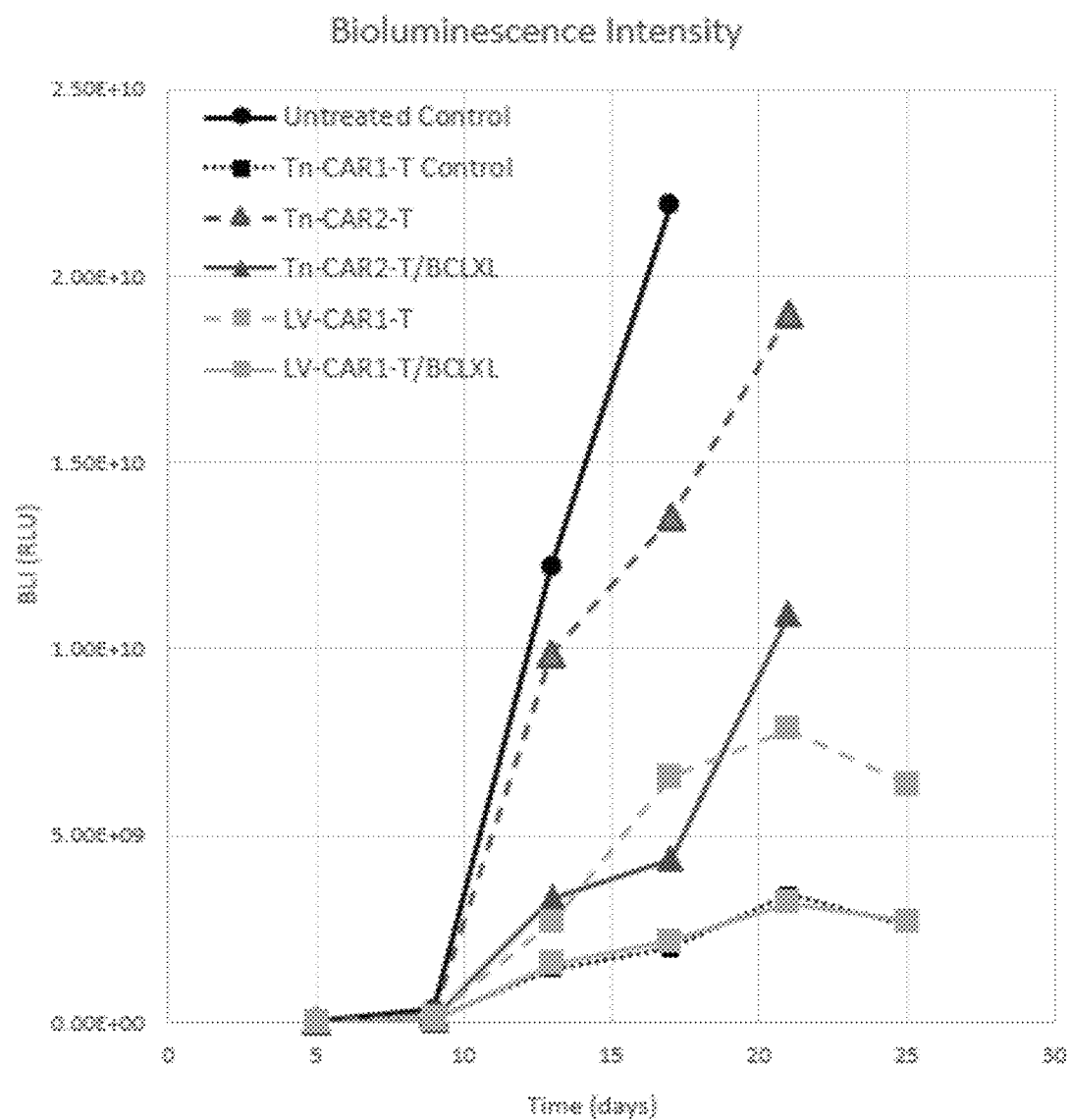
FIG. 41 shows the average tumor progression over time in Raji-luc tumor bearing NSG mice when treated with T cells transduced with a lentivirus comprising genes encoding a CAR, with or without Bcl-xL; or when treated with T cells transfected with a transposon, with or without Bcl-xL, each represented by average bioluminescence. All treated groups show lower tumor burden at each timepoint than the corresponding untreated control.
Figure 42:
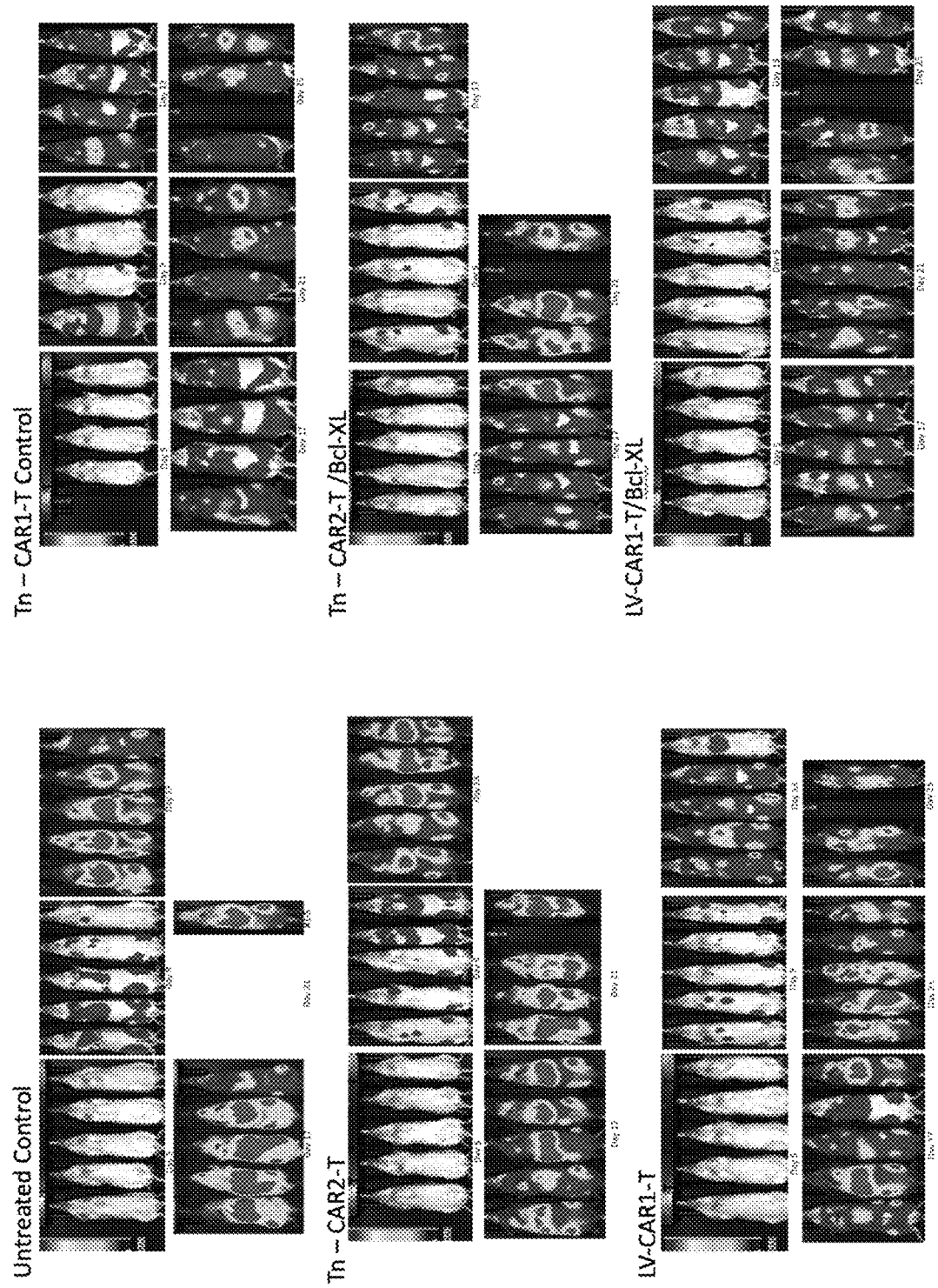
FIG. 42 shows BLI from which the data in FIG. 41 were derived.

FIG. 41 shows the average tumor progression in each treatment group over time, represented by average bioluminescence. All treated groups show lower tumor burden at each timepoint than the untreated control. The group treated with the Tn-CAR1-T cells show lower tumor burden than those either treated with Tn-CAR2-T cells or the transduced LV-CAR1-T cells. Those with Bcl-xL show a smaller tumor burden compared to those with only the respective CAR1 or CAR2. FIG. 42 shows BLI images from which these data were derived.

What is claimed is:

1. A modified T cell expressing a heterologous polynucleotide, the heterologous polynucleotide comprising:

(A) a first gene comprising a nucleotide sequence encoding a protein selected from the group consisting of Bcl-xL, Survivin, or CD28-D124E/T195P, wherein the first gene is operably linked to a first heterologous regulatory sequence effective for expression of the protein within a T cell, thereby enhancing survival of the T cell; and (B) a second gene comprising a nucleotide sequence encoding a chimeric antigen receptor (CAR), wherein the CAR comprises an extracellular domain that specifically binds to a CD19 antigen, and wherein the second gene is operably linked to a second heterologous regulatory sequence effective for expression of the CAR in the T cell, wherein the first heterologous regulatory sequence and the second heterologous regulatory sequence are separate regulatory sequences, and wherein the heterologous polynucleotide is integrated into the genome of the modified T cell.

2. The modified immune cell of claim 1, wherein the CAR further comprises a costimulatory polypeptide selected from CD28 or 4-1BB.

3. A pharmaceutical composition comprising the modified T cell of claim 1.

4. A method for preparing a modified T cell, wherein the method comprises:

introducing a heterologous polynucleotide into a T cell ex-vivo, the heterologous polynucleotide comprising:

(A) a first gene comprising a nucleotide sequence encoding a protein selected from the group consisting of Bcl-xL, Survivin, or CD28-D124E/T195P, wherein the first gene is operably linked to a first heterologous regulatory sequence effective for expression of the protein within the T cell, thereby enhancing survival of the T cell; and (B) a second gene comprising a nucleotide sequence encoding a chimeric antigen receptor (CAR), wherein the CAR comprises an extracellular domain that specifically binds to a CD19 antigen, and wherein the second gene is operably linked to a second heterologous regulatory sequence effective for expression of the CAR in the T cell, wherein the first heterologous regulatory sequence and the second heterologous regulatory sequence are separate regulatory sequences.

5. The method of claim 4, wherein the heterologous polynucleotide comprises a transposon.

6. The method of claim 5, wherein:

the heterologous polynucleotide is flanked by a pair of transposon ends, wherein a corresponding transposase is introduced into the T cell, and wherein the heterologous polynucleotide is transposable by the transposase.

7. The method of claim 6, wherein the transposase is introduced as a nucleic acid encoding the transposase.

8. The method of claim 7, wherein the nucleic acid encoding the transposase is an mRNA.

9. The method of claim 4, wherein the heterologous polynucleotide comprises a lentivirus.

10. The modified T cell of claim 1, wherein the protein is Bcl-xL.

11. The modified T cell of claim 1, wherein the protein is Survivin.

12. The modified T cell of claim 1, wherein the protein is CD28-D124E/T195P.

13. The modified T cell of claim 2, wherein the costimulatory polypeptide is CD28.

14. The modified T cell of claim 2, wherein the costimulatory polypeptide is 4-1BB.

15. A polynucleotide, comprising:

(A) a first gene comprising a nucleotide sequence encoding a protein selected from the group consisting of Bcl-xL, Survivin, or CD28-D124E/T195P, wherein the first gene is operably linked to a first regulatory sequence effective for expression of the protein within a T cell, thereby enhancing survival of the T cell; and (B) a second gene comprising a nucleotide sequence encoding a chimeric antigen receptor (CAR), wherein the CAR comprises an extracellular domain that specifically binds to a CD19 antigen, and wherein the second gene is operably linked to a second regulatory sequence effective for expression of the CAR in the T cell, wherein the first regulatory sequence and the second regulatory sequence are separate sequences.

16. The polynucleotide of claim 15, wherein the CAR further comprises a costimulatory polypeptide selected from CD28 or 4-1BB.

17. The polynucleotide of claim 16, wherein the costimulatory polypeptide is CD28.

18. The polynucleotide of claim 16, wherein the costimulatory polypeptide is 4-1BB.

19. A transposon comprising the polynucleotide according to claim 15.

20. A lentiviral vector comprising the polynucleotide according to claim 15.

* * * * *